US009046530B2

(12) United States Patent
Zhong

(10) Patent No.: US 9,046,530 B2
(45) Date of Patent: Jun. 2, 2015

(54) METHODS AND COMPOSITIONS FOR CHLAMYDIAL ANTIGENS AS REAGENTS FOR DIAGNOSIS OF TUBAL FACTOR INFERTILITY AND CHLAMYDIAL INFECTION

(71) Applicant: Board of Regents, The University of Texas System, Austin, TX (US)

(72) Inventor: Guangming Zhong, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 7 days.

(21) Appl. No.: 13/691,260

(22) Filed: Nov. 30, 2012

(65) Prior Publication Data

US 2013/0143757 A1    Jun. 6, 2013

Related U.S. Application Data

(60) Provisional application No. 61/566,089, filed on Dec. 2, 2011.

(51) Int. Cl.
*G01N 33/68* (2006.01)
*G01N 33/569* (2006.01)

(52) U.S. Cl.
CPC ...... *G01N 33/6893* (2013.01); *G01N 33/56927* (2013.01); *G01N 2800/367* (2013.01); *G01N 2800/52* (2013.01)

(58) Field of Classification Search
USPC .......................................................... 506/9
See application file for complete search history.

(56) References Cited

U.S. PATENT DOCUMENTS

| | | | |
|---|---|---|---|
| 7,892,567 B2 | 2/2011 | Arulanandam et al. | |
| 8,092,812 B2 | 1/2012 | Arulanandam et al. | |
| 2010/0119549 A1 | 5/2010 | Zhong | |
| 2011/0256094 A1 | 10/2011 | Zhong | |
| 2013/0045181 A1 | 2/2013 | Zhong | |

FOREIGN PATENT DOCUMENTS

WO    WO2010/100632 A2 *   9/2010   ............ A61K 39/118

OTHER PUBLICATIONS

Mouton et al, International Journal of STD and AIDS, 2002: 13 (Suppl. 2): 26-29.*
Bax et al. "Comparison of Serological Assays for Detection of *Chlamydia trachomatis* Antibodies in Different Groups of Obstetrical and Gynecological Patients" *Clinical and Diagnostic Laboratory Immunology* 10(1):174-176 (2003).
Budrys et al. "Genome-Wide Identification of *Chlamydia trachomatis* Antigens Associated with Tubal Factor Infertility"

Abstract from the American Society for Reproductive Medicine 67th Annual Meeting (Oct. 15-19, 2011) Orlando, Florida (2 pages).
Cappello et al. "*Chlamydia trachomatis* Infection and Anti-Hsp60 Immunity: The Two Sides of the Coin" *PLoS Pathogens* 5(8):e1000552 (2009).
Chen et al. "The Hypothetical Protein CT813 is Localized in the *Chlamydia trachomatis* Inclusion Membrane and is Immunogenic in Women Urogenitally Infected with *C. trachomatis*" *Infection and Immunity* 74(8):4826-4840 (2006).
Chen et al. "Characterization of Pgp3 a *Chlamydia trachomatis* Plasmid-Encoded Immunodominant Antigen" *Journal of Bacteriology* 192(22):6017-6024 (2010).
Claman et al. "The Presence of Serum Antibody to the Chlamydial Heat Shock Protein (CHSP60) as a Diagnostic Test for Tubal Factor Infertility" *Fertil Steril* 67(3):501-504 (1997).
Coppus et al. "*Chlamydia trachomatis* IgG Seropositivity is Associated with Lower Natural Conception Rates in Ovulatory Subfertile Women without Visible Tubal Pathology" *Human Reproduction* 26(11):3061-3067 (2011).
Den Hartog et al. "*Chlamydia trachomatis*-Associated Tubal Factor Subfertility: Immunogenetic Aspects and Serological Screening" *Human Reproduction Update* 12(6):719-730 (2006).
Fan et al. "*Chlamydia pneumoniae* Secretion of a Protease-Like Activity Factor for Degrading Host Cell Transcription Factors is Required for Major Histocompatibility Complex Antigen Expression" *Infection and Immunity* 70(1):345-349 (2002).
Fan et al. "Inhibition of Apoptosis in *Chlamydia*-Infected Cells: Blockade of Mitochondrial Cytochrome c Release and Caspase Activation" *J. Exp. Med.* 187(4):487-496 (1998).
Fling et al. CD8[+]T Cells Recognize an Inclusion Membrane-Associated Protein from the Vacuolar Pathogen *Chlamydia trachomatis* *PNAS* 98(3):1160-1165 (2001).
Gervassi et al. "Human CD8[+]T Cells Recognize the 60-kDa Cystein-Rich Outer Membrane Protein from *Chlamydia trachomatis*[1]" *The Journal of Immunology* 173:6905-6913 (2004).
Greene et al. "Inhibition of Host Cell Cytokinesis by *Chlamydia trachomatis* Infection" *Journal of Infection* 47:45-51 (2003).
Greene et al. "*Chlamydia*-Infected Cells Continue to Undergo Mitosis and Resist Induction of Apoptosis" *Infection and Immunity* 72(1):451-460 (2004).
Koh et al. "Seroprevalence of IgG Antibodies Against *Chlamydia pneumoniae* in Chinese, Malays and Asian Indians in Singapore" *International Journal of Epidemiology* 31:1001-1007 (2002).
Hower et al. "Evidence that CT694 is a Novel *Chlamydia trachomatis* T3S Substrate Capable of Functioning During Invasion or Early Cycle Development" *Molecular Microbiology* 72(6):1423-1437 (2009).
Lei et al. "Localization of *Chlamydia trachomatis* Hypothetical Protein CT311 in Host Cell Cytoplasm" *Microb Pathog.* 51(3):101-109 (2011).

(Continued)

*Primary Examiner* — Jennifer McDonald
*Assistant Examiner* — Valerie Toodle
(74) *Attorney, Agent, or Firm* — Myers Bigel Sibley & Sajovec, P.A.

(57) ABSTRACT

The present invention provides *Chlamydia* proteins and fragments thereof and methods of use in diagnostic assays.

7 Claims, 6 Drawing Sheets

(56) References Cited

OTHER PUBLICATIONS

Li et al. "Characterization of Fifty Putative Inclusion Membrane Proteins Encoded in the *Chlamydia trachomatis* Genome" *Infection and Immunity* 76(6): 2746-2757 (2008).

Li et al. "The Chlamydial Plasmid-Encoded Protein pgp3 is Secreted into the Cytosol of *Chlamydia*-Infected Cells" *Infection and Immunity* 76(8):3415-3428 (2008).

Logan et al. "Can History, Ultrasound, or ELISA Chlamydial Antibodies, Alone or in Combination, Predict Tubal Factor Infertility in Subfertile Women?" *Human Reproduction* 18(11):2350-2356 (2003).

Peeling et al. "Antibody to Chlamydial hsp60 Predicts an Increased Risk for Chlamydial Pelvic Inflammatory Disease" *The Journal of Infectious Diseases* 175:1153-1158 (1997).

Qi et al. "A *Chlamydia trachomatis* OmcB C-Terminal Fragment is Released into the Host Cell Cytoplasm and is Immunogenic in Humans" *Infection and Immunity* 79(6):2193-2203 (2011).

Ridker et al. "Prospective Study of *Chlamydia pneumoniae* IgG Seropositivity and Risks of Future Myocardial Infarction" *Circulation* 99:1161-1164 (1999).

Rodgers et al. "Association of Tubal Factor Infertility with Elevated Antibodies to *Chlamydia trachomatis* Caseinolytic Protease P" *Am J Obstet Gynecol.* 203(5):494.e7-494.e14 (2010).

Rodgers et al. "Genome-Wide Identification of *Chlamydia trachomatis* Antigens Associated with Tubal Factor Infertility" *Fertil Steril.* 96(3):715-721 (2011).

Sharma et al. "Human Antibody Responses to a *Chlamydia*-Secreted Protease Factor" *Infection and Immunity* 72(12):7164-7171 (2004).

Sharma et al. "Profiling of Human Antibody Responses to *Chlamydia trachomatis* Urogenital Tract Infection Using Microplates Arrayed with 156 Chlamydial Fusion Proteins" *Infection and Immunity* 74(3):1490-1499 (2006).

Stephens et al. "Antichlamydial Antibodies, Human Fertility, and Pregnancy Wastage" *Infect Dis Obstet Gynecol* vol. 2011, Article ID 525182 (9 pages) (2011).

Veenemans et al. "The Value of *Chlamydia trachomatis* Antibody Testing in Predicting Tubal Factor Infertility" *Human Reproduction* 17(3):695-698 (2002).

Wang et al. "A Genome-Wide Profiling of the Humoral Immune Response to *Chlamydia trachomatis* Infection Reveals Vaccine Candidate Antigens Expressed in Humans" *The Journal of Immunology* 185:1670-1680 (2010).

Zhong et al. "Identification of a Chlamydial Protease-Like Activity Factor Responsible for the Degradation of Host Transcription Factors" *J. Exp. Med.* 193(8):935-942 (2001).

Ault et al. "Antibodies to the Chlamydial 60 Kilodalton Heat Shock Protein in Women with Tubal Factor Infertility" *Dis. Obstet. and Gynecol.* 6:163-167 (1998).

Barlow et al. "The Prevalence of *Chlamydia trachomatis* in Fresh Tissue Specimens from Patients with Ectopic Pregnancy or Tubal Factor Infertility as Determined by PCR and in-situ Hybridisation" *J. Med. Microbiol.* 50:902-908 (2001).

Beatty et al. "Repeated and Persistent Infection with *Chlamydia* and the Development of Chronic Inflammation and Disease" *Trends in Microbiology* 2(3):94-98 (1994).

Brunham et al. *Chlamydia trachomatis*: Its Role in Tubal Infertility *The Journal of Infectious Diseases* 152(6):1275-1282 (1985).

Budrys et al. "*Chlamydia trachomatis* Antigens Recognized in Women with Tubal Factor Infertility, Normal Fertility, and Acute Infection" *Obstet Gynecol* 119:1009-1016 (2012).

Bulut et al. "Chlamydial Heat Shock Protein 60 Activates Macrophages and Endothelial Cells Through Toll-Like Receptor 4 and MD2 in a MyD88-Dependent Pathway" *The Journal of Immunology* 168:1435-1440 (2002).

Campanella et al. "A Comparative Analysis of the Products of GROEL-1 Gene from *Chlamydia trachomatis* Serovar D and the HSP60 var1 Transcript from *Homo sapiens* Suggests a Possible Autoimmune Response" *International Journal of Immunogenetics* 36:73-78 (2008).

Cheng et al. "Intracellular Interleukin-1α Mediates Interleukin-8 Production Induced by *Chlamydia trachomatis* Infection via a Mechanism Independent of Type I Interleukin-1 Receptor" *Infection and Immunity* 76(3):942-951 (2008).

Cheng et al. "Caspase-1 Contributes to *Chlamydia trachomatis*-Induced Upper Urogenital Tract Inflammatory Pathologies without Affecting the Course of Infection" *Infection and Immunity* 76(2):515-522 (2008).

Confino et al. "Transcervical Balloon Tuboplasty" *JAMA* 264(16):2079-2082 (1990).

Dadamessi et al. "Combined Detection of *Chlamydia trachomatis*-Specific Antibodies Against the 10 and 60-kDa Heat Shock Proteins as a Diagnostic Tool for Tubal Factor Infertility: Results from a Case-Control Study in Cameroon" *FEMS Immunology and Medical Microbiology* 45:31-35 (2005).

Den Hartog et al. "Screening Strategies for Tubal Factor Subfertility" *Human Reproduction* 23(8):1840-1848 (2008).

Dieterle et al, "Humoral Immune Response to the Chlamydial Heat Shock Proteins hsp60 and hsp70 in *Chlamydia*-Associated Chronic Salpingitis with Tubal Occlusion" *Human Reproduction* 11(6):1352-1356 (1996).

Domeika et al. "Humoral Immune Response to Conserved Epitopes of *Chlamydia trachomatis* and Human 60-kDa Heat-Shock Protein in Women with Pelvic Inflammatory Disease" *The Journal of Infectious Diseases* 177:714-719 (1998).

Dutta et al. "*Chlamydia trachomatis*-Specific Heat Shock Proteins 60 Antibodies Can Serve as Prognostic Marker in Secondary Infertile Women" *Infection* 36(4):374-378 (2008).

El Hakim et al. "Significance of Positive *Chlamydia* Serology in Women with Normal-Looking Fallopian Tubes" *RBMOnline* 19(6):847-851 (2009).

Equils et al. "*Chlamydia* Heat Shock Protein 60 Induces Trophoblast Apoptosis Through TLR4[1,2]" *The Journal of Immunology* 177:1257-1263 (2006).

Gijsen et al. "*Chlamydia pneumoniae* and Screening for Tubal Factor Subfertility" *Human Reproduction* 16(3):487-491 (2001).

Goodall et al. "Identification of *Chlamydia trachomatis* Antigens Recognized by Human CD4[+] T Lymphocytes by Screening an Expression Library" *Eur. J. Immunol.* 31:1513-1522 (2001).

Haggerty "Evidence for a Role of *Mycoplasma genitalium* in Pelvic Inflammatory Disease" *Current Opinion in Infectious Diseases* 21:65-69 (2008).

Healy et al. "Female Infertility: Causes and Treatment" *The Lancet* 343:1539-1544 (1994).

Hjelholt et al. "Tubal Factor Infertility is Associated with Antibodies Against *Chlamydia trachomatis* Heat Shock Protein 60 (HSP60) but not Human HSP60" *Human Reproduction* 26(8):2069-2076 (2011).

Jakus et al. "Antibody to the *Chlamydia trachomatis* 60 kDa Heat Shock Protein in Follicular Fluid and in Vitro Fertilization Outcome" *American Journal of Reproductive Immunology* 59:85-89 (2008).

Karinen et al. "Association Between *Chlamydia trachomatis* Antibodies and Subfertility in the Northern Finland Birth Cohort 1966 (NFBC 1966), at the Age of 31 Years" *Epidemiol. Infect.* 132:977-984 (2004).

Karinen et al. "Antibodies to *Chlamydia trachomatis* Heat Shock Proteins Hsp60 and Hsp10 and Subfertility in General Population at Age 31" *AJRI* 52:291-297 (2004).

Kinnunen et al. "Chlamydial Heat Shock Protein 60-Specific T Cells in Inflamed Salpingeal Tissue" *Fertility and Sterility* 77(1):162-166 (2002).

Kinnunen et al. "Heat Shock Protein 60 Specific T-Cell Response in Chlamydial Infections" *Scand. J. Immunol.* 54:76-81 (2001).

Laverda et al. "Chlamydial Heat Shock Proteins and Disease Pathology: New Paradigms for Old Problems?" *Infect. Dis. Obstet. Gynecol.* 7:64-71 (1999).

Moreno et al. "Immunopathogenic Consequences of *Chlamydia trachomatis* 60 kDa Heat Shock Protein Expression in the Female Reproductive Tract" *Cell Stress and Chaperones* 15:467-473 (2010).

Lunenfeld et al. "The Association Between Chlamydial-Specific IgG and IgA Antibodies and Pregnancy Outcome in an In Vitro Fertilization Program" *Journal of in Vitro Fertilization and Embryo Transfer* 6(4):222-227 (1989).

(56) References Cited

OTHER PUBLICATIONS

Malik et al. "*Chlamydia trachomatis* Infection in Women with Secondary Infertility" *Fertility and Sterility* 91(1):91-95 (2009).

Mol et al. "The Accuracy of Serum Chlamydial Antibodies in the Diagnosis of Tubal Pathology: a Meta-Analysis" *Fertil Steril* 67(6):1031-1037 (1997).

Morales et al. "Infection of Human Fallopian Tube Epithelial Cells with *Neisseria gonorrhoeae* Protects Cells from Tumor Necrosis Factor Alpha-Induced Apoptosis" *Infection and Immunity* 74(6):3643-3650 (2006).

Mygind et al. "Analysis of the Humoral Immune Response to *Chlamydia* Outer Membrane Protein 2" *Clinical and Diagnostic Laboratory Immunology* 5(3):313-318 (1998).

Pellati et al. "Genital Tract Infections and Infertility" *Reproductive Biology* 140:3-11 (2008).

Persson et al. "Antibodies to *Chlamydia trachomatis* Heat Shock Proteins in Women with Tubal Factor Infertility are Associated with Prior Infection by *C. trachomatis* but not by *C. pneumoniae*" *Human Reproduction* 14(8):1969-1973 (1999).

Sarov et al. "*Chlamydia* Specific IgG and IgA Antibodies in Women with Obstructive Infertility as Determined by Immunoblotting and Immunoperoxidase Assays" *Eur. J. Epidemiol.* 4(2):216-223 (1988).

Stephens "The Cellular Paradigm of Chlamydial Pathogenesis" *Trends in Microbiology* 11(1):44-51 (2003).

Svenstrup et al. "*Mycoplasma genitalim, Chlamydia trachomatis*, and Tubal Factor Infertility—a Prospective Study" *Fertility and Sterility* 90(3):513-520 (2008).

Sziller et al. "Circulating Antibodies to a Conserved Epitope of the *Chlamydia trachomatis* 60-kDa Heat Shock Protein is Associated with Decreased Spontaneous Fertility Rate in Ectopic Pregnant Women Treated by Salpingectomy" *Am J Reprod Immunol* 59:99-104 (2008).

Tiitinen et al. "*Chlamydia trachomatis* and Chlamydial Heat Shock Protein 60-Specific Antibody and Cell-Mediated Responses Predict Tubal Factor Infertility" *Human Reproduction* 21(6):1533-1538 (2006).

Westrom et al. "Pelvic Inflammatory Disease and Fertility. A Cohort Study of 1,844 Women with Laparoscopically Verified Disease and 657 Control Women with Normal Laparoscopic Results" *Sex Transm Dis* 19:185-192 (1992).

Toye et al. "Association Between Antibody to the Chlamydial Heat-Shock Protein and Tubal Infertility" *The Journal of Infectious Diseases* 168(5):1236-1240 (1993).

Wang et al. "A *Chlamydial* Type III-Secreted Effector Protein (Tarp) is Predominantly Recognized by Antibodies from Humans Infected with *Chlamydia trachomatis* and Induces Protective Immunity Against Upper Genital Tract Pathologies in Mice" *Vaccine* 27:2967-2980 (2009).

Wilkowska-Trojniel et al. "*Chlamydia trachomatis* Urogenital Infection in Women with Infertility" *Advances in Medical Sciences* 54(1):82-85 (2009).

Witkin et al. "Cell-Mediated Immune Response to the Recombinant 57-kDa Heat-Shock Protein of *Chlamydia trachomatis* in Women with Salpingitis" *The Journal of Infectious Diseases* 167(6):1379-1383 (1993).

\* cited by examiner

| CT ORF | | CT110 | CT376 | CT111 | CT557 | CT579 |
|---|---|---|---|---|---|---|
| TFI | Total | 24 | 24 | 24 | 24 | 24 |
| | +Ve | 9 | 6 | 4 | 4 | 4 |
| FC | Total | 25 | 25 | 25 | 25 | 25 |
| | +Ve | 0 | 0 | 0 | 0 | 0 |

Summary

B

*14 out of 24 (58%) TFI antisera reacted with CT110, CT376 or CT557

Positive Reactivity Distribution

24 TFI antisera

*C. trachomatis* ORF fusion proteins used for reacting with human antisera

Comparison of a potential chlamydia Ab test with HSG for identifying tubal factor fertility (TFI)

METHODS AND COMPOSITIONS FOR CHLAMYDIAL ANTIGENS AS REAGENTS FOR DIAGNOSIS OF TUBAL FACTOR INFERTILITY AND CHLAMYDIAL INFECTION

STATEMENT OF PRIORITY

This application claims the benefit, under 35 U.S.C. §119 (e), of U.S. Provisional Application Ser. No. 61/566,089, filed Dec. 2, 2011, the entire contents of which are incorporated by reference herein.

STATEMENT OF GOVERNMENT SUPPORT

The present invention was funded in part by government support under grant numbers R01AI064537 and R01AI047997 from the National Institutes of Health. The United States Government has certain rights in this invention.

STATEMENT REGARDING ELECTRONIC FILING OF A SEQUENCE LISTING

A Sequence Listing in ASCII text format, submitted under 37 C.F.R. §1.821, entitled 9237-50_ST25.txt, 1,098,928 bytes in size, generated on Nov. 29, 2012 and filed via EFS-Web, is provided in lieu of a paper copy. This Sequence Listing is hereby incorporated herein by reference into the specification for its disclosures.

BACKGROUND OF THE INVENTION

1. Field of the Invention

The present invention relates to the field of diagnosis/determination of chlamydial infection and disease as well as diagnosis/determination of tubal factor infertility.

2. Background Art

Twenty-five to 35% of patients presenting for infertility evaluation have tubal disease (1-4). *Chlamydia trachomatis* is the primary sexually transmitted infection responsible for tubal factor infertility (TFI) (5-7) with *C. trachomatis* antibodies in approximately 70% of human patients (8). *C. trachomatis* infected cells produce inflammatory cytokines (9-10) which may contribute to upper genital tract inflammatory damage (11-13). Lunefeld et al. found that among patients undergoing in vitro fertilization, those with *C. trachomatis* antibodies had decreased pregnancy rates (14).

*C. trachomatis* infection is often asymptomatic so patient history cannot dictate the presence of tubal disease (15-16). Elevated titers of anti-*C. trachomatis* antibodies are associated with TFI, but detection of overall antibody levels lacks the sensitivity and specificity required for differential diagnosis (17).

The present invention provides chlamydial antigens that can be used to develop rapid and convenient means for diagnosing/determining tubal factor infertility, as well as chlamydial antigens that can be used to develop rapid and convenient means for diagnosing/determining acute chlamydial invention.

SUMMARY OF THE INVENTION

In one aspect, the present invention provides a method of diagnosing tubal factor infertility in a subject, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof, and *Chlamydia trachomatis* CT875 or an immunologically reactive fragment thereof; and (b) detecting formation of an antigen/antibody complex with each of the antigen of *Chlamydia trachomatis* CT443 or an immunologically reactive fragment thereof and the antigen of *Chlamydia trachomatis* CT381 or an immunologically reactive fragment thereof and detecting the absence of formation of an antigen/antibody complex (e.g., detecting no antigen/antibody complex) with the antigen of *Chlamydia trachomatis* CT875 or an immunologically reactive fragment thereof in the sample, thereby diagnosing tubal factor infertility in the subject.

Also provided herein is a method of identifying a subject as having an increased likelihood of having or developing tubal factor infertility, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or an immunologically reactive fragment thereof and the antigen of *Chlamydia trachomatis* CT381 or an immunologically reactive fragment thereof and detecting the absence of formation of an antigen/antibody complex (e.g., detecting no antigen/antibody complex) with the antigen of *Chlamydia trachomatis* CT875 or an immunologically reactive fragment thereof in the sample, thereby identifying the subject as having an increased likelihood of having or developing tubal factor infertility.

In further aspects, the present invention provides a method of diagnosing acute *Chlamydia trachomatis* infection in a subject, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or immunologically reactive fragment thereof, the antigen of *Chlamydia trachomatis* CT381 or immunologically reactive fragment thereof and the antigen of *Chlamydia trachomatis* CT875 or the immunologically reactive fragment in the sample, thereby diagnosing acute *Chlamydia trachomatis* infection in the subject.

Additionally provided herein is a method of diagnosing acute *Chlamydia trachomatis* infection in a subject, comprising: (a) contacting a biological sample from the subject with an antigen of *Chlamydia trachomatis* CT875 or immunologically reactive fragment thereof; and (b) detecting formation of an antigen/antibody complex with the antigen of *Chlamydia trachomatis* CT875 or immunologically reactive fragment thereof in the sample, thereby diagnosing acute *Chlamydia trachomatis* infection in the subject.

The present invention also provides a method of identifying a subject as having an increased likelihood of having an acute *Chlamydia trachomatis* infection, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or immunologically reactive fragment thereof, the antigen of *Chlamydia trachomatis* CT381 or immunologically reactive fragment thereof and the antigen of *Chlamydia trachomatis* CT875 or the immunologically reactive fragment in the sample, thereby identifying the subject as having an increased likelihood of having an acute *Chlamydia trachomatis* infection.

Additionally provided herein is a method of identifying a subject as having an increased likelihood of having an acute *Chlamydia trachomatis* infection, comprising: (a) contacting a biological sample from the subject with an antigen of *Chlamydia trachomatis* CT875 or immunologically reactive fragment thereof; and (b) detecting formation of an antigen/antibody complex with the antigen of *Chlamydia trachomatis* CT875 or immunologically reactive fragment thereof in the sample, thereby identifying the subject as having an increased likelihood of having an acute *Chlamydia trachomatis* infection.

Additionally provided herein is a method of identifying a subject for whom antibiotic therapy for *Chlamydia trachomatis* infection is likely to be or would be beneficial, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or immunologically reactive fragment thereof, the antigen of *Chlamydia trachomatis* CT381 or immunologically reactive fragment thereof and the antigen of *Chlamydia trachomatis* CT875 or the immunologically reactive fragment in the sample, thereby identifying a subject for whom antibiotic therapy to treat *Chlamydia trachomatis* infection is likely to be or would be beneficial. The method above can further comprise the step of applying antibiotic therapy for *Chlamydia trachomatis* infection and/or anti-inflammatory treatment procedures to the subject.

Also provided herein is a method of identifying a subject for whom antibiotic therapy for *Chlamydia trachomatis* infection is likely to be or would be beneficial, comprising: (a) contacting a biological sample from the subject with an antigen of *Chlamydia trachomatis* CT875 or immunologically reactive fragment thereof; and (b) detecting formation of an antigen/antibody complex with the antigen of *Chlamydia trachomatis* CT875 or immunologically reactive fragment thereof in the sample, thereby identifying a subject for whom antibiotic therapy for *Chlamydia trachomatis* infection is likely to be or would be beneficial. The method above can further comprise the step of applying antibiotic therapy for *Chlamydia trachomatis* infection and/or anti-inflammatory treatment procedures to the subject.

In further aspects, the present invention provides a kit comprising a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof.

Additionally provided is a kit comprising a diagnostic panel comprising an antigen of *Chlamydia trachomatis* CT875 or immunologically reactive fragment thereof. In particular embodiments, a kit of this invention can further comprise an antigen of *Chlamydia trachomatis* CT147 or immunologically reactive fragment thereof.

BRIEF DESCRIPTION OF THE DRAWINGS

FIGS. 2A-B. Distribution Patterns of Reactivity of 5 Antigens with 24 TFI Samples. The reactivity of each of 5 antigens (listed along the X-axis at the top of bottom) with 24 TFI and 25 FC human sera (each at a final dilution of 1:1000) was summarized in panel A and the reactivity with the 24 TFI samples (listed along Y-axis) was displayed in panel B. Each horizontal bar indicates a positive reactivity as determined based on the mean plus 2 standard deviations. Star indicates antisera uniquely reacted with a given antigen. Please note that CT110, CT376 & CT557 together positively detected a total of 14 unique TFI antisera (58%).

DETAILED DESCRIPTION OF THE INVENTION

Figure 1:
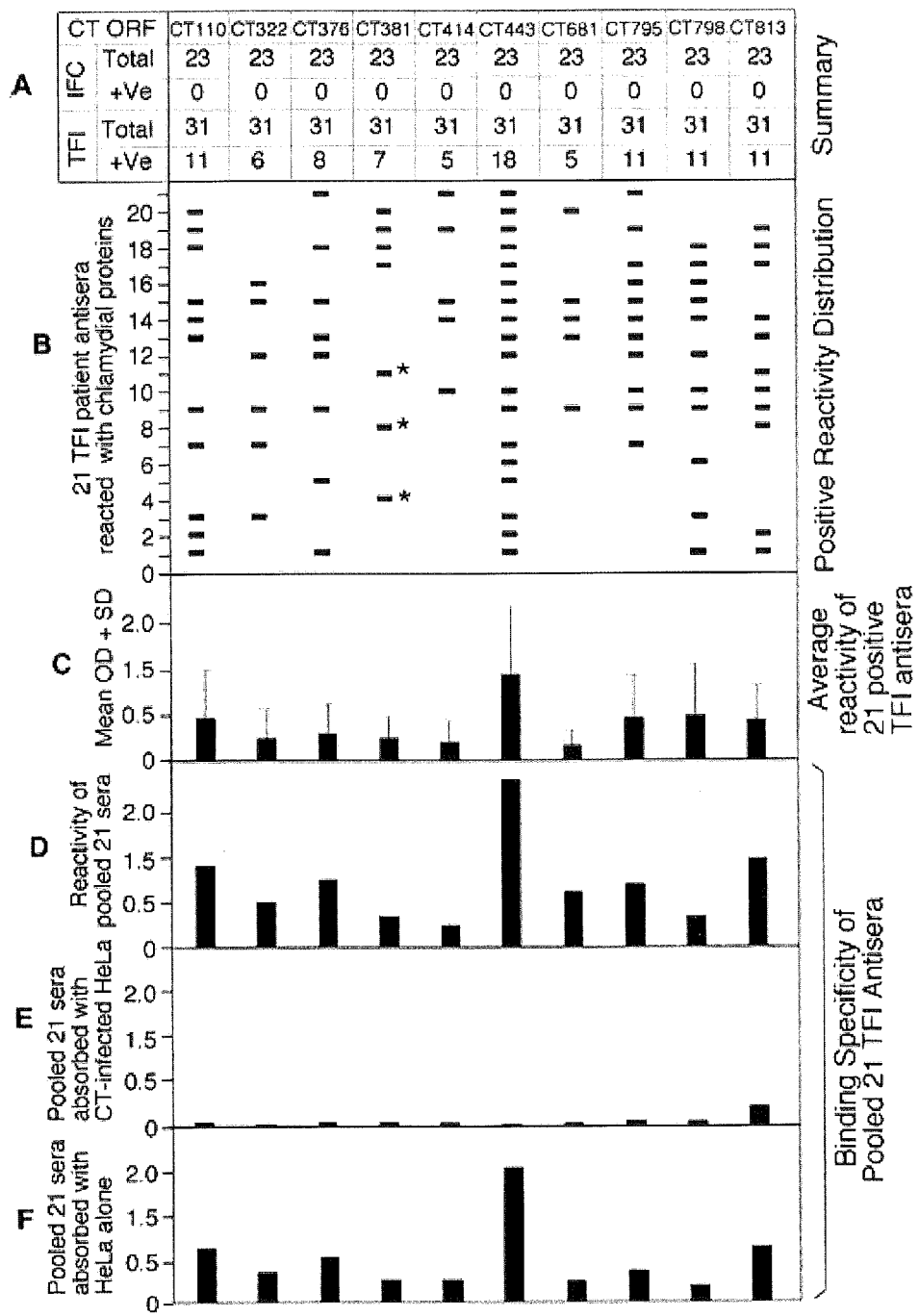
FIGS. 1A-F. Reactivity of 30 *C. trachomatis* Antigens with 54 Patient Sera at 1:4000 Dilution. The 30 antigens were reacted with the 54 human sera as described in Table 2 except that each serum was diluted 1:4000 (data not shown). (A) Ten of the 30 antigens, failing to react with any of the 23 IFC sera, were thus presented in the figure. Note that HSP60 (CT110) and OmcB (CT443) maintained a detection sensitivity of 35.5% and 58%, respectively. (B) The reactivity of each of the 10 antigens was analyzed at individual antiserum level. Note that the combinations of CT443 with CT381 or HSP60 with CT376, CT381 and CT798 can have the highest sensitivity of 67.7% while maintaining 100% specificity. (C) The reactivity intensity between each antigen and the 21 positive sera (measured at individual antiserum level) was expressed as mean OD plus standard deviation, (D) Each of the 10 antigens was reacted with an antiserum sample pooled from the 21 sera at equal ratio without (D) or with absorption with *C. trachomatis* (CT)-infected HeLa lysate (E) or HeLa alone lysate (F). Note that absorption with CT-HeLa but not HeLa alone lysates removed the reactivity of each antigen with the pooled antiserum.

The present invention is based on the unexpected identification of immunodominant proteins of *Chlamydia trachomatis* and combinations thereof that allow for the diagnosis of tubal factor infertility as well as for the identification of subjects having an increased likelihood of having or developing tubal factor infertility. The present invention is also based on the unexpected identification of immunodominant proteins of *Chlamydia trachomatis* and combinations thereof that allow for the diagnosis of acute infection by *Chlamydia trachomatis*. These immunodominant proteins have been identified by the screening fusion protein arrays described herein in the EXAMPLES section. These immunodominant proteins, immunologically reactive fragments thereof and/or homologues of these proteins or immunologically reactive fragments thereof from other chlamydial species can be employed in methods of detection and diagnosis by identifying the presence of an antibody to the protein(s) and/or immunologically reactive fragment(s) thereof in a sample, such as a biological sample from a subject.

Thus, in one embodiment, the present invention provides a method of diagnosing tubal factor infertility in a subject, comprising, consisting essentially of or consisting of: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof, and *Chlamydia trachomatis* CT875 or an immunologically reactive fragment thereof; and (b) detecting formation of an antigen/antibody complex with each of the antigen of *Chlamydia trachomatis* CT443 or an immunologically reactive fragment thereof and the antigen of *Chlamydia trachomatis* CT381 or an immunologically reactive fragment thereof and not detecting formation of an antigen/antibody complex with the antigen of *Chlamydia trachomatis* CT875 or an immunologically reactive fragment thereof in the sample, thereby diagnosing tubal factor infertility in the subject.

When a subject's infertility is diagnosed to be due to tubal factor as a result of chlamydial infection, a treatment option for the woman's infertility can be in vitro fertilization (IVF). Furthermore, applying both anti-chlamydial and anti-inflammatory treatment procedures to the subjects prior to IVF can increase the chance of success for IVF. Thus, in some embodiments, the method above can further comprise the step of advising and/or having the subject that has been diagnosed with tubal factor infertility to initiate IVF procedures to become pregnant. Such methods can further comprise the step of applying anti-chlamydial and/or anti-inflammatory treatment procedures to the subject.

Furthermore, the present invention provides a method of identifying a subject as having an increased likelihood of having or developing tubal factor infertility, comprising, consisting essentially of or consisting of: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or an immunologically reactive fragment thereof and the antigen of *Chlamydia trachomatis* CT381 or an immunologically reactive fragment thereof and not detecting formation of an antigen/antibody complex with the antigen of *Chlamydia trachomatis* CT875 or an immunologically reactive fragment thereof in the sample, thereby identifying the subject as having an increased likelihood of having or developing tubal factor infertility.

When a subject is identified as having an increased likelihood of having or developing tubal factor infertility as a result of chlamydial infection, the subject can undergo an infertility evaluation and both anti-chlamydial and anti-inflammatory treatment procedures can be applied to subject if the subject desires to have children. Thus, in some embodiments, the method above can further comprise the step of advising and/or having the subject that has been identified as having an increased likelihood of having or developing tubal factor infertility as a result of chlamydial infection to undergo an infertility evaluation. Such methods can further comprise the step of applying anti-chlamydial and/or anti-inflammatory treatment procedures to the subject.

Establishing that the cause of a woman's infertility is tubal factor infertility according to the methods described herein allows the woman and her physician to avoid approaches that are likely to be unsuccessful, such as hormone replacement and artificial insemination in order to overcome or bypass the woman's infertility and to select more effective methods of establishing a successful pregnancy in the woman, such as in vitro fertilization. The knowledge that the cause of a woman's infertility is tubal factor infertility also informs the woman and her physician that the use of invasive and costly procedures such as hysterosalpingogram (HSG) or laparoscopy may be unnecessary.

Thus, in one embodiment, the present invention also provides a method of identifying a subject as a good or suitable candidate for in vitro fertilization or surgical repair of tubal damage, comprising, consisting essentially of or consisting of: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or an immunologically reactive fragment thereof and the antigen of *Chlamydia trachomatis* CT381 or an immunologically reactive fragment thereof and not detecting formation of an antigen/antibody complex with the antigen of *Chlamydia trachomatis* CT875 or an immunologically reactive fragment thereof in the sample, thereby identifying the subject as a good or suitable candidate for in vitro fertilization or surgical repair of tubal damage. Thus, in some embodiments, the method above can further comprise the step of advising and/or having the subject that has been identified as a good or suitable candidate for in vitro fertilization (IVF) or surgical repair of tubal damage to undergo such IVF or surgery. Such methods can further comprise the step of applying anti-chlamydial and/or anti-inflammatory treatment procedures to the subject.

In some embodiments, the subject of this invention can be a human female and in some embodiments, the subject of this invention can be an infertile human female. In some embodiments, the tubal factor infertility can be caused by chlamydial infection and in some embodiments, the tubal factor infertility can be caused by infection by *Chlamydia trachomatis*.

In certain embodiments of the methods described above regarding tubal factor infertility, the diagnostic panel can further comprise, consist essentially of or consist of an additional antigen selected from the group consisting of a) *Chlamydia trachomatis* HSP60 or an immunologically reactive fragment thereof, b) *Chlamydia trachomatis* CT376 or an immunologically reactive fragment thereof, c) *Chlamydia trachomatis* CT557 or an immunologically reactive fragment thereof, and d) any combination thereof, and the method can further comprise, consist essentially of or consist of detecting an antigen/antibody complex in the sample for each of said additional antigen(s).

In further embodiments, the present invention provides a method of diagnosing acute *Chlamydia trachomatis* infection in a subject, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or immunologically reactive fragment thereof, the antigen of *Chlamydia trachomatis* CT381 or immunologically reactive fragment thereof and the antigen of *Chlamydia trachomatis* CT875 or the immunologically reactive fragment in the sample, thereby diagnosing acute *Chlamydia trachomatis* infection in the subject. The method above can further comprise the step of applying anti-chlamydial and/or anti-inflammatory treatment procedures to the subject.

Also provided herein is a method of diagnosing acute *Chlamydia trachomatis* infection in a subject, comprising: (a) contacting a biological sample from the subject with an antigen of *Chlamydia trachomatis* CT875 or immunologically reactive fragment thereof; and (b) detecting formation of an antigen/antibody complex with the antigen of *Chlamydia trachomatis* CT875 or immunologically reactive fragment thereof in the sample, thereby diagnosing acute *Chlamydia trachomatis* infection in the subject. The method above can further comprise the step of applying anti-chlamydial and/or anti-inflammatory treatment procedures to the subject.

The present invention also provides a method of identifying a subject as having an increased likelihood of having an acute *Chlamydia trachomatis* infection, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or immunologically reactive fragment thereof, the antigen of *Chlamydia trachomatis* CT381 or immunologically reactive fragment thereof and the antigen of *Chlamydia trachomatis* CT875 or the immunologically reactive fragment in the sample, thereby identifying the subject as having an increased likelihood of having an acute *Chlamydia trachomatis* infection. The method above can further comprise the step of applying anti-chlamydial and/or anti-inflammatory treatment procedures to the subject.

Additionally provided herein is a method of identifying a subject as having an increased likelihood of having an acute *Chlamydia trachomatis* infection, comprising: (a) contacting a biological sample from the subject with an antigen of *Chlamydia trachomatis* CT875 or immunologically reactive fragment thereof; and (b) detecting formation of an antigen/antibody complex with the antigen of *Chlamydia trachomatis* CT875 or immunologically reactive fragment thereof in the sample, thereby identifying the subject as having an increased likelihood of having an acute *Chlamydia trachomatis* infection. The method above can further comprise the step of applying anti-chlamydial and/or anti-inflammatory treatment procedures to the subject.

Additionally provided herein is a method of identifying a subject for whom antibiotic therapy for *Chlamydia trachomatis* infection is likely to be or would be beneficial, comprising: (a) contacting a biological sample from the subject with a diagnostic panel comprising an antigen of each of *Chlamydia trachomatis* CT443 or an immunologically reactive fragment thereof, *Chlamydia trachomatis* CT381 or an immunologically reactive fragment thereof and *Chlamydia trachomatis* CT875 or an immunologically reactive fragment thereof; and (b) detecting formation of an antigen/antibody complex with each of the antigen of *Chlamydia trachomatis* CT443 or immunologically reactive fragment thereof, the antigen of *Chlamydia trachomatis* CT381 or immunologically reactive fragment thereof and the antigen of *Chlamydia trachomatis* CT875 or the immunologically reactive fragment in the sample, thereby identifying a subject for whom antibiotic therapy to treat *Chlamydia trachomatis* infection is likely to be or would be beneficial. The method above can further comprise the step of applying antibiotic therapy for *Chlamydia trachomatis* infection and/or anti-inflammatory treatment procedures to the subject.

Also provided herein is a method of identifying a subject for whom antibiotic therapy for *Chlamydia trachomatis* infection is likely to be or would be beneficial, comprising: (a) contacting a biological sample from the subject with an antigen of *Chlamydia trachomatis* CT875 or immunologically reactive fragment thereof; and (b) detecting formation of an antigen/antibody complex with the antigen of *Chlamydia trachomatis* CT875 or immunologically reactive fragment thereof in the sample, thereby identifying a subject for whom antibiotic therapy for *Chlamydia trachomatis* infection is likely to be or would be beneficial. The method above can further comprise the step of applying antibiotic therapy for *Chlamydia trachomatis* infection and/or anti-inflammatory treatment procedures to the subject.

In some embodiments the method of diagnosing acute chlamydial infection or identifying a subject as having an increased likelihood of having an acute *Chlamydia trachomatis* infection or identifying a subject for whom antibiotic therapy for *Chlamydia trachomatis* infection can further comprise, consist essentially of or consist of contacting the sample with an antigen of *Chlamydia trachomatis* CT147 or immunologically reactive fragment thereof and detecting an antigen/antibody complex in the sample with the antigen of *Chlamydia trachomatis* CT147 or immunologically reactive fragment thereof.

A biological sample of this invention can be any biological fluid and/or tissue in which antibodies can be detected. Non-limiting examples of a sample of this invention can include vaginal fluid, vaginal tissue, vaginal washing, vaginal swab, vaginal discharge, cervical swab, cervical tissue urethral swab, urethral discharge, rectal swab, rectal material, rectal washing, urine, blood, serum, plasma, saliva, tears, skin swab, semen, seminal fluid, sputum, bronchial fluid, bronchial washing, peritoneal fluid, peritoneal washing, pleural fluid, pleural washing, cerebrospinal fluid, eye fluid and/or tissue, fluid and/or tissue from lung, liver, heart, brain, kidney, spleen or muscle and any combination thereof.

In some embodiments, the biological sample of this invention to be used in the methods of this invention can be diluted 1:10, 1:100, 1:200, 1:300, 1:400, 1:500, 1:600, 1:700, 1:800, 1:900, 1:1000, 1:1500, 1:2000, 1:3000, 1:4000, 1:5000, 1:6000, 1:7000, 1:8000, 1:9000, 1:10,000, 1:20,000, 1:30,000, 1:40,000, 1:50,000, 1:100,000, etc. Such a dilution can be carried out according to protocols well known in the art and as described in the EXAMPLES section herein. Such dilution can be used to increase the specificity of the method, as described herein.

In the methods of this invention, the biological sample can be preabsorbed, e.g., to reduce or minimize cross-reactivity and/or background. As nonlimiting examples, in some embodiments, the biological sample can be preabsorbed with a lysate of bacteria expressing glutathione-S-transferase (GST) and/or a lysate of normal (e.g., non-chlamydial infected mammalian cells. In some embodiments absorption of the sample can be with a lysate of *Chlamydia*-infected mammalian cells, to remove and/or block chlamydial antigen-specific antibodies from human samples, which can help confirm the specificity of human antibody binding to the test antigen.

A subject of this invention that has an "increased likelihood" or "increased risk" of having or tubal factor infertility can be a subject having symptoms and/or signs of infertility and/or meets criteria known in the art for being infertile or such a subject can be a subject who is not having symptoms and/or signs of infertility and/or does not meet criteria know in the art for being infertile. By "increased likelihood" or "increased risk" of having tubal factor infertility it is meant that the increase is relative to a control (e.g., a subject whose biological sample is not positive for antibodies to CT443 and CT381 and negative for antibodies to CT875).

Furthermore, a subject of this invention that has an "increased likelihood" or "increased risk" of having an acute *Chlamydia trachomatis* infection can be a subject having symptoms and/or signs of *Chlamydia trachomatis* infection or such a subject can be a subject who is not having symptoms and/or signs of *Chlamydia trachomatis* infection. By "increased likelihood" or "increased risk" of acute *Chlamydia trachomatis* infection it is meant that the increase is relative to a control (e.g., a subject whose biological sample is not positive for antibodies to CT443 and CT381 and CT875 or a subject whose biological sample is not positive for antibodies to CT875).

In additional embodiments of this invention, the chlamydial proteins listed herein can also be employed in the methods and compositions of this invention, either singly or in any combination with one another and/or in combination with any other chlamydial protein and/or reagent of this invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "isolated" as used herein means the protein or polypeptide or immunologically reactive fragment or nucleic acid of this invention is sufficiently free of contaminants or cell components with which polypeptides and/or nucleic acids normally occur. "Isolated" does not mean that the preparation is technically pure (homogeneous), but it is sufficiently pure to provide the polypeptide or nucleic acid in a form in which it can be used in methods of this invention.

The term "epitope" as used herein refers to at least about 3 to about 5, or about 5 to about 10 or about 5 to about 15, and not more than about 1,000 amino acids (or any integer therebetween) (e.g., 5-12 amino acids or 3-10 amino acids or 4-8 amino acids or 6-15 amino acids, etc.), which define a sequence that by itself or as part of a larger sequence, binds to an antibody generated in response to such sequence or stimulates a cellular immune response. There is no critical upper limit to the length of the fragment, which can comprise nearly the full-length of the protein sequence, or even a fusion protein comprising two or more epitopes from a single or multiple chlamydial proteins. An epitope for use in the subject invention is not limited to a polypeptide having the exact sequence of the portion of the parent protein from which it is derived. Indeed, there are many known strains or isolates of *Chlamydia* and there are several variable domains that exhibit relatively high degrees of variability between isolates. Thus, the term "epitope" encompasses sequences identical to the native sequence, as well as modifications to the native sequence, such as deletions, additions and substitutions (generally, but not always, conservative in nature). In some embodiments, an "immunologically reactive fragment" of this invention can comprise one, two, three, four or more epitopes of a protein of this invention.

Regions of a given polypeptide or fragment thereof that include an epitope can be identified using any number of epitope mapping techniques, well known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci.* USA 81:3998-4002; Geysen et al. (1986) *Molec. Immunol.* 23:709-715, all incorporated herein by reference in their entireties.

Similarly, conformational epitopes are readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

As used herein, the term "polypeptide" or "protein" is used to describe a chain of amino acids that correspond to those encoded by a nucleic acid. A polypeptide or protein of this invention can be a peptide, which usually describes a chain of amino acids of from two to about 30 to about 50 amino acids. The term polypeptide as used herein also describes a chain of amino acids having more than about 30 amino acids or more than about 50 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 or 50 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences of this invention are presented in the amino to carboxy direction, from left to right. The "carboxy terminus" or "C terminus" of a protein or amino acid sequence as used herein refers to a portion or fragment or domain of a protein or amino acid sequence that makes up about ⅔, about ½, about ⅓ or about ¼ of the total amino acid sequence at the carboxy end of the sequence (i.e., the right end or right-sided end or the "end" of the sequence). The "amino terminus" or "N terminus" of a protein or amino acid sequence as used herein refers to a portion or fragment or domain of a protein or amino acid sequence that makes up about ⅔, about ½, about ⅓ or about ¼ of the total amino acid sequence at the amino end of the sequence (i.e., the left end or left sided end or the "beginning" of the sequence).

Nucleotide sequences are presented herein by single strand only, in the 5' to 3' direction, from left to right. However, it is intended that the nucleic acids of this invention can be either single or double stranded (i.e., including the complementary nucleic acid). A nucleic acid of this invention can be the complement of a nucleic acid described herein.

A "biologically active fragment" includes a polypeptide or peptide of this invention that comprises a sufficient number of amino acids to have one or more of the biological activities of the polypeptides of this invention. Such biological activities can include, but are not limited to, in any combination, binding activity and/or immunogenic activity, as well as any other activity now known or later identified for the polypeptides and/or fragments of this invention.

An "immunologically reactive fragment," "immunogenic fragment" or "antigenic fragment" of a protein refers to a portion of the protein or peptide that is immunologically reactive with a binding partner, e.g., an antibody, which is immunologically reactive with the protein or peptide itself.

In some embodiments, the terms "immunologically reactive fragment," "immunogenic fragment" or "antigenic fragment" are used to describe a fragment or portion of a protein or peptide that can stimulate a humoral and/or cellular immune response in a subject. An immunologically reactive fragment, immunogenic fragment or antigenic fragment of this invention can comprise, consist essentially of and/or consist of one, two, three, four or more epitopes of a protein of this invention. An immunologically reactive fragment, immunogenic fragment or antigenic fragment can be any fragment of contiguous amino acids of a *Chlamydia trachomatis* protein of this invention, including but not limited to CT443, CT381, CT875, CT147, HSP60, CT376, CT557, CT858 (CPAF), Pgp3, CT823 (cHtrA), CT681 (MOMP), CT119 (IncA), CT813, CT795, CT621 and CT622, the amino acid sequences of each of which are provided herein and are available at www.ncbi.nlm.nih.gov/protein/15605169) and can be for example, 5, 10, 15, 20, 25, 30, 35, 40, 45, 50, 75, 100, 150, 200, 250, 300, 350, 400, 450, 500, 550, 600, 650, 700, 750, 800, 850, 900, 950 or 1000 amino acids in length, dependent upon the total number of amino acids of the full length protein. Identification of any such immunologically reactive, immunogenic or antigenic fragment(s) is routine in the art.

Nonlimiting examples of an immunologically reactive fragment of *Chlamydia trachomatis* CT443 protein (GenBank Database® Accession No. NP_219955.1) include amino acids 41-269 (F1), amino acids 166-269 (F2), amino acids 211-269 (F3), amino acids 101-210 (F4), amino acids 166-210 (F5), amino acids 41-165 (F6), amino acids 101-165 (F7), amino acids 41-100 (F8), amino acids 211-410 (F9), amino acids 270-410 (F10), amino acids 270-553 (F11) and amino acids 411-553 (F12), with amino acid numbering starting with amino acid 1 and ending with amino acid 553 of the 553 amino acid CT443 protein, the amino acid sequence of which is provided herein. As described herein, in some embodiments, fragments identified above as F1 through F8 could be described as N terminal or amino terminal fragments. As also described herein, in some embodiments, fragments identified above as F9 through F12 could be described as C terminal or carboxy terminal fragments. In some embodiments of this invention, the CT443 protein or immunologically reactive fragment employed in methods of this invention can be a C terminal fragment.

Nonlimiting examples of an immunologically reactive fragment of *Chlamydia trachomatis* CPAF protein (GenBank Database® Accession No. AAC68456.1) include amino acids 1-200, amino acids 136-609, amino acids 242-609, amino acids 284-609 and amino acids 387-609 with numbering starting from amino acid 1 at the amino terminus through amino acid 609 at the carboxy terminus of the 609 amino acid CPAF protein, the amino acid sequence of which is provided herein and is available under GenBank Database® Accession No. AAC68456.1.

Also provided herein is an isolated peptide comprising, consisting essentially of or consisting of about five amino acids to about 15, 20, 25, 30, 35, 40, 45, 50, 50, 70, 80, 90 or 100 amino acids (including any value between 5 and 100 not explicitly recited herein), wherein the peptide comprises one or more (e.g., 2, 3, 4, 5, 6, 7, 8, 9, 10, 11, 12, 13, 14, 15, 16, 17, 18, 19 or 20) of the 5 mer peptides listed in Table 6, as well as a composition comprising any of these isolated peptides, singly or in any combination in a carrier (e.g., a pharmaceutically acceptable carrier). Such peptides can be employed as immunologically reactive fragments in the methods of this invention.

It is further provided herein that in the methods of this invention, an immunologically reactive fragment of this invention and a biological sample diluted as described herein can be employed in any combination in the methods described herein to increase the specificity of the method. As one nonlimiting example, a biological sample diluted 1:3000 was reacted with the F11 fragment of chlamydial protein CT443 resulting in an increase in specificity of the assay and further diluting the sample 1:10,000 increased specificity even more (see Example 2). Optimization of the sample dilution and immunologically reactive fragment reactivity can be carried out as described herein and according to methods well known in the art.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known.

Such fragments can be tested for one or more of the biological activities of this invention according to the methods described herein, which are routine methods for testing activities of polypeptides, and/or according to any art-known and routine methods for identifying such activities. Such production and testing to identify biologically active fragments and/or immunologically reactive fragments of the polypeptides described herein would be well within the scope of one of ordinary skill in the art and would be routine.

As used herein, the term "antibody" includes intact immunoglobin molecules as well as fragments thereof, such as Fab, F(ab')2, and Fc, which are capable of binding the epitopic determinant of an antigen (i.e., antigenic determinant). Antibodies that bind the polypeptides of this invention are prepared using intact polypeptides or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize the animal (e.g., a mouse, rat, or rabbit). The polypeptide or peptide antigens can also be administered with an adjuvant, as described herein and as otherwise known in the art. The term "antibody" as used herein, includes, but is not limited to a polypeptide encoded by an immunoglobulin gene or immunoglobulin genes, or a fragment thereof. "Antibody" also includes, but is not limited to, a polypeptide encoded by an immunoglobulin gene or immunoglobulin genes, or a fragment thereof, which specifically binds to and recognizes the biomarkers of this invention.

The term "epitope" means an antigenic determinant that is specifically bound by an antibody. Epitopes usually consist of surface groupings of molecules such as amino acids and/or sugar side chains and usually have specific three-dimensional structural characteristics, as well as specific charge characteristics.

The terms "specifically binds to" and "specifically reactive with" refer to a binding reaction that is determinative of the presence of the antigen and antibody or aptamer and target in the presence of a heterogeneous population of proteins, nucleic acids and/or other biologics. Thus, under designated assay conditions, the specified antibodies and antigens and/or aptamers and targets bind to one another and do not bind in a significant amount to other components present in a sample.

In some embodiments employing antibodies, a variety of immunoassay formats can be used to select antibodies specifically reactive with a particular antigen. For example, solid-phase ELISA immunoassays are routinely used to select monoclonal antibodies specifically immunoreactive with an analyte. See Harlow and Lane (ANTIBODIES: A LABORATORY MANUAL, Cold Springs Harbor Publications, New York, (1988)) for a description of immunoassay formats and conditions that can be used to determine specific immunoreactivity. Typically a specific or selective reaction will be at least twice background signal to noise and more typically more than 10 to 100 times greater than background.

Various immunoassays can be used to detect antibodies of this invention. Such immunoassays typically involve the measurement of antigen/antibody complex formation between a protein or peptide and its specific antibody.

The immunoassays of the invention can be either competitive or noncompetitive and both types of assays are well-known and well-developed in the art. In competitive binding assays, antigen or antibody competes with a detectably labeled antigen or antibody for specific binding to a capture site bound to a solid surface. The concentration of labeled antigen or antibody bound to the capture agent is inversely proportional to the amount of free antigen or antibody present in the sample.

Noncompetitive assays of this invention can be sandwich assays, in which, for example, the antigen is bound between two antibodies. One of the antibodies is used as a capture agent and is bound to a solid surface. The other antibody is labeled and is used to measure or detect the resultant antigen/antibody complex by e.g., visual or instrument means. A number of combinations of antibody and labeled antibody can be used, as are well known in the art. In some embodiments, the antigen/antibody complex can be detected by other proteins capable of specifically binding human immunoglobulin constant regions, such as protein A, protein L or protein G. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401-1406 (1973); Akerstrom et al., *J. Immunol.*, 135: 2589-2542 (1985).)

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}S$, $^{125}I$, $^{32}P$, $^{13}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993); the entire contents of which are incorporated herein by reference for teachings directed to immunoassays).

The methods of this invention can also be carried out using a variety of solid phase systems, such as described in U.S. Pat. No. 5,879,881, as well as in a dry strip lateral flow system (e.g., a "dipstick" system), such as described, for example, in U.S. Patent Publication No. 20030073147, the entire contents of each of which are incorporated by reference herein.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein, (1975) *Nature* 265:495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope of interest.

The term "sample" as used herein is used in its broadest sense. A biological sample suspected of containing a polypeptide, fragment, antibody and/or nucleic acid of this invention can be any biological fluid, an extract from a cell, an extracellular matrix isolated from a cell, a cell (in solution or bound to a solid support), a tissue, a tissue print, and the like.

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents.

A variety of protocols for detecting the presence of and/or measuring the amount of an antibody or antibodies in a sample are known in the art. Such protocols are well known in the art and non-limiting examples include enzyme immunoassays (ETA), agglutination assays, immunoblots (Western blot; dot/slot blot, etc.), radioimmunoassays (RIA), immunodiffusion assays, chemiluminescence assays, antibody library screens, expression arrays, enzyme-linked immunosorbent assays (ELISA), radioimmunoassays (RIA), immunoprecipitation, Western blotting, competitive binding assays, immunofluorescence, immunohistochemical staining precipitation/flocculation assays and fluorescence-activated cell sorting (FACS). These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

The present invention further provides isolated polypeptides, peptides, proteins and/or fragments that are substantially equivalent to those described for this invention. As used herein, "substantially equivalent" can refer both to nucleic acid and amino acid sequences, for example a mutant sequence, that varies from a reference sequence by one or more substitutions (e.g., substitution with conservative amino acids as are well known in the art), deletions and/or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologues, as well as methods of obtaining homologues, of the polypeptides and/or fragments of this invention from other strains of *Chlamydia* and/or other organisms included in this invention. As used herein, an amino acid sequence or protein is defined as a homologue of a polypeptide or fragment of the present invention if it shares significant homology to one of the polypeptides and/or fragments of the present invention. Significant homology means at least 75%, 80%, 85%, 90%, 95%, 98% and/or 100% homology with another amino acid sequence. Specifically, by using the nucleic acids that encode the chlamydial proteins of this invention (as are known in the art and incorporated by reference herein), as a probe or primer, and techniques such as PCR amplification and colony/plaque hybridization, one skilled in the art can identify homologues of the polypeptides and/or fragments of this invention in *Chlamydia* and/or other organisms on the basis of information available in the art. A homologue of a *Chlamydia trachomatis* protein of this invention can include a protein of *Chlamydia muridarum, Chlamydia pneumoniae, Chlamydia psittaci* or *Chlamydia caviae* identified to be a homologue according to methods well known in the art and as described herein. It would be well understood by one of ordinary skill in the art that such homologues (either complete proteins and/or immunologically reactive fragments thereof) can be employed in the methods of this invention. The identification and testing of such homologues for suitability as antigens in the methods of this invention is well within the skill of one in the art. Such homologues among the proteins of *Chlamydia trachomatis, Chlamydia muridarum, Chlamydia pneumoniae, Chlamydia psittaci* and *Chlamydia caviae* are well known in the art. As one non-limiting example, a listing of *Chlamydia pneumoniae* proteins and the *Chlamydia trachomatis* homologues of these proteins can be found in U.S. Pat. No. 6,822,071, the entire contents of which are incorporated by reference herein for these teachings.

In some embodiments, the present invention provides the antigens of this invention immobilized on a solid support (e.g., beads, plates, slides or wells formed from materials such as, e.g., latex or polystyrene). Nonlimiting examples of such solid supports include polycarbonate, agarose, nitrocellulose, sepharose, acrylic resins, polyacrylamide and latex beads, as well as any other solid support known in the art. Techniques for coupling antibodies and antigens to such solid supports are well known in the art (Weir et al., *Handbook of Experimental Immunology* 4th Ed., Blackwell Scientific Publications, Oxford, England, Chapter 10 (1986)). Antibodies and/or antigens of this invention can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Conditions suitable for the formation of an antigen/antibody complex are routine in the art and form the basis for all immunoassays. Such conditions may vary depending on the particular reagents, samples and/or steps employed in a given immunoassay, as would be readily determined by one of ordinary skill in the art. Determination of the formation of an antibody/antigen complex in the methods of this invention can be by detection of, for example, precipitation, agglutination, flocculation, radioactivity, color development or change, fluorescence, luminescence, etc., as is well know in the art.

It is further contemplated that the present invention provides kits for detection, in a biological sample, of antibodies specifically reactive to antigens of this invention. In one embodiment, the kit can comprise one or more antigens of this invention, along with suitable buffers, wash solutions and/or other reagents for the detection of antibody/antigen complex formation.

In one embodiment, a kit of this invention can comprise, consist essentially of and/or consist of antigens (e.g., a diagnostic panel) and reagents for detecting, in a biological sample, the presence or absence of 1) an antibody that specifically reacts with *Chlamydia trachomatis* CT443 protein or an immunologically reactive fragment thereof, 2) an antibody that specifically reacts with *Chlamydia trachomatis* CT875 protein or an immunologically reactive fragment thereof and 3) *Chlamydia trachomatis* CT381 protein or an immunologically reactive fragment thereof. In some embodiments, the kit described in this paragraph can further comprise, consist essentially of or consist of antigens (e.g., as additional components of a diagnostic panel) and reagents for detecting, in a biological sample, the presence or absence of *Chlamydia trachomatis* HSP60 protein or an immunologically reactive fragment thereof, *Chlamydia trachomatis* CT376 protein or an immunologically reactive fragment thereof, *Chlamydia trachomatis* CT557 protein or an immunologically reactive fragment thereof, and any combination thereof. Thus, a kit of this invention can include a diagnostic panel that comprises, consists essentially of or consists of an antigen of *Chlamydia trachomatis* CT443 protein or an immunologically reactive fragment thereof, an antigen of *Chlamydia trachomatis* CT875 protein or an immunologically reactive fragment thereof, an antigen of *Chlamydia trachomatis* CT381 protein or an immunologically reactive fragment thereof. Such a kit can further include, in its diagnostic panel, an antigen of *Chlamydia trachomatis* HSP60 protein or an immunologically reactive fragment thereof, an antigen of *Chlamydia trachomatis* CT376 protein or an immunologically reactive fragment thereof, an antigen of *Chlamydia trachomatis* CT557 protein or an immunologically reactive fragment thereof, and any combination thereof.

In a further embodiment, a kit of this invention can comprise, consist essentially of and/or consist of antigens (e.g., a diagnostic panel) and reagents for detecting, in a biological sample, the presence or absence of 1) an antibody that specifically reacts with *Chlamydia trachomatis* CT443 protein or an immunologically reactive fragment thereof, 2) an antibody that specifically reacts with *Chlamydia trachomatis* CT875 protein or an immunologically reactive fragment thereof, 3) *Chlamydia trachomatis* CT381 protein or an immunologically reactive fragment thereof and 4) an antigen of *Chlamydia trachomatis* CT147 protein or an immunologically reactive fragment thereof. Thus, a kit of this invention can include a diagnostic panel that comprises, consists essentially of or consists of an antigen of *Chlamydia trachomatis* CT443 protein or an immunologically reactive fragment thereof, an antigen of *Chlamydia trachomatis* CT875 protein or an immunologically reactive fragment thereof, an antigen of *Chlamydia trachomatis* CT381 protein or an immunologically reactive fragment thereof and an antigen of *Chlamydia trachomatis* CT147 protein or an immunologically reactive fragment thereof.

In another embodiment, a kit of this invention comprise, consist essentially of and/or consist of antigens (e.g., a diagnostic panel) and reagents for detecting, in a biological sample, the presence or absence of an antibody that specifically reacts with *Chlamydia trachomatis* CT875 protein or an immunologically reactive fragment thereof. Such a kit can further comprise, consist essentially of or consist of antigens (e.g., as additional components of a diagnostic panel) and reagents for detecting in a biological sample, the presence or absence of an antibody that specifically reacts with *Chlamydia trachomatis* CT147 protein or an immunologically reactive fragment thereof. Thus a kit of this invention can include a diagnostic panel that comprises, consists essentially of or consists of an antigen of *Chlamydia trachomatis* CT875 protein or an immunologically reactive fragment thereof. In some embodiments, such a kit can further comprise, consist essentially of or consist of *Chlamydia trachomatis* CT147 protein or an immunologically reactive fragment thereof.

It would be well understood by one of ordinary skill in the art that the kits of this invention can comprise one or more containers and/or receptacles to hold the reagents (e.g., antibodies, antigens, nucleic acids) of the kit, along with appropriate buffers and/or wash solutions and directions for using the kit, as would be well known in the art.

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Genome-Wide Identification of *Chlamydia trachomatis* Antigens Associated with Tubal Factor Infertility Objective.

To identify *C. trachomatis* antigens that can be used to differentially diagnose tubal factor infertility in comparison to previously reported Heat Shock Protein 60 (HSP60).

Design.

In Vitro Study

Patients.

Infertile women with and without tubal pathology diagnosed laparoscopically.

Setting.

Academic medical center.

Main Outcome Measures.

Antibody responses to *C. trachomatis* in infertile women with or without tubal pathologies using a *C. trachomatis* genome-wide proteome array.

Results.

Comparison of the antibody profiles revealed 30 *C. trachomatis* antigens that were preferentially recognized by tubal factor infertility women with a detection sensitivity and specificity of 80.6% and 56.5%, respectively, 10 of which showed 100% specificity. A combination of CT443 and CT381 antigens yielded the highest detection sensitivity (67.7%) while maintaining 100% specificity.

Conclusion.

These findings have demonstrated that antibodies to CT443 and CT381, when used in combination, have higher sensitivity and specificity in predicting tubal factor infertility than other indicators for tubal factor infertility such as HSP60 antibodies (35.5%, 100%) or hysterosalpingogram (65%, 83%). Using a panel of *C. trachomatis* antigens to serologically diagnose tubal factor infertility can save the patients from undertaking expensive and invasive procedures for determining tubal pathology and choosing treatment plans.

Introduction.

Twenty-five to 35% of patients presenting for infertility evaluation have tubal disease (1-4). *Chlamydia trachomatis* is the primary sexually transmitted infection responsible for tubal factor infertility (TFI) (5-7) with *C. trachomatis* antibodies in approximately 70% of patients (8). *C. trachomatis* infected cells produce inflammatory cytokines (9-10) which may contribute to upper genital tract inflammatory damage (11-13). Lunefeld et al. found that among patients undergoing in vitro fertilization, those with *C. trachomatis* antibodies had decreased pregnancy rates (14).

*C. trachomatis* infection is often asymptomatic so patient history cannot dictate the presence of tubal disease (15-16). Elevated titers of anti-*C. trachomatis* antibodies are associated with TFI, but detection of overall antibody levels lacks the sensitivity and specificity required for differential diagnosis (17).

Measuring anti-*C. trachomatis* antibodies at the single antigen level may offer increased sensitivity and specificity for predicting TFI. Elevated anti-chlamydial heat shock protein 60 (HSP60, CT110) antibodies are associated with TFI (18-27). Anti-HSP60 antibodies are associated with decreased pregnancy rates in patients with an ectopic pregnancy history (17). When HSP60 antibodies are in follicular fluid, there are decreased implantation rates (28-29). Some have postulated that chlamydial HSP60 incites a strong inflammatory response that may cross-react with the highly conserved human HSP60 (25, 30-31). HSP60 may induce T-cell responses that contribute to the tubal damage (32-33).

In the present study a *C. trachomatis* whole-genome scale protein array has been developed that can profile antigen specificities of anti-*Chlamydia trachomatis* antibodies (34).

Human Patients.

Thirty one TFI and 23 IFC patients were enrolled at the University of Texas Health Science Center at San Antonio following Institutional Review Board approval. All women were at least 21 years old and underwent diagnostic laparoscopy with chromotubation as part of their infertility evaluation. Diagnosis of tubal infertility was defined as fallopian pathology consistent with hydrosalpinx, fimbrial phimosis, or peri-tubal adhesions. Exclusion criteria included prior tubal ligation, surgical finding of endometriosis, or a history of pelvic infection or inflammation other than pelvic inflammatory disease such as appendicitis. IFC patients had normal pelvic findings and tubal patency at laparoscopy. After the blood draw, serum samples were stored at −20° C. until analyzed.

Cell Culture and Chlamydial Infection.

As previously described, HeLa cells (American Type Culture Collection, Manassas Va. 20108) were cultured in DMEM (GIBCO PRL, Rockville, Md.) with 10% fetal calf serum (FCS; GIBCO BRL) at 37° C. with 5% carbon dioxide ($CO_2$) (34-36). *C. trachomatis* serovar D or *Chlamydia pneumoniae* AR39 organisms were grown, purified and titrated as previously described (36-38). For immunofluorescence assay, chlamydial organisms were used to infect HeLa cells grown on glass coverslips in 24-well plates. The sub-confluent HeLa cells were treated with DMEM containing 304 ml of DEAE-Dextran (Sigma, St. Louis, Mo.) for 10 minutes at 37° C. After removal of DEAE-Dextran solution, chlamydial organisms were added to the wells for 2 hours at 37° C. The infected cells were continuously cultured in DMEM with 10% FCS and 2 µg/ml of cycloheximide (Sigma, St. Louis, Mo.).

Immunofluorescence Assay (IFA).

Anti-chlamydial organism antibodies in human sera were titrated using an Immunofluorescence assay (IFA) as previously described (34, 36, 39, 40). Briefly, HeLa cells grown on coverslips were infected with *C. trachomatis* or *C. pneumoniae* organisms, fixed 48 h post-infection for *C. trachomatis* and 72 h for *C. pneumoniae* with 2% paraformaldehyde, and permeabilized with 2% saponin at room temperature for 1 hour. After blocking, human sera were added to the *Chlamydia*-infected cell samples. The primary Ab binding was visualized with a goat anti-human IgG conjugated with Cy3 (red; Jackson ImmunoResearch Laboratories, West Grove, Pa.), and DNA was labeled with Hoechst dye (blue; Sigma-Aldrich). The highest dilution of a serum that still gave a positive reactivity was defined as the titer of the given serum sample. Serum samples were serially diluted and the appropriate dilutions were repeated multiple times based on the results obtained from prior dilutions in order to obtain a more accurate titer for each serum. Images were acquired with an Olympus AX70 fluorescence microscope equipped with multiple filter sets (Olympus, Melville, N.Y.) as previously described (36, 40).

Chlamydial Fusion Protein-Arrayed Microplate Enzyme-Linked Immunosorbent Assay (ELISA).

Glutathione S-transferase (GST) fusion protein enzyme-linked immunosorbent assay (ELISA) for detecting human antibody recognition of chlamydial proteins was carried out as previously described (36). Bacterial lysates containing individual chlamydial GST fusion proteins were added to 96 well microplates pre-coated with glutathione (Pierce, Rockford, Ill.) at a 1:10 dilution in PBS with a total volume of 200 μl/well. Lysates containing GST alone, as negative, and GST-chlamydial protease-like activity factor (CPAF), as positive controls, were also included on each plate. The plates were incubated overnight at 4° C. to allow GST fusion proteins to bind to the plate-immobilized glutathione then blocked with 2.5% milk in PBS and washing with PBST (PBS with 0.05% Tween 20; Sigma Aldrich).

The human sera were pre-absorbed with bacterial lysates containing GST at 4° C. overnight, then incubated with glutathione beads (bioWorld, Dublin, Ohio) for 1 hour at room temperature to reduce background caused by non-specific human antibodies. The human antibody reactivity was detected with a goat anti-human-IgG, IgA and IgM conjugated with horse-radish peroxidase (HRP; Jackson ImmunoResearch Laboratories) plus the substrate 2,2'-azino-bi(2-ethylbenzothiazoline-6-sulforic acid)diammonium salt (ABTS; Sigma). The optical density (OD) was measured at 405 nm using a microplate reader (Molecular Devices Corporation, Sunnyvale, Calif.). To confirm the antibody binding specificity, all sera were further absorbed with lysates made from either HeLa cells alone or *C. trachomatis* serovar D-infected HeLa cells prior to reacting with the fusion protein-coated plates. The absorption was carried out as follows: HeLa cells with or without chlamydial infection were lysed via sonication at $2 \times 10^7$ cells per ml of PBS containing a cocktail of protease inhibitors. The pre-diluted serum samples were incubated with cell lysates overnight at 4° C. prior to reacting with the plate-immobilized chlamydial fusion proteins. The antibody binding that remained positive after HeLa-alone lysate absorption but significantly reduced by *Chlamydia*-HeLa lysate absorption was considered true positive.

Data Analyses.

Data were analyzed using SPSS v. 15.0 software (IBM, Chicago, Ill.) as previously described (36, 39). Briefly, titer values were log-transformed to produce a normal distribution and analyses were performed on transformed values. Student's t-Test was utilized to assess anti-*C. trachomatis* and anti-*C. pneumoniae* antibodies to evaluate overall mean differences between the 2 groups of patients. Because the a priori hypothesis was that the TFI group would have higher titers than the IFC group, a one-tailed analysis was used for the *C. trachomatis* data, but a two-tailed analysis was performed on the *C. pneumonia* data because there was no a priori hypothesis. Because the antibody titers had large variations within a given group, the serum titers were evaluated by ranges of <1:10 (Negative), 1:10 to 1:10,000 (Low), and >1:10,000 (High). Chi-Squared and Fisher's Exact Test were employed to compare overall antibodies to *C. trachomatis* and antibodies to *C. pneumoniae*.

ELISA results were analyzed using Student's t-Test and Fisher's Exact Test as appropriate. For the genome-wide ELISA, both Student's t-Test (for comparing quantitative OD value data) and Fisher's Exact Test (for comparing the number of sera positively reacted with a given antigen) were preformed. Using both methods allows for the identification of *C. trachomatis* antigens that are both clinically and statistically significant. When Student's t-Test was utilized, the OD values after subtracting background from the same plate were used. When Fisher's Exact Test was utilized, a response was determined positive when the OD value was equal to or greater than 2 standard deviations above the mean calculated from the same 96 well plate as described previously (39, 41).

Infertile Women with Laparoscopy-Identified Tubal Pathologies Developed Significantly Higher Titers of Anti-*C. trachomatis* Antibodies.

Sera from TFI or IFC were titrated using HeLa cells infected with either *C. trachomatis* or *C. pneumoniae* organisms as antigens in an IFA. TFI Patients developed high titers of antibodies to *C. trachomatis* (p<0.001) but not C, *pneumoniae* (p=0.269) (Table 1). When the patients were categorized based on levels of anti-chlamydial antibodies, most TFI patients developed high titers of anti-*C. trachomatis* antibodies (61.3%) while most IFC patients displayed lower titers (82.6%; p<0.001).

Table 1 shows titers of human antibodies against *C. trachomatis* and *C. pneumoniae*. Serum samples from women with TFI and IFC were 2 fold serially diluted starting with 1:10 and reacted with HeLa cells infected with either *C. trachomatis* or *C. pneumoniae*. The antibody reactivity was detected using an immunofluorescence assay as described herein. The highest dilution that still gave a positive reactivity was defined as the serum titer. Each serum sample was titrated in triplicate and the average was used as the geometric titer of a given serum sample. Student's t-Test was used to quantitatively analyze the differences between the two groups of patients. There is a statistically significant difference in titers of antibodies against *C. trachomatis* (p<0.001) but not *C. pneumoniae* (p=0.269) organisms. When the serum samples were divided into 3 categories (negative, low and high) based on antibody titers, the qualitative analysis with Chi-squared test still revealed a significant difference in the number of sera in different categories between the two groups of patients for antibodies against *C. trachomatis* (p<0.001) but not *C. pneumoniae* (p=0.634) organisms. Further pairwise Chi-squared analyses of the anti-*C. trachomatis* antibodies revealed significant differences between the high vs. low and high vs. negative groups. The number of individuals with high titers of anti-*C. trachomatis* antibodies in the TFI group is significantly higher than that in the IFC group.

Table 2 shows reactivity of 30 *C. trachomatis* antigens with 54 patient sera at 1:800 dilution. The 30 *C. trachomatis* antigens significantly recognized by 24 TFI patients were reacted with 54 patient sera (33 TFI and 21 IFC). All sera were diluted at 1:800 regardless of their overall anti-C, trachomatis antibody titers as determined with the immunofluorescence assay. The mean ODs of each antigen were compared between TFI and IFC groups using Student t-Test and the corresponding p values confirmed that all 30 antigens were significantly recognized by TFI patients. The number of positive recognition by either TFI or IFC was used to calculate recognition specificity and sensitivity as well as positive or negative predicting values (PPV or NPV; right panel). HSP60 (CT110) displayed a detection specificity of 82.6% and sensitivity of 71% and many other immunodominant antigens such as pCTO3 (Pgp3, a plasmid-encoded secreted protein), CT858 (CPAF, a chlamydial protease/proteasome-like activity factor that is secreted into host cell cytosol), CT823 (cHtrA, a secreted stress response serine protease), CT813 (an inclusion membrane protein), CT443 (OmcB, outer membrane complex protein B) and CT143 (a hypothetical protein) behaved similarly. Only the hypothetical protein CT557 had 100% specificity but its sensitivity was only 29%. Thus, under this assay condition, no single antigen or combinations of antigens can achieve 100% specificity with a sensitivity of >50%.

Identification of *C. trachomatis* Antigens Preferentially Recognized by Infertile Women with or without Tubal Pathology.

It is difficult to use the quantitative difference in overall anti-*C. trachomatis* antibodies to diagnose TFI. To identify antigens that are recognized by TFI patients, anti-*C. trachomatis* antibodies in 24 TFI and 11 IFC patients were mapped at the genome-wide scale since these patients displayed an overall anti-*C. trachomatis* antibody titer above 1:1000. These 35 sera recognized *C. trachomatis* antigens distributed across the genome with 265 antigens recognized by at least one antiserum and 643 antigens not detected by any sera. Many *C. trachomatis* antigens are recognized by both groups of patients, but there are antigens preferentially recognized by either group. Thirty antigens were significantly recognized by TFI based on either mean OD values (Student's t-test) or recognition frequency (Fisher's exact test). Reactivity was confirmed using absorption against either HeLa alone or *C. trachomatis*-infected HeLa lysates as described previously (36).

Identification of *C. trachomatis* Antigens Uniquely Recognized by TFI Patients.

To identify antigens that can be used to predict TFI in infertility clinics, antigens were identified that were uniquely recognized by TFI patients. The 30 antigens preferentially recognized by TFI patients (Table 2) were reacted with sera from all 54 patients (including 31 TFI and 23 IFC) regardless of their overall anti-*C. trachomatis* antibody titers. The HSP60 (CT110) reacted with 22 of the 31 TFI and 4 of the 23 IFC sera with a specificity and sensitivity of 82.6% and 71.0%, respectively, in predicting TFI.

To further increase specificity, a 5-fold dilution (final dilution of 1:4000) was used to reduce the false-positive rate. At this dilution, 10 of the 30 antigens, including CT110, CT322, CT376, CT381, CT414, CT443, CT681, CT795, CT798 and CT813, failed to react with any sera from the IFC group. Thus, these 10 antigens were uniquely recognized by TFI patients with a detection specificity of 100%. Dilution of the samples decreased detection sensitivity. HSP60 (CT110) only reacted with 11 out of 31 TFI sera, dropping the detection sensitivity to 35.5% along with three immunodominant antigens (CT795, CT798, CT813). CT443 reacted with 18 of the 31 TFI sera, maintaining a sensitivity of 58.1%. When the reactivity of the 10 antigens was analyzed at each individual antiserum level, it was found that the 10 antigens all together reacted with 21 independent sera of 31 total TFI sera, with a sensitivity of 67.7%. More importantly, this sensitivity can be maintained using fewer antigens. Combining HSP60 with CT376, CT381 and CT798 (total 4 antigens) or CT443 with CT381 (only 2 antigens) maintains sensitivity of 67.7%. As for other immunodominant antigens with a detection specificity of <100%, their detection sensitivity can be 80% even after serum dilution. Due to their ability to generate false positive results by reacting with IFC samples, it is clinically undesirable to use these antigens for screening for TFI.

*C. trachomatis* organisms cause pathologies in the fallopian tubes, leading to complications such as ectopic pregnancy and infertility. Since infertility can be caused by many different factors, distinguishing tubal infertility from other causes is useful for guiding treatment plans. The goal of the current study is to identify *C. trachomatis* antigens that can improve specificity and sensitivity in detecting TFI.

The finding that anti-*C. trachomatis* but not anti-*C. pneumoniae* antibodies are highly associated with TFI is consistent with the literature (42-44). Efforts have been made to develop individual *C. trachomatis* antigen-based detection methods. Previous reports demonstrate that anti-HSP60 antibodies are detected in 70-80% of TFI patients (21-22, 45-46). The present genome-wide search for additional markers of TFI not only confirmed these findings but also revealed new information for further increasing specificity and sensitivity in detecting TFI.

Thirty antigens were preferentially recognized by TFI patients. At 1:800 dilution, HSP60 reacted with 22 of the 31 TFI sera (71% sensitivity) and 4 of the 23 IFC sera (82.6% specificity), which is consistent with previous findings and suggests that the ELISA described herein is comparable to other assays. When the sera were diluted to 1:4000 in order to further increase specificity, 10 of the 30 antigens achieved 100% specificity. Although the sensitivity decreased, careful examination revealed that a combination of 2 antigens [CT381 and CT443 (Outer membrane complex B, OmcB)], or 4 antigens [CT110 (HSP60), CT376, CT381 & CT798] detected TFI with a specificity and sensitivity of 100% and 67.7%, respectively. These combinations of antigens improved the *C. trachomatis* serology approach for diagnosing tubal infertility over using HSP60 alone (35.5% sensitivity), which represents a clinically significant improvement.

Hysterosalpingogram (HSG) has a detection specificity and sensitivity of 83% and 65% respectively for detecting tubal pathology (47). *C. trachomatis* antigen-based serology diagnosis has numerous advantages over HSG besides improved detection, including sparing patients from the discomfort, radiation, and potential for infectious sequellae. This conclusion is consistent with previous reports that elevated chlamydial antibody levels are comparable to HSG (48) in diagnosing TFI and that HSG does not add to the medical knowledge on whether *C. trachomatis* infection contribute to tubal pathology (49).

It is unknown whether these antigens themselves or antigen-specific immune responses contribute to the inflammatory pathologies in the fallopian tubes. The protein CT443, or OmcB, displayed the highest rate of reactivity with TFI patient sera. OmcB is a highly conserved immunodominant antigen, but the precise location of OmcB in the organisms and its role during infection is poorly understood (34, 50-52).

Despite the overwhelming evidence of *C. trachomatis* infection association with TFI, not every patient is infected with *C. trachomatis* or developed immune responses to *C. trachomatis*. Interventions such as early antibiotic therapy may cause a negative or low titer in patients, but it is unlikely that tubal pathology would be attributed to the *C. trachomatis* infection in these patients. Tubal pathology in TFI patients without positive *C. trachomatis* titers might be caused by other sources of infection such as *Neisseria gonorrhoeae* (53-54) and *Mycoplasma genitalium* (55-56). Thus, to further increase the sensitivity in diagnosing TFI, other infection causes should also be taken into account.

REFERENCES FOR EXAMPLE 1

1. Healy D L, Trounson A O, Andersen A N. Female infertility: causes and treatment. *Lancet* 1994; 343:1539-1544.
2. Musich J R, Behrman S J. Surgical management of tubal obstruction at the uterotubal junction. *Fertil Steril* 1983; 40:423-441.
3. Serafini P, Batzofin J. Diagnosis of female infertility. A comprehensive approach. *J Reprod Med* 1989; 34:29-40.
4. Wilkowska-Trojniel M, Zdrodowska-Stefanow B, Ostaszewska-Puchalska I, Zbucka M, Wolczynski S, Grygoruk C, et al. *Chlamydia trachomatis* urogenital infection in women with infertility. *Adv Med Sci* 2009; 54:82-85.
5. Confino E, Tur-Kaspa I, DeCherney A, Corfman R, Coulam C, Robinson E, et al. Transcervical balloon tuboplasty. A multicenter study. *JAMA* 1990; 264:2079-2082.

6. Grant A. Infertility surgery of the oviduct. *Fertil Steril* 1971; 22:496-503.
7. Malik A, Jain S, Rizvi M, Shukla I, Hakim S. *Chlamydia trachomatis* infection in women with secondary infertility. *Fertil Steril* 2009; 91:91-95.
8. Barlow R E, Cooke I D, Odukoya O, Heatley M K, Jenkins J, Narayansingh G, et al. The prevalence of *Chlamydia trachomatis* in fresh tissue specimens from patients with ectopic pregnancy or tubal factor infertility as determined by PCR and in-situ hybridisation; *J Med Microbiol* 2001; 50:902-908.
9. Stephens R S, The cellular paradigm of chlamydial pathogenesis. *Trends Microbiol* 2003; 11:44-51.
10. Cheng W, Shivshankar P, Zhong Y, Chen D, Li Z, Zhong G. Intracellular interleukin-1alpha mediates interleukin-8 production induced by *Chlamydia trachomatis* infection via a mechanism independent of type I interleukin-1 receptor. *Infect Immun* 2008; 76:942-951.
11. Ajonuma L C, Ng E H, Chan H C. New insights into the mechanisms underlying hydrosalpinx fluid formation and its adverse effect on IVF outcome. *Hum Reprod Update* 2002; 8:255-264.
12. Sharma M, Sethi S, Daftari S, Malhotra S. Evidence of chlamydial infection in infertile women with fallopian tube obstruction. *Indian J Pathol Microbiol* 2003; 46:680-683.
13. Cheng W, Shivshankar P, Li Z, Chen L, Yeh I T, Zhong G. Capase-1 contributes to *Chlamydia trachomatis*-induced upper urogenital tract inflammatory pathologies without affecting the course of infection. *Infect Immun* 2008; 76:515-522.
14. Lunenfeld E, Shapiro B S, Sarov B, Sarov I, Insler V, Decherney A H. The association between chlamydial-specific IgG and IgA antibodies and pregnancy outcome in an in vitro fertilization program. *J In Vitro Fert Embryo Transf* 1989; 6:222-227.
15. El Hakim E A, Epee M, Draycott T, Gordon U D, Akande V A. Significance of positive *Chlamydia* serology in women with normal-looking Fallopian tubes. *Reprod Biomed Online* 2009; 19:847-851.
16. Westrom L, Joesoef R, Reynolds G, Hagdu A, Thompson S E. Pelvic inflammatory disease and fertility. A cohort study of 1,844 women with laparoscopically verified disease and 657 control women with normal laparoscopic results. *Sex Transm Dis* 1992; 19:185-192.
17. Sziller I, Fedorcsak P, Csapo Z, Szirmai K, Linhares I M, Papp Z, et al. Circulating antibodies to a conserved epitope of the *Chlamydia trachomatis* 60-kDa heat shock protein is associated with decreased spontaneous fertility rate in ectopic pregnant women treated by salpingectomy. *Am J Reprod Immunol* 2008; 59:99-104.
18. Brunham R C, Maclean I W, Binns B, Peeling R W. *Chlamydia trachomatis*: its role in tubal infertility. *J Infect Dis* 1985; 152:1275-1282.
19. LaVerda D, Kalayoglu M V, Byrne G I. Chlamydial heat shock proteins and disease pathology: new paradigms for old problems? *Infect Dis Obstet Gynecol* 1999; 7:64-71.
20. Witkin S S, Jeremias J, Toth M, Ledger W J. Cell-mediated immune response to the recombinant 57-kDa heat-shock protein of *Chlamydia trachomatis* in women with salpingitis. *J Infect Dis* 1993; 167:1379-1383.
21. Toye B, Laferriere C, Claman P, Jessamine P, Peeling R. Association between antibody to the chlamydial heat-shock protein and tubal infertility. *J Infect Dis* 1993; 168:1236-1240.
22. Ault K A, Statland B D, King M M, Dozier D I, Joachims M L, Gunter J. Antibodies to the chlamydial 60 kilodalton heat shock protein in women with tubal factor infertility. *Infect Dis Obstet Gynecol* 1998; 6:163-167.
23. Dieterle S, Wollenhaupt J. Humoral immune response to the chlamydial heat shock proteins hsp60 and hsp70 in *Chlamydia*-associated chronic salpingitis with tubal occlusion. *Hum Reprod* 1996; 11:1352-1356.
24. Tiitinen A, Surcel H M, Halttunen M, Birkelund S, Bloigu A, Christiansen G, et al. *Chlamydia trachomatis* and chlamydial heat shock protein 60-specific antibody and cell-mediated responses predict tubal factor infertility. *Hum Reprod* 2006; 21:1533-1538.
25. Linhares I M, Witkin S S. Immunopathogenic consequences of *Chlamydia trachomatis* 60 kDa heat shock protein expression in the female reproductive tract. *Cell Stress Chaperones* 2010; 15:467-473.
26. Karinen L, Pouta A, Hartikainen A L, Bloigu A, Paldanius M, Leinonen M, et al. Antibodies to *Chlamydia trachomatis* heat shock proteins Hsp60 and Hsp10 and subfertility in general population at age 31. *Am J Reprod Immunol* 2004; 52:291-297.
27. Karinen L, Pouta A, Hartikainen A L, Bloigu A, Paldanius M, Leinonen M, et al. Association between *Chlamydia trachomatis* antibodies and subfertility in the Northern Finland Birth Cohort 1966 (NFBC 1966), at the age of 31 years. *Epidemiol Infect* 2004; 132:977-984,
28. Jakus S, Neuer A, Dieterle S, Bongiovanni A M, Witkin S S. Antibody to the *Chlamydia trachomatis* 60 kDa heat shock protein in follicular fluid and in vitro fertilization outcome. *Am J Reprod Immunol* 2008; 59:85-89.
29. Equils O, Lu D, Gatter M, Witkin S S, Bertolotto C, Arditi M, et al. *Chlamydia* heat shock protein 60 induces trophoblast apoptosis through TLR4. *J Immunol* 2006; 177:1257-1263.
30. Beatty W L, Byrne G I, Morrison R P. Repeated and persistent infection with *Chlamydia* and the development of chronic inflammation and disease. *Trends Microbiol* 1994; 2:94-98.
31. Campanella C, Marino Gammazza A, Mularoni L, Cappello F, Zummo G, Di Felice V. A comparative analysis of the products of GROEL-1 gene from *Chlamydia trachomatis* serovar D and the HSP60 var1 transcript from *Homo sapiens* suggests a possible autoimmune response. *International Journal of Immunogenetics* 2009; 36:73-78.
32. Kinnunen A, Molander P, Morrison R, Lehtinen M, Karttunen R, Tiitinen A, et al. Chlamydial heat shock protein 60-specific T cells in inflamed salpingeal tissue. *Fertil Steril* 2002; 77:162-166.
33. Kinnunen A, Surcel H M, Halttunen M, Tiitinen A, Morrison R P, Morrison S G, et al. *Chlamydia trachomatis* heat shock protein-60 induced interferon-gamma and interleukin-10 production in infertile women. *Clin Exp Immunol* 2003; 131:299-303.
34. Wang J, Zhang Y, Lu C, Lei L, Yu P, Zhong G. A genome-wide profiling of the humoral immune response to *Chlamydia trachomatis* infection reveals vaccine candidate antigens expressed in humans. *J Immunol* 2010; 185:1670-1680.
35. Zhong G, Fan P, Ji H, Dong F, Huang Y. Identification of a chlamydial protease-like activity factor responsible for the degradation of host transcription factors. *J Exp Med* 2001; 193:935-942.
36. Rodgers A K, Wang J, Zhang Y, Holden A, Berryhill B, Budrys N M, et al. Association of tubal factor infertility with elevated antibodies to *Chlamydia trachomatis* caseinolytic protease P. *Am J Obstet Gynecol* 2010; 203: 494 e497-494 e414.

37. Li Z, Chen D, Zhong Y, Wang S, Zhong G. The chlamydial plasmid-encoded protein pgp3 is secreted into the cytosol of *Chlamydia*-infected cells. *Infect Immun* 2008; 76:3415-3428.
38. Luo J, Liu G, Zhong Y, Jia T, Liu K, Chen D, et al. Characterization of hypothetical proteins Cpn0146, 0147, 0284 & 0285 that are predicted to be in the *Chlamydia pneumoniae* inclusion membrane. *BMC Microbiol* 2007; 7:38.
39. Wang J, Chen L, Chen F, Zhang X, Zhang Y, Baseman J, et al. A chlamydial type III-secreted effector protein (Tarp) is predominantly recognized by antibodies from humans infected with *Chlamydia trachomatis* and induces protective immunity in mice against inflammatory pathologies in the upper genital tract. *J Immunol* revision. 2008.
40. Sharma J, Zhong Y, Dong F, Piper J M, Wang G, Zhong G. Profiling of human antibody responses to *Chlamydia trachomatis* urogenital tract infection using microplates arrayed with 156 chlamydial fusion proteins. *Infect Immun* 2006; 74:1490-1499.
41. Dutta R, Jha R, Salhan S, Mittal A. *Chlamydia trachomatis*-specific heat shock proteins 60 antibodies can serve as prognostic marker in secondary infertile women. *Infection* 2008; 36:374-378.
42. Persson K, Osser S, Birkelund S, Christiansen G, Brade H. Antibodies to *Chlamydia trachomatis* heat shock proteins in women with tubal factor infertility are associated with prior infection by *C. trachomatis* but not by *C. pneumoniae*. *Hum Reprod* 1999; 14:1969-1973.
43. Gijsen A P, Land J A, Goossens V J, Leffers P, Bruggeman C A, Evers J L. *Chlamydia pneumoniae* and screening for tubal factor subfertility. *Hum Reprod* 2001; 16:487-491.
44. Sarov I, Lunenfeld E, Sarov B, Hanuka N, Rosenzweig R, Potashnik G, et al. *Chlamydia* specific IgG and IgA antibodies in women with obstructive infertility as determined by immunoblotting and immunoperoxidase assays. *Eur J Epidemiol* 1988; 4:216-223.
45. Arno J N, Yuan Y, Cleary R E, Morrison R P. Serologic responses of infertile women to the 60-kd chlamydial heat shock protein (hsp60). *Fertil Steril* 1995; 64:730-735.
46. Dadamessi I, Eb F, Betsou F. Combined detection of *Chlamydia trachomatis*-specific antibodies against the 10 and 60-kDa heat shock proteins as a diagnostic tool for tubal factor infertility: Results from a case-control study in Cameroon. *FEMS Immunology & Medical Microbiology* 2005; 45:31-35.
47. Swart P, Mol B W, van der Veen F, van Beurden M, Redekop W K, Bossuyt P M. The accuracy of hysterosalpingography in the diagnosis of tubal pathology: a meta-analysis. *Fertility & Sterility* 1995.64:486-491.
48. Mol B W, Dijkman B, Wertheim P, Lijmer J, van der Veen F, Bossuyt P M. The accuracy of serum chlamydial antibodies in the diagnosis of tubal pathology: a meta-analysis. *Fertility & Sterility* 1997; 67:1031-1037.
49. den Hartog J E, Lardenoije C M, Severens J L, Land J A, Evers J L, Kessels A G. Screening strategies for tubal factor subfertility. *Hum Reprod* 2008; 23:1840-1848.
50. Mygind P, Christiansen G, Persson K, Birkelund S. Analysis of the humoral immune response to *Chlamydia* outer membrane protein 2. *Clin Diagn Lab Immunol* 1998; 5:313-318.
51. Gervassi A L, Grabstein K H, Probst P, Hess B, Alderson M R, Fling S P. Human CD8+ T cells recognize the 60-kDa cysteine-rich outer membrane protein from *Chlamydia trachomatis*. *J Immunol* 2004; 173:6905-6913.
52. Goodall J C, Yeo G, Huang M, Raggiaschi R, Gaston J S. Identification of *Chlamydia trachomatis* antigens recognized by human CD4+ T lymphocytes by screening an expression library. *Eur J Immunol* 2001; 31:1513-1522.
53. Pellati D, Mylonakis I, Bertoloni G, Fiore C, Andrisani A, Ambrosini G, et al. Genital tract infections and infertility. *Eur J Obstet Gynecol Reprod Biol* 2008; 140:3-11.
54. Morales P, Reyes P, Vargas M, Rios M, Imarai M, Cardenas H, et al. Infection of human fallopian tube epithelial cells with *Neisseria gonorrhoeae* protects cells from tumor necrosis factor alpha-induced apoptosis. *Infect Immun* 2006; 74:3643-3650.
55. Svenstrup H F, Fedder J, Kristoffersen S E, Trolle B, Birkelund S, Christiansen G. 2008. *Mycoplasma genitalium, Chlamydia trachomatis*, and tubal factor infertility—a prospective study. *Fertil Steril* 2008; 90:513-520.
56. Haggerty C L, Evidence for a role of *Mycoplasma genitalium* in pelvic inflammatory disease. *Curr Opin Infect Dis* 2008; 21:65-69.

Example 2

*Chlamydia trachomatis* Antigens Recognized by Women with Tubal Factor Infertility, Normal Fertility and Acute Infection Abstract.

To identify C, trachomatis antigens associated with tubal factor infertility, a whole genome scale *C. trachomatis* proteome array was used to compare antibody specificity profiles among women with tubal factor infertility, normal fertility and acute *C. trachomatis* infection. Thirteen immunodominant antigens reacted with ≥50% antisera from all women. Ten *C. trachomatis* antigens were uniquely recognized by women diagnosed with tubal factor infertility. Assessing antigen fragments with serum sample dilution, chlamydial antigens HSP60, CT376, CT557 & CT443 could discriminate between women with tubal factor infertility and women with normal fertility at a sensitivity of 63% and specificity of 100%, respectively. However, these antigens also strongly reacted with antisera from women diagnosed with acute *C. trachomatis* infections. Nevertheless, women with an acute infection preferentially recognized a new set of 21 antigens. Of these, CT875 & CT147 together distinguished women with acute infection from all other *C. trachomatis*-exposed women with a detection sensitivity of 63% and specificity of 100%, respectively. A combination of both sets of antigens may be useful to screen all women for tubal factor infertility and identify acute *C. trachomatis* infection.

Introduction.

*Chlamydia trachomatis* is a leading cause of sexually transmitted bacterial infection (STI) in the US, affecting over one million women in 2008 alone (1). The incidence of *C. trachomatis* infection has steadily increased since it was first recorded in 1984, and continues to rise yearly. *C. trachomatis* infection is often undiagnosed and untreated because it is asymptomatic. If untreated, *C. trachomatis* infection may lead to ascending infection, causing complications such as ectopic pregnancy and tubal factor infertility (1-2). However, not all women infected with *C. trachomatis* develop tubal damage. Up to 50% of women with normal fallopian tubes on laparoscopy or normal fertility have developed high titers of anti-*C. trachomatis* antibodies (3). It is not clear what determines whether a *C. trachomatis*-exposed woman will develop tubal pathology and complications. Nevertheless, the severity and number of episodes of *C. trachomatis* infection can contribute to tubal pathology. Since host immune responses reflect both infection status and host responsiveness to infection, monitoring specific antibody responses to *C. trachoma-* tis infection may lead to the identification of biomarkers that correlate with tubal pathology. Women with robust antibody responses to the *C. trachomatis* major outer membrane protein (MOMP) are less likely to develop tubal pathology while those who generate high titers of anti-HSP60 antibodies are at a significantly higher risk of developing tubal factor infertility (TFI) (4). High resolution mapping of host antibody responses to *C. trachomatis* infection may aid in the identification of *C. trachomatis* antigens associated with TFI.

Previous studies have revealed a strong association of anti-*C. trachomatis* and anti-HSP60 antibodies with TFI (3-9). Using a high-resolution whole genome scale protein array assay, the profiles of antigen specificities of anti-C, trachomatis antibodies were compared between women with TFI and women with infertility due to other causes (infertility control, IFC). The association of HSP60 antibodies with TFI was confirmed and additional new *C. trachomatis* antigens associated with TFI were identified (5). However, these and other studies focused on well-defined study subjects for comparison. When more diverse patient populations were included in the comparison, the anti-*C. trachomatis* and HSP60 antibodies no longer significantly correlated with tubal factor infertility or subfertility (10). The goal of the current study is to identify *C. trachomatis* antigens that are preferentially recognized by different groups of women with diverse socio-economic status. It was found that *C. trachomatis* antigens such as HSP60, which have previously been shown to be associated with TFI (5), were also highly reactive with anti-sera from women with acute *C. trachomatis* urogenital tract infection. Thus, TFI-associated antigens including HSP60 cannot predict tubal factor infertility in the general female population. Here, a whole genome scale proteome array was used to define a set of 21 antigens for distinguishing women with acute *C. trachomatis* infection from other *C. trachomatis*-exposed women. It is demonstrated that distinct panels of *C. trachomatis* antigens may be used to predict pathology and/or clinic phenotypes caused by *C. trachomatis* infection.

Human Subjects.

All patients were enrolled at the University of Texas Health Science Center at San Antonio after receipt of Institutional Review Board (IRB) approval. All participants underwent a single blood draw. Serum samples were stored at −20° C. until analyzed. Subjects were composed of three distinct socioeconomic and demographic groups. The TFI group (N=24) was recruited from a university-based infertility clinic. The typical payer mix is 13% privately insured, 69% self pay, and 18% military. Subjects with TFI were eligible if they were at least 21 years of age and had a pelvic laparoscopy demonstrating hydrosalpinx, fimbrial phimosis, or peritubal adhesions. Exclusion criteria included prior tubal ligation, surgical finding of endometriosis, or a history of pelvic infection or inflammation other than pelvic inflammatory disease, such as appendicitis. The fertile control (FC) group (N=25) was recruited from a university affiliated county hospital. The typical payer mix is 31% privately insured, 29% Medicare, 36% Medicaid. FC subjects were eligible if they were at least 21 years of age and had at least one live birth and normal pelvic findings at the time of tubal ligation. FC patients were enrolled at the time of their scheduled tubal ligation. Sterilization was performed either via laparoscopy or via mini-laparotomy. The sexually transmitted infection (STI) group (N=24) was referred by the health department to a university based STI clinic after diagnosis of any sexually transmitted infections or diseases. Patients reported their insurance as 11% privately insured, 25% Medicaid, 25% uninsured and 14% did not respond. STI patients were eligible if they were of reproductive age (15-45 years of age) and had a recent diagnosis of *C. trachomatis* infection. The diagnosis was based on positive *C. trachomatis* nucleic acid detection in vaginal swab samples as described previously (11-12). Blood was taken within 2 weeks of the diagnosis.

Cell Culture and Chlamydial Infection.

As previously described (13-14), HeLa cells (American Type Culture Collection) were cultured in Dulbecco's minimum essential medium (DMEM; GIBCO) with 10% fetal calf serum (GIBCO) at 37° C. with 5% $CO_2$. *C. trachomatis* serovar D or *C. pneumoniae* AR39 organisms were grown, purified, and titrated as previously described (3, 5, 13, 15). For immunofluorescence assay, chlamydial organisms were used to infect HeLa cells grown on glass coverslips in 24-well plates. The subconfluent HeLa cells were treated with DMEM containing 30 mg/mL of DEAE-Dextran (Sigma) for 10 minutes at 37° C. After removal of DEAE-Dextran solution, chlamydial organisms were added to the wells for 2 hours at 37° C. The infected cells were continuously cultured in DMEM with 10% fetal calf serum and 2 mg/mL of cycloheximide (Sigma) for 48 h (*C. trachomatis*) or 72 h (*C. pneumoniae*) before sample processing.

Immunofluorescence Assay.

Antichlamydial organism antibodies in human sera were titrated using an immunofluorescence assay as previously described (3, 5). Briefly, HeLa cells grown on coverslips were infected with *C. trachomatis* or *C. pneumoniae* organisms, fixed with 2% paraformaldehyde, and permeabilized with 2% saponin at room temperature for 1 hour. After blocking, human sera were added to the *Chlamydia*-infected cell samples. The primary antibody binding was visualized with a goat anti-human IgG conjugated with Cy3 (red; Jackson ImmunoResearch Laboratories), and DNA was labeled with Hoechst dye (blue; Sigma-Aldrich). The highest dilution of a serum that still gave a positive reactivity was defined as the titer of the given serum sample. Serum samples were serially diluted, and the appropriate dilutions were repeated multiple times according to the results obtained from prior dilutions, to obtain a more accurate titer for each serum. Images were acquired with an Olympus AX70 fluorescence microscope equipped with multiple filter sets, as previously described (16-17).

Chlamydial Fusion Protein-Arrayed Microplate ELISA.

Glutathione S-transferase (GST) fusion protein ELISA for detecting human antibody recognition of chlamydial proteins was carried out as previously described (11-12). Bacterial lysates containing individual chlamydial GST fusion proteins were added to 96-well microplates precoated with glutathione (Pierce) at a 1:10 dilution in PBS, with a total volume of 200 µL per well. Lysates containing GST alone, as negative, and GST-chlamydial protease/proteasome-like activity factor (CPAF), as positive controls, were also included on each plate. The plates were incubated overnight at 4° C. to allow GST fusion proteins to bind to the plate-immobilized glutathione, then blocked with 2.5% milk in phosphate-buffered saline (PBS) and washed with PBST (PBS with 0.05% Tween 20; Sigma-Aldrich). The human sera were preabsorbed with a bacterial lysate containing GST at 4° C. overnight, then incubated with glutathione beads (bioWorld) for 1 hour at room temperature to reduce background caused by nonspecific human antibodies. The human antibody reactivity was detected with a goat anti-human IgG, IgA, and IgM conjugated with horseradish peroxidase (Jackson ImmunoResearch Laboratories) plus the substrate 2,20-azino-bi (2-ethylbenzothiazoline-6-sulforic acid)diammonium salt (Sigma). The optical density (OD) was measured at 405 nm using a microplate reader (Molecular Devices). To confirm the antibody binding specificity, all sera were further absorbed with lysates made from either HeLa cells alone or *C. trachomatis* serovar D-infected HeLa cells before reacting with the fusion protein-coated plates. The absorption was carried out as follows: HeLa cells with or without chlamydial infection were lysed via sonication at $2 \times 10^7$ cells per milliliter of PBS containing a cocktail of protease inhibitors. The prediluted serum samples were incubated with cell lysates overnight at 4° C. before reacting with the plate-immobilized chlamydial fusion proteins. The antibody binding that remained positive after HeLa-alone lysate absorption but significantly reduced by *Chlamydia*-HeLa lysate absorption was considered true positive.

Data Analyses.

Data were analyzed using Microsoft Excel 2007. ANOVA was used to compare anti-*C. trachomatis* and anti-*C. pneumoniae* antibody titers between all three groups of patients. Student's t-Test was used to identify statistical differences between given two groups. Results from ELISA were analyzed using both Student's t-Test (for comparing quantitative OD value data) and Chi-squared or Fisher's Exact test (for comparing the number of sera positively reacted with a given antigen). Combination of these two methods allowed for the identification of *C. trachomatis* antigens that are both clinically and statistically significant. When Student's t-Test was used, the OD values after subtracting background from the same plate were used. When the Chi squared test was used, positive reactivity frequency was used. A reaction was determined positive when the OD value was 2 standard deviations (SD) above the mean calculated from the same 96-well plate (5).

Overall Anti-*C. trachomatis* and Anti-*C. pneumoniae* Antibodies in Three Groups of Women.

Serially diluted serum samples from women with tubal factor infertility (TFI), normal fertility (FC) and acute *C. trachomatis* infection (STI) were reacted with *C. trachomatis* and *C. pneumoniae*-infected HeLa cells to measure the titers of the corresponding antibodies (Table 3). STI women displayed the lowest levels of anti-*C. pneumoniae* antibodies compared to TFI and FC groups (P<0.05 for both, Student's t-Test) while TFI and FC displayed similar levels of the antibodies (p=0.34). The distribution of anti-*C. pneumoniae* antibodies correlated well with the age distribution among the three groups of women. STI women were significantly younger (mean age 21.8±3.1 years) than both TFI (34.6±4.4, p<0.05) and FC (32.5±5.7, p<0.05), respectively, while the TFI and FC women displayed similar ages (p>0.05). These results are consistent with a general concept that anti-*C. pneumoniae* antibody levels increase as age increases (18-19).

However, the anti-*C. trachomatis* antibody titers were highest in the STI group compared to those in either the TFI or FC groups (p=0.0748 & p=0.0099, respectively) while there was no significant difference between TFI and FC groups (p=0.2229). The STI group was significantly younger than both the TFI and FC groups as noted above. Thus, in contrast to the age-dependent increase in anti-*C. pneumoniae* antibody titers, the anti-*C. trachomatis* antibody titers decreased as age progressed, probably due to reduced exposure to *C. trachomatis*. This observation is consistent with CDC data showing that adolescents and young women ages 15 to 24 are at the highest risk for STIs (2). Although the titer of anti-*C. trachomatis* antibodies in TFI women (35483.33±39950.49) appeared to be higher than that in FC women (23760.00±23974.4), the difference was not statistically significant (p=0.2229), which stands in contrast to the previous report that women with tubal factor infertility displayed significantly higher levels of anti-*C. trachomatis* antibodies than women with infertility due to non-tubal causes (3, 5). The previous studies focused on infertile women recruited from an infertility clinic while the above analysis compared tubal factor infertility women from the infertility clinic with women of normal fertility. Clearly, when diverse female populations are included, the overall anti-*C. trachomatis* antibody levels are no longer associated with tubal factor infertility. A whole genome scale protein array was used next to profile antigen-specificities of antibodies in the serum samples from this diverse population of women.

Genome-Wide Antibody Profiles Reveal Immunodominant Antigens Commonly Recognized by all Three Groups of Women.

Anti-*C. trachomatis* antibodies from 24 TFI, 25 FC and 24 STI women were profiled for their antigen-specificities at a genome-wide scale. These 73 antisera recognized *C. trachomatis* antigens distributed across the entire genome with 541 antigens recognized by at least one antiserum and 367 antigens not detected by any antisera. Many *C. trachomatis* antigens were recognized by all 3 groups of women although some antigens were preferentially recognized by individual or combinations of groups. Regardless of which groups the women were from, 50% or more of the 73 women recognized a total of 13 antigens, including pCT03 (93% frequency) (Pgp3, a plasmid-encoded hypothetical protein that is secreted into host cell cytosol (20-21)), CT858 (90% frequency) (CPAF, a chlamydial protease/proteasome-like activity factor known to be secreted into host cell cytosol (14)), CT101 (79% frequency) (hypothetical protein, HP), CT841 (77% frequency) (FtsH, ATP-dependent Zinc protease), CT240 (73% frequency) (Recombination protein RecR), CT443 (73% frequency) (outer membrane complex protein B, OmcB (22)), CT142 (60% frequency) and CT143 (71% frequency) (both HPs), CT813 (68% frequency) and CT529 (62% frequency) (both inclusion membrane proteins, Incs (23, 24)), CT694 (66% frequency) (a putative effector of the type III secretion pathway (25)), CT022 (55% frequency) (50S ribosomal protein L31 type B) and CT806 (55% frequency) (insulinase family/protease III, Ptr). These proteins are designated as immunodominant antigens in these women.

Identification of Antigens Preferentially Recognized by TFI Women.

Figure 3:
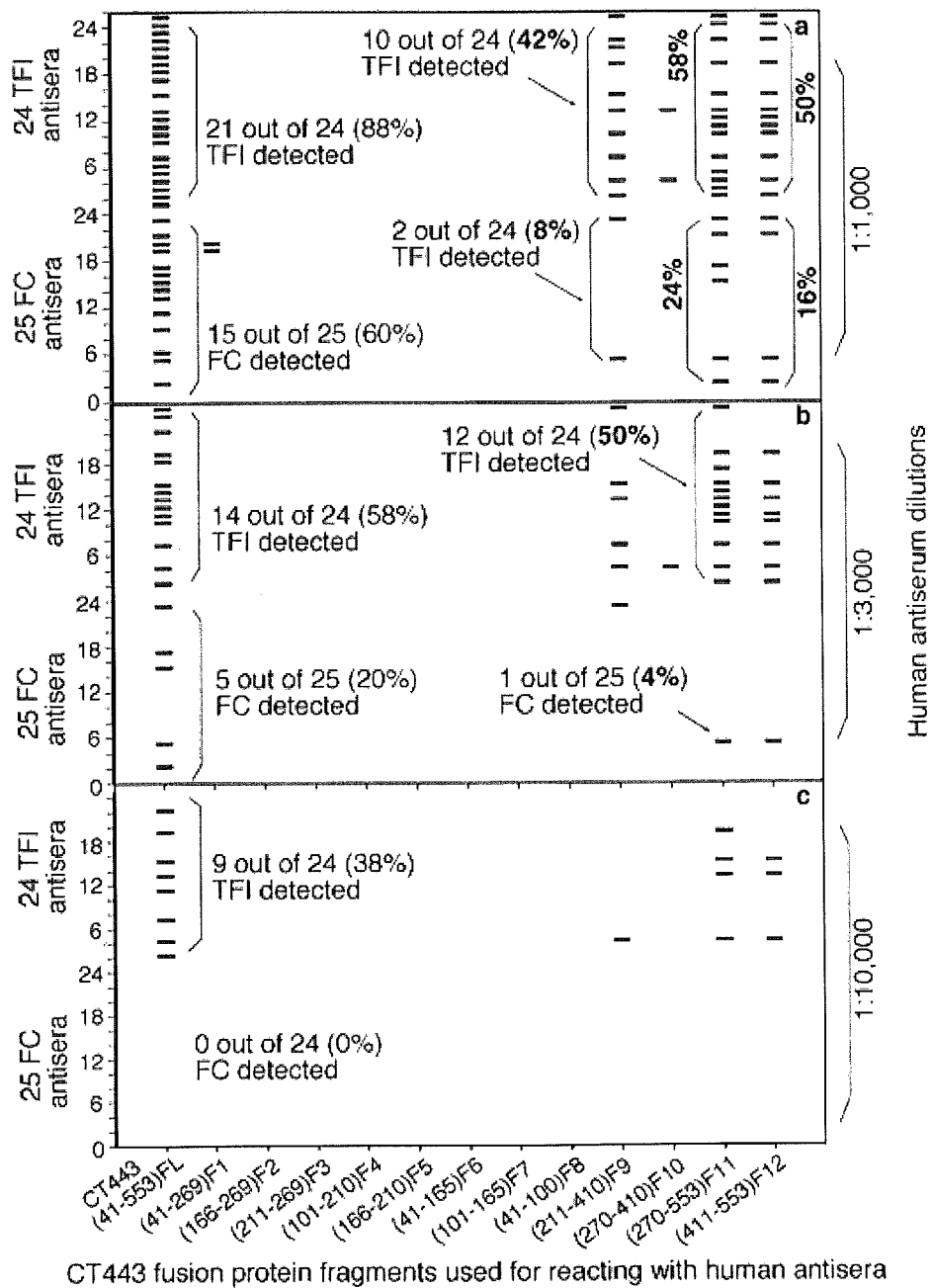
FIGS. 3A-C. Reactivity Patterns of CT443 and its 12 Fragments with TFI & FC Serum Samples. CT443 full length (FL) and its 12 fragments (F1 to F12) as shown along the X-axis at the bottom were reacted with 24 TFI and 25 FC antisera (listed along the Y-axis on the left) at different dilutions (as shown along the Y-axis on the right), including 1:1,000 (A), 1:3,000 (B) and 1:10,000 (C). A positive reactivity was indicated with a horizontal bar. Number of or percentage of antisera reacted with a given antigen were spelled out in text in corresponding panels. Please note that most antibody reactivity was localized at the C-terminal fragments, including fragment 10 (F9), F11 and F12 and the fragments displayed better discrimination of TFI from FC samples than the full length CT443 at different serum dilutions.
Figure 4:
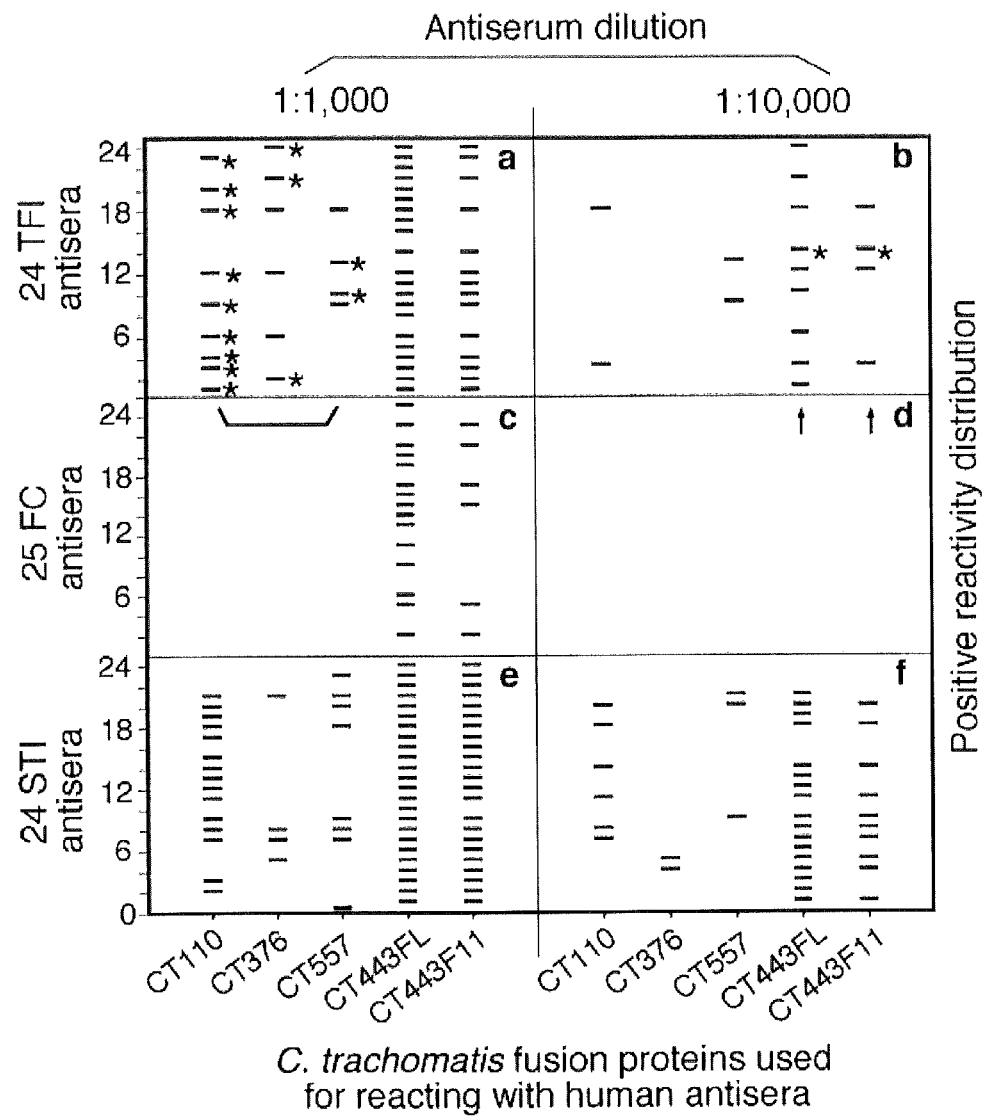
FIGS. 4A-F. Reactivity Patterns of Antigens Preferentially Recognized by TFI Women with Serum Samples from 3 Different Groups of Women. The reactivity of CT110, CT376, CT557, CT443 and CT443F11 as listed along the X-axis at the bottom with 24 TFI (A-B), 25 FC(C-D) and 24 STI (E-F) antisera as shown along the Y-axis at the left side. A positive reactivity was indicated with a horizontal bar. The human sera were used at either 1:1000 (A, C, E) or 1:10,000 (B, D, F) dilution. Antisera from the TFI group uniquely detected by a given antigen are marked with stars. Antigens preferentially recognized by TFI women were also highly reactive with STI women samples.
Figure 5:
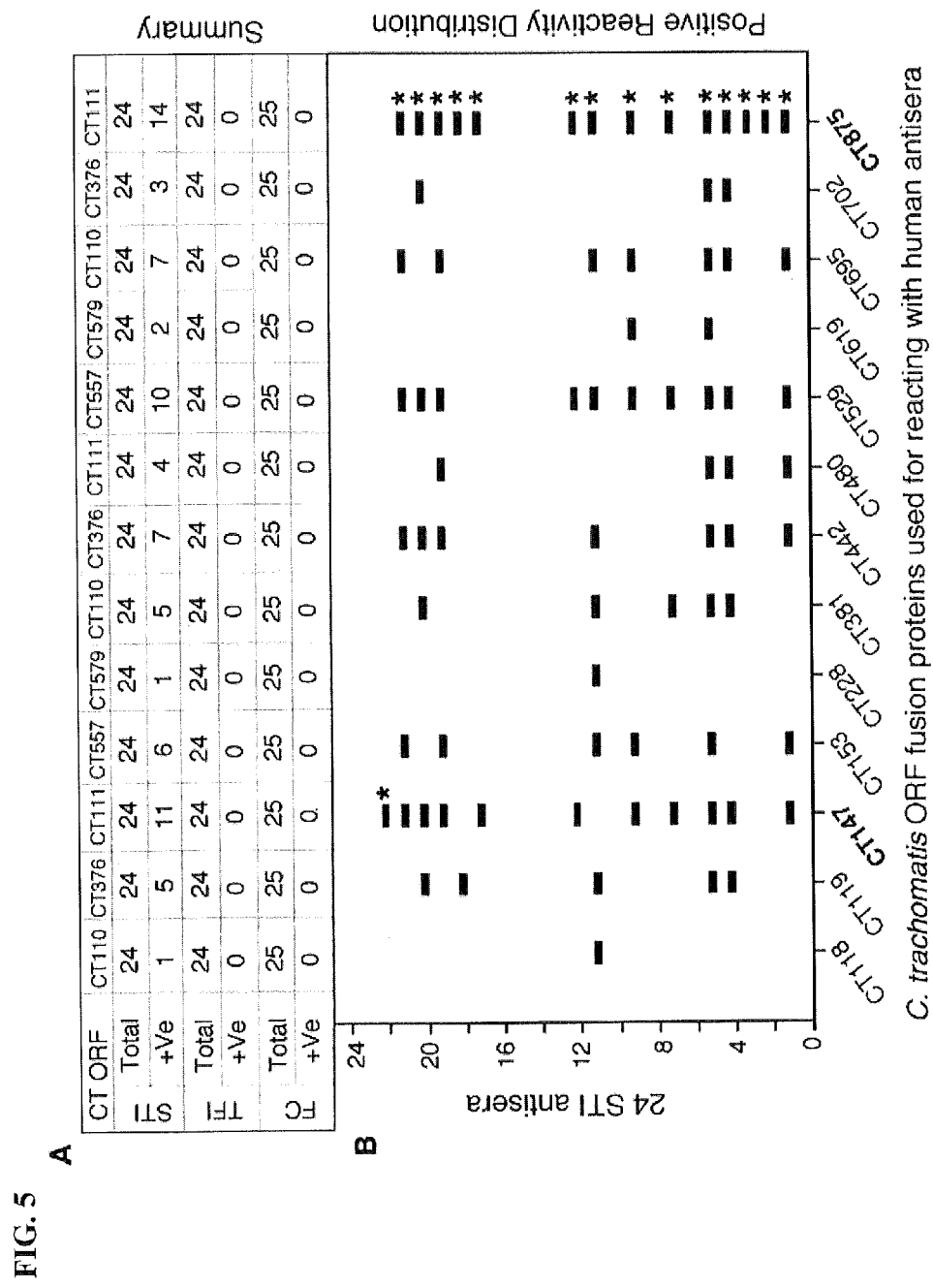
FIGS. 5A-B. Reactivity Patterns of 13 Antigens with STI Women Samples. When the 21 antigens listed in Table 5 were reacted with human sera at 1:10,000 dilution, 13 antigens (listed at top and bottom of the figure) completely lost reactivity with either TFI or FC women samples but each maintained a certain level of reactivity with STI samples as summarized in panel A. The patterns of reactivity of the 13 antigens with 24 STI samples are shown in panel B. Each horizontal bar indicates a positive reactivity and antisera uniquely reacted with CT875 and CT147 are marked with a star. CT875 and CT147 detected 15 out of the 24 STI sera with a sensitivity of 63% while maintaining 100% specificity.

The reactivity of the antiserum samples with each of the 908 *C. trachomatis* antigens was compared between the 3 groups of women both quantitatively (comparison of OD values using ANOVA) and qualitatively (comparison of recognition frequency using Fisher's Exact test). Antigens that displayed statistically significant differences in antibody reactivity (either quantitatively or qualitatively) and were recognized by 10% or more of the antisera from at least one group of women were selected. There were a total of 97 antigens that met both the above requirements. The use of 10% cutoff for recognition frequency was set to eliminate antigens with extremely low reactivities that were no longer biologically significant, although statistically significant. Many antigens shown at the bottom half of the figure were visually identifiable as antigens preferentially recognized by women from one or two groups but not all groups. Since a major goal of the current study is to identify TFI-associated antigens, the antigens that displayed statistically significant differences in recognition by TFI versus FC women were analyzed first (Table 4). Among the 10 antigens that were preferentially recognized by TFI women, 5 failed to react with any antisera from FC women under the current serum dilution (1:1000), suggesting that these antigens can distinguish TFI from FC women with 100% specificity. When the reactivity patterns of these 5 antigens with TFI women were revealed (FIG. 2), it was found that CT110, the chlamydial HSP60, reacted with antisera from 9 out of 24 TFI women, thus with a detection sensitivity of 38%. Antigen CT376 reacted with additional 3 TFI samples while CT557 reacted with another 2 TFI samples. Together, these 3 antigens detected TFI samples with a sensitivity of 58% while still maintaining 100% specificity. Among the remaining 5 antigens recognized by both TFI and FC women, CT443, the outer membrane complex protein B (OmcB) was recognized by TFI women with the highest frequency and intensity (both were significantly higher compared to FC women). Testing was done to determine whether a combination of human serum dilution and CT443 fragments could help to further differentiate TFI from FC women (FIG. 3). The CT443 full length (FL) proteins were expressed in 12 different fragments, all of which were used to react with both TFI and FC women antisera at different dilutions. Only the fragments representing the C-terminal portion of CT443, including fragments 9 (F9), 11 and 12, were reactive with human antisera. Nevertheless, at each human serum dilution, the CT443 fragments produced significantly greater differences than the full length CT443 did in antibody reactivity between TFI and FC samples. For example, at 1:1000 dilution of human sera, the full length CT443 reacted with 88% of TFI and 60% of FC women (a 32% decrease in reactivity with FC women antibodies) while F9 reacted with 42% TFI and only 8% FC (81% decrease), F11 reacted with 58% TFI and 24% FC (59% decrease) and F12 reacted with 50% TFI and 16% FC (48% decrease). When the human antiserum was used at 1:3000 dilution, F11 still reacted with 50% TFI but only 4% FC, representing a 92% decrease in reactivity with FC. Only one of the 25 FC antisera remained reactive with F11. Further modification of F11 may lead to the elimination of the FC reactivity while maintaining high levels of reactivity with TFI. These results have provided proof of principle that fragmentation of immunodominant cross-reactive antigens may represent a viable approach for identifying antigens with increasing differential diagnosis power. Interestingly, when human sera were diluted to 1:10,000, the full length CT443 no longer reacted with any FC women samples but retained reactivity with 38% of TFI samples, suggesting that serum sample dilution may represent another strategy to increase the ability to differentiate between women with different phenotypes. When the reactivity patterns of CT443 and its fragment 11 were compared with those of HSP60, CT376 and CT557, one additional TFI antiserum was detected (FIGS. 4A-B). Thus, a combination of these 4 antigens achieved a detection sensitivity of 63% for TFI women while still maintaining 100% detection specificity when both TFI and FC women were included.

Identification of Antigens Preferentially Recognized by Women with Acute *C. trachomatis* Infection.

When the antigens that were demonstrated to be able to discriminate TFI from FC samples with 100% specificity were applied to women diagnosed with acute *C. trachomatis* infection from a STI clinic, these antigens also strongly reacted with the STI serum samples even when the samples were highly diluted (FIG. 4). This is because STI women were all diagnosed with acute *C. trachomatis* infection when sera were collected and they developed high titers of antibodies to many antigens as revealed in Table 3. Fortunately, the whole genome scale proteome array also allowed the identification of *C. trachomatis* antigens that were preferentially recognized by STI but not TFI women (Table 5). A total of 21 antigens that displayed the greatest differences in reactivity between STI and TFI women were selected based on both quantitative and qualitative statistical analyses. It appeared that all 21 antigens strongly reacted with samples from patients with STIs, but were poorly recognized by either TFI or FC women serum samples. For example, when human serum samples were diluted at 1:1000, CT147 reacted with 88% of STI, but only 21% of TFI or 16% of FC samples and CT875 was recognized by 75% STI women, but only 17% of TFI or 16% FC women. Clearly, these 21 antigens were highly associated with acute infection since only the STI women were detected positive for *C. trachomatis* DNA in vaginal swab samples at the time when sera were taken while neither TFI nor FC women displayed any sign of acute *C. trachomatis* infection. These antigens could be used to distinguish STI patients from those in other groups. These antigens have been designated as acute infection-associated antigens. When human serum samples were diluted at 1:10,000, 13 of the 21 acute infection-associated antigens maintained positive reactivity with STI samples, but failed to react with any serum samples from either TFI or FC women (FIG. 5). The reactivity patterns of these 13 acute infection-associated antigens revealed that CT875 reacted with 14 out of the 24 STI serum samples. CT147 reacted with an additional STI sample (although the rest reacted with STI samples already detected by CT875 and CT147). Thus, antigens CT875 and CT147 together can be used to distinguish STI women from the rest of women with a detection sensitivity of 63% and a specificity of 100%. Continuing optimization of the detection system and use of acute infection-associated antigen fragments may allow for further increases in detection sensitivity while maintaining high specificity.

Table 3 shows titers of antibodies against *C. trachomatis* and *C. pneumoniae* in women with tubal factor infertility (TFI), normal fertility (FC) or acute infection (STI). Serum samples from women with TFI, FC, or STI were 2-fold serially diluted starting with 1:10 and reacted with HeLa cells infected with either *C trachomatis* or *C pneumoniae*. The highest dilution that still gave a positive reactivity was defined as the serum titer. ANOVA was used to analyze the overall differences among the 3 groups. There is a statistically significant difference in titers of antibodies against both *C. trachomatis* and *C. pneumoniae*. However, further pairwise analyses with Student's t-Test reveals significantly higher titers of anti-*C. trachomatis* but lower titers of anti-*C. pneumoniae* antibodies in STI women.

Table 4 shows antigens preferentially recognized by women with tubal factor infertility (TFI) but not normal fertility (FC). When Fisher's Exact test and Student's t-Test were used to compare each of 908 protein reactivities between TFI and FC groups, 10 antigens displayed statistically significantly differences by either method. Their corresponding ORF names, reactivity frequency (Freq) and intensity (OD values: mean plus/minus standard deviations) along with the p values were listed in corresponding columns. Five of the 10 antigens (CT110, CT376, CT111, CT557 & CT579) reacted with no FC samples.

Table 5 shows antigens that are most significantly recognized by women with acute *C. trachomatis* infection. Each of the 541 human antibody-reactive *C. trachomatis* antigens was compared for their reactivities with antisera from STI versus TFI or FC women using Student's t-Test (for comparing OD values in mean plus/minus standard deviations) and Fisher's Exact Test (for comparing reactive frequencies, Freq; a positive reaction was identified if the OD value is equal to or above the mean plus 2 standard deviations). Antigens that displayed the most differences and were recognized by STI women with a recognition frequency of 30% or higher were selected. A total of 21 antigens met the two requirements and were listed from top to bottom based on the extent of differential recognition by STI versus TFI or FC women. The reactivity was measured using a human serum dilution of 1:1000. All antigens were highly reactive with STI women samples and significantly less reactive with both TFI and FC samples.

In this study, the whole genome scale proteome array analyses have been extended to women with TFI, normal fertility or acute infection from a diverse socioeconomic group of women in San Antonio, Tex. The overall goal is to define C. trachomatis antigens that can be used to differentiate women with different clinical phenotypes after C. trachomatis infection with a focus on identifying biomarkers for predicting/diagnosing tubal factor infertility. The 3 groups of women recruited into the current study can largely represent the general female population since their overall anti-C. pneumoniae antibody levels increase as ages progress as demonstrated in other populations of women (18-19) while the overall anti-C. trachomatis antibody levels are the highest in STI women with an age range that is known to be most susceptible to C. trachomatis infection in the US (2). Although the 3 groups of women recognized many common antigens, quantitative and qualitative statistical analyses have allowed for the identification of 10 antigens that were preferentially recognized by TFI but not FC groups. Using serum sample dilution and antigen fragmentation to increase differentiating capacity, a 4-antigen combination consisting of HSP60, CT376, CT557 and CT443 distinguished tubal factor infertility from normal fertility women with a detection sensitivity of 63% and specificity of 100%. However, these same antigens also strongly reacted with antisera from women diagnosed with acute C. trachomatis from a STI clinic. Fortunately, the whole genome proteome array has led to the identification of 21 antigens that are highly associated with acute infection, two of which, CT875 & CT147, distinguished women with acute infection from other C. trachomatis-exposed women with a detection sensitivity of 63% and specificity of 100%. Thus, it is possible to use a combination of antigens to screen all women for predicting/diagnosing chlamydial infection and diseases.

Many previous studies have shown an association of anti-C. trachomatis antibodies with tubal factor infertility or subfertility (3, 5-7). Many of these studies focused on the comparison between women with tubal factor infertility and infertile women due to non-tubal causes but both visiting the same infertility clinics. However, when more diverse female populations were analyzed and included in the comparison, the anti-C. trachomatis antibodies were no longer significantly higher in patients with tubal factor infertility (10). In the current study, no statistically significant difference in anti-C. trachomatis antibody titers was found between women diagnosed with tubal factor infertility from a infertility clinic and women with normal fertility undergoing tubal ligation procedures. Thus, the overall anti-C. trachomatis antibodies, although highly associated with tubal factor infertility when compared to infertile women, cannot predict tubal factor infertility among C. trachomatis-exposed women.

Figure 6:
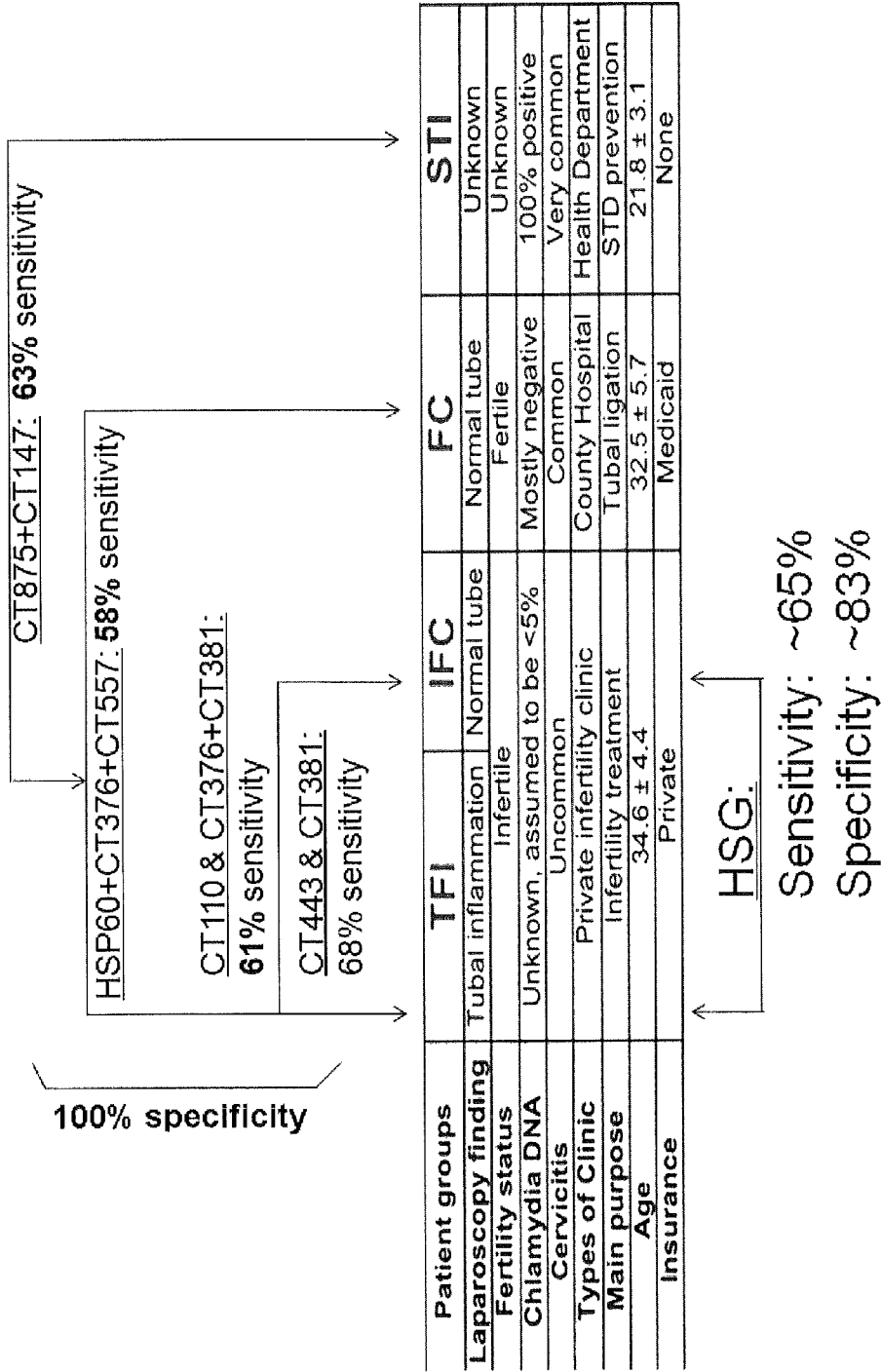
FIG. 6. Comparison of *Chlamydia* Antibody Test with Hysterosalpingogram (HSG) for Identifying Tubal Factor Infertility (TFI).

It has been previously shown that chlamydial HSP60 detected tubal factor infertility with a sensitivity of 36% and a specificity of 100% while a combination of antigens CT443 and CT381 provided a detection sensitivity of 68% while still maintaining 100% specificity (5). In the current study, when the antigen specificity profiles of anti-C. trachomatis antibodies in the TFI women were compared with those in FC women undergoing tubal ligation, these previous overall findings still held true. The chlamydial HSP60 along with antigens CT376 & CT557 positively detected 14 out of the 24 TFI samples with a sensitivity of 58%, but failed to react with any serum samples from FC women (100% specificity) (FIG. 6). CT443 or OmcB (outer membrane complex protein B) was found to react with serum samples only from tubal factor but not non-tubal infertility patients in the previous study (5). Although CT443 was recognized by both TFI and FC women in the current study, the reactivity of CT443 with TFI women was significantly stronger than that with FC women.

Using antigen fragmentation and serum dilution, it was possible to increase specificity of this diagnosis. By increasing the serum dilution, CT443 or CT443 fragments were able to differentiate TFI from FC samples. Using a dilution of 1:3,000, CT443 F11 reacted with 50% TFI but only 4% FC. Additional modifications of F11 may eliminate the residual FC reactivity. Further dilution of human sera to 1:10,000 completely removed the reactivity of CT443 with FC samples but allowed reactivity of CT443 with 38% of TFI samples. Together, these observations have provided a proof of principle that serum dilution and fragmentation of immunodominant cross-reactive antigens may represent viable approaches for identifying biomarkers to diagnose pathologies or predict clinic phenotypes associated with C. trachomatis.

Although the antigens identified above can distinguish TFI from FC women with 100% specificity, these antigens were also found to be strongly reactive with serum samples from women diagnosed with acute C. trachomatis infection from a STI clinic. Fortunately, the power of the whole genome scale proteome array has also allowed or the identification of 21 C. trachomatis antigens that were preferentially recognized by STI but not TFI nor FC women. Two of the 21 acute infection-associated antigens, CT875 and CT147, distinguished STI women from TFI and FC women with a detection sensitivity of 63% and a specificity of 100%. Continued optimization of the detection system and use of acute infection-associated antigen fragments may allow for further increases in detection sensitivity while maintaining high specificities. The observation that the acute infection-associated antigens were all poorly recognized by both TFI and FC women suggests that women in the TFI and FC groups were exposed to C. trachomatis in the past without ongoing infection. All STI women were detected positive for C. trachomatis DNA in vaginal swab samples at the time when sera were taken (11-12). However, the C. trachomatis status in either TFI or FC women was not specifically monitored when blood samples were collected. Nevertheless, physical examination revealed that none of the TFI and FC women displayed any sign of acute C. trachomatis infection in the lower genital tract (data not shown) and the nucleic acid detection rate was very low in patients who visited the same infertility or OB/GYN clinics in the past. Thus, the acute infection-associated antigens may represent useful biomarkers for indicating recent infection.

Identification of biomarkers associated with pathologies and/or clinic phenotypes caused by C. trachomatis infection will not only provide safer means for diagnosis or prognosis of C. trachomatis infection and diseases but may also promote better understanding of the mechanisms of C. trachomatis pathogenesis. It is widely believed that the association of chlamydial HSP60 with TFI suggests a role of HSP60 or host immune responses to HSP60 in tubal pathologies. Due to the high degree of amino acid sequence homology between chlamydial and human HSP60, anti-chlamydial HSP60 antibodies may cross-react with host HSP60 (26-27) or anti-HSP60 T cell responses may attack fallopian tube tissues (28-29). However, a recent study has shown that although antibodies reactive with chlamydial HSP60 were significantly higher in TFI women than those in control group, antibodies reactive with human HSP60 were at similar levels in both groups (30), suggesting that the anti-HSP60 cross-reactive antibodies may not significantly contribute to chlamydial pathogenesis. Chlamydial HSP60 has been shown to activate inflammatory pathways in macrophages (31), which may allow HSP60 to exacerbate inflammatory damage in fallopian tubes. The other *C. trachomatis* antigens that are significantly associated with TFI including CT376, CT557 & CT443 may also contribute to tubal pathology. Both CT376 and CT557 are highly conserved metabolic enzymes: malate dehydrogenase (334 amino acids) and dihydrolipoamide dehydrogenase (pyruvate dehydrogenase E3 component, 465 amino acids), respectively. These enzymes share high degrees of amino acid sequence homology with their host counterparts with 43% for CT376 and 38% for CT557, respectively. These metabolic enzymes are supposed to be localized in the cytoplasm of chlamydial organisms and should not be leaked into host cells during chlamydial infection. As with the cytoplasmic HSP60, CT376 and CT557 may be released into host environments after RB lysis. Clearly, both CT376 and CT557 are exposed to human immune cells during chlamydial infection in humans since humans developed robust antibody responses to these proteins. The question is whether CT376 and CT557 can be as inflammatory as HSP60 and immune responses to these proteins can contribute to chlamydial pathogenesis. CT443 or OmcB is an immunodominant protein in the outer membrane complex known as outer membrane complex protein B, although its precise location in chlamydial organisms remains unclear. It has been shown that a CT443 C-terminal fragment is released into host cell cytosol (22), which may explain the high immunogenicity of CT443 C-terminus since chlamydial proteins secreted into or exposed to host cell cytosol are known to be more immunogenic (32-33). Consistent with this concept is the current finding that most human antibodies recognized CT443 fragments covering the C-terminal regions and a previous report that a CD8+ T cell epitope was mapped to CT443 C-terminus (34).

REFERENCES FOR EXAMPLE 2

1. Centers for Disease Control and Prevention C. Sexually Transmitted Disease Surveillance, 2008. In: *Services USDoHaH*, editor. Atlanta, Ga.: www.cdc.gov/std/stats08/toc; November 2009.
2. Centers for Disease Control and Prevention C. Sexually transmitted disease surveillance 2008 supplement, *Chlamydia* Prevalence Monitoring Project Annual Report 2007. In: *U.S. Department of Health and Human Services CfDCaP*, editor. Atlanta, Ga.: U.S. Department of Health and Human Services, Centers for Disease Control and Prevention; January 2009.
3. Rodgers et al. Association of tubal factor infertility with elevated antibodies to *Chlamydia trachomatis* caseinolytic protease P. *Am J Obstet Gynecol* 2010 November; 203(5): 494 e7-e14.
4. Claman et al. The presence of serum antibody to the chlamydial heat shock protein (CHSP60) as a diagnostic test for tubal factor infertility. *Fertil Steril* 1997 March; 67(3):501-4.
5. Rodgers et al. Genome-wide identification of *Chlamydia trachomatis* antigens associated with tubal factor infertility. *Fertil Steril* 2011 September; 96(3):715-21.
6. den Hartog et al. *Chlamydia trachomatis*-associated tubal factor subfertility: Immunogenetic aspects and serological screening. *Hum Reprod Update* 2006 November-December; 12(6):719-30.
7. Stephens et al. Antichlamydial antibodies, human fertility, and pregnancy wastage. *Infect Dis Obstet Gynecol* 2011; 2011:525182.
8. Veenemans and van der Linden. The value of *Chlamydia trachomatis* antibody testing in predicting tubal factor infertility. *Hum Reprod* 2002 March; 17(3):695-8.
9. Peeling et al. Antibody to chlamydial hsp60 predicts an increased risk for chlamydial pelvic inflammatory disease. *J Infect Dis* 1997 May; 175(5): 1153-8.
10. Bax et al. Comparison of serological assays for detection of *Chlamydia trachomatis* antibodies in different groups of obstetrical and gynecological patients. *Clin Diagn Lab Immunol* 2003 January; 10(1):174-6.
11. Wang et al. A Genome-Wide Profiling of the Humoral Immune Response to *Chlamydia trachomatis* Infection Reveals Vaccine Candidate Antigens Expressed in Humans. *J Immunol* 2010 Aug. 1; 185(3):1670-80.
12. Sharma et al. Profiling of human antibody responses to *Chlamydia trachomatis* urogenital tract infection using microplates arrayed with 156 chlamydial fusion proteins. *Infect Immun* 2006 March; 74(3):1490-9.
13. Greene et al. *Chlamydia*-infected cells continue to undergo mitosis and resist induction of apoptosis. *Infect Immun* 2004 January; 72(1):451-60.
14. Zhong et al. Identification of a chlamydial protease-like activity factor responsible for the degradation of host transcription factors. *J Exp Med* 2001 Apr. 16; 193(8):935-42.
15. Greene and Zhong. Inhibition of host cell cytokinesis by *Chlamydia trachomatis* infection. *J Infect* 2003 July; 47(1):45-51.
16. Fan et al. *Chlamydia pneumoniae* secretion of a protease-like activity factor for degrading host cell transcription factors required for [correction of factors is required for] major histocompatibility complex antigen expression. *Infect Immun* 2002 January; 70(1):345-9.
17. Fan et al. Inhibition of apoptosis in chlamydia-infected cells: blockade of mitochondrial cytochrome c release and caspase activation. *J Exp Med* 1998 Feb. 16; 187(4):487-96.
18. Koh et al. Seroprevalence of IgG antibodies against *Chlamydia pneumoniae* in Chinese, Malays and Asian Indians in Singapore. *Int J Epidemiol* 2002 October; 31(5): 1001-7.
19. Ridker et al. Prospective study of *Chlamydia pneumoniae* IgG seropositivity and risks of future myocardial infarction. *Circulation* 1999 Mar. 9; 99(9):1161-4.
20. Li et al. The chlamydial plasmid-encoded protein pgp3 is secreted into the cytosol of *Chlamydia*-infected cells. *Infect Immun* 2008 August; 76(8):3415-28.
21. Chen et al. Characterization of Pgp3, a *Chlamydia trachomatis* plasmid-encoded immunodominant antigen. *J Bacteriol* 2010 Sep. 17.
22. Qi et al. A *Chlamydia trachomatis* OmcB C-terminal fragment is released into host cell cytoplasm and is immunogenic in humans. *Infect Immun* 2011 Mar. 21.
23. Chen et al. The hypothetical protein CT813 is localized in the *Chlamydia trachomatis* inclusion membrane and is immunogenic in women urogenitally infected with *C. trachomatis*. *Infect Immun* 2006 August; 74(8):4826-40.
24. Fling et al. CD8+ T *cells recognize an inclusion membrane-associated protein from the vacuolar pathogen Chlamydia trachomatis*. *Proc Natl Acad Sci USA* 2001 Jan. 30; 98(3):1160-5.
25. Hower et al. Evidence that CT694 is a novel *Chlamydia trachomatis* T3 S substrate capable of functioning during invasion or early cycle development. *Mol Microbiol* 2009 June; 72(6):1423-37.
26. Cappello et al. *Chlamydia trachomatis* infection and anti-Hsp60 immunity: the two sides of the coin. *PLoS Pathog* 2009 August; 5(8):e1000552.

27. Domeika et al. Humoral immune response to conserved epitopes of *Chlamydia trachomatis* and human 60-kDa heat-shock protein in women with pelvic inflammatory disease. *J Infect Dis* 1998 March; 177(3):714-9.
28. Ausiello et al. 60-kDa heat shock protein of *Chlamydia pneumoniae* is a target of T-cell immune response. *J Biol Regul Homeost Agents* 2005 July-December; 19(3-4):136-40.
29. Kinnunen et al. Heat shock protein 60 specific T-cell response in chlamydial infections. *Scand J Immunol* 2001 July-August; 54(1-2):76-81.
30. Hjelholt et al. Tubal factor infertility is associated with antibodies against *Chlamydia trachomatis* heat shock protein 60 (HSP60) but not human HSP60. *Hum Reprod* 2011 August; 26(8):2069-76.
31. Bulut Y et al. Chlamydial heat shock protein 60 activates macrophages and endothelial cells through Toll-like receptor 4 and MD2 in a MyD88-dependent pathway. *J Immunol* 2002 Feb. 1; 168(3):1435-40.
32. Sharma et al. Human antibody responses to a *Chlamydia*-secreted protease factor. *Infect Immun* 2004 December; 72(12):7164-71.
33. Li et al. Characterization of fifty putative inclusion membrane proteins encoded in the *Chlamydia trachomatis* genome. *Infect Immun* 2008 June; 76(6):2746-57.
34. Gervassi et al. Human CD8+ T cells recognize the 60-kDa cysteine-rich outer membrane protein from *Chlamydia trachomatis*. *J Immunol* 2004 Dec. 1; 173(11):6905-13.

TABLE 1

Titers of antibodies against *C. trachomatis* and *C. pneumoniae* in infertile women with or without tubal pathology

| | | Antibodies to *C. trachomatis* | | Antibodies to *C. pneumoniae* | |
|---|---|---|---|---|---|
| | | TFI (n = 31) | IFC (n = 23) | TFI (n = 31) | IFC (n = 23) |
| Quantitative analyses | Mean | 69928 | 3814 | 41503 | 25861 |
| | Standard Deviation | 106709 | 8270 | 65848 | 35847 |
| | Student's t Test | $p = 0.0009$ | | $p = 0.269$ | |
| Categorization of serum samples into Negative, Low and High titer groups | | | | | |
| Qualitative analyses | Negative titers (<1:10) | 1 (3.2%) | 3 (13.0%) | 3 (9.7%) | 4 (17.4%) |
| | Low titers (1:10-1:10000) | 11 (35.5%) | 19 (82.6%) | 11 (34.5%) | 6 (26.1%) |
| | High titers (>1:10000) | 19 (61.3%) | 1 (4.4%) | 17 (54.8%) | 13 (56.5%) |
| | $\chi^2$ Test | $p < 0.001$ | | $p = 0.634$ | |
| | Pairwise $\chi^2$ Tests | High vs. Negative | $p = 0.008$ | N/A | |
| | | High vs. Low | $p < 0.001$ | | |
| | | Low vs. Negative | $p = 0.556$ | | |

TABLE 2

Reactivity of 30 significant *C. trachomatis* proteins with 31 TFI and 23 IFC patient antisera (1:800 dilution)

| CT ORF | TFI (n = 31) X +/− SD | IFC (n = 23) X +/− SD | t-Test | Specificity | Sensitivity | PPV | NPV |
|---|---|---|---|---|---|---|---|
| CT067 | 0.407 ± 0.483 | 0.045 ± 0.115 | <0.001 | 87.0% | 51.6% | 84.2% | 57.1% |
| CT089 | 0.645 ± 0.936 | 0.189 ± 0.407 | 0.020 | 78.3% | 45.2% | 73.7% | 51.4% |
| CT110 | 0.679 ± 0.756 | 0.069 ± 0.112 | <0.001 | 82.6% | 71.0% | 84.6% | 67.9% |
| CT116 | 0.176 ± 0.252 | 0.012 ± 0.059 | 0.001 | 95.7% | 32.3% | 90.9% | 51.2% |
| CT119 | 0.375 ± 0.501 | 0.082 ± 0.196 | 0.005 | 87.0% | 48.4% | 83.3% | 55.6% |
| CT142 | 0.468 ± 0.522 | 0.098 ± 0.138 | 0.001 | 78.3% | 54.8% | 77.3% | 56.3% |
| CT143 | 1.012 ± 0.818 | 0.166 ± 0.220 | <0.001 | 73.9% | 71.0% | 78.6% | 65.4% |
| CT147 | 0.789 ± 0.678 | 0.303 ± 0.185 | 0.001 | 34.8% | 80.6% | 62.5% | 57.1% |
| CT153 | 0.404 ± 0.561 | 0.071 ± 0.110 | 0.003 | 91.3% | 45.2% | 87.5% | 55.3% |
| CT322 | 0.366 ± 0.586 | 0.055 ± 0.112 | 0.007 | 95.7% | 41.9% | 92.9% | 55.0% |
| CT376 | 0.453 ± 0.616 | 0.072 ± 0.097 | 0.002 | 95.7% | 41.9% | 92.9% | 55.0% |
| CT381 | 0.330 ± 0.346 | 0.059 ± 0.074 | <0.001 | 95.7% | 51.6% | 94.1% | 59.5% |
| CT414 | 0.327 ± 0.469 | 0.061 ± 0.082 | 0.004 | 95.7% | 51.6% | 94.1% | 59.5% |
| CT442 | 0.486 ± 0.622 | 0.055 ± 0.070 | 0.001 | 91.3% | 48.4% | 88.2% | 56.8% |
| CT443 | 1.145 ± 1.020 | 0.110 ± 0.173 | <0.001 | 87.0% | 71.0% | 88.0% | 69.0% |
| CT456 | 0.803 ± 0.879 | 0.241 ± 0.558 | 0.006 | 73.9% | 64.5% | 76.9% | 60.7% |
| CT529 | 0.854 ± 0.644 | 0.444 ± 0.310 | 0.003 | 13.0% | 87.1% | 57.4% | 42.9% |
| CT557 | 0.358 ± 0.638 | 0.028 ± 0.057 | 0.007 | 100% | 29.0% | 100% | 51.1% |
| CT603 | 0.579 ± 0.654 | 0.141 ± 0.161 | 0.001 | 78.3% | 61.3% | 79.2% | 60.0% |
| CT681 | 0.363 ± 0.386 | 0.060 ± 0.078 | <0.001 | 87.0% | 51.6% | 84.2% | 57.1% |
| CT694 | 0.698 ± 0.848 | 0.150 ± 0.293 | 0.002 | 78.3% | 54.8% | 77.3% | 56.3% |

TABLE 2-continued

Reactivity of 30 significant *C. trachomatis* proteins with 31 TFI and 23 IFC patient antisera (1:800 dilution)

| CT ORF | TFI (n = 31) X +/− SD | IFC (n = 23) X +/− SD | t-Test | Specificity | Sensitivity | PPV | NPV |
|---|---|---|---|---|---|---|---|
| CT795 | 0.647 ± 0.771 | 0.034 ± 0.101 | <0.001 | 95.7% | 61.3% | 95.0% | 64.7% |
| CT798 | 0.622 ± 0.827 | 0.038 ± 0.089 | <0.001 | 91.3% | 51.6% | 88.9% | 58.3% |
| CT806 | 0.673 ± 0.772 | 0.104 ± 0.212 | <0.001 | 82.6% | 54.8% | 81.0% | 57.6% |
| CT812 | 0.555 ± 0.667 | 0.061 ± 0.087 | <0.001 | 91.3% | 54.8% | 89.5% | 60.0% |
| CT813 | 0.673 ± 0.689 | 0.095 ± 0.165 | <0.001 | 78.3% | 67.7% | 80.8% | 64.3% |
| CT823 | 0.649 ± 0.709 | 0.071 ± 0.074 | <0.001 | 91.3% | 71.0% | 91.7% | 70.0% |
| CT858 | 1.947 ± 1.276 | 0.338 ± 0.666 | <0.001 | 78.3% | 74.2% | 82.1% | 69.2% |
| CT866 | 0.574 ± 0.738 | 0.062 ± 0.079 | 0.001 | 91.3% | 48.4% | 88.2% | 56.8% |
| pCT03 | 1.761 ± 1.366 | 0.166 ± 0.573 | <0.001 | 82.6% | 74.2% | 85.2% | 70.4% |

TABLE 3

Titers of antibodies against *C. trachomatis* and *C. pneumoniae* in women with tubal factor infertility (TFI), normal fertility (FC) or acute infection (STI)

| | Antibodies to *C. trachomatis* | | | Antibodies to *C. pneumoniae* | | |
|---|---|---|---|---|---|---|
| Groups | TFI (n = 24) | FC (n = 25) | STI (n = 24) | TFI (n = 24) | FC (n = 25) | STI (n = 24) |
| Mean | 35483.33 | 23760.00 | 65500.00 | 23000.00 | 17136.00 | 7875.00 |
| Standard deviation | 39950.49 | 23974.43 | 70078.87 | 23083.97 | 19709.45 | 6295.70 |
| ANOVA | | PP = 0.0108 | | | PP = 0.0166 | |
| | TFI vs FC | FC vs. STI | TFI vs. STI | TFI vs FC | FC vs STI | TFI vs. STI |
| Student's t-Test | P = 0.2229 | P = 0.0099 | P = 0.0748 | P = 0.3431 | PP = 0.0331 | P = 0.0033 |

TABLE 4

Antigens preferentially recognized by woman with Tubal Factor Infertility but not normal fertility

| Groups | TFI (N = 24) | | FC (N = 25) | | P value | |
|---|---|---|---|---|---|---|
| ORFs | Freq. | Mean ± SD | Freq. | Mean ± SD | Fisher's | t-Test |
| CT110 | 38% | 0.308 ± 0.512 | 0% | 0.018 ± 0.054 | <0.001 | 0.011 |
| CT376 | 25% | 0.137 ± 0.186 | 0% | 0.005 ± 0.037 | 0.010 | 0.001 |
| CT111 | 17% | 0.129 ± 0.238 | 0% | 0.043 ± 0.062 | 0.050 | 0.098 |
| CT557 | 17% | 0.142 ± 0.289 | 0% | 0.008 ± 0.047 | 0.050 | 0.035 |
| CT579 | 17% | 0.077 ± 0.163 | 0% | 0.004 ± 0.040 | 0.050 | 0.025 |
| CT443 | 88% | 0.717 ± 0.576 | 60% | 0.306 ± 0.258 | 0.030 | 0.003 |
| CT798 | 58% | 0.374 ± 0.403 | 28% | 0.182 ± 0.328 | 0.031 | 0.074 |
| CT603 | 42% | 0.187 ± 0.203 | 16% | 0.071 ± 0.140 | 0.047 | 0.025 |
| CT381 | 21% | 0.102 ± 0.149 | 4% | 0.027 ± 0.072 | 0.086 | 0.031 |
| CT823 | 17% | 0.122 ± 0.158 | 4% | 0.034 ± 0.109 | 0.162 | 0.029 |

TABLE 5

21 antigens most significantly recognized by women with acute *C. trachomatis* infection (antiserum dilution 1:1.000)

| Groups | STI (n = 24) | | TFI (n = 24) | | FC (n = 25) | | STI vs. TFI | | STI vs. FC | | TFI vs. FC | |
|---|---|---|---|---|---|---|---|---|---|---|---|---|
| ORFs | Freq | Mean ± SD | Freq | Mean ± SD | Freq | Mean ± SD | t-Test | Fisher's | t-Test | Fisher's | t-Test | Fisher's |
| CT147 | 88% | 0.937 ± 0.776 | 21% | 0.161 ± 0.191 | 16% | 0.117 ± 0.213 | <0.001 | <0.001 | <0.001 | <0.001 | 0.455 | 0.661 |
| CT442 | 83% | 0.841 ± 0.701 | 17% | 0.151 ± 0.303 | 20% | 0.113 ± 0.229 | <0.001 | <0.001 | <0.001 | <0.001 | 0.623 | 0.763 |
| CT529 | 100% | 1.040 ± 0.620 | 42% | 0.293 ± 0.310 | 32% | 0.227 ± 0.341 | <0.001 | <0.001 | <0.001 | <0.001 | 0.483 | 0.482 |
| CT119 | 75% | 0.603 ± 0.681 | 13% | 0.124 ± 0.212 | 4% | 0.040 ± 0.072 | 0.002 | <0.001 | <0.001 | <0.001 | 0.077 | 0.277 |
| CT089 | 92% | 1.364 ± 0.995 | 33% | 0.274 ± 0.456 | 28% | 0.208 ± 0.388 | <0.001 | <0.001 | <0.001 | <0.001 | 0.586 | 0.685 |
| CT695 | 92% | 0.825 ± 0.731 | 33% | 0.274 ± 0.342 | 24% | 0.144 ± 0.149 | 0.002 | <0.001 | <0.001 | <0.001 | 0.098 | 0.469 |
| CT806 | 88% | 0.739 ± 0.643 | 29% | 0.152 ± 0.231 | 20% | 0.102 ± 0.152 | <0.001 | <0.001 | <0.001 | <0.001 | 0.387 | 0.455 |
| CT875 | 75% | 0.956 ± 0.727 | 17% | 0.145 ± 0.269 | 16% | 0.098 ± 0.170 | <0.001 | <0.001 | <0.001 | <0.001 | 0.472 | 0.949 |
| CT841 | 96% | 1.093 ± 0.625 | 42% | 0.282 ± 0.468 | 48% | 0.232 ± 0.255 | <0.001 | <0.001 | <0.001 | <0.001 | 0.643 | 0.655 |
| CT694 | 92% | 1.235 ± 0.763 | 38% | 0.261 ± 0.375 | 32% | 0.311 ± 0.505 | <0.001 | <0.001 | <0.001 | <0.001 | 0.695 | 0.685 |

TABLE 5-continued 21 antigens most significantly recognized by women with acute *C. trachomatis* infection
(antiserum dilution 1:1.000)

| Groups | STI (n = 24) | | TFI (n = 24) | | FC (n = 25) | | STI vs. TFI | | STI vs. FC | | TFI vs. FC | |
|---|---|---|---|---|---|---|---|---|---|---|---|---|
| ORFs | Freq | Mean ± SD | Freq | Mean ± SD | Freq | Mean ± SD | t-Test | Fisher's | t-Test | Fisher's | t-Test | Fisher's |
| CT480 | 54% | 0.447 ± 0.529 | 4% | 0.046 ± 0.143 | 8% | 0.027 ± 0.101 | <0.001 | <0.001 | <0.001 | <0.001 | 0.594 | 0.575 |
| CT812 | 63% | 0.654 ± 0.731 | 13% | 0.137 ± 0.286 | 4% | 0.028 ± 0.075 | 0.002 | <0.001 | <0.001 | <0.001 | 0.083 | 0.277 |
| CT228 | 50% | 0.377 ± 0.675 | 4% | 0.037 ± 0.063 | 0% | 0.009 ± 0.041 | 0.018 | <0.001 | 0.013 | <0.001 | 0.078 | 0.302 |
| CT153 | 83% | 0.765 ± 0.785 | 33% | 0.238 ± 0.312 | 16% | 0.112 ± 0.134 | 0.004 | <0.001 | <0.001 | <0.001 | 0.079 | 0.158 |
| CT381 | 71% | 0.537 ± 0.579 | 21% | 0.102 ± 0.148 | 4% | 0.026 ± 0.071 | <0.001 | <0.001 | <0.001 | <0.001 | 0.031 | 0.072 |
| CT118 | 46% | 0.298 ± 0.494 | 4% | 0.041 ± 0.077 | 0% | 0.018 ± 0.046 | 0.016 | <0.001 | 0.011 | <0.001 | 0.216 | 0.302 |
| CT149 | 67% | 0.594 ± 0.941 | 21% | 0.136 ± 0.285 | 12% | 0.067 ± 0.192 | 0.027 | 0.001 | 0.012 | <0.001 | 0.331 | 0.402 |
| CT142 | 92% | 1.173 ± 0.686 | 50% | 0.265 ± 0.310 | 28% | 0.204 ± 0.337 | <0.001 | 0.001 | <0.001 | <0.001 | 0.512 | 0.114 |
| CT619 | 33% | 0.184 ± 0.428 | 0% | 0.005 ± 0.035 | 4% | 0.003 ± 0.054 | 0.047 | 0.002 | 0.050 | 0.008 | 0.866 | 0.322 |
| CT702 | 33% | 0.279 ± 0.649 | 0% | 0.017 ± 0.038 | 4% | 0.015 ± 0.067 | 0.030 | 0.002 | 0.037 | 0.008 | 0.875 | 0.322 |
| CT143 | 100% | 1.324 ± 0.681 | 67% | 0.355 ± 0.317 | 40% | 0.202 ± 0.219 | <0.001 | 0.002 | <0.001 | <0.001 | 0.058 | 0.060 |

TABLE 6

5-mer CT443 (OmcB or CRP60, 553 amino acids), ACCESSION#: NP219955.1, GI: 15605169 (SEQ ID NOS: 1-549)

| | |
|---|---|
| 1. | MRIGD |
| 2. | RIGDP |
| 3. | IGDPM |
| 4. | GDPMN |
| 5. | DPMNK |
| 6. | PMNKL |
| 7. | MNKLI |
| 8. | NKLIR |
| 9. | KLIRR |
| 10. | LIRRA |
| 11. | IRRAV |
| 12. | RRAVT |
| 13. | RAVTI |
| 14. | AVTIF |
| 15. | VTIFA |
| 16. | TIFAV |
| 17. | IFAVT |
| 18. | FAVTS |
| 19. | AVTSV |
| 20. | VTSVA |
| 21. | TSVAS |
| 22. | SVASL |
| 23. | VASLF |
| 24. | ASLFA |
| 25. | SLFAS |
| 26. | LFASG |
| 27. | FASGV |
| 28. | ASGVL |
| 29. | SGVLE |
| 30. | GVLET |
| 31. | VLETS |
| 32. | LETSM |
| 33. | ETSMA |
| 34. | TSMAE |
| 35. | SMAES |
| 36. | MAESL |
| 37. | AESLS |
| 38. | ESLST |
| 39. | SLSTN |
| 40. | YATVG |
| 41. | STNVI |
| 42. | TNVIS |
| 43. | NVISL |
| 44. | VISLA |
| 45. | ISLAD |
| 46. | SLADT |
| 47. | LADTK |
| 48. | ADTKA |
| 49. | DTKAK |
| 50. | TKAKD |
| 51. | KAKDN |
| 52. | AKDNT |
| 53. | KDNTS |
| 54. | DNTSH |
| 55. | NTSHK |
| 56. | TSHKS |
| 57. | SHKSK |
| 58. | HKSKK |
| 59. | KSKKA |
| 60. | SKKAR |
| 61. | KKARK |
| 62. | KARKN |
| 63. | ARKNH |
| 64. | RKNHS |
| 65. | KNHSK |
| 66. | NHSKE |
| 67. | HSKET |
| 68. | SKETP |
| 69. | KETPV |
| 70. | ETPVD |
| 71. | TPVDR |
| 72. | PVDRK |
| 73. | VDRKE |
| 74. | DRKEV |
| 75. | RKEVA |
| 76. | KEVAP |
| 77. | EVAPV |
| 78. | VAPVH |
| 79. | APVHE |
| 80. | PVHES |
| 81. | TTPTA |
| 82. | HESKA |
| 83. | ESKAT |
| 84. | SKATG |
| 85. | KATGP |
| 86. | ATGPK |
| 87. | TGPKQ |
| 88. | GPKQD |
| 89. | PKQDS |
| 90. | KQDSC |
| 91. | QDSCF |
| 92. | DSCFG |
| 93. | SCFGR |
| 94. | CFGRM |
| 95. | FGRMY |
| 96. | GRMYT |
| 97. | RMYTV |
| 98. | MYTVK |
| 99. | YTVKV |
| 100. | TVKVN |
| 101. | VKVND |
| 102. | KVNDD |
| 103. | VNDDR |
| 104. | NDDRN |
| 105. | DDRNV |
| 106. | DRNVE |
| 107. | RNVEI |
| 108. | NVEIT |

TABLE 6-continued

| | |
|---|---|
| 109. | VEITQ |
| 110. | EITQA |
| 111. | ITQAV |
| 112. | TQAVP |
| 113. | QAVPE |
| 114. | AVPEY |
| 115. | VPEYA |
| 116. | PEYAT |
| 117. | EYATV |
| 118. | YATVG |
| 119. | ATVGS |
| 120. | TVGSP |
| 121. | VGSPY |
| 122. | GSPYP |
| 123. | SPYPI |
| 124. | PYPIE |
| 125. | YPIEI |
| 126. | PIEIT |
| 127. | IEITA |
| 128. | EITAT |
| 129. | ITATG |
| 130. | TATGK |
| 131. | ATGKR |
| 132. | TGKRD |
| 133. | GKRDC |
| 134. | KRDCV |
| 135. | RDCVD |
| 136. | DCVDV |
| 137. | CVDVI |
| 138. | VDVII |
| 139. | DVIIT |
| 140. | VIITQ |
| 141. | IITQQ |
| 142. | ITQQL |
| 143. | TQQLP |
| 144. | QQLPC |
| 145. | QLPCE |
| 146. | LPCEA |
| 147. | PCEAE |
| 148. | CEAEF |
| 149. | EAEFV |
| 150. | AEFVR |
| 151. | EFVRS |
| 152. | FVRSD |
| 153. | VRSDP |
| 154. | RSDPA |
| 155. | SDPAT |
| 156. | DPATT |
| 157. | PATTP |
| 158. | ATTPT |
| 159. | TTPTA |
| 160. | TPTAD |
| 161. | PTADG |
| 162. | TADGK |
| 163. | ADGKL |
| 164. | DGKLV |
| 165. | GKLVW |
| 166. | KLVWK |
| 167. | LVWKI |
| 168. | VWKID |
| 169. | WKIDR |
| 170. | KIDRL |
| 171. | IDRLG |
| 172. | DRLGQ |
| 173. | RLGQG |
| 174. | LGQGE |
| 175. | GQGEK |
| 176. | QGEKS |
| 177. | GEKSK |
| 178. | EKSKI |
| 179. | KSKIT |
| 180. | SKITV |
| 181. | KITVW |
| 182. | ITVWV |
| 183. | TVWVK |
| 184. | VWVKP |
| 185. | WVKPL |
| 186. | VKPLK |
| 187. | KPLKE |
| 188. | PLKEG |

TABLE 6-continued

| | |
|---|---|
| 189. | LKEGC |
| 190. | KEGCC |
| 191. | EGCCF |
| 192. | GCCFT |
| 193. | CCFTA |
| 194. | CFTAA |
| 195. | FTAAT |
| 196. | TAATV |
| 197. | AATVC |
| 198. | ATVCA |
| 199. | TVCAC |
| 200. | VCACP |
| 201. | CACPE |
| 202. | ACPEI |
| 203. | CPEIR |
| 204. | PEIRS |
| 205. | EIRSV |
| 206. | IRSVT |
| 207. | RSVTK |
| 208. | SVTKC |
| 209. | VTKCG |
| 210. | TKCGQ |
| 211. | KCGQP |
| 212. | CGQPA |
| 213. | GQPAI |
| 214. | QPAIC |
| 215. | PAICV |
| 216. | AICVK |
| 217. | ICVKQ |
| 218. | CVKQE |
| 219. | VKQEG |
| 220. | KQEGP |
| 221. | QEGPE |
| 222. | EGPEN |
| 223. | GPENA |
| 224. | PENAC |
| 225. | ENACL |
| 226. | NACLR |
| 227. | ACLRC |
| 228. | CLRCP |
| 229. | LRCPV |
| 230. | RCPVV |
| 231. | CPVVY |
| 232. | PVVYK |
| 233. | VVYKI |
| 234. | VYKIN |
| 235. | YKINI |
| 236. | KINIV |
| 237. | INIVN |
| 238. | NIVNQ |
| 239. | IVNQG |
| 240. | VNQGT |
| 241. | NQGTA |
| 242. | QGTAT |
| 243. | GTATA |
| 244. | TATAR |
| 245. | ATARN |
| 246. | TARNV |
| 247. | ARNVV |
| 248. | RNVVV |
| 249. | NVVVE |
| 250. | VVVEN |
| 251. | VVENP |
| 252. | VENPV |
| 253. | ENPVP |
| 254. | NPVPD |
| 255. | PVPDG |
| 256. | VPDGY |
| 257. | PDGYA |
| 258. | DGYAH |
| 259. | GYAHS |
| 260. | YAHSS |
| 261. | AHSSG |
| 262. | HSSGQ |
| 263. | SSGQR |
| 264. | SGQRV |
| 265. | GQRVL |
| 266. | QRVLT |
| 267. | RVLTF |
| 268. | VLTFT |

TABLE 6-continued

| | |
|---|---|
| 269. | LTFTL |
| 270. | TFTLG |
| 271. | FTLGD |
| 272. | TLGDM |
| 273. | LGDMQ |
| 274. | GDMQP |
| 275. | DMQPG |
| 276. | MQPGE |
| 277. | QPGEH |
| 278. | PGEHR |
| 279. | GEHRT |
| 280. | EHRTI |
| 281. | HRTIT |
| 282. | RTITV |
| 283. | TITVE |
| 284. | ITVEF |
| 285. | TVEFC |
| 286. | VEFCP |
| 287. | EFCPL |
| 288. | FCPLK |
| 289. | CPLKR |
| 290. | PLKRG |
| 291. | LKRGR |
| 292. | KRGRA |
| 293. | RGRAT |
| 294. | GRATN |
| 295. | RATNI |
| 296. | ATNIA |
| 297. | TNIAT |
| 298. | NIATV |
| 299. | IATVS |
| 300. | ATVSY |
| 301. | TVSYC |
| 302. | VSYCG |
| 303. | SYCGG |
| 304. | YCGGH |
| 305. | CGGHK |
| 306. | GGHKN |
| 307. | GHKNT |
| 308. | HKNTA |
| 309. | KNTAS |
| 310. | NTASV |
| 311. | TASVT |
| 312. | ASVTT |
| 313. | SVTTV |
| 314. | VTTVI |
| 315. | TTVIN |
| 316. | TVINE |
| 317. | VINEP |
| 318. | INEPC |
| 319. | NEPCV |
| 320. | EPCVQ |
| 321. | PCVQV |
| 322. | CVQVS |
| 323. | VQVSI |
| 324. | QVSIA |
| 325. | VSIAG |
| 326. | SIAGA |
| 327. | IAGAD |
| 328. | AGADW |
| 329. | GADWS |
| 330. | ADWSY |
| 331. | DWSYV |
| 332. | WSYVC |
| 333. | SYVCK |
| 334. | YVCKP |
| 335. | VCKPV |
| 336. | CKPVE |
| 337. | KPVEY |
| 338. | PVEYV |
| 339. | VEYVI |
| 340. | EYVIS |
| 341. | YVISV |
| 342. | VISVS |
| 343. | ISVSN |
| 344. | SVSNP |
| 345. | VSNPG |
| 346. | SNPGD |
| 347. | NPGDL |
| 348. | PGDLV |
| 349. | GDLVL |
| 350. | DLVLR |
| 351. | LVLRD |
| 352. | VLRDV |
| 353. | LRDVV |
| 354. | RDVVV |
| 355. | DVVVE |
| 356. | VVVED |
| 357. | VVEDT |
| 358. | VEDTL |
| 359. | EDTLS |
| 360. | DTLSP |
| 361. | TLSPG |
| 362. | LSPGV |
| 363. | SPGVT |
| 364. | PGVTV |
| 365. | GVTVL |
| 366. | VTVLE |
| 367. | TVLEA |
| 368. | VLEAA |
| 369. | LEAAG |
| 370. | EAAGA |
| 371. | AAGAQ |
| 372. | AGAQI |
| 373. | GAQIS |
| 374. | AQISC |
| 375. | QISCN |
| 376. | ISCNK |
| 377. | SCNKV |
| 378. | CNKVV |
| 379. | NKVVW |
| 380. | KVVWT |
| 381. | VVWTV |
| 382. | VWTVK |
| 383. | WTVKE |
| 384. | TVKEL |
| 385. | VKELN |
| 386. | KELNP |
| 387. | ELNPG |
| 388. | LNPGE |
| 389. | NPGES |
| 390. | PGESL |
| 391. | GESLQ |
| 392. | ESLQY |
| 393. | SLQYK |
| 394. | LQYKV |
| 395. | QYKVL |
| 396. | YKVLV |
| 397. | KVLVR |
| 398. | VLVRA |
| 399. | LVRAQ |
| 400. | VRAQT |
| 401. | RAQTP |
| 402. | AQTPG |
| 403. | QTPGQ |
| 404. | TPGQF |
| 405. | PGQFT |
| 406. | GQFTN |
| 407. | QFTNN |
| 408. | FTNNV |
| 409. | TNNVV |
| 410. | NNVVV |
| 411. | NVVVK |
| 412. | VVVKS |
| 413. | VVKSC |
| 414. | VKSCS |
| 415. | KSCSD |
| 416. | SCSDC |
| 417. | CSDCG |
| 418. | SDCGT |
| 419. | DCGTC |
| 420. | CGTCT |
| 421. | GTCTS |
| 422. | TCTSC |
| 423. | CTSCA |
| 424. | TSCAE |
| 425. | SCAEA |
| 426. | CAEAT |
| 427. | AEATT |
| 428. | EATTY |

TABLE 6-continued

| | |
|---|---|
| 429. | ATTYW |
| 430. | TTYWK |
| 431. | TYWKG |
| 432. | YWKGV |
| 433. | WKGVA |
| 434. | KGVAA |
| 435. | GVAAT |
| 436. | VAATH |
| 437. | AATHM |
| 438. | ATHMC |
| 439. | THMCV |
| 440. | HMCVV |
| 441. | MCVVD |
| 442. | CVVDT |
| 443. | VVDTC |
| 444. | VDTCD |
| 445. | DTCDP |
| 446. | TCDPV |
| 447. | CDPVC |
| 448. | DPVCV |
| 449. | PVCVG |
| 450. | VCVGE |
| 451. | CVGEN |
| 452. | VGENT |
| 453. | GENTV |
| 454. | ENTVY |
| 455. | NTVYR |
| 456. | TVYRI |
| 457. | VYRIC |
| 458. | YRICV |
| 459. | RICVT |
| 460. | ICVTN |
| 461. | CVTNR |
| 462. | VTNRG |
| 463. | TNRGS |
| 464. | NRGSA |
| 465. | RGSAE |
| 466. | GSAED |
| 467. | SAEDT |
| 468. | AEDTN |
| 469. | EDTNV |
| 470. | DTNVS |
| 471. | TNVSL |
| 472. | NVSLM |
| 473. | VSLML |
| 474. | SLMLK |
| 475. | LMLKF |
| 476. | MLKFS |
| 477. | LKFSK |
| 478. | KFSKE |
| 479. | FSKEL |
| 480. | SKELQ |
| 481. | KELQP |
| 482. | ELQPV |
| 483. | LQPVS |
| 484. | QPVSF |
| 485. | PVSFS |
| 486. | VSFSG |
| 487. | SFSGP |
| 488. | FSGPT |
| 489. | SGPTK |
| 490. | GPTKG |
| 491. | PTKGT |
| 492. | TKGTI |
| 493. | KGTIT |
| 494. | GTITG |
| 495. | TITGN |
| 496. | ITGNT |
| 497. | TGNTV |
| 498. | GNTVV |
| 499. | NTVVF |
| 500. | TVVFD |
| 501. | VVFDS |
| 502. | VFDSL |
| 503. | FDSLP |
| 504. | DSLPR |
| 505. | SLPRL |
| 506. | LPRLG |
| 507. | PRLGS |
| 508. | RLGSK |

TABLE 6-continued

| | |
|---|---|
| 509. | LGSKE |
| 510. | GSKET |
| 511. | SKETV |
| 512. | KETVE |
| 513. | ETVEF |
| 514. | TVEFS |
| 515. | VEFSV |
| 516. | EFSVT |
| 517. | FSVTL |
| 518. | SVTLK |
| 519. | VTLKA |
| 520. | TLKAV |
| 521. | LKAVS |
| 522. | KAVSA |
| 523. | AVSAG |
| 524. | VSAGD |
| 525. | SAGDA |
| 526. | AGDAR |
| 527. | GDARG |
| 528. | DARGE |
| 529. | ARGEA |
| 530. | RGEAI |
| 531. | GEAIL |
| 532. | EAILS |
| 533. | AILSS |
| 534. | ILSSD |
| 535. | LSSDT |
| 536. | SSDTL |
| 537. | SDTLT |
| 538. | DTLTV |
| 539. | TLTVP |
| 540. | LTVPV |
| 541. | TVPVS |
| 542. | VPVSD |
| 543. | PVSDT |
| 544. | VSDTE |
| 545. | SDTEN |
| 546. | DTENT |
| 547. | TENTH |
| 548. | ENTHI |
| 549. | NTHIY |

5-mer peptides of CT381 (ArtJ, 257 amino acids), accession#: NP 219890.1, GI: 15605105 (SEQ ID NOS: 550-802)

| | |
|---|---|
| 550. | MCIKR |
| 551. | CIKRK |
| 552. | IKRKK |
| 553. | KRKKT |
| 554. | RKKTW |
| 555. | KKTWI |
| 556. | KTWIA |
| 557. | TWIAF |
| 558. | WIAFL |
| 559. | IAFLA |
| 560. | AFLAV |
| 561. | FLAVV |
| 562. | LAVVC |
| 563. | AVVCS |
| 564. | VVCSF |
| 565. | VCSFC |
| 566. | CSFCL |
| 567. | SFCLT |
| 568. | FCLTG |
| 569. | CLTGC |
| 570. | LTGCL |
| 571. | TGCLK |
| 572. | GCLKE |
| 573. | CLKEG |
| 574. | LKEGG |
| 575. | KEGGD |
| 576. | EGGDS |
| 577. | GGDSN |
| 578. | GDSNS |
| 579. | DSNSE |
| 580. | SNSEK |
| 581. | NSEKF |
| 582. | SEKFI |
| 583. | EKFIV |

TABLE 6-continued

| | |
|---|---|
| 584. | KFIVG |
| 585. | FIVGT |
| 586. | IVGTN |
| 587. | VGTNA |
| 588. | GTNAT |
| 589. | TNATY |
| 590. | NATYP |
| 591. | ATYPP |
| 592. | TYPPF |
| 593. | YPPFE |
| 594. | PPFEF |
| 595. | PFEFV |
| 596. | FEFVD |
| 597. | EFVDK |
| 598. | FVDKR |
| 599. | VDKRG |
| 600. | DKRGE |
| 601. | KRGEV |
| 602. | RGEVV |
| 603. | GEVVG |
| 604. | EVVGF |
| 605. | VVGFD |
| 606. | VGFDI |
| 607. | GFDID |
| 608. | FDIDL |
| 609. | DIDLA |
| 610. | IDLAR |
| 611. | DLARE |
| 612. | LAREI |
| 613. | AREIS |
| 614. | REISN |
| 615. | EISNK |
| 616. | ISNKL |
| 617. | SNKLG |
| 618. | NKLGK |
| 619. | KLGKT |
| 620. | LGKTL |
| 621. | GKTLD |
| 622. | KTLDV |
| 623. | TLDVR |
| 624. | LDVRE |
| 625. | DVREF |
| 626. | VREFS |
| 627. | REFSF |
| 628. | EFSFD |
| 629. | FSFDA |
| 630. | SFDAL |
| 631. | FDALI |
| 632. | DALIL |
| 633. | ALILN |
| 634. | LILNL |
| 635. | ILNLK |
| 636. | LNLKQ |
| 637. | NLKQH |
| 638. | LKQHR |
| 639. | KQHRI |
| 640. | QHRID |
| 641. | HRIDA |
| 642. | RIDAV |
| 643. | IDAVI |
| 644. | DAVIT |
| 645. | AVITG |
| 646. | VITGM |
| 647. | ITGMS |
| 648. | TGMSI |
| 649. | GMSIT |
| 650. | MSITP |
| 651. | SITPS |
| 652. | ITPSR |
| 653. | TPSRL |
| 654. | PSRLK |
| 655. | SRLKE |
| 656. | RLKEI |
| 657. | LKEIL |
| 658. | KEILM |
| 659. | EILMI |
| 660. | ILMIP |
| 661. | LMIPY |
| 662. | MIPYY |
| 663. | IPYYG |

TABLE 6-continued

| | |
|---|---|
| 664. | PYYGE |
| 665. | YYGEE |
| 666. | YGEEI |
| 667. | GEEIK |
| 668. | EEIKH |
| 669. | EIKHL |
| 670. | IKHLV |
| 671. | KHLVL |
| 672. | HLVLV |
| 673. | LVLVF |
| 674. | VLVFK |
| 675. | LVFKG |
| 676. | VFKGE |
| 677. | FKGEN |
| 678. | KGENK |
| 679. | GENKH |
| 680. | ENKHP |
| 681. | NKHPL |
| 682. | KHPLP |
| 683. | HPLPL |
| 684. | PLPLT |
| 685. | LPLTQ |
| 686. | PLTQY |
| 687. | LTQYR |
| 688. | TQYRS |
| 689. | QYRSV |
| 690. | YRSVA |
| 691. | RSVAV |
| 692. | SVAVQ |
| 693. | VAVQT |
| 694. | AVQTG |
| 695. | VQTGT |
| 696. | QTGTY |
| 697. | TGTYQ |
| 698. | GTYQE |
| 699. | TYQEA |
| 700. | YQEAY |
| 701. | QEAYL |
| 702. | EAYLQ |
| 703. | AYLQS |
| 704. | YLQSL |
| 705. | LQSLS |
| 706. | QSLSE |
| 707. | SLSEV |
| 708. | LSEVH |
| 709. | SEVHI |
| 710. | EVHIR |
| 711. | VHIRS |
| 712. | HIRSF |
| 713. | IRSFD |
| 714. | RSFDS |
| 715. | SFDST |
| 716. | FDSTL |
| 717. | DSTLE |
| 718. | STLEV |
| 719. | TLEVL |
| 720. | LEVLM |
| 721. | EVLME |
| 722. | VLMEV |
| 723. | LMEVM |
| 724. | MEVMH |
| 725. | EVMHG |
| 726. | VMHGK |
| 727. | MHGKS |
| 728. | HGKSP |
| 729. | GKSPV |
| 730. | KSPVA |
| 731. | SPVAV |
| 732. | PVAVL |
| 733. | VAVLE |
| 734. | AVLEP |
| 735. | VLEPS |
| 736. | LEPSI |
| 737. | EPSIA |
| 738. | PSIAQ |
| 739. | SIAQV |
| 740. | IAQVV |
| 741. | AQVVL |
| 742. | QVVLK |
| 743. | VVLKD |

TABLE 6-continued

| | |
|---|---|
| 744. | VLKDF |
| 745. | LKDFP |
| 746. | KDFPA |
| 747. | DFPAL |
| 748. | FPALS |
| 749. | PALST |
| 750. | ALSTA |
| 751. | LSTAT |
| 752. | STATI |
| 753. | TATID |
| 754. | ATIDL |
| 755. | TIDLP |
| 756. | IDLPE |
| 757. | DLPED |
| 758. | LPEDQ |
| 759. | PEDQW |
| 760. | EDQWV |
| 761. | DQWVL |
| 762. | QWVLG |
| 763. | WVLGY |
| 764. | VLGYG |
| 765. | LGYGI |
| 766. | GYGIG |
| 767. | YGIGV |
| 768. | GIGVA |
| 769. | IGVAS |
| 770. | GVASD |
| 771. | VASDR |
| 772. | ASDRP |
| 773. | SDRPA |
| 774. | DRPAL |
| 775. | RPALA |
| 776. | PALAL |
| 777. | ALALK |
| 778. | LALKI |
| 779. | ALKIE |
| 780. | LKIEA |
| 781. | KIEAA |
| 782. | IEAAV |
| 783. | EAAVQ |
| 784. | AAVQE |
| 785. | AVQEI |
| 786. | VQEIR |
| 787. | QEIRK |
| 788. | EIRKE |
| 789. | IRKEG |
| 790. | RKEGV |
| 791. | KEGVL |
| 792. | EGVLA |
| 793. | GVLAE |
| 794. | VLAEL |
| 795. | LAELE |
| 796. | AELEQ |
| 797. | ELEQK |
| 798. | LEQKW |
| 799. | EQKWG |
| 800. | QKWGL |
| 801. | KWGLN |
| 802. | WGLNN |

5-mer peptides of CT875 (hypothetical protein, 591 amino acids), ACCESSION#: NP_219502.1, GI: 15604718 (SEQ ID NOS: 803-1389)

| | |
|---|---|
| 803. | MSIRG |
| 804. | SIRGV |
| 805. | IRGVG |
| 806. | RGVGG |
| 807. | GVGGN |
| 808. | VGGNG |
| 809. | GNGNS |
| 810. | NGNSR |
| 811. | GNSRI |
| 812. | NSRIP |
| 813. | SRIPS |
| 814. | RIPSH |
| 815. | IPSHN |
| 816. | PSHNG |
| 817. | SHNGD |
| 818. | HNGDG |

TABLE 6-continued

| | |
|---|---|
| 819. | NGDGS |
| 820. | GDGSN |
| 821. | DGSNR |
| 822. | GSNRR |
| 823. | SNRRS |
| 824. | NRRSQ |
| 825. | RRSQN |
| 826. | RSQNT |
| 827. | SQNTK |
| 828. | QNTKG |
| 829. | NTKGN |
| 830. | TKGNN |
| 831. | KGNNK |
| 832. | GNNKV |
| 833. | NNKVE |
| 834. | NKVED |
| 835. | KVEDR |
| 836. | VEDRV |
| 837. | VEDRV |
| 838. | EDRVC |
| 839. | DRVCS |
| 840. | RVCSL |
| 841. | VCSLY |
| 842. | CSLYS |
| 843. | SLYSS |
| 844. | LYSSR |
| 845. | YSSRS |
| 846. | SSRSN |
| 847. | SRSNE |
| 848. | RSNEN |
| 849. | SNENR |
| 850. | NENRE |
| 851. | ENRES |
| 852. | NRESP |
| 853. | RESPY |
| 854. | ESPYA |
| 855. | SPYAV |
| 856. | PYAVV |
| 857. | YAVVD |
| 858. | AVVDV |
| 859. | VVDVS |
| 860. | VDVSS |
| 861. | DVSSM |
| 862. | VSSMI |
| 863. | SSMIE |
| 864. | SMIES |
| 865. | MIEST |
| 866. | IESTP |
| 867. | ESTPT |
| 868. | STPTS |
| 869. | TPTSG |
| 870. | PTSGE |
| 871. | TSGET |
| 872. | SGETT |
| 873. | GETTR |
| 874. | ETTRA |
| 875. | TTRAS |
| 876. | TRASR |
| 877. | RASRG |
| 878. | ASRGV |
| 879. | SRGVF |
| 880. | RGVFS |
| 881. | GVFSR |
| 882. | VFSRF |
| 883. | FSRFQ |
| 884. | SRFQR |
| 885. | RFQRG |
| 886. | FQRGL |
| 887. | QRGLV |
| 888. | RGLVR |
| 889. | GLVRV |
| 890. | LVRVA |
| 891. | VRVAD |
| 892. | RVADK |
| 893. | VADKV |
| 894. | ADKVR |
| 895. | DKVRR |
| 896. | KVRRA |
| 897. | VRRAV |
| 898. | RRAVQ |

TABLE 6-continued

| | |
|---|---|
| 899. | RAVQC |
| 900. | AVQCA |
| 901. | VQCAW |
| 902. | QCAWS |
| 903. | CAWSS |
| 904. | AWSSV |
| 905. | WSSVS |
| 906. | SSVST |
| 907. | SVSTR |
| 908. | VSTRR |
| 909. | STRRS |
| 910. | TRRSS |
| 911. | RRSSA |
| 912. | RSSAT |
| 913. | SSATR |
| 914. | SATRA |
| 915. | ATRAA |
| 916. | TRAAE |
| 917. | RAAES |
| 918. | AAESG |
| 919. | AESGS |
| 920. | ESGSS |
| 921. | SGSSS |
| 922. | GSSSR |
| 923. | SSSRT |
| 924. | SSRTA |
| 925. | SRTAR |
| 926. | RTARG |
| 927. | TARGA |
| 928. | ARGAS |
| 929. | RGASS |
| 930. | GASSG |
| 931. | ASSGY |
| 932. | SSGYR |
| 933. | SGYRE |
| 934. | GYREY |
| 935. | YREYS |
| 936. | REYSP |
| 937. | EYSPS |
| 938. | YSPSA |
| 939. | SPSAA |
| 940. | PSAAR |
| 941. | SAARG |
| 942. | AARGL |
| 943. | ARGLR |
| 944. | RGLRL |
| 945. | GLRLM |
| 946. | LRLMF |
| 947. | RLMFT |
| 948. | LMFTD |
| 949. | MFTDF |
| 950. | FTDFW |
| 951. | TDFWR |
| 952. | DFWRT |
| 953. | FWRTR |
| 954. | WRTRV |
| 955. | RTRVL |
| 956. | TRVLR |
| 957. | RVLRQ |
| 958. | VLRQT |
| 959. | LRQTS |
| 960. | RQTSP |
| 961. | QTSPM |
| 962. | TSPMA |
| 963. | SPMAG |
| 964. | PMAGV |
| 965. | MAGVF |
| 966. | AGVFG |
| 967. | GVFGN |
| 968. | VFGNL |
| 969. | FGNLD |
| 970. | GNLDV |
| 971. | NLDVN |
| 972. | LDVNE |
| 973. | DVNEA |
| 974. | VNEAR |
| 975. | NEARL |
| 976. | EARLM |
| 977. | ARLMA |
| 978. | RLMAA |
| 979. | LMAAY |
| 980. | MAAYT |
| 981. | AAYTS |
| 982. | AYTSE |
| 983. | YTSEC |
| 984. | TSECA |
| 985. | SECAD |
| 986. | ECADH |
| 987. | CADHL |
| 988. | ADHLE |
| 989. | DHLEA |
| 990. | HLEAN |
| 991. | LEANK |
| 992. | EANKL |
| 993. | ANKLA |
| 994. | NKLAG |
| 995. | KLAGP |
| 996. | LAGPD |
| 997. | AGPDG |
| 998. | GPDGV |
| 999. | PDGVA |
| 1000. | DGVAA |
| 1001. | GVAAA |
| 1002. | VAAAR |
| 1003. | AAARE |
| 1004. | AAREI |
| 1005. | AREIA |
| 1006. | REIAK |
| 1007. | EIAKR |
| 1008. | IAKRW |
| 1009. | AKRWE |
| 1010. | KRWEQ |
| 1011. | RWEQR |
| 1012. | WEQRV |
| 1013. | EQRVR |
| 1014. | QRVRD |
| 1015. | RVRDL |
| 1016. | VRDLQ |
| 1017. | RDLQD |
| 1018. | DLQDK |
| 1019. | LQDKG |
| 1020. | QDKGA |
| 1021. | DKGAA |
| 1022. | KGAAR |
| 1023. | GAARK |
| 1024. | AARKL |
| 1025. | ARKLL |
| 1026. | RKLLN |
| 1027. | KLLND |
| 1028. | LLNDP |
| 1029. | LNDPL |
| 1030. | NDPLG |
| 1031. | DPLGR |
| 1032. | PLGRR |
| 1033. | LGRRT |
| 1034. | GRRTP |
| 1035. | RRTPN |
| 1036. | RTPNY |
| 1037. | TPNYQ |
| 1038. | PNYQS |
| 1039. | NYQSK |
| 1040. | YQSKN |
| 1041. | QSKNP |
| 1042. | SKNPG |
| 1043. | KNPGE |
| 1044. | NPGEY |
| 1045. | PGEYT |
| 1046. | GEYTV |
| 1047. | EYTVG |
| 1048. | YTVGN |
| 1049. | TVGNS |
| 1050. | VGNSM |
| 1051. | GNSMF |
| 1052. | NSMFY |
| 1053. | SMFYD |
| 1054. | MFYDG |
| 1055. | FYDGP |
| 1056. | YDGPQ |
| 1057. | DGPQV |
| 1058. | GPQVA |

TABLE 6-continued

| | |
|---|---|
| 1059. | PQVAN |
| 1060. | QVANL |
| 1061. | VANLQ |
| 1062. | ANLQN |
| 1063. | NLQNV |
| 1064. | LQNVD |
| 1065. | QNVDT |
| 1066. | NVDTG |
| 1067. | VDTGF |
| 1068. | DTGFW |
| 1069. | TGFWL |
| 1070. | GFWLD |
| 1071. | FWLDM |
| 1072. | WLDMS |
| 1073. | LDMSN |
| 1074. | DMSNL |
| 1075. | MSNLS |
| 1076. | SNLSD |
| 1077. | NLSDV |
| 1078. | LSDVV |
| 1079. | SDVVL |
| 1080. | DVVLS |
| 1081. | VVLSR |
| 1082. | VLSRE |
| 1083. | LSREI |
| 1084. | SREIQ |
| 1085. | REIQT |
| 1086. | EIQTG |
| 1087. | IQTGL |
| 1088. | QTGLR |
| 1089. | TGLRA |
| 1090. | GLRAR |
| 1091. | LRARA |
| 1092. | RARAT |
| 1093. | ARATL |
| 1094. | RATLE |
| 1095. | ATLEE |
| 1096. | TLEES |
| 1097. | LEESM |
| 1098. | EESMP |
| 1099. | ESMPM |
| 1100. | SMPML |
| 1101. | MPMLE |
| 1102. | PMLEN |
| 1103. | MLENL |
| 1104. | LENLE |
| 1105. | ENLEE |
| 1106. | NLEER |
| 1107. | LEERF |
| 1108. | EERFR |
| 1109. | ERFRR |
| 1110. | RFRRL |
| 1111. | FRRLQ |
| 1112. | RRLQE |
| 1113. | RLQET |
| 1114. | LQETC |
| 1115. | QETCD |
| 1116. | ETCDA |
| 1117. | TCDAA |
| 1118. | CDAAR |
| 1119. | DAART |
| 1120. | AARTE |
| 1121. | ARTEI |
| 1122. | RTEIE |
| 1123. | TEIEE |
| 1124. | EIEES |
| 1125. | IEESG |
| 1126. | EESGW |
| 1127. | ESGWT |
| 1128. | SGWTR |
| 1129. | GWTRE |
| 1130. | WTRES |
| 1131. | TRESA |
| 1132. | RESAS |
| 1133. | ESASR |
| 1134. | SASRM |
| 1135. | ASRME |
| 1136. | SRMEG |
| 1137. | RMEGD |
| 1138. | MEGDE |
| 1139. | EGDEA |
| 1140. | GDEAQ |
| 1141. | DEAQG |
| 1142. | EAQGP |
| 1143. | AQGPS |
| 1144. | QGPSR |
| 1145. | GPSRA |
| 1146. | PSRAQ |
| 1147. | SRAQQ |
| 1148. | RAQQA |
| 1149. | AQQAF |
| 1150. | QQAFQ |
| 1151. | QAFQS |
| 1152. | AFQSF |
| 1153. | FQSFV |
| 1154. | QSFVN |
| 1155. | SFVNE |
| 1156. | FVNEC |
| 1157. | VNECN |
| 1158. | NECNS |
| 1159. | ECNSI |
| 1160. | CNSIE |
| 1161. | NSIEF |
| 1162. | SIEFS |
| 1163. | IEFSF |
| 1164. | EFSFG |
| 1165. | FSFGS |
| 1166. | SFGSF |
| 1167. | FGSFG |
| 1168. | GSFGE |
| 1169. | SFGEH |
| 1170. | FGEHV |
| 1171. | GEHVR |
| 1172. | EHVRV |
| 1173. | HVRVL |
| 1174. | VRVLC |
| 1175. | RVLCA |
| 1176. | VLCAR |
| 1177. | LCARV |
| 1178. | CARVS |
| 1179. | ARVSR |
| 1180. | RVSRG |
| 1181. | VSRGL |
| 1182. | SRGLA |
| 1183. | RGLAA |
| 1184. | GLAAA |
| 1185. | LAAAG |
| 1186. | AAAGE |
| 1187. | AAGEA |
| 1188. | AGEAI |
| 1189. | GEAIR |
| 1190. | EAIRR |
| 1191. | AIRRC |
| 1192. | IRRCF |
| 1193. | RRCFS |
| 1194. | RCFSC |
| 1195. | CFSCC |
| 1196. | FSCCK |
| 1197. | SCCKG |
| 1198. | CCKGS |
| 1199. | CKGST |
| 1200. | KGSTH |
| 1201. | GSTHR |
| 1202. | STHRY |
| 1203. | THRYA |
| 1204. | HRYAP |
| 1205. | RYAPR |
| 1206. | YAPRD |
| 1207. | APRDD |
| 1208. | PRDDL |
| 1209. | RDDLS |
| 1210. | DDLSP |
| 1211. | DLSPE |
| 1212. | LSPEG |
| 1213. | SPEGA |
| 1214. | PEGAS |
| 1215. | EGASL |
| 1216. | GASLA |
| 1217. | ASLAE |
| 1218. | SLAET |

TABLE 6-continued

| | |
|---|---|
| 1219. | LAETL |
| 1220. | AETLA |
| 1221. | ETLAR |
| 1222. | TLARF |
| 1223. | LARFA |
| 1224. | ARFAD |
| 1225. | RFADD |
| 1226. | FADDM |
| 1227. | ADDMG |
| 1228. | DDMGI |
| 1229. | DMGIE |
| 1230. | MGIER |
| 1231. | GIERG |
| 1232. | IERGA |
| 1233. | ERGAD |
| 1234. | RGADG |
| 1235. | GADGT |
| 1236. | ADGTY |
| 1237. | DGTYD |
| 1238. | GTYDI |
| 1239. | TYDIP |
| 1240. | YDIPL |
| 1241. | DIPLV |
| 1242. | IPLVD |
| 1243. | PLVDD |
| 1244. | LVDDW |
| 1245. | VDDWR |
| 1246. | DDWRR |
| 1247. | DWRRG |
| 1248. | WRRGV |
| 1249. | RRGVP |
| 1250. | RGVPS |
| 1251. | GVPSI |
| 1252. | VPSIE |
| 1253. | PSIEG |
| 1254. | SIEGE |
| 1255. | IEGEG |
| 1256. | EGEGS |
| 1257. | GEGSD |
| 1258. | EGSDS |
| 1259. | GSDSI |
| 1260. | SDSIY |
| 1261. | DSIYE |
| 1262. | SIYEI |
| 1263. | IYEIM |
| 1264. | YEIMM |
| 1265. | EIMMP |
| 1266. | IMMPI |
| 1267. | MMPIY |
| 1268. | MPIYE |
| 1269. | PIYEV |
| 1270. | IYEVM |
| 1271. | YEVMD |
| 1272. | EVMDM |
| 1273. | VMDMD |
| 1274. | MDMDL |
| 1275. | DMDLE |
| 1276. | MDLET |
| 1277. | DLETR |
| 1278. | LETRR |
| 1279. | ETRRS |
| 1280. | TRRSF |
| 1281. | RRSFA |
| 1282. | RSFAV |
| 1283. | SFAVQ |
| 1284. | FAVQQ |
| 1285. | AVQQG |
| 1286. | VQQGH |
| 1287. | QQGHY |
| 1288. | QGHYQ |
| 1289. | GHYQD |
| 1290. | HYQDP |
| 1291. | YQDPR |
| 1292. | QDPRA |
| 1293. | DPRAS |
| 1294. | PRASD |
| 1295. | RASDY |
| 1296. | ASDYD |
| 1297. | SDYDL |
| 1298. | DYDLP |
| 1299. | YDLPR |
| 1300. | DLPRA |
| 1301. | LPRAS |
| 1302. | PRASD |
| 1303. | RASDY |
| 1304. | ASDYD |
| 1305. | SDYDL |
| 1306. | DYDLP |
| 1307. | YDLPR |
| 1308. | DLPRS |
| 1309. | LPRSP |
| 1310. | PRSPY |
| 1311. | RSPYP |
| 1312. | SPYPT |
| 1313. | PYPTP |
| 1314. | YPTPP |
| 1315. | PTPPL |
| 1316. | TPPLP |
| 1317. | PPLPP |
| 1318. | PLPPR |
| 1319. | LPPRY |
| 1320. | PPRYQ |
| 1321. | PRYQL |
| 1322. | RYQLQ |
| 1323. | YQLQN |
| 1324. | QLQNM |
| 1325. | LQNMD |
| 1326. | QNMDV |
| 1327. | NMDVE |
| 1328. | MDVEA |
| 1329. | DVEAG |
| 1330. | VEAGF |
| 1331. | EAGFR |
| 1332. | AGFRE |
| 1333. | GFREA |
| 1334. | FREAV |
| 1335. | REAVY |
| 1336. | EAVYA |
| 1337. | AVYAS |
| 1338. | VYASF |
| 1339. | YASFV |
| 1340. | ASFVA |
| 1341. | SFVAG |
| 1342. | FVAGM |
| 1343. | VAGMY |
| 1344. | AGMYN |
| 1345. | GMYNY |
| 1346. | MYNYV |
| 1347. | YNYVV |
| 1348. | NYVVT |
| 1349. | YVVTQ |
| 1350. | VVTQP |
| 1351. | VTQPQ |
| 1352. | TQPQE |
| 1353. | QPQER |
| 1354. | PQERI |
| 1355. | QERIP |
| 1356. | ERIPN |
| 1357. | RIPNS |
| 1358. | IPNSQ |
| 1359. | PNSQQ |
| 1360. | NSQQV |
| 1361. | SQQVE |
| 1362. | QQVEG |
| 1363. | QVEGI |
| 1364. | VEGIL |
| 1365. | EGILR |
| 1366. | GILRD |
| 1367. | ILRDM |
| 1368. | LRDML |
| 1369. | RDMLT |
| 1370. | DMLTN |
| 1371. | MLTNG |
| 1372. | LTNGS |
| 1373. | TNGSQ |
| 1374. | NGSQT |
| 1375. | GSQTF |
| 1376. | SQTFR |
| 1377. | QTFRD |
| 1378. | TFRDL |

TABLE 6-continued

| | | |
|---|---|---|
| 1379. | FRDLM | |
| 1380. | RDLMR | |
| 1381. | DLMRR | |
| 1382. | LMRRW | |
| 1383. | MRRWN | |
| 1384. | RRWNR | |
| 1385. | RWNRE | |
| 1386. | WNREV | |
| 1387. | NREVD | |
| 1388. | REVDR | |
| 1389. | EVDRE | |

5-mer peptides of CT147 (hypothetical protein, 1449 amino acids), ACCESSION# NP 219650.1, GI: 15604866 (SEQ ID NOS: 1390-2834)

| | |
|---|---|
| 1390. | MANPS |
| 1391. | ANPST |
| 1392. | NPSTP |
| 1393. | PSTPS |
| 1394. | STPSF |
| 1395. | TPSFN |
| 1396. | PSFNH |
| 1397. | SFNHS |
| 1398. | FNHSD |
| 1399. | NHSDL |
| 1400. | HSDLS |
| 1401. | SDLSL |
| 1402. | DLSLQ |
| 1403. | LSLQG |
| 1404. | SLQGR |
| 1405. | LQGRL |
| 1406. | QGRLR |
| 1407. | GRLRA |
| 1408. | RLRAS |
| 1409. | LRASS |
| 1410. | RASSQ |
| 1411. | ASSQQ |
| 1412. | SSQQC |
| 1413. | SQQCT |
| 1414. | QQCTQ |
| 1415. | QCTQA |
| 1416. | CTQAG |
| 1417. | TQAGQ |
| 1418. | QAGQG |
| 1419. | AGQGD |
| 1420. | GQGDP |
| 1421. | QGDPQ |
| 1422. | GDPQP |
| 1423. | DPQPL |
| 1424. | PQPLS |
| 1425. | QPLSP |
| 1426. | PLSPE |
| 1427. | LSPES |
| 1428. | SPESR |
| 1429. | PESRG |
| 1430. | ESRGL |
| 1431. | SRGLT |
| 1432. | RGLTS |
| 1433. | GLTSN |
| 1434. | LTSNF |
| 1435. | TSNFS |
| 1436. | SNFST |
| 1437. | NFSTR |
| 1438. | FSTRR |
| 1439. | STRRD |
| 1440. | TRRDL |
| 1441. | RRDLI |
| 1442. | RDLID |
| 1443. | DLIDV |
| 1444. | LIDVV |
| 1445. | IDVVE |
| 1446. | DVVEE |
| 1447. | VVEES |
| 1448. | VEESI |
| 1449. | EESIE |
| 1450. | ESIET |
| 1451. | SIETA |
| 1452. | IETAK |
| 1453. | ETAKG |

TABLE 6-continued

| | |
|---|---|
| 1454. | TAKGS |
| 1455. | AKGSE |
| 1456. | KGSEL |
| 1457. | GSELK |
| 1458. | SELKK |
| 1459. | ELKKL |
| 1460. | LKKLR |
| 1461. | KKLRI |
| 1462. | KLRIY |
| 1463. | LRIYE |
| 1464. | RIYEI |
| 1465. | IYEIA |
| 1466. | YEIAL |
| 1467. | EIALK |
| 1468. | IALKI |
| 1469. | ALKIL |
| 1470. | LKILT |
| 1471. | KILTI |
| 1472. | ILTII |
| 1473. | LTIIG |
| 1474. | TIIGA |
| 1475. | IIGAA |
| 1476. | IGAAI |
| 1477. | GAAIL |
| 1478. | AAILF |
| 1479. | AILFA |
| 1480. | ILFAV |
| 1481. | LFAVP |
| 1482. | FAVPL |
| 1483. | AVPLC |
| 1484. | VPLCM |
| 1485. | PLCML |
| 1486. | LCMLL |
| 1487. | CMLLG |
| 1488. | MLLGV |
| 1489. | LLGVP |
| 1490. | LGVPL |
| 1491. | GVPLW |
| 1492. | VPLWI |
| 1493. | PLWIP |
| 1494. | LWIPI |
| 1495. | WIPIV |
| 1496. | IPIVT |
| 1497. | PIVTC |
| 1498. | IVTCI |
| 1499. | VTCIG |
| 1500. | TCIGV |
| 1501. | CIGVG |
| 1502. | IGVGI |
| 1503. | GVGIA |
| 1504. | VGIAF |
| 1505. | GIAFS |
| 1506. | IAFSI |
| 1507. | AFSIA |
| 1508. | FSIAK |
| 1509. | SIAKG |
| 1510. | IAKGC |
| 1511. | AKGCL |
| 1512. | KGCLQ |
| 1513. | GCLQK |
| 1514. | CLQKR |
| 1515. | LQKRC |
| 1516. | QKRCQ |
| 1517. | KRCQQ |
| 1518. | RCQQI |
| 1519. | CQQIR |
| 1520. | QQIRE |
| 1521. | QIREE |
| 1522. | IREEY |
| 1523. | REEYR |
| 1524. | EEYRA |
| 1525. | EYRAL |
| 1526. | YRALH |
| 1527. | RALHL |
| 1528. | ALHLY |
| 1529. | LHLYH |
| 1530. | HLYHR |
| 1531. | LYHRY |
| 1532. | YHRYL |
| 1533. | HRYLL |

TABLE 6-continued

| | |
|---|---|
| 1534. | RYLLS |
| 1535. | YLLSN |
| 1536. | LLSNK |
| 1537. | LSNKD |
| 1538. | SNKDS |
| 1539. | NKDSI |
| 1540. | KDSID |
| 1541. | DSIDG |
| 1542. | SIDGT |
| 1543. | IDGTL |
| 1544. | DGTLL |
| 1545. | GTLLS |
| 1546. | TLLSR |
| 1547. | LLSRF |
| 1548. | LSRFD |
| 1549. | SRFDI |
| 1550. | RFDIR |
| 1551. | FDIRF |
| 1552. | DIRFR |
| 1553. | IRFRK |
| 1554. | RFRKA |
| 1555. | FRKAE |
| 1556. | RKAEE |
| 1557. | KAEEK |
| 1558. | AEEKL |
| 1559. | EEKLH |
| 1560. | EKLHG |
| 1561. | KLHGL |
| 1562. | LHGLD |
| 1563. | HGLDL |
| 1564. | GLDLD |
| 1565. | LDLDK |
| 1566. | DLDKR |
| 1567. | LDKRE |
| 1568. | DKREA |
| 1569. | KREAN |
| 1570. | REANH |
| 1571. | EANHP |
| 1572. | ANHPL |
| 1573. | NHPLE |
| 1574. | HPLEA |
| 1575. | PLEAD |
| 1576. | LEADK |
| 1577. | EADKR |
| 1578. | ADKRY |
| 1579. | DKRYD |
| 1580. | KRYDF |
| 1581. | RYDFA |
| 1582. | YDFAG |
| 1583. | DFAGL |
| 1584. | FAGLA |
| 1585. | AGLAH |
| 1586. | GLAHQ |
| 1587. | LAHQR |
| 1588. | AHQRY |
| 1589. | HQRYQ |
| 1590. | QRYQV |
| 1591. | RYQVD |
| 1592. | YQVDA |
| 1593. | QVDAA |
| 1594. | VDAAL |
| 1595. | DAALG |
| 1596. | AALGI |
| 1597. | ALGIS |
| 1598. | LGISS |
| 1599. | GISSS |
| 1600. | ISSSQ |
| 1601. | SSSQD |
| 1602. | SSQDA |
| 1603. | SQDAF |
| 1604. | QDAFW |
| 1605. | DAFWR |
| 1606. | AFWRG |
| 1607. | FWRGV |
| 1608. | WRGVA |
| 1609. | RGVAQ |
| 1610. | GVAQQ |
| 1611. | VAQQV |
| 1612. | AQQVK |
| 1613. | QQVKS |

TABLE 6-continued

| | |
|---|---|
| 1614. | QVKSV |
| 1615. | VKSVK |
| 1616. | KSVKD |
| 1617. | SVKDD |
| 1618. | VKDDV |
| 1619. | KDDVV |
| 1620. | DDVVL |
| 1621. | DVVLG |
| 1622. | VVLGD |
| 1623. | VLGDK |
| 1624. | LGDKA |
| 1625. | GDKAS |
| 1626. | DKAST |
| 1627. | KASTD |
| 1628. | ASTDL |
| 1629. | STDLY |
| 1630. | TDLYP |
| 1631. | DLYPI |
| 1632. | LYPIA |
| 1633. | YPIAQ |
| 1634. | PIAQQ |
| 1635. | IAQQA |
| 1636. | AQQAL |
| 1637. | QQALQ |
| 1638. | QALQA |
| 1639. | ALQAA |
| 1640. | LQAAG |
| 1641. | QAAGV |
| 1642. | AAGVG |
| 1643. | AGVGF |
| 1644. | GVGFS |
| 1645. | VGFSG |
| 1646. | GFSGA |
| 1647. | FSGAA |
| 1648. | SGAAG |
| 1649. | GAAGK |
| 1650. | AAGKE |
| 1651. | AGKES |
| 1652. | GKESL |
| 1653. | KESLL |
| 1654. | ESLLD |
| 1655. | SLLDL |
| 1656. | LLDLA |
| 1657. | LDLAK |
| 1658. | DLAKS |
| 1659. | LAKSL |
| 1660. | AKSLS |
| 1661. | KSLSS |
| 1662. | SLSSL |
| 1663. | LSSLF |
| 1664. | SSLFA |
| 1665. | SLFAW |
| 1666. | LFAWG |
| 1667. | FAWGS |
| 1668. | AWGSQ |
| 1669. | WGSQV |
| 1670. | GSQVG |
| 1671. | SQVGK |
| 1672. | QVGKD |
| 1673. | VGKDS |
| 1674. | GKDSH |
| 1675. | KDSHE |
| 1676. | DSHEA |
| 1677. | SHEAL |
| 1678. | HEALQ |
| 1679. | EALQQ |
| 1680. | ALQQY |
| 1681. | LQQYQ |
| 1682. | QQYQM |
| 1683. | QYQMR |
| 1684. | YQMRF |
| 1685. | QMRFL |
| 1686. | MRFLS |
| 1687. | RFLSS |
| 1688. | FLSSP |
| 1689. | LSSPI |
| 1690. | SSPIL |
| 1691. | SPILA |
| 1692. | PILAT |
| 1693. | ILATW |

TABLE 6-continued

| | |
|---|---|
| 1694. | LATWC |
| 1695. | ATWCG |
| 1696. | TWCGA |
| 1697. | WCGAG |
| 1698. | CGAGF |
| 1699. | GAGFS |
| 1700. | AGFSA |
| 1701. | GFSAS |
| 1702. | FSASA |
| 1703. | SASAQ |
| 1704. | ASAQD |
| 1705. | SAQDF |
| 1706. | AQDFV |
| 1707. | QDFVL |
| 1708. | DFVLK |
| 1709. | FVLKG |
| 1710. | VLKGE |
| 1711. | LKGEN |
| 1712. | KGENI |
| 1713. | GENIL |
| 1714. | ENILD |
| 1715. | NILDI |
| 1716. | ILDIA |
| 1717. | LDIAS |
| 1718. | DIASE |
| 1719. | IASEN |
| 1720. | ASENH |
| 1721. | SENHT |
| 1722. | ENHTK |
| 1723. | NHTKM |
| 1724. | HTKMQ |
| 1725. | TKMQN |
| 1726. | KMQNA |
| 1727. | MQNAI |
| 1728. | QNAIK |
| 1729. | NAIKR |
| 1730. | AIKRV |
| 1731. | IKRVQ |
| 1732. | KRVQL |
| 1733. | RVQLV |
| 1734. | VQLVS |
| 1735. | QLVSV |
| 1736. | LVSVL |
| 1737. | VSVLG |
| 1738. | SVLGK |
| 1739. | VLGKM |
| 1740. | LGKMR |
| 1741. | GKMRN |
| 1742. | KMRNW |
| 1743. | MRNWK |
| 1744. | RNWKE |
| 1745. | NWKEK |
| 1746. | WKEKI |
| 1747. | KEKID |
| 1748. | EKIDT |
| 1749. | KIDTL |
| 1750. | IDTLI |
| 1751. | DTLIQ |
| 1752. | TLIQN |
| 1753. | LIQNK |
| 1754. | IQNKN |
| 1755. | QNKNL |
| 1756. | NKNLD |
| 1757. | KNLDQ |
| 1758. | NLDQD |
| 1759. | LDQDS |
| 1760. | DQDSL |
| 1761. | QDSLR |
| 1762. | DSLRK |
| 1763. | SLRKL |
| 1764. | LRKLY |
| 1765. | RKLYQ |
| 1766. | KLYQD |
| 1767. | LYQDI |
| 1768. | YQDIE |
| 1769. | QDIEK |
| 1770. | DIEKA |
| 1771. | IEKAM |
| 1772. | EKAMH |
| 1773. | KAMHK |
| 1774. | AMHKV |
| 1775. | MHKVC |
| 1776. | HKVCI |
| 1777. | KVCIE |
| 1778. | VCIED |
| 1779. | CIEDG |
| 1780. | IEDGV |
| 1781. | EDGVS |
| 1782. | DGVST |
| 1783. | GVSTS |
| 1784. | VSTSI |
| 1785. | STSIQ |
| 1786. | TSIQT |
| 1787. | SIQTQ |
| 1788. | IQTQV |
| 1789. | QTQVR |
| 1790. | TQVRK |
| 1791. | QVRKV |
| 1792. | VRKVT |
| 1793. | RKVTQ |
| 1794. | KVTQK |
| 1795. | VTQKY |
| 1796. | TQKYL |
| 1797. | QKYLR |
| 1798. | KYLRQ |
| 1799. | YLRQD |
| 1800. | LRQDL |
| 1801. | RQDLQ |
| 1802. | QDLQE |
| 1803. | DLQEL |
| 1804. | LQELL |
| 1805. | QELLN |
| 1806. | ELLNK |
| 1807. | LLNKK |
| 1808. | LNKKA |
| 1809. | NKKAP |
| 1810. | KKAPL |
| 1811. | KAPLN |
| 1812. | APLNE |
| 1813. | PLNES |
| 1814. | LNESD |
| 1815. | NESDL |
| 1816. | ESDLS |
| 1817. | SDLSK |
| 1818. | DLSKM |
| 1819. | LSKMQ |
| 1820. | SKMQK |
| 1821. | KMQKG |
| 1822. | MQKGI |
| 1823. | QKGIS |
| 1824. | KGISS |
| 1825. | GISSC |
| 1826. | ISSCA |
| 1827. | SSCAN |
| 1828. | SCANL |
| 1829. | CANLV |
| 1830. | ANLVV |
| 1831. | NLVVT |
| 1832. | LVVTL |
| 1833. | VVTLL |
| 1834. | VTLLE |
| 1835. | TLLES |
| 1836. | LLESQ |
| 1837. | LESQL |
| 1838. | ESQLG |
| 1839. | SQLGT |
| 1840. | QLGTS |
| 1841. | LGTSG |
| 1842. | GTSGQ |
| 1843. | TSGQT |
| 1844. | SGQTP |
| 1845. | GQTPI |
| 1846. | QTPIK |
| 1847. | TPIKE |
| 1848. | PIKEV |
| 1849. | IKEVE |
| 1850. | KEVEE |
| 1851. | EVEES |
| 1852. | VEESI |
| 1853. | EESIY |

TABLE 6-continued

| | | |
|---|---|---|
| 1854. | ESIYR | |
| 1855. | SIYRD | |
| 1856. | IYRDL | |
| 1857. | YRDLI | |
| 1858. | RDLIA | |
| 1859. | DLIAT | |
| 1860. | LIATI | |
| 1861. | IATIL | |
| 1862. | ATILQ | |
| 1863. | TILQM | |
| 1864. | ILQMG | |
| 1865. | LQMGS | |
| 1866. | QMGSA | |
| 1867. | MGSAA | |
| 1868. | GSAAG | |
| 1869. | SAAGG | |
| 1870. | AAGGV | |
| 1871. | AGGVT | |
| 1872. | GGVTP | |
| 1873. | GVTPL | |
| 1874. | VTPLV | |
| 1875. | TPLVD | |
| 1876. | PLVDG | |
| 1877. | LVDGV | |
| 1878. | VDGVH | |
| 1879. | DGVHK | |
| 1880. | GVHKA | |
| 1881. | VHKAI | |
| 1882. | HKAIR | |
| 1883. | KAIRE | |
| 1884. | AIREG | |
| 1885. | IREGK | |
| 1886. | REGKA | |
| 1887. | EGKAL | |
| 1888. | GKALR | |
| 1889. | KALRS | |
| 1890. | ALRSE | |
| 1891. | LRSEL | |
| 1892. | RSELS | |
| 1893. | SELSR | |
| 1894. | ELSRA | |
| 1895. | LSRAM | |
| 1896. | SRAMS | |
| 1897. | RAMSL | |
| 1898. | AMSLH | |
| 1899. | MSLHP | |
| 1900. | SLHPR | |
| 1901. | LHPRQ | |
| 1902. | HPRQS | |
| 1903. | PRQSF | |
| 1904. | RQSFL | |
| 1905. | QSFLG | |
| 1906. | SFLGV | |
| 1907. | FLGVQ | |
| 1908. | LGVQS | |
| 1909. | GVQSA | |
| 1910. | VQSAV | |
| 1911. | QSAVE | |
| 1912. | SAVEK | |
| 1913. | AVEKL | |
| 1914. | VEKLQ | |
| 1915. | EKLQA | |
| 1916. | KLQAF | |
| 1917. | LQAFI | |
| 1918. | QAFIR | |
| 1919. | AFIRD | |
| 1920. | FIRDP | |
| 1921. | IRDPK | |
| 1922. | RDPKW | |
| 1923. | DPKWG | |
| 1924. | PKWGA | |
| 1925. | KWGAS | |
| 1926. | WGASA | |
| 1927. | GASAV | |
| 1928. | ASAVH | |
| 1929. | SAVHT | |
| 1930. | AVHTS | |
| 1931. | VHTSA | |
| 1932. | HTSAE | |
| 1933. | TSAEE | |

TABLE 6-continued

| | | |
|---|---|---|
| 1934. | SAEET | |
| 1935. | AEETL | |
| 1936. | EETLA | |
| 1937. | ETLAQ | |
| 1938. | TLAQK | |
| 1939. | LAQKQ | |
| 1940. | AQKQK | |
| 1941. | QKQKF | |
| 1942. | KQKFV | |
| 1943. | QKFVS | |
| 1944. | KFVSD | |
| 1945. | FVSDL | |
| 1946. | VSDLT | |
| 1947. | SDLTR | |
| 1948. | DLTRI | |
| 1949. | LTRIQ | |
| 1950. | TRIQT | |
| 1951. | RIQTS | |
| 1952. | IQTSL | |
| 1953. | QTSLA | |
| 1954. | TSLAD | |
| 1955. | SLADW | |
| 1956. | LADWR | |
| 1957. | ADWRE | |
| 1958. | DWRER | |
| 1959. | WRERY | |
| 1960. | RERYG | |
| 1961. | ERYGL | |
| 1962. | RYGLF | |
| 1963. | YGLFE | |
| 1964. | GLFEE | |
| 1965. | LFEET | |
| 1966. | FEETK | |
| 1967. | EETKL | |
| 1968. | ETKLN | |
| 1969. | TKLNH | |
| 1970. | KLNHI | |
| 1971. | LNHIV | |
| 1972. | NHIVS | |
| 1973. | HIVST | |
| 1974. | IVSTD | |
| 1975. | VSTDF | |
| 1976. | STDFV | |
| 1977. | TDFVS | |
| 1978. | DFVSR | |
| 1979. | FVSRT | |
| 1980. | VSRTE | |
| 1981. | SRTEA | |
| 1982. | RTEAF | |
| 1983. | TEAFL | |
| 1984. | EAFLD | |
| 1985. | AFLDT | |
| 1986. | FLDTL | |
| 1987. | LDTLK | |
| 1988. | DTLKN | |
| 1989. | TLKNV | |
| 1990. | LKNVA | |
| 1991. | KNVAE | |
| 1992. | NVAEA | |
| 1993. | VAEAC | |
| 1994. | AEACS | |
| 1995. | EACSL | |
| 1996. | ACSLE | |
| 1997. | CSLEQ | |
| 1998. | SLEQA | |
| 1999. | LEQAV | |
| 2000. | EQAVA | |
| 2001. | QAVAE | |
| 2002. | AVAEL | |
| 2003. | VAELK | |
| 2004. | AELKD | |
| 2005. | ELKDC | |
| 2006. | LKDCE | |
| 2007. | KDCED | |
| 2008. | DCEDA | |
| 2009. | CEDAM | |
| 2010. | EDAMK | |
| 2011. | DAMKA | |
| 2012. | AMKAD | |
| 2013. | MKADL | |

TABLE 6-continued

| | |
|---|---|
| 2014. | KADLT |
| 2015. | ADLTH |
| 2016. | DLTHV |
| 2017. | LTHVE |
| 2018. | THVEQ |
| 2019. | HVEQK |
| 2020. | VEQKM |
| 2021. | EQKMN |
| 2022. | QKMNP |
| 2023. | KMNPT |
| 2024. | MNPTE |
| 2025. | NPTEI |
| 2026. | PTEIE |
| 2027. | TEIES |
| 2028. | EIESA |
| 2029. | IESAR |
| 2030. | ESARE |
| 2031. | SAREE |
| 2032. | AREEF |
| 2033. | REEFK |
| 2034. | EEFKR |
| 2035. | EFKRL |
| 2036. | FKRLM |
| 2037. | KRLME |
| 2038. | RLMEE |
| 2039. | LMEEL |
| 2040. | MEELA |
| 2041. | EELAG |
| 2042. | ELAGI |
| 2043. | LAGIQ |
| 2044. | AGIQE |
| 2045. | GIQEQ |
| 2046. | IQEQL |
| 2047. | QEQLE |
| 2048. | EQLEQ |
| 2049. | QLEQI |
| 2050. | LEQIA |
| 2051. | EQIAQ |
| 2052. | QIAQP |
| 2053. | IAQPI |
| 2054. | AQPIY |
| 2055. | QPIYE |
| 2056. | PIYEE |
| 2057. | IYEEG |
| 2058. | YEEGV |
| 2059. | EEGVS |
| 2060. | EGVSG |
| 2061. | GVSGE |
| 2062. | VSGER |
| 2063. | SGERL |
| 2064. | GERLL |
| 2065. | ERLLL |
| 2066. | RLLLN |
| 2067. | LLLNT |
| 2068. | LLNTV |
| 2069. | LNTVF |
| 2070. | NTVFF |
| 2071. | TVFFH |
| 2072. | VFFHP |
| 2073. | FFHPE |
| 2074. | FHPEV |
| 2075. | HPEVL |
| 2076. | PEVLR |
| 2077. | EVLRK |
| 2078. | VLRKK |
| 2079. | LRKKV |
| 2080. | RKKVQ |
| 2081. | KKVQA |
| 2082. | KVQAK |
| 2083. | VQAKE |
| 2084. | QAKEA |
| 2085. | AKEAS |
| 2086. | KEASL |
| 2087. | EASLE |
| 2088. | ASLEA |
| 2089. | SLEAL |
| 2090. | LEALT |
| 2091. | EALTK |
| 2092. | ALTKG |
| 2093. | LTKGE |
| 2094. | TKGEQ |
| 2095. | KGEQP |
| 2096. | GEQPS |
| 2097. | EQPSP |
| 2098. | QPSPT |
| 2099. | PSPTK |
| 2100. | SPTKK |
| 2101. | PTKKK |
| 2102. | TKKKT |
| 2103. | KKKTL |
| 2104. | KKTLK |
| 2105. | KTLKQ |
| 2106. | TLKQL |
| 2107. | LKQLS |
| 2108. | KQLSE |
| 2109. | QLSEG |
| 2110. | LSEGC |
| 2111. | SEGCE |
| 2112. | EGCEY |
| 2113. | GCEYF |
| 2114. | CEYFS |
| 2115. | EYFSS |
| 2116. | YFSSL |
| 2117. | FSSLV |
| 2118. | SSLVS |
| 2119. | SLVSK |
| 2120. | LVSKI |
| 2121. | VSKIN |
| 2122. | SKINA |
| 2123. | KINAL |
| 2124. | INALK |
| 2125. | NALKT |
| 2126. | ALKTI |
| 2127. | LKTIL |
| 2128. | KTILE |
| 2129. | TILEG |
| 2130. | ILEGS |
| 2131. | LEGSR |
| 2132. | EGSRG |
| 2133. | GSRGK |
| 2134. | SRGKK |
| 2135. | RGKKI |
| 2136. | GKKIA |
| 2137. | KKIAS |
| 2138. | KIASQ |
| 2139. | IASQD |
| 2140. | ASQDI |
| 2141. | SQDIR |
| 2142. | QDIRQ |
| 2143. | DIRQL |
| 2144. | IRQLI |
| 2145. | RQLIG |
| 2146. | QLIGL |
| 2147. | LIGLT |
| 2148. | IGLTD |
| 2149. | GLTDE |
| 2150. | LTDEL |
| 2151. | TDELA |
| 2152. | DELAL |
| 2153. | ELALE |
| 2154. | LALEL |
| 2155. | ALELS |
| 2156. | LELSS |
| 2157. | ELSSF |
| 2158. | LSSFQ |
| 2159. | SSFQQ |
| 2160. | SFQQD |
| 2161. | FQQDS |
| 2162. | QQDSL |
| 2163. | QDSLE |
| 2164. | DSLES |
| 2165. | SLESL |
| 2166. | LESLL |
| 2167. | ESLLY |
| 2168. | SLLYG |
| 2169. | LLYGL |
| 2170. | LYGLE |
| 2171. | YGLEG |
| 2172. | GLEGL |
| 2173. | LEGLS |

TABLE 6-continued

| | |
|---|---|
| 2174. | EGLSI |
| 2175. | GLSIP |
| 2176. | LSIPA |
| 2177. | SIPAA |
| 2178. | IPAAS |
| 2179. | PAASI |
| 2180. | AASIE |
| 2181. | ASIEQ |
| 2182. | SIEQK |
| 2183. | IEQKK |
| 2184. | EQKKG |
| 2185. | QKKGS |
| 2186. | KKGSP |
| 2187. | KGSPK |
| 2188. | GSPKS |
| 2189. | SPKSS |
| 2190. | PKSSS |
| 2191. | KSSSI |
| 2192. | SSSIA |
| 2193. | SSIAE |
| 2194. | SIAEK |
| 2195. | IAEKV |
| 2196. | AEKVV |
| 2197. | EKVVY |
| 2198. | KVVYA |
| 2199. | VVYAS |
| 2200. | VYASH |
| 2201. | YASHQ |
| 2202. | ASHQR |
| 2203. | SHQRV |
| 2204. | HQRVH |
| 2205. | QRVHN |
| 2206. | RVHNG |
| 2207. | VHNGV |
| 2208. | HNGVK |
| 2209. | NGVKA |
| 2210. | GVKAK |
| 2211. | VKAKV |
| 2212. | KAKVN |
| 2213. | AKVNR |
| 2214. | KVNRT |
| 2215. | VNRTL |
| 2216. | NRTLE |
| 2217. | RTLEA |
| 2218. | TLEAF |
| 2219. | LEAFS |
| 2220. | EAFSQ |
| 2221. | AFSQL |
| 2222. | FSQLI |
| 2223. | SQLIK |
| 2224. | QLIKG |
| 2225. | LIKGL |
| 2226. | IKGLR |
| 2227. | KGLRG |
| 2228. | GLRGS |
| 2229. | LRGSL |
| 2230. | RGSLR |
| 2231. | GSLRN |
| 2232. | SLRNA |
| 2233. | LRNAM |
| 2234. | RNAMI |
| 2235. | NAMIT |
| 2236. | AMITK |
| 2237. | MITKA |
| 2238. | ITKAV |
| 2239. | TKAVV |
| 2240. | KAVVA |
| 2241. | AVVAA |
| 2242. | VVAAV |
| 2243. | VAAVL |
| 2244. | AAVLS |
| 2245. | AVLSV |
| 2246. | VLSVA |
| 2247. | LSVAF |
| 2248. | SVAFS |
| 2249. | VAFSC |
| 2250. | AFSCL |
| 2251. | FSCLA |
| 2252. | SCLAI |
| 2253. | CLAIA |

TABLE 6-continued

| | |
|---|---|
| 2254. | LAIAL |
| 2255. | AIALF |
| 2256. | IALFS |
| 2257. | ALFSV |
| 2258. | LFSVQ |
| 2259. | FSVQL |
| 2260. | SVQLT |
| 2261. | VQLTW |
| 2262. | QLTWL |
| 2263. | LTWLP |
| 2264. | TWLPI |
| 2265. | WLPIM |
| 2266. | LPIML |
| 2267. | PIMLC |
| 2268. | IMLCV |
| 2269. | MLCVL |
| 2270. | LCVLA |
| 2271. | CVLAL |
| 2272. | VLALV |
| 2273. | LALVL |
| 2274. | ALVLE |
| 2275. | LVLEA |
| 2276. | VLEAI |
| 2277. | LEAIP |
| 2278. | EAIPS |
| 2279. | AIPSA |
| 2280. | IPSAL |
| 2281. | PSALS |
| 2282. | SALSI |
| 2283. | ALSIW |
| 2284. | LSIWV |
| 2285. | SIWVE |
| 2286. | IWVEK |
| 2287. | WVEKR |
| 2288. | VEKRN |
| 2289. | EKRNW |
| 2290. | KRNWK |
| 2291. | RNWKY |
| 2292. | NWKYE |
| 2293. | WKYEV |
| 2294. | KYEVA |
| 2295. | YEVAS |
| 2296. | EVASL |
| 2297. | VASLA |
| 2298. | ASLAK |
| 2299. | SLAKQ |
| 2300. | LAKQL |
| 2301. | AKQLV |
| 2302. | KQLVS |
| 2303. | QLVSD |
| 2304. | LVSDG |
| 2305. | VSDGR |
| 2306. | SDGRK |
| 2307. | DGRKL |
| 2308. | GRKLP |
| 2309. | RKLPY |
| 2310. | KLPYP |
| 2311. | LPYPD |
| 2312. | PYPDL |
| 2313. | YPDLG |
| 2314. | PDLGD |
| 2315. | DLGDQ |
| 2316. | LGDQN |
| 2317. | GDQNI |
| 2318. | DQNIK |
| 2319. | QNIKH |
| 2320. | NIKHL |
| 2321. | IKHLE |
| 2322. | KHLEK |
| 2323. | HLEKI |
| 2324. | LEKIR |
| 2325. | EKIRD |
| 2326. | KIRDV |
| 2327. | IRDVY |
| 2328. | RDVYG |
| 2329. | DVYGL |
| 2330. | VYGLD |
| 2331. | YGLDG |
| 2332. | GLDGV |
| 2333. | LDGVA |

TABLE 6-continued

| | |
|---|---|
| 2334. | DGVAE |
| 2335. | GVAEL |
| 2336. | VAELR |
| 2337. | AELRV |
| 2338. | ELRVA |
| 2339. | LRVAE |
| 2340. | RVAEA |
| 2341. | VAEAA |
| 2342. | AEAAL |
| 2343. | EAALL |
| 2344. | AALLG |
| 2345. | ALLGV |
| 2346. | LLGVQ |
| 2347. | LGVQK |
| 2348. | GVQKL |
| 2349. | VQKLP |
| 2350. | QKLPE |
| 2351. | KLPEE |
| 2352. | LPEEQ |
| 2353. | PEEQK |
| 2354. | EEQKQ |
| 2355. | EQKQE |
| 2356. | QKQES |
| 2357. | KQESL |
| 2358. | QESLK |
| 2359. | ESLKS |
| 2360. | SLKSA |
| 2361. | LKSAV |
| 2362. | KSAVK |
| 2363. | SAVKA |
| 2364. | AVKAL |
| 2365. | VKALR |
| 2366. | KALRA |
| 2367. | ALRAD |
| 2368. | LRADA |
| 2369. | RADAK |
| 2370. | ADAKV |
| 2371. | DAKVL |
| 2372. | AKVLN |
| 2373. | KVLNK |
| 2374. | VLNKK |
| 2375. | LNKKF |
| 2376. | NKKFK |
| 2377. | KKFKK |
| 2378. | KFKKL |
| 2379. | FKKLP |
| 2380. | KKLPE |
| 2381. | KLPES |
| 2382. | LPESY |
| 2383. | PESYQ |
| 2384. | ESYQP |
| 2385. | SYQPQ |
| 2386. | YQPQH |
| 2387. | QPQHS |
| 2388. | PQHSE |
| 2389. | QHSEV |
| 2390. | HSEVT |
| 2391. | SEVTG |
| 2392. | EVTGV |
| 2393. | VTGVQ |
| 2394. | TGVQG |
| 2395. | GVQGV |
| 2396. | VQGVT |
| 2397. | QGVTE |
| 2398. | GVTEQ |
| 2399. | VTEQE |
| 2400. | TEQES |
| 2401. | EQESR |
| 2402. | QESRD |
| 2403. | ESRDD |
| 2404. | SRDDV |
| 2405. | RDDVL |
| 2406. | DDVLV |
| 2407. | DVLVA |
| 2408. | VLVAQ |
| 2409. | LVAQD |
| 2410. | VAQDM |
| 2411. | AQDMA |
| 2412. | QDMAA |
| 2413. | DMAAI |

TABLE 6-continued

| | |
|---|---|
| 2414. | MAAIE |
| 2415. | AAIEE |
| 2416. | AIEEL |
| 2417. | IEELQ |
| 2418. | EELQD |
| 2419. | ELQDQ |
| 2420. | LQDQY |
| 2421. | QDQYH |
| 2422. | DQYHA |
| 2423. | QYHAA |
| 2424. | YHAAC |
| 2425. | HAACL |
| 2426. | AACLQ |
| 2427. | ACLQF |
| 2428. | CLQFE |
| 2429. | LQFES |
| 2430. | QFESV |
| 2431. | FESVS |
| 2432. | ESVST |
| 2433. | SVSTR |
| 2434. | VSTRF |
| 2435. | STRFL |
| 2436. | TRFLA |
| 2437. | RFLAE |
| 2438. | FLAEQ |
| 2439. | LAEQR |
| 2440. | AEQRK |
| 2441. | EQRKA |
| 2442. | QRKAK |
| 2443. | RKAKF |
| 2444. | KAKFL |
| 2445. | AKFLE |
| 2446. | KFLEE |
| 2447. | FLEEL |
| 2448. | LEELL |
| 2449. | EELLV |
| 2450. | ELLVQ |
| 2451. | LLVQK |
| 2452. | LVQKR |
| 2453. | VQKRR |
| 2454. | QKRRD |
| 2455. | KRRDV |
| 2456. | RRDVS |
| 2457. | RDVSH |
| 2458. | DVSHL |
| 2459. | VSHLS |
| 2460. | SHLSH |
| 2461. | HLSHQ |
| 2462. | LSHQE |
| 2463. | SHQEA |
| 2464. | HQEAH |
| 2465. | QEAHY |
| 2466. | EAHYT |
| 2467. | AHYTQ |
| 2468. | HYTQV |
| 2469. | YTQVV |
| 2470. | TQVVS |
| 2471. | QVVSH |
| 2472. | VVSHL |
| 2473. | VSHLK |
| 2474. | SHLKE |
| 2475. | HLKEL |
| 2476. | LKELI |
| 2477. | KELIS |
| 2478. | ELISM |
| 2479. | LISMR |
| 2480. | ISMRK |
| 2481. | SMRKG |
| 2482. | MRKGA |
| 2483. | RKGAS |
| 2484. | KGAST |
| 2485. | GASTQ |
| 2486. | ASTQH |
| 2487. | STQHA |
| 2488. | TQHAS |
| 2489. | QHASK |
| 2490. | HASKE |
| 2491. | ASKEE |
| 2492. | SKEET |
| 2493. | KEEIS |

TABLE 6-continued

| | |
|---|---|
| 2494. | EEIST |
| 2495. | EISTK |
| 2496. | ISTKM |
| 2497. | STKMR |
| 2498. | TKMRE |
| 2499. | KMREL |
| 2500. | MRELL |
| 2501. | RELLS |
| 2502. | ELLSL |
| 2503. | LLSLD |
| 2504. | LSLDD |
| 2505. | SLDDQ |
| 2506. | LDDQL |
| 2507. | DDQLL |
| 2508. | DQLLK |
| 2509. | QLLKA |
| 2510. | LLKAH |
| 2511. | LKAHT |
| 2512. | KAHTA |
| 2513. | AHTAQ |
| 2514. | HTAQD |
| 2515. | TAQDV |
| 2516. | AQDVN |
| 2517. | QDVNR |
| 2518. | DVNRD |
| 2519. | VNRDN |
| 2520. | NRDNS |
| 2521. | RDNSI |
| 2522. | DNSIN |
| 2523. | NSING |
| 2524. | SINGQ |
| 2525. | INGQL |
| 2526. | NGQLQ |
| 2527. | GQLQQ |
| 2528. | QLQQQ |
| 2529. | LQQQF |
| 2530. | QQQFK |
| 2531. | QQFKK |
| 2532. | QFKKL |
| 2533. | FKKLS |
| 2534. | KKLSE |
| 2535. | KLSEE |
| 2536. | LSEEG |
| 2537. | SEEGS |
| 2538. | EEGSL |
| 2539. | EGSLQ |
| 2540. | GSLQK |
| 2541. | SLQKV |
| 2542. | LQKVK |
| 2543. | QKVKA |
| 2544. | KVKAL |
| 2545. | VKALL |
| 2546. | KALLE |
| 2547. | ALLEL |
| 2548. | LLELN |
| 2549. | LELNM |
| 2550. | ELNMC |
| 2551. | LNMCL |
| 2552. | NMCLG |
| 2553. | MCLGN |
| 2554. | CLGNA |
| 2555. | LGNAG |
| 2556. | GNAGQ |
| 2557. | NAGQT |
| 2558. | AGQTL |
| 2559. | GQTLY |
| 2560. | QTLYH |
| 2561. | TLYHS |
| 2562. | LYHSR |
| 2563. | YHSRL |
| 2564. | HSRLK |
| 2565. | SRLKR |
| 2566. | RLKRE |
| 2567. | LKREV |
| 2568. | KREVF |
| 2569. | REVFE |
| 2570. | EVFEA |
| 2571. | VFEAS |
| 2572. | FEASL |
| 2573. | EASLS |
| 2574. | ASLSG |
| 2575. | SLSGT |
| 2576. | LSGTS |
| 2577. | SGTSR |
| 2578. | GTSRQ |
| 2579. | TSRQL |
| 2580. | SRQLL |
| 2581. | RQLLQ |
| 2582. | QLLQY |
| 2583. | LLQYG |
| 2584. | LQYGE |
| 2585. | QYGED |
| 2586. | YGEDL |
| 2587. | GEDLF |
| 2588. | EDLFA |
| 2589. | DLFAS |
| 2590. | LFASY |
| 2591. | FASYD |
| 2592. | ASYDG |
| 2593. | SYDGS |
| 2594. | YDGSD |
| 2595. | DGSDR |
| 2596. | GSDRS |
| 2597. | SDRSA |
| 2598. | DRSAL |
| 2599. | RSALL |
| 2600. | SALLR |
| 2601. | ALLRF |
| 2602. | LLRFV |
| 2603. | LRFVL |
| 2604. | RFVLG |
| 2605. | FVLGS |
| 2606. | VLGSG |
| 2607. | LGSGY |
| 2608. | GSGYE |
| 2609. | SGYEM |
| 2610. | GYEMI |
| 2611. | YEMIS |
| 2612. | EMISE |
| 2613. | MISEA |
| 2614. | ISEAS |
| 2615. | SEASS |
| 2616. | EASSE |
| 2617. | ASSEL |
| 2618. | SSELK |
| 2619. | SELKS |
| 2620. | ELKSL |
| 2621. | LKSLR |
| 2622. | KSLRK |
| 2623. | SLRKR |
| 2624. | LRKRW |
| 2625. | RKRWK |
| 2626. | KRWKR |
| 2627. | RWKRS |
| 2628. | WKRSA |
| 2629. | KRSAS |
| 2630. | RSASQ |
| 2631. | SASQA |
| 2632. | ASQAA |
| 2633. | SQAAI |
| 2634. | QAAIA |
| 2635. | AAIAP |
| 2636. | AIAPE |
| 2637. | IAPED |
| 2638. | APEDY |
| 2639. | PEDYE |
| 2640. | EDYEK |
| 2641. | DYEKV |
| 2642. | YEKVC |
| 2643. | EKVCR |
| 2644. | KVCRV |
| 2645. | VCRVL |
| 2646. | CRVLE |
| 2647. | RVLER |
| 2648. | VLERF |
| 2649. | LERFL |
| 2650. | ERFLK |
| 2651. | RFLKA |
| 2652. | FLKAR |
| 2653. | LKARD |

TABLE 6-continued

| | |
|---|---|
| 2654. | KARDS |
| 2655. | ARDSL |
| 2656. | RDSLR |
| 2657. | DSLRP |
| 2658. | SLRPK |
| 2659. | LRPKL |
| 2660. | RPKLG |
| 2661. | PKLGL |
| 2662. | KLGLP |
| 2663. | LGLPL |
| 2664. | GLPLG |
| 2665. | LPLGK |
| 2666. | PLGKS |
| 2667. | LGKSS |
| 2668. | GKSSD |
| 2669. | KSSDA |
| 2670. | SSDAT |
| 2671. | SDATV |
| 2672. | DATVG |
| 2673. | ATVGL |
| 2674. | TVGLQ |
| 2675. | VGLQH |
| 2676. | GLQHQ |
| 2677. | LQHQI |
| 2678. | QHQIR |
| 2679. | HQIRD |
| 2680. | QIRDN |
| 2681. | IRDNQ |
| 2682. | RDNQR |
| 2683. | DNQRV |
| 2684. | NQRVK |
| 2685. | QRVKA |
| 2686. | RVKAR |
| 2687. | VKARV |
| 2688. | KARVT |
| 2689. | ARVTA |
| 2690. | RVTAC |
| 2691. | VTACY |
| 2692. | TACYQ |
| 2693. | ACYQE |
| 2694. | CYQES |
| 2695. | YQESC |
| 2696. | QESCR |
| 2697. | ESCRN |
| 2698. | SCRNV |
| 2699. | CRNVL |
| 2700. | RNVLQ |
| 2701. | NVLQH |
| 2702. | VLQHL |
| 2703. | LQHLE |
| 2704. | QHLED |
| 2705. | HLEDW |
| 2706. | LEDWV |
| 2707. | EDWVR |
| 2708. | DWVRK |
| 2709. | WVRKT |
| 2710. | VRKTR |
| 2711. | RKTRQ |
| 2712. | KTRQE |
| 2713. | TRQES |
| 2714. | RQESA |
| 2715. | QESAE |
| 2716. | ESAEC |
| 2717. | SAECQ |
| 2718. | AECQK |
| 2719. | ECQKV |
| 2720. | CQKVE |
| 2721. | QKVET |
| 2722. | KVETK |
| 2723. | VETKI |
| 2724. | ETKIR |
| 2725. | TKIRE |
| 2726. | KIREF |
| 2727. | IREFC |
| 2728. | REFCQ |
| 2729. | EFCQK |
| 2730. | FCQKA |
| 2731. | CQKAG |
| 2732. | QKAGS |
| 2733. | KAGSK |
| 2734. | AGSKE |
| 2735. | GSKEN |
| 2736. | SKENL |
| 2737. | KENLA |
| 2738. | ENLAE |
| 2739. | NLAES |
| 2740. | LAEST |
| 2741. | AESTE |
| 2742. | ESTEM |
| 2743. | STEML |
| 2744. | TEMLF |
| 2745. | EMLFS |
| 2746. | MLFSS |
| 2747. | LFSSL |
| 2748. | FSSLE |
| 2749. | SSLEE |
| 2750. | SLEED |
| 2751. | LEEDL |
| 2752. | EEDLN |
| 2753. | EDLNK |
| 2754. | DLNKI |
| 2755. | LNKIP |
| 2756. | NKIPL |
| 2757. | KIPLD |
| 2758. | IPLDV |
| 2759. | PLDVL |
| 2760. | LDVLR |
| 2761. | DVLRA |
| 2762. | VLRAI |
| 2763. | LRAIL |
| 2764. | RAILR |
| 2765. | AILRS |
| 2766. | ILRSL |
| 2767. | LRSLS |
| 2768. | RSLSS |
| 2769. | SLSSK |
| 2770. | LSSKV |
| 2771. | SSKVL |
| 2772. | SKVLH |
| 2773. | KVLHI |
| 2774. | VLHIR |
| 2775. | LHIRD |
| 2776. | HIRDQ |
| 2777. | IRDQK |
| 2778. | RDQKL |
| 2779. | DQKLE |
| 2780. | QKLEL |
| 2781. | KLELE |
| 2782. | LELEK |
| 2783. | ELEKL |
| 2784. | LEKLE |
| 2785. | EKLEE |
| 2786. | KLEEQ |
| 2787. | LEEQF |
| 2788. | EEQFA |
| 2789. | EQFAK |
| 2790. | QFAKT |
| 2791. | FAKTN |
| 2792. | AKTNA |
| 2793. | KTNAI |
| 2794. | TNAIV |
| 2795. | NAIVK |
| 2796. | AIVKA |
| 2797. | IVKAK |
| 2798. | VKAKE |
| 2799. | KAKEA |
| 2800. | AKEAE |
| 2801. | KEAEF |
| 2802. | EAEFE |
| 2803. | AEFEK |
| 2804. | EFEKN |
| 2805. | FEKNG |
| 2806. | EKNGE |
| 2807. | KNGEV |
| 2808. | NGEVW |
| 2809. | GEVWH |
| 2810. | EVWHN |
| 2811. | VWHNQ |
| 2812. | WHNQY |
| 2813. | HNQYQ |

TABLE 6-continued

| | |
|---|---|
| 2814. | NQYQM |
| 2815. | QYQML |
| 2816. | YQMLK |
| 2817. | QMLKS |
| 2818. | MLKSQ |
| 2819. | LKSQM |
| 2820. | KSQME |
| 2821. | SQMEK |
| 2822. | QMEKL |
| 2823. | MEKLE |
| 2824. | EKLES |
| 2825. | KLESQ |
| 2826. | LESQK |
| 2827. | ESQKR |
| 2828. | SQKRR |
| 2829. | QKRRL |
| 2830. | KRRLT |
| 2831. | RRLTD |
| 2832. | RLTDK |
| 2833. | LTDKK |
| 2834. | TDKKE |

5-mer peptides of HSP60 (CT110, 544 amino acids), ACCESSION# AAS19616.1, GI: 42541742 (SEQ ID NOS: 2835-3374)

| | |
|---|---|
| 2835. | MVAKN |
| 2836. | VAKNI |
| 2837. | AKNIK |
| 2838. | KNIKY |
| 2839. | NIKYN |
| 2840. | IKYNE |
| 2841. | KYNEE |
| 2842. | YNEEA |
| 2843. | NEEAR |
| 2844. | EEARK |
| 2845. | EARKK |
| 2846. | ARKKI |
| 2847. | RKKIQ |
| 2848. | KKIQK |
| 2849. | KIQKG |
| 2850. | IQKGV |
| 2851. | QKGVK |
| 2852. | KGVKT |
| 2853. | GVKTL |
| 2854. | VKTLA |
| 2855. | KTLAE |
| 2856. | TLAEA |
| 2857. | LAEAV |
| 2858. | AEAVK |
| 2859. | EAVKV |
| 2860. | AVKVT |
| 2861. | VKVTL |
| 2862. | KVTLG |
| 2863. | VTLGP |
| 2864. | TLGPK |
| 2865. | LGPKG |
| 2866. | GPKGR |
| 2867. | PKGRH |
| 2868. | KGRHV |
| 2869. | GRHVV |
| 2870. | RHVVI |
| 2871. | HVVID |
| 2872. | VVIDK |
| 2873. | VIDKS |
| 2874. | IDKSF |
| 2875. | DKSFG |
| 2876. | KSFGS |
| 2877. | SFGSP |
| 2878. | FGSPQ |
| 2879. | GSPQV |
| 2880. | SPQVT |
| 2881. | PQVTK |
| 2882. | QVTKD |
| 2883. | VTKDG |
| 2884. | TKDGV |
| 2885. | KDGVT |
| 2886. | DGVTV |
| 2887. | GVTVA |
| 2888. | VTVAK |
| 2889. | TVAKE |
| 2890. | VAKEV |
| 2891. | AKEVE |
| 2892. | KEVEL |
| 2893. | EVELA |
| 2894. | VELAD |
| 2895. | ELADK |
| 2896. | LADKH |
| 2897. | ADKHE |
| 2898. | DKHEN |
| 2899. | KHENM |
| 2900. | HENMG |
| 2901. | ENMGA |
| 2902. | NMGAQ |
| 2903. | MGAQM |
| 2904. | GAQMV |
| 2905. | AQMVK |
| 2906. | QMVKE |
| 2907. | MVKEV |
| 2908. | VKEVA |
| 2909. | KEVAS |
| 2910. | EVASK |
| 2911. | VASKT |
| 2912. | ASKTA |
| 2913. | SKTAD |
| 2914. | KTADK |
| 2915. | TADKA |
| 2916. | ADKAG |
| 2917. | DKAGD |
| 2918. | KAGDG |
| 2919. | AGDGT |
| 2920. | GDGTT |
| 2921. | DGTTT |
| 2922. | GTTTA |
| 2923. | TTTAT |
| 2924. | TTATV |
| 2925. | TATVL |
| 2926. | ATVLA |
| 2927. | TVLAE |
| 2928. | VLAEA |
| 2929. | LAEAI |
| 2930. | AEAIY |
| 2931. | EAIYT |
| 2932. | AIYTE |
| 2933. | IYTEG |
| 2934. | YTEGL |
| 2935. | TEGLR |
| 2936. | EGLRN |
| 2937. | GLRNV |
| 2938. | LRNVT |
| 2939. | RNVTA |
| 2940. | NVTAG |
| 2941. | VTAGA |
| 2942. | TAGAN |
| 2943. | AGANP |
| 2944. | GANPM |
| 2945. | ANPMD |
| 2946. | NPMDL |
| 2947. | PMDLK |
| 2948. | MDLKR |
| 2949. | DLKRG |
| 2950. | LKRGI |
| 2951. | KRGID |
| 2952. | RGIDK |
| 2953. | GIDKA |
| 2954. | IDKAV |
| 2955. | DKAVK |
| 2956. | KAVKV |
| 2957. | AVKVV |
| 2958. | VKVVV |
| 2959. | KVVVD |
| 2960. | VVVDQ |
| 2961. | VVDQI |
| 2962. | VDQIR |
| 2963. | DQIRK |
| 2964. | QIRKI |
| 2965. | IRKIS |
| 2966. | RKISK |
| 2967. | KISKP |
| 2968. | ISKPV |

TABLE 6-continued

| | |
|---|---|
| 2969. | SKPVQ |
| 2970. | KPVQH |
| 2971. | PVQHH |
| 2972. | VQHHK |
| 2973. | QHHKE |
| 2974. | HHKEI |
| 2975. | HKEIA |
| 2976. | KEIAQ |
| 2977. | EIAQV |
| 2978. | IAQVA |
| 2979. | AQVAT |
| 2980. | QVATI |
| 2981. | VATIS |
| 2982. | ATISA |
| 2983. | TISAN |
| 2984. | ISANN |
| 2985. | SANND |
| 2986. | ANNDA |
| 2987. | NNDAE |
| 2988. | NDAEI |
| 2989. | DAEIG |
| 2990. | AEIGN |
| 2991. | EIGNL |
| 2992. | IGNLI |
| 2993. | GNLIA |
| 2994. | NLIAE |
| 2995. | LIAEA |
| 2996. | IAEAM |
| 2997. | AEAME |
| 2998. | EAMEK |
| 2999. | AMEKV |
| 3000. | MEKVG |
| 3001. | EKVGK |
| 3002. | KVGKN |
| 3003. | VGKNG |
| 3004. | GKNGS |
| 3005. | KNGSI |
| 3006. | NGSIT |
| 3007. | GSITV |
| 3008. | SITVE |
| 3009. | ITVEE |
| 3010. | TVEEA |
| 3011. | VEEAK |
| 3012. | EEAKG |
| 3013. | EAKGF |
| 3014. | AKGFE |
| 3015. | KGFET |
| 3016. | GFETV |
| 3017. | FETVL |
| 3018. | ETVLD |
| 3019. | TVLDV |
| 3020. | VLDVV |
| 3021. | LDVVE |
| 3022. | DVVEG |
| 3023. | VVEGM |
| 3024. | VEGMN |
| 3025. | EGMNF |
| 3026. | GMNFN |
| 3027. | MNFNR |
| 3028. | NFNRG |
| 3029. | FNRGY |
| 3030. | NRGYL |
| 3031. | RGYLS |
| 3032. | GYLSS |
| 3033. | YLSSY |
| 3034. | LSSYF |
| 3035. | SSYFA |
| 3036. | SYFAT |
| 3037. | YFATN |
| 3038. | FATNP |
| 3039. | ATNPE |
| 3040. | TNPET |
| 3041. | NPETQ |
| 3042. | PETQE |
| 3043. | ETQEC |
| 3044. | TQECV |
| 3045. | QECVL |
| 3046. | ECVLE |
| 3047. | CVLED |
| 3048. | VLEDA |
| 3049. | LEDAL |
| 3050. | EDALV |
| 3051. | DALVL |
| 3052. | ALVLI |
| 3053. | LVLIY |
| 3054. | VLIYD |
| 3055. | LIYDK |
| 3056. | IYDKK |
| 3057. | YDKKI |
| 3058. | DKKIS |
| 3059. | KKISG |
| 3060. | KISGI |
| 3061. | ISGIK |
| 3062. | SGIKD |
| 3063. | GIKDF |
| 3064. | IKDFL |
| 3065. | KDFLP |
| 3066. | DFLPV |
| 3067. | FLPVL |
| 3068. | LPVLQ |
| 3069. | PVLQQ |
| 3070. | VLQQV |
| 3071. | LQQVA |
| 3072. | QQVAE |
| 3073. | QVAES |
| 3074. | VAESG |
| 3075. | AESGR |
| 3076. | ESGRP |
| 3077. | SGRPL |
| 3078. | GRPLL |
| 3079. | RPLLI |
| 3080. | PLLII |
| 3081. | LLIIA |
| 3082. | LIIAE |
| 3083. | IIAED |
| 3084. | IAEDI |
| 3085. | AEDIE |
| 3086. | EDIEG |
| 3087. | DIEGE |
| 3088. | IEGEA |
| 3089. | EGEAL |
| 3090. | GEALA |
| 3091. | EALAT |
| 3092. | ALATL |
| 3093. | LATLV |
| 3094. | ATLVV |
| 3095. | TLVVN |
| 3096. | LVVNR |
| 3097. | VVNRI |
| 3098. | VNRIR |
| 3099. | NRIRG |
| 3100. | RIRGG |
| 3101. | IRGGF |
| 3102. | RGGFR |
| 3103. | GGFRV |
| 3104. | GFRVC |
| 3105. | FRVCA |
| 3106. | RVCAV |
| 3107. | VCAVK |
| 3108. | CAVKA |
| 3109. | AVKAP |
| 3110. | VKAPG |
| 3111. | KAPGF |
| 3112. | APGFG |
| 3113. | PGFGD |
| 3114. | GFGDR |
| 3115. | FGDRR |
| 3116. | GDRRK |
| 3117. | DRRKA |
| 3118. | RRKAM |
| 3119. | RKAML |
| 3120. | KAMLE |
| 3121. | AMLED |
| 3122. | MLEDI |
| 3123. | LEDIA |
| 3124. | EDIAI |
| 3125. | DIAIL |
| 3126. | IAILT |
| 3127. | AILTG |
| 3128. | ILTGG |

TABLE 6-continued

| | |
|---|---|
| 3129. | LTGGQ |
| 3130. | TGGQL |
| 3131. | GGQLI |
| 3132. | GQLIS |
| 3133. | QLISE |
| 3134. | LISEE |
| 3135. | ISEEL |
| 3136. | SEELG |
| 3137. | EELGM |
| 3138. | ELGMK |
| 3139. | LGMKL |
| 3140. | GMKLE |
| 3141. | MKLEN |
| 3142. | KLENA |
| 3143. | LENAN |
| 3144. | ENANL |
| 3145. | NANLA |
| 3146. | ANLAM |
| 3147. | NLAML |
| 3148. | LAMLG |
| 3149. | AMLGK |
| 3150. | MLGKA |
| 3151. | LGKAK |
| 3152. | GKAKK |
| 3153. | KAKKV |
| 3154. | AKKVI |
| 3155. | KKVIV |
| 3156. | KVIVS |
| 3157. | VIVSK |
| 3158. | IVSKE |
| 3159. | VSKED |
| 3160. | SKEDT |
| 3161. | KEDTT |
| 3162. | EDTTI |
| 3163. | DTTIV |
| 3164. | TTIVE |
| 3165. | TIVEG |
| 3166. | IVEGM |
| 3167. | VEGMG |
| 3168. | EGMGE |
| 3169. | GMGEK |
| 3170. | MGEKE |
| 3171. | GEKEA |
| 3172. | EKEAL |
| 3173. | KEALE |
| 3174. | EALEA |
| 3175. | ALEAR |
| 3176. | LEARC |
| 3177. | EARCE |
| 3178. | ARCES |
| 3179. | RCESI |
| 3180. | CESIK |
| 3181. | ESIKK |
| 3182. | SIKKQ |
| 3183. | IKKQI |
| 3184. | KKQIE |
| 3185. | KQIED |
| 3186. | QIEDS |
| 3187. | IEDSS |
| 3188. | EDSSS |
| 3189. | DSSSD |
| 3190. | SSSDY |
| 3191. | SSDYD |
| 3192. | SDYDK |
| 3193. | DYDKE |
| 3194. | YDKEK |
| 3195. | DKEKL |
| 3196. | KEKLQ |
| 3197. | EKLQE |
| 3198. | KLQER |
| 3199. | LQERL |
| 3200. | QERLA |
| 3201. | ERLAK |
| 3202. | RLAKL |
| 3203. | LAKLS |
| 3204. | AKLSG |
| 3205. | KLSGG |
| 3206. | LSGGV |
| 3207. | SGGVA |
| 3208. | GGVAV |
| 3209. | GVAVI |
| 3210. | VAVIR |
| 3211. | AVIRV |
| 3212. | VIRVG |
| 3213. | IRVGA |
| 3214. | RVGAA |
| 3215. | VGAAT |
| 3216. | GAATE |
| 3217. | AATEI |
| 3218. | ATEIE |
| 3219. | TEIEM |
| 3220. | EIEMK |
| 3221. | IEMKE |
| 3222. | EMKEK |
| 3223. | MKEKK |
| 3224. | KEKKD |
| 3225. | EKKDR |
| 3226. | KKDRV |
| 3227. | KDRVD |
| 3228. | DRVDD |
| 3229. | RVDDA |
| 3230. | VDDAQ |
| 3231. | DDAQH |
| 3232. | DAQHA |
| 3233. | AQHAT |
| 3234. | QHATI |
| 3235. | HATIA |
| 3236. | ATIAA |
| 3237. | TIAAV |
| 3238. | IAAVE |
| 3239. | AAVEE |
| 3240. | AVEEG |
| 3241. | VEEGI |
| 3242. | EEGIL |
| 3243. | EGILP |
| 3244. | GILPG |
| 3245. | ILPGG |
| 3246. | LPGGG |
| 3247. | PGGGT |
| 3248. | GGGTA |
| 3249. | GGTAL |
| 3250. | GTALI |
| 3251. | TALIR |
| 3252. | ALIRC |
| 3253. | LIRCI |
| 3254. | IRCIP |
| 3255. | RCIPT |
| 3256. | CIPTL |
| 3257. | IPTLE |
| 3258. | PTLEA |
| 3259. | TLEAF |
| 3260. | LEAFL |
| 3261. | EAFLP |
| 3262. | AFLPM |
| 3263. | FLPML |
| 3264. | LPMLT |
| 3265. | PMLTN |
| 3266. | MLTNE |
| 3267. | LTNED |
| 3268. | TNEDE |
| 3269. | NEDEQ |
| 3270. | EDEQI |
| 3271. | DEQIG |
| 3272. | EQIGA |
| 3273. | QIGAR |
| 3274. | IGARI |
| 3275. | GARIV |
| 3276. | ARIVL |
| 3277. | RIVLK |
| 3278. | IVLKA |
| 3279. | VLKAL |
| 3280. | LKALS |
| 3281. | KALSA |
| 3282. | ALSAP |
| 3283. | LSAPL |
| 3284. | SAPLK |
| 3285. | APLKQ |
| 3286. | PLKQI |
| 3287. | LKQIA |
| 3288. | KQIAA |

TABLE 6-continued

| | |
|---|---|
| 3289. | QIAAN |
| 3290. | IAANA |
| 3291. | AANAG |
| 3292. | ANAGK |
| 3293. | NAGKE |
| 3294. | AGKEG |
| 3295. | GKEGA |
| 3296. | KEGAI |
| 3297. | EGAII |
| 3298. | GAIIF |
| 3299. | AIIFQ |
| 3300. | IIFQQ |
| 3301. | IFQQV |
| 3302. | FQQVM |
| 3303. | QQVMS |
| 3304. | QVMSR |
| 3305. | VMSRS |
| 3306. | MSRSA |
| 3307. | SRSAN |
| 3308. | RSANE |
| 3309. | SANEG |
| 3310. | ANEGY |
| 3311. | NEGYD |
| 3312. | EGYDA |
| 3313. | GYDAL |
| 3314. | YDALR |
| 3315. | DALRD |
| 3316. | ALRDA |
| 3317. | LRDAY |
| 3318. | RDAYT |
| 3319. | DAYTD |
| 3320. | AYTDM |
| 3321. | YTDML |
| 3322. | TDMLE |
| 3323. | DMLEA |
| 3324. | MLEAG |
| 3325. | LEAGI |
| 3326. | EAGIL |
| 3327. | AGILD |
| 3328. | GILDP |
| 3329. | ILDPA |
| 3330. | LDPAK |
| 3331. | DPAKV |
| 3332. | PAKVT |
| 3333. | AKVTR |
| 3334. | KVTRS |
| 3335. | VTRSA |
| 3336. | TRSAL |
| 3337. | RSALE |
| 3338. | SALES |
| 3339. | ALESA |
| 3340. | LESAA |
| 3341. | ESAAS |
| 3342. | SAASV |
| 3343. | AASVA |
| 3344. | ASVAG |
| 3345. | SVAGL |
| 3346. | VAGLL |
| 3347. | AGLLL |
| 3348. | GLLLT |
| 3349. | LLLTT |
| 3350. | LLTTE |
| 3351. | LTTEA |
| 3352. | TTEAL |
| 3353. | TEALI |
| 3354. | EALIA |
| 3355. | ALIAE |
| 3356. | LIAEI |
| 3357. | IAEIP |
| 3358. | AEIPE |
| 3359. | EIPEE |
| 3360. | IPEEK |
| 3361. | PEEKP |
| 3362. | EEKPA |
| 3363. | EKPAA |
| 3364. | KPAAA |
| 3365. | PAAAP |
| 3366. | AAAPA |
| 3367. | AAPAM |
| 3368. | APAMP |

TABLE 6-continued

| | |
|---|---|
| 3369. | PAMPG |
| 3370. | AMPGA |
| 3371. | MPGAG |
| 3372. | PGAGM |
| 3373. | GAGMD |
| 3374. | AGMDY |

5-mer peptides of CT376 (malate dehydrogenase, 326 amino acids) ACCESSION# NP 219885.1, GI: 15605100 (SEQ ID NOS: 3375-3696)

| | |
|---|---|
| 3375. | MVSQT |
| 3376. | VSQTV |
| 3377. | SQTVS |
| 3378. | QTVSV |
| 3379. | TVSVA |
| 3380. | VSVAV |
| 3381. | SVAVT |
| 3382. | VAVTG |
| 3383. | AVTGG |
| 3384. | VTGGT |
| 3385. | TGGTG |
| 3386. | GGTGQ |
| 3387. | GTGQI |
| 3388. | TGQIA |
| 3389. | GQIAY |
| 3390. | QIAYS |
| 3391. | IAYSF |
| 3392. | AYSFL |
| 3393. | YSFLF |
| 3394. | SFLFS |
| 3395. | FLFSL |
| 3396. | LFSLA |
| 3397. | FSLAH |
| 3398. | SLAHG |
| 3399. | LAHGD |
| 3400. | AHGDV |
| 3401. | HGDVF |
| 3402. | GDVFG |
| 3403. | DVFGL |
| 3404. | VFGLD |
| 3405. | FGLDC |
| 3406. | GLDCG |
| 3407. | LDCGI |
| 3408. | DCGID |
| 3409. | CGIDL |
| 3410. | GIDLR |
| 3411. | IDLRI |
| 3412. | DLRIY |
| 3413. | LRIYD |
| 3414. | RIYDI |
| 3415. | IYDIP |
| 3416. | YDIPG |
| 3417. | DIPGT |
| 3418. | IPGTE |
| 3419. | PGTER |
| 3420. | GTERA |
| 3421. | TERAL |
| 3422. | ERALS |
| 3423. | RALSG |
| 3424. | ALSGV |
| 3425. | LSGVR |
| 3426. | SGVRM |
| 3427. | GVRME |
| 3428. | VRMEL |
| 3429. | RMELD |
| 3430. | MELDD |
| 3431. | ELDDG |
| 3432. | LDDGA |
| 3433. | DDGAF |
| 3434. | DGAFP |
| 3435. | GAFPL |
| 3436. | AFPLL |
| 3437. | FPLLQ |
| 3438. | PLLQR |
| 3439. | LLQRV |
| 3440. | LQRVQ |
| 3441. | QRVQV |
| 3442. | RVQVT |
| 3443. | VQVTT |

TABLE 6-continued

| # | Seq |
|---|---|
| 3444. | QVTTS |
| 3445. | VTTSL |
| 3446. | TTSLH |
| 3447. | TSLHD |
| 3448. | SLHDA |
| 3449. | LHDAF |
| 3450. | HDAFD |
| 3451. | DAFDG |
| 3452. | AFDGI |
| 3453. | FDGID |
| 3454. | DGIDA |
| 3455. | GIDAA |
| 3456. | IDAAF |
| 3457. | DAAFL |
| 3458. | AAFLI |
| 3459. | AFLIG |
| 3460. | FLIGS |
| 3461. | LIGSV |
| 3462. | IGSVP |
| 3463. | GSVPR |
| 3464. | SVPRG |
| 3465. | VPRGP |
| 3466. | PRGPG |
| 3467. | RGPGM |
| 3468. | GPGME |
| 3469. | PGMER |
| 3470. | GMERR |
| 3471. | MERRD |
| 3472. | ERRDL |
| 3473. | RRDLL |
| 3474. | RDLLK |
| 3475. | DLLKK |
| 3476. | LLKKN |
| 3477. | LKKNG |
| 3478. | KKNGE |
| 3479. | KNGEI |
| 3480. | NGEIF |
| 3481. | GEIFA |
| 3482. | EIFAT |
| 3483. | IFATQ |
| 3484. | FATQG |
| 3485. | ATQGK |
| 3486. | TQGKA |
| 3487. | QGKAL |
| 3488. | GKALN |
| 3489. | KALNT |
| 3490. | ALNTT |
| 3491. | LNTTA |
| 3492. | NTTAK |
| 3493. | TTAKR |
| 3494. | TAKRD |
| 3495. | AKRDA |
| 3496. | KRDAK |
| 3497. | RDAKI |
| 3498. | DAKIF |
| 3499. | AKIFV |
| 3500. | KIFVV |
| 3501. | IFVVG |
| 3502. | FVVGN |
| 3503. | VVGNP |
| 3504. | VGNPV |
| 3505. | GNPVN |
| 3506. | NPVNT |
| 3507. | PVNTN |
| 3508. | VNTNC |
| 3509. | NTNCW |
| 3510. | TNCWI |
| 3511. | NCWIA |
| 3512. | CWIAM |
| 3513. | WIAMN |
| 3514. | IAMNH |
| 3515. | AMNHA |
| 3516. | MNHAP |
| 3517. | NHAPR |
| 3518. | HAPRL |
| 3519. | APRLL |
| 3520. | PRLLR |
| 3521. | RLLRK |
| 3522. | LLRKN |
| 3523. | LRKNF |
| 3524. | RKNFH |
| 3525. | KNFHA |
| 3526. | NFHAM |
| 3527. | FHAML |
| 3528. | HAMLR |
| 3529. | AMLRL |
| 3530. | MLRLD |
| 3531. | LRLDQ |
| 3532. | RLDQN |
| 3533. | LDQNR |
| 3534. | DQNRM |
| 3535. | QNRMH |
| 3536. | NRMHS |
| 3537. | RMHSM |
| 3538. | MHSML |
| 3539. | HSMLS |
| 3540. | SMLSH |
| 3541. | MLSHR |
| 3542. | LSHRA |
| 3543. | SHRAE |
| 3544. | HRAEV |
| 3545. | RAEVP |
| 3546. | AEVPL |
| 3547. | EVPLS |
| 3548. | VPLSA |
| 3549. | PLSAV |
| 3550. | LSAVS |
| 3551. | SAVSQ |
| 3552. | AVSQV |
| 3553. | VSQVV |
| 3554. | SQVVV |
| 3555. | QVVVW |
| 3556. | VVVWG |
| 3557. | VVWGN |
| 3558. | VWGNH |
| 3559. | WGNHS |
| 3560. | GNHSA |
| 3561. | NHSAK |
| 3562. | HSAKQ |
| 3563. | SAKQV |
| 3564. | AKQVP |
| 3565. | KQVPD |
| 3566. | QVPDF |
| 3567. | VPDFT |
| 3568. | PDFTQ |
| 3569. | DFTQA |
| 3570. | FTQAL |
| 3571. | TQALI |
| 3572. | QALIN |
| 3573. | ALIND |
| 3574. | LINDR |
| 3575. | INDRP |
| 3576. | NDRPI |
| 3577. | DRPIA |
| 3578. | RPIAE |
| 3579. | PIAET |
| 3580. | IAETI |
| 3581. | AETIA |
| 3582. | ETIAD |
| 3583. | TIADR |
| 3584. | IADRD |
| 3585. | ADRDW |
| 3586. | DRDWL |
| 3587. | RDWLE |
| 3588. | DWLEN |
| 3589. | WLENI |
| 3590. | LENIM |
| 3591. | ENIMV |
| 3592. | NIMVP |
| 3593. | IMVPS |
| 3594. | MVPSV |
| 3595. | VPSVQ |
| 3596. | PSVQS |
| 3597. | SVQSR |
| 3598. | VQSRG |
| 3599. | QSRGS |
| 3600. | SRGSA |
| 3601. | RGSAV |
| 3602. | GSAVI |
| 3603. | SAVIE |

TABLE 6-continued

| | |
|---|---|
| 3604. | AVIEA |
| 3605. | VIEAR |
| 3606. | IEARG |
| 3607. | EARGK |
| 3608. | ARGKS |
| 3609. | RGKSS |
| 3610. | GKSSA |
| 3611. | KSSAA |
| 3612. | SSAAS |
| 3613. | SAASA |
| 3614. | AASAA |
| 3615. | ASAAR |
| 3616. | SAARA |
| 3617. | AARAL |
| 3618. | ARALA |
| 3619. | RALAE |
| 3620. | ALAEA |
| 3621. | LAEAA |
| 3622. | AEAAR |
| 3623. | EAARS |
| 3624. | AARSI |
| 3625. | ARSIY |
| 3626. | RSIYQ |
| 3627. | SIYQP |
| 3628. | IYQPK |
| 3629. | YQPKE |
| 3630. | QPKEG |
| 3631. | PKEGE |
| 3632. | KEGEW |
| 3633. | EGEWF |
| 3634. | GEWFS |
| 3635. | EWFSS |
| 3636. | WFSSG |
| 3637. | FSSGV |
| 3638. | SSGVC |
| 3639. | SGVCS |
| 3640. | GVCSD |
| 3641. | VCSDH |
| 3642. | CSDHN |
| 3643. | SDHNP |
| 3644. | DHNPY |
| 3645. | HNPYG |
| 3646. | NPYGL |
| 3647. | PYGLP |
| 3648. | YGLPE |
| 3649. | GLPED |
| 3650. | LPEDL |
| 3651. | PEDLI |
| 3652. | EDLIF |
| 3653. | DLIFG |
| 3654. | LIFGF |
| 3655. | IFGFP |
| 3656. | FGFPC |
| 3657. | GFPCR |
| 3658. | FPCRM |
| 3659. | PCRML |
| 3660. | CRMLA |
| 3661. | RMLAT |
| 3662. | MLATG |
| 3663. | LATGE |
| 3664. | ATGEY |
| 3665. | TGEYE |
| 3666. | GEYEV |
| 3667. | EYEVI |
| 3668. | YEVIP |
| 3669. | EVIPR |
| 3670. | VIPRL |
| 3671. | IPRLP |
| 3672. | PRLPW |
| 3673. | RLPWD |
| 3674. | LPWDA |
| 3675. | PWDAF |
| 3676. | WDAFI |
| 3677. | DAFIR |
| 3678. | AFIRG |
| 3679. | FIRGK |
| 3680. | IRGKM |
| 3681. | RGKMQ |
| 3682. | GKMQI |
| 3683. | KMQIS |

TABLE 6-continued

| | |
|---|---|
| 3684. | MQISL |
| 3685. | QISLD |
| 3686. | ISLDE |
| 3687. | SLDEI |
| 3688. | LDEIL |
| 3689. | DEILQ |
| 3690. | EILQE |
| 3691. | ILQEK |
| 3692. | LQEKA |
| 3693. | QEKAS |
| 3694. | EKASV |
| 3695. | KASVS |
| 3696. | ASVSL |

5-mer peptides of CT557 (dihydrolipoamide dehydrogenase, 465 amino acids), ACCESSION# NP 220072.1, GI: 15605286 (SEQ ID NOS: 3697-4018)

| | |
|---|---|
| 3697. | MVSQT |
| 3698. | VSQTV |
| 3699. | SQTVS |
| 3700. | QTVSV |
| 3701. | TVSVA |
| 3702. | VSVAV |
| 3703. | SVAVT |
| 3704. | VAVTG |
| 3705. | AVTGG |
| 3706. | VTGGT |
| 3707. | TGGTG |
| 3708. | GGTGQ |
| 3709. | GTGQI |
| 3710. | TGQIA |
| 3711. | GQIAY |
| 3712. | QIAYS |
| 3713. | IAYSF |
| 3714. | AYSFL |
| 3715. | YSFLF |
| 3716. | SFLFS |
| 3717. | FLFSL |
| 3718. | LFSLA |
| 3719. | FSLAH |
| 3720. | SLAHG |
| 3721. | LAHGD |
| 3722. | AHGDV |
| 3723. | HGDVF |
| 3724. | GDVFG |
| 3725. | DVFGL |
| 3726. | VFGLD |
| 3727. | FGLDC |
| 3728. | GLDCG |
| 3729. | LDCGI |
| 3730. | DCGID |
| 3731. | CGIDL |
| 3732. | GIDLR |
| 3733. | IDLRI |
| 3734. | DLRIY |
| 3735. | LRIYD |
| 3736. | RIYDI |
| 3737. | IYDIP |
| 3738. | YDIPG |
| 3739. | DIPGT |
| 3740. | IPGTE |
| 3741. | PGTER |
| 3742. | GTERA |
| 3743. | TERAL |
| 3744. | ERALS |
| 3745. | RALSG |
| 3746. | ALSGV |
| 3747. | LSGVR |
| 3748. | SGVRM |
| 3749. | GVRME |
| 3750. | VRMEL |
| 3751. | RMELD |
| 3752. | MELDD |
| 3753. | ELDDG |
| 3754. | LDDGA |
| 3755. | DDGAF |
| 3756. | DGAFP |
| 3757. | GAFPL |
| 3758. | AFPLL |

TABLE 6-continued

| | |
|---|---|
| 3759. | FPLLQ |
| 3760. | PLLQR |
| 3761. | LLQRV |
| 3762. | LQRVQ |
| 3763. | QRVQV |
| 3764. | RVQVT |
| 3765. | VQVTT |
| 3766. | QVTTS |
| 3767. | VTTSL |
| 3768. | TTSLH |
| 3769. | TSLHD |
| 3770. | SLHDA |
| 3771. | LHDAF |
| 3772. | HDAFD |
| 3773. | DAFDG |
| 3774. | AFDGI |
| 3775. | FDGID |
| 3776. | DGIDA |
| 3777. | GIDAA |
| 3778. | IDAAF |
| 3779. | DAAFL |
| 3780. | AAFLI |
| 3781. | AFLIG |
| 3782. | FLIGS |
| 3783. | LIGSV |
| 3784. | IGSVP |
| 3785. | GSVPR |
| 3786. | SVPRG |
| 3787. | VPRGP |
| 3788. | PRGPG |
| 3789. | RGPGM |
| 3790. | GPGME |
| 3791. | PGMER |
| 3792. | GMERR |
| 3793. | MERRD |
| 3794. | ERRDL |
| 3795. | RRDLL |
| 3796. | RDLLK |
| 3797. | DLLKK |
| 3798. | LLKKN |
| 3799. | LKKNG |
| 3800. | KKNGE |
| 3801. | KNGEI |
| 3802. | NGEIF |
| 3803. | GEIFA |
| 3804. | EIFAT |
| 3805. | IFATQ |
| 3806. | FATQG |
| 3807. | ATQGK |
| 3808. | TQGKA |
| 3809. | QGKAL |
| 3810. | GKALN |
| 3811. | KALNT |
| 3812. | ALNTT |
| 3813. | LNTTA |
| 3814. | NTTAK |
| 3815. | TTAKR |
| 3816. | TAKRD |
| 3817. | AKRDA |
| 3818. | KRDAK |
| 3819. | RDAKI |
| 3820. | DAKIF |
| 3821. | AKIFV |
| 3822. | KIFVV |
| 3823. | IFVVG |
| 3824. | FVVGN |
| 3825. | VVGNP |
| 3826. | VGNPV |
| 3827. | GNPVN |
| 3828. | NPVNT |
| 3829. | PVNTN |
| 3830. | VNTNC |
| 3831. | NTNCW |
| 3832. | TNCWI |
| 3833. | NCWIA |
| 3834. | CWIAM |
| 3835. | WIAMN |
| 3836. | IAMNH |
| 3837. | AMNHA |
| 3838. | MNHAP |
| 3839. | NHAPR |
| 3840. | HAPRL |
| 3841. | APRLL |
| 3842. | PRLLR |
| 3843. | RLLRK |
| 3844. | LLRKN |
| 3845. | LRKNF |
| 3846. | RKNFH |
| 3847. | KNFHA |
| 3848. | NFHAM |
| 3849. | FHAML |
| 3850. | HAMLR |
| 3851. | AMLRL |
| 3852. | MLRLD |
| 3853. | LRLDQ |
| 3854. | RLDQN |
| 3855. | LDQNR |
| 3856. | DQNRM |
| 3857. | QNRMH |
| 3858. | NRMHS |
| 3859. | RMHSM |
| 3860. | MHSML |
| 3861. | HSMLS |
| 3862. | SMLSH |
| 3863. | MLSHR |
| 3864. | LSHRA |
| 3865. | SHRAE |
| 3866. | HRAEV |
| 3867. | RAEVP |
| 3868. | AEVPL |
| 3869. | EVPLS |
| 3870. | VPLSA |
| 3871. | PLSAV |
| 3872. | LSAVS |
| 3873. | SAVSQ |
| 3874. | AVSQV |
| 3875. | VSQVV |
| 3876. | SQVVV |
| 3877. | QVVVW |
| 3878. | VVVWG |
| 3879. | VVWGN |
| 3880. | VWGNH |
| 3881. | WGNHS |
| 3882. | GNHSA |
| 3883. | NHSAK |
| 3884. | HSAKQ |
| 3885. | SAKQV |
| 3886. | AKQVP |
| 3887. | KQVPD |
| 3888. | QVPDF |
| 3889. | VPDFT |
| 3890. | PDFTQ |
| 3891. | DFTQA |
| 3892. | FTQAL |
| 3893. | TQALI |
| 3894. | QALIN |
| 3895. | ALIND |
| 3896. | LINDR |
| 3897. | INDRP |
| 3898. | NDRPI |
| 3899. | DRPIA |
| 3900. | RPIAE |
| 3901. | PIAET |
| 3902. | IAETI |
| 3903. | AETIA |
| 3904. | ETIAD |
| 3905. | TIADR |
| 3906. | IADRD |
| 3907. | ADRDW |
| 3908. | DRDWL |
| 3909. | RDWLE |
| 3910. | DWLEN |
| 3911. | WLENI |
| 3912. | LENIM |
| 3913. | ENIMV |
| 3914. | NIMVP |
| 3915. | IMVPS |
| 3916. | MVPSV |
| 3917. | VPSVQ |
| 3918. | PSVQS |

TABLE 6-continued

| | |
|---|---|
| 3919. | SVQSR |
| 3920. | VQSRG |
| 3921. | QSRGS |
| 3922. | SRGSA |
| 3923. | RGSAV |
| 3924. | GSAVI |
| 3925. | SAVIE |
| 3926. | AVIEA |
| 3927. | VIEAR |
| 3928. | IEARG |
| 3929. | EARGK |
| 3930. | ARGKS |
| 3931. | RGKSS |
| 3932. | GKSSA |
| 3933. | KSSAA |
| 3934. | SSAAS |
| 3935. | SAASA |
| 3936. | AASAA |
| 3937. | ASAAR |
| 3938. | SAARA |
| 3939. | AARAL |
| 3940. | ARALA |
| 3941. | RALAE |
| 3942. | ALAEA |
| 3943. | LAEAA |
| 3944. | AEAAR |
| 3945. | EAARS |
| 3946. | AARSI |
| 3947. | ARSIY |
| 3948. | RSIYQ |
| 3949. | SIYQP |
| 3950. | IYQPK |
| 3951. | YQPKE |
| 3952. | QPKEG |
| 3953. | PKEGE |
| 3954. | KEGEW |
| 3955. | EGEWF |
| 3956. | GEWFS |
| 3957. | EWFSS |
| 3958. | WFSSG |
| 3959. | FSSGV |
| 3960. | SSGVC |
| 3961. | SGVCS |
| 3962. | GVCSD |
| 3963. | VCSDH |
| 3964. | CSDHN |
| 3965. | SDHNP |
| 3966. | DHNPY |
| 3967. | HNPYG |
| 3968. | NPYGL |
| 3969. | PYGLP |
| 3970. | YGLPE |
| 3971. | GLPED |
| 3972. | LPEDL |
| 3973. | PEDLI |
| 3974. | EDLIF |
| 3975. | DLIFG |
| 3976. | LIFGF |
| 3977. | IFGFP |
| 3978. | FGFPC |
| 3979. | GFPCR |
| 3980. | FPCRM |
| 3981. | PCRML |
| 3982. | CRMLA |
| 3983. | RMLAT |
| 3984. | MLATG |
| 3985. | LATGE |
| 3986. | ATGEY |
| 3987. | TGEYE |
| 3988. | GEYEV |
| 3989. | EYEVI |
| 3990. | YEVIP |
| 3991. | EVIPR |
| 3992. | VIPRL |
| 3993. | IPRLP |
| 3994. | PRLPW |
| 3995. | RLPWD |
| 3996. | LPWDA |
| 3997. | PWDAF |
| 3998. | WDAFI |

TABLE 6-continued

| | |
|---|---|
| 3999. | DAFIR |
| 4000. | AFIRG |
| 4001. | FIRGK |
| 4002. | IRGKM |
| 4003. | RGKMQ |
| 4004. | GKMQI |
| 4005. | KMQIS |
| 4006. | MQISL |
| 4007. | QISLD |
| 4008. | ISLDE |
| 4009. | SLDEI |
| 4010. | LDEIL |
| 4011. | DEILQ |
| 4012. | EILQE |
| 4013. | ILQEK |
| 4014. | LQEKA |
| 4015. | QEKAS |
| 4016. | EKASV |
| 4017. | KASVS |
| 4018. | ASVSL |

5-mer peptides of CT858 (CPAF, total of 609 amino acids), ACCESSION# AAC68456.1, GI: 3329332 (SEQ ID NOS: 4019-4623)

| | |
|---|---|
| 4019. | MGFWR |
| 4020. | GFWRT |
| 4021. | FWRTS |
| 4022. | WRTSI |
| 4023. | RTSIM |
| 4024. | TSIMK |
| 4025. | SIMKM |
| 4026. | IMKMN |
| 4027. | MKMNR |
| 4028. | KMNRI |
| 4029. | MNRIW |
| 4030. | NRIWL |
| 4031. | RIWLL |
| 4032. | IWLLL |
| 4033. | WLLLL |
| 4034. | LLLLT |
| 4035. | LLLTF |
| 4036. | LLTFS |
| 4037. | LTFSS |
| 4038. | TFSSA |
| 4039. | FSSAI |
| 4040. | SSAIH |
| 4041. | SAIHS |
| 4042. | AIHSP |
| 4043. | IHSPV |
| 4044. | HSPVQ |
| 4045. | SPVQG |
| 4046. | PVQGE |
| 4047. | VQGES |
| 4048. | QGESL |
| 4049. | GESLV |
| 4050. | ESLVC |
| 4051. | SLVCK |
| 4052. | LVCKN |
| 4053. | VCKNA |
| 4054. | CKNAL |
| 4055. | KNALQ |
| 4056. | NALQD |
| 4057. | ALQDL |
| 4058. | LQDLS |
| 4059. | QDLSF |
| 4060. | DLSFL |
| 4061. | LSFLE |
| 4062. | SFLEH |
| 4063. | FLEHL |
| 4064. | LEHLL |
| 4065. | EHLLQ |
| 4066. | HLLQV |
| 4067. | LLQVK |
| 4068. | LQVKY |
| 4069. | QVKYA |
| 4070. | VKYAP |
| 4071. | KYAPK |
| 4072. | YAPKT |
| 4073. | APKTW |

TABLE 6-continued

| | |
|---|---|
| 4074. | PKTWK |
| 4075. | KTWKE |
| 4076. | TWKEQ |
| 4077. | WKEQY |
| 4078. | KEQYL |
| 4079. | EQYLG |
| 4080. | QYLGW |
| 4081. | YLGWD |
| 4082. | LGWDL |
| 4083. | GWDLV |
| 4084. | WDLVQ |
| 4085. | DLVQS |
| 4086. | LVQSS |
| 4087. | VQSSV |
| 4088. | QSSVS |
| 4089. | SSVSA |
| 4090. | SVSAQ |
| 4091. | VSAQQ |
| 4092. | SAQQK |
| 4093. | AQQKL |
| 4094. | QQKLR |
| 4095. | QKLRT |
| 4096. | KLRTQ |
| 4097. | LRTQE |
| 4098. | RTQEN |
| 4099. | TQENP |
| 4100. | QENPS |
| 4101. | ENPST |
| 4102. | NPSTS |
| 4103. | PSTSF |
| 4104. | STSFC |
| 4105. | TSFCQ |
| 4106. | SFCQQ |
| 4107. | FCQQV |
| 4108. | CQQVL |
| 4109. | QQVLA |
| 4110. | QVLAD |
| 4111. | VLADF |
| 4112. | LADFI |
| 4113. | ADFIG |
| 4114. | DFIGG |
| 4115. | FIGGL |
| 4116. | IGGLN |
| 4117. | GGLND |
| 4118. | GLNDF |
| 4119. | LNDFH |
| 4120. | NDFHA |
| 4121. | DFHAG |
| 4122. | FHAGV |
| 4123. | HAGVT |
| 4124. | AGVTF |
| 4125. | GVTFF |
| 4126. | VTFFA |
| 4127. | TFFAI |
| 4128. | FFAIE |
| 4129. | FAIES |
| 4130. | AIESA |
| 4131. | IESAY |
| 4132. | ESAYL |
| 4133. | SAYLP |
| 4134. | AYLPY |
| 4135. | YLPYT |
| 4136. | LPYTV |
| 4137. | PYTVQ |
| 4138. | YTVQK |
| 4139. | TVQKS |
| 4140. | VQKSS |
| 4141. | QKSSD |
| 4142. | KSSDG |
| 4143. | SSDGR |
| 4144. | SDGRF |
| 4145. | DGRFY |
| 4146. | GRFYF |
| 4147. | RFYFV |
| 4148. | FYFVD |
| 4149. | YFVDI |
| 4150. | FVDIM |
| 4151. | VDIMT |
| 4152. | DIMTF |
| 4153. | IMTFS |
| 4154. | MTFSS |
| 4155. | TFSSE |
| 4156. | FSSEI |
| 4157. | SSEIR |
| 4158. | SEIRV |
| 4159. | EIRVG |
| 4160. | IRVGD |
| 4161. | RVGDE |
| 4162. | VGDEL |
| 4163. | GDELL |
| 4164. | DELLE |
| 4165. | ELLEV |
| 4166. | LLEVD |
| 4167. | LEVDG |
| 4168. | EVDGA |
| 4169. | VDGAP |
| 4170. | DGAPV |
| 4171. | GAPVQ |
| 4172. | APVQD |
| 4173. | PVQDV |
| 4174. | VQDVL |
| 4175. | QDVLA |
| 4176. | DVLAT |
| 4177. | VLATL |
| 4178. | LATLY |
| 4179. | ATLYG |
| 4180. | TLYGS |
| 4181. | LYGSN |
| 4182. | YGSNH |
| 4183. | GSNHK |
| 4184. | SNHKG |
| 4185. | NHKGT |
| 4186. | HKGTA |
| 4187. | KGTAA |
| 4188. | GTAAE |
| 4189. | TAAEE |
| 4190. | AAEES |
| 4191. | AEESA |
| 4192. | EESAA |
| 4193. | ESAAL |
| 4194. | SAALR |
| 4195. | AALRT |
| 4196. | ALRTL |
| 4197. | LRTLF |
| 4198. | RTLFS |
| 4199. | TLFSR |
| 4200. | LFSRM |
| 4201. | FSRMA |
| 4202. | SRMAS |
| 4203. | RMASL |
| 4204. | MASLG |
| 4205. | ASLGH |
| 4206. | SLGHK |
| 4207. | LGHKV |
| 4208. | GHKVP |
| 4209. | HKVPS |
| 4210. | KVPSG |
| 4211. | VPSGR |
| 4212. | PSGRT |
| 4213. | SGRTT |
| 4214. | GRTTL |
| 4215. | RTTLK |
| 4216. | TTLKI |
| 4217. | TLKIR |
| 4218. | LKIRR |
| 4219. | KIRRP |
| 4220. | IRRPF |
| 4221. | RRPFG |
| 4222. | RPFGT |
| 4223. | PFGTT |
| 4224. | FGTTR |
| 4225. | GTTRE |
| 4226. | TTREV |
| 4227. | TREVR |
| 4228. | REVRV |
| 4229. | EVRVK |
| 4230. | VRVKW |
| 4231. | RVKWR |
| 4232. | VKWRY |
| 4233. | KWRYV |

TABLE 6-continued

| | |
|---|---|
| 4234. | WRYVP |
| 4235. | RYVPE |
| 4236. | YVPEG |
| 4237. | VPEGV |
| 4238. | PEGVG |
| 4239. | EGVGD |
| 4240. | GVGDL |
| 4241. | VGDLA |
| 4242. | GDLAT |
| 4243. | DLATI |
| 4244. | LATIA |
| 4245. | ATIAP |
| 4246. | TIAPS |
| 4247. | IAPSI |
| 4248. | APSIR |
| 4249. | PSIRA |
| 4250. | SIRAP |
| 4251. | IRAPQ |
| 4252. | RAPQL |
| 4253. | APQLQ |
| 4254. | PQLQK |
| 4255. | QLQKS |
| 4256. | LQKSM |
| 4257. | QKSMR |
| 4258. | KSMRS |
| 4259. | SMRSF |
| 4260. | MRSFF |
| 4261. | RSFFP |
| 4262. | SFFPK |
| 4263. | FFPKK |
| 4264. | FPKKD |
| 4265. | PKKDD |
| 4266. | KKDDA |
| 4267. | KDDAF |
| 4268. | DDAFH |
| 4269. | DAFHR |
| 4270. | AFHRS |
| 4271. | FHRSS |
| 4272. | HRSSS |
| 4273. | RSSSL |
| 4274. | SSSLF |
| 4275. | SSLFY |
| 4276. | SLFYS |
| 4277. | LFYSP |
| 4278. | FYSPM |
| 4279. | YSPMV |
| 4280. | SPMVP |
| 4281. | PMVPH |
| 4282. | MVPHF |
| 4283. | VPHFW |
| 4284. | PHFWA |
| 4285. | HFWAE |
| 4286. | FWAEL |
| 4287. | WAELR |
| 4288. | AELRN |
| 4289. | ELRNH |
| 4290. | LRNHY |
| 4291. | RNHYA |
| 4292. | NHYAT |
| 4293. | HYATS |
| 4294. | YATSG |
| 4295. | ATSGL |
| 4296. | TSGLK |
| 4297. | SGLKS |
| 4298. | GLKSG |
| 4299. | LKSGY |
| 4300. | KSGYN |
| 4301. | SGYNI |
| 4302. | GYNIG |
| 4303. | YNIGS |
| 4304. | NIGST |
| 4305. | IGSTD |
| 4306. | GSTDG |
| 4307. | STDGF |
| 4308. | TDGFL |
| 4309. | DGFLP |
| 4310. | GFLPV |
| 4311. | FLPVI |
| 4312. | LPVIG |
| 4313. | PVIGP |

TABLE 6-continued

| | |
|---|---|
| 4314. | VIGPV |
| 4315. | IGPVI |
| 4316. | GPVIW |
| 4317. | PVIWE |
| 4318. | VIWES |
| 4319. | IWESE |
| 4320. | WESEG |
| 4321. | ESEGL |
| 4322. | SEGLF |
| 4323. | EGLFR |
| 4324. | GLFRA |
| 4325. | LFRAY |
| 4326. | FRAYI |
| 4327. | RAYIS |
| 4328. | AYISS |
| 4329. | YISSV |
| 4330. | ISSVT |
| 4331. | SSVTD |
| 4332. | SVTDG |
| 4333. | VTDGD |
| 4334. | TDGDG |
| 4335. | DGDGK |
| 4336. | GDGKS |
| 4337. | DGKSH |
| 4338. | GKSHK |
| 4339. | KSHKV |
| 4340. | SHKVG |
| 4341. | HKVGF |
| 4342. | KVGFL |
| 4343. | VGFLR |
| 4344. | GFLRI |
| 4345. | FLRIP |
| 4346. | LRIPT |
| 4347. | RIPTY |
| 4348. | IPTYS |
| 4349. | PTYSW |
| 4350. | TYSWQ |
| 4351. | YSWQD |
| 4352. | SWQDM |
| 4353. | WQDME |
| 4354. | QDMED |
| 4355. | DMEDF |
| 4356. | MEDFD |
| 4357. | EDFDP |
| 4358. | DFDPS |
| 4359. | FDPSG |
| 4360. | DPSGP |
| 4361. | PSGPP |
| 4362. | SGPPP |
| 4363. | GPPPW |
| 4364. | PPPWE |
| 4365. | PPWEE |
| 4366. | PWEEF |
| 4367. | WEEFA |
| 4368. | EEFAK |
| 4369. | EFAKI |
| 4370. | FAKII |
| 4371. | AKIIQ |
| 4372. | KIIQV |
| 4373. | IIQVF |
| 4374. | IQVFS |
| 4375. | QVFSS |
| 4376. | VFSSN |
| 4377. | FSSNT |
| 4378. | SSNTE |
| 4379. | SNTEA |
| 4380. | NTEAL |
| 4381. | TEALI |
| 4382. | EALII |
| 4383. | ALIID |
| 4384. | LIIDQ |
| 4385. | IIDQT |
| 4386. | IDQTN |
| 4387. | DQTNN |
| 4388. | QTNNP |
| 4389. | TNNPG |
| 4390. | NNPGG |
| 4391. | NPGGS |
| 4392. | PGGSV |
| 4393. | GGSVL |

TABLE 6-continued

| | | |
|---|---|---|
| 4394. | GSVLY | |
| 4395. | SVLYL | |
| 4396. | VLYLY | |
| 4397. | LYLYA | |
| 4398. | YLYAL | |
| 4399. | LYALL | |
| 4400. | YALLS | |
| 4401. | ALLSM | |
| 4402. | LLSML | |
| 4403. | LSMLT | |
| 4404. | SMLTD | |
| 4405. | MLTDR | |
| 4406. | LTDRP | |
| 4407. | TDRPL | |
| 4408. | DRPLE | |
| 4409. | RPLEL | |
| 4410. | PLELP | |
| 4411. | LELPK | |
| 4412. | ELPKH | |
| 4413. | LPKHR | |
| 4414. | PKHRM | |
| 4415. | KHRMI | |
| 4416. | HRMIL | |
| 4417. | RMILT | |
| 4418. | MILTQ | |
| 4419. | ILTQD | |
| 4420. | LTQDE | |
| 4421. | TQDEV | |
| 4422. | QDEVV | |
| 4423. | DEVVD | |
| 4424. | EVVDA | |
| 4425. | VVDAL | |
| 4426. | VDALD | |
| 4427. | DALDW | |
| 4428. | ALDWL | |
| 4429. | LDWLT | |
| 4430. | DWLTL | |
| 4431. | WLTLL | |
| 4432. | LTLLE | |
| 4433. | TLLEN | |
| 4434. | LLENV | |
| 4435. | LENVD | |
| 4436. | ENVDT | |
| 4437. | NVDTN | |
| 4438. | VDTNV | |
| 4439. | DTNVE | |
| 4440. | TNVES | |
| 4441. | NVESR | |
| 4442. | VESRL | |
| 4443. | ESRLA | |
| 4444. | SRLAL | |
| 4445. | RLALG | |
| 4446. | LALGD | |
| 4447. | ALGDN | |
| 4448. | LGDNM | |
| 4449. | GDNME | |
| 4450. | DNMEG | |
| 4451. | NMEGY | |
| 4452. | MEGYT | |
| 4453. | EGYTV | |
| 4454. | GYTVD | |
| 4455. | YTVDL | |
| 4456. | TVDLQ | |
| 4457. | VDLQV | |
| 4458. | DLQVA | |
| 4459. | LQVAE | |
| 4460. | QVAEY | |
| 4461. | VAEYL | |
| 4462. | AEYLK | |
| 4463. | EYLKS | |
| 4464. | YLKSF | |
| 4465. | LKSFG | |
| 4466. | KSFGR | |
| 4467. | SFGRQ | |
| 4468. | FGRQV | |
| 4469. | GRQVL | |
| 4470. | RQVLN | |
| 4471. | QVLNC | |
| 4472. | VLNCW | |
| 4473. | LNCWS | |
| 4474. | NCWSK | |
| 4475. | CWSKG | |
| 4476. | WSKGD | |
| 4477. | SKGDI | |
| 4478. | KGDIE | |
| 4479. | GDIEL | |
| 4480. | DIELS | |
| 4481. | IELST | |
| 4482. | ELSTP | |
| 4483. | LSTPI | |
| 4484. | STPIP | |
| 4485. | TPIPL | |
| 4486. | PIPLF | |
| 4487. | IPLFG | |
| 4488. | PLFGF | |
| 4489. | LFGFE | |
| 4490. | FGFEK | |
| 4491. | GFEKI | |
| 4492. | FEKIH | |
| 4493. | EKIHP | |
| 4494. | KIHPH | |
| 4495. | IHPHP | |
| 4496. | HPHPR | |
| 4497. | PHPRV | |
| 4498. | HPRVQ | |
| 4499. | PRVQY | |
| 4500. | RVQYS | |
| 4501. | VQYSK | |
| 4502. | QYSKP | |
| 4503. | YSKPI | |
| 4504. | SKPIC | |
| 4505. | KPICV | |
| 4506. | PICVL | |
| 4507. | ICVLI | |
| 4508. | CVLIN | |
| 4509. | VLINE | |
| 4510. | LINEQ | |
| 4511. | INEQD | |
| 4512. | NEQDF | |
| 4513. | EQDFS | |
| 4514. | QDFSC | |
| 4515. | DFSCA | |
| 4516. | FSCAD | |
| 4517. | SCADF | |
| 4518. | CADFF | |
| 4519. | ADFFP | |
| 4520. | DFFPV | |
| 4521. | FFPVV | |
| 4522. | FPVVL | |
| 4523. | PVVLK | |
| 4524. | VVLKD | |
| 4525. | VLKDN | |
| 4526. | LKDND | |
| 4527. | KDNDR | |
| 4528. | DNDRA | |
| 4529. | NDRAL | |
| 4530. | DRALI | |
| 4531. | RALIV | |
| 4532. | ALIVG | |
| 4533. | LIVGT | |
| 4534. | IVGTR | |
| 4535. | VGTRT | |
| 4536. | GTRTA | |
| 4537. | TRTAG | |
| 4538. | RTAGA | |
| 4539. | TAGAG | |
| 4540. | AGAGG | |
| 4541. | GAGGF | |
| 4542. | AGGFV | |
| 4543. | GGFVF | |
| 4544. | GFVFN | |
| 4545. | FVFNV | |
| 4546. | VFNVQ | |
| 4547. | FNVQF | |
| 4548. | NVQFP | |
| 4549. | VQFPN | |
| 4550. | QFPNR | |
| 4551. | FPNRT | |
| 4552. | PNRTG | |
| 4553. | NRTGI | |

TABLE 6-continued

| | |
|---|---|
| 4554. | RTGIK |
| 4555. | TGIKT |
| 4556. | GIKTC |
| 4557. | IKTCS |
| 4558. | KTCSL |
| 4559. | TCSLT |
| 4560. | CSLTG |
| 4561. | SLTGS |
| 4562. | LTGSL |
| 4563. | TGSLA |
| 4564. | GSLAV |
| 4565. | SLAVR |
| 4566. | LAVRE |
| 4567. | AVREH |
| 4568. | VREHG |
| 4569. | REHGA |
| 4570. | EHGAF |
| 4571. | HGAFI |
| 4572. | GAFIE |
| 4573. | AFIEN |
| 4574. | FIENI |
| 4575. | IENIG |
| 4576. | ENIGV |
| 4577. | NIGVE |
| 4578. | IGVEP |
| 4579. | GVEPH |
| 4580. | VEPHI |
| 4581. | EPHID |
| 4582. | PHIDL |
| 4583. | HIDLP |
| 4584. | IDLPF |
| 4585. | DLPFT |
| 4586. | LPFTA |
| 4587. | PFTAN |
| 4588. | FTAND |
| 4589. | TANDI |
| 4590. | ANDIR |
| 4591. | NDIRY |
| 4592. | DIRYK |
| 4593. | IRYKG |
| 4594. | RYKGY |
| 4595. | YKGYS |
| 4596. | KGYSE |
| 4597. | GYSEY |
| 4598. | YSEYL |
| 4599. | SEYLD |
| 4600. | EYLDK |
| 4601. | YLDKV |
| 4602. | LDKVK |
| 4603. | DKVKK |
| 4604. | KVKKL |
| 4605. | VKKLV |
| 4606. | KKLVC |
| 4607. | KLVCQ |
| 4608. | LVCQL |
| 4609. | VCQLI |
| 4610. | CQLIN |
| 4611. | QLINN |
| 4612. | LINND |
| 4613. | INNDG |
| 4614. | NNDGT |
| 4615. | NDGTI |
| 4616. | DGTII |
| 4617. | GTIIL |
| 4618. | TIILA |
| 4619. | IILAE |
| 4620. | ILAED |
| 4621. | LAEDG |
| 4622. | AEDGS |
| 4623. | EDGSF |

5-mer peptides of Pgp3 (plasmid-encoded secretion protein, total of 264 amino acids), ACCESSION# ADI51551.1, GI: 297749006 (SEQ ID NOS: 4624-4883)

| | |
|---|---|
| 4624. | MGNSG |
| 4625. | GNSGF |
| 4626. | NSGFY |
| 4627. | SGFYL |
| 4628. | GFYLY |
| 4629. | FYLYN |
| 4630. | YLYNT |
| 4631. | LYNTE |
| 4632. | YNTEN |
| 4633. | NTENC |
| 4634. | TENCV |
| 4635. | ENCVF |
| 4636. | NCVFA |
| 4637. | CVFAD |
| 4638. | VFADN |
| 4639. | FADNI |
| 4640. | ADNIK |
| 4641. | DNIKV |
| 4642. | NIKVG |
| 4643. | IKVGQ |
| 4644. | KVGQM |
| 4645. | VGQMT |
| 4646. | GQMTE |
| 4647. | QMTEP |
| 4648. | MTEPL |
| 4649. | TEPLK |
| 4650. | EPLKD |
| 4651. | PLKDQ |
| 4652. | LKDQQ |
| 4653. | KDQQI |
| 4654. | DQQII |
| 4655. | QQIIL |
| 4656. | QIILG |
| 4657. | IILGT |
| 4658. | ILGTK |
| 4659. | LGTKS |
| 4660. | GTKST |
| 4661. | TKSTP |
| 4662. | KSTPV |
| 4663. | STPVA |
| 4664. | TPVAA |
| 4665. | PVAAK |
| 4666. | VAAKM |
| 4667. | AAKMT |
| 4668. | AKMTA |
| 4669. | KMTAS |
| 4670. | MTASD |
| 4671. | TASDG |
| 4672. | ASDGI |
| 4673. | SDGIS |
| 4674. | DGISL |
| 4675. | GISLT |
| 4676. | ISLTV |
| 4677. | SLTVS |
| 4678. | LTVSN |
| 4679. | TVSNN |
| 4680. | VSNNS |
| 4681. | SNNSS |
| 4682. | NNSST |
| 4683. | NSSTN |
| 4684. | SSTNA |
| 4685. | STNAS |
| 4686. | TNASI |
| 4687. | NASIT |
| 4688. | ASITI |
| 4689. | SITIG |
| 4690. | ITIGL |
| 4691. | TIGLD |
| 4692. | IGLDA |
| 4693. | GLDAE |
| 4694. | LDAEK |
| 4695. | DAEKA |
| 4696. | AEKAY |
| 4697. | EKAYQ |
| 4698. | KAYQL |
| 4699. | AYQLI |
| 4700. | YQLIL |
| 4701. | QLILE |
| 4702. | LILEK |
| 4703. | ILEKL |
| 4704. | LEKLG |
| 4705. | EKLGN |
| 4706. | KLGNQ |
| 4707. | LGNQI |
| 4708. | GNQIL |

TABLE 6-continued

| | |
|---|---|
| 4709. | NQILD |
| 4710. | QILDG |
| 4711. | ILDGI |
| 4712. | LDGIA |
| 4713. | DGIAD |
| 4714. | GIADT |
| 4715. | IADTI |
| 4716. | ADTIV |
| 4717. | DTIVD |
| 4718. | TIVDS |
| 4719. | IVDST |
| 4720. | VDSTV |
| 4721. | DSTVQ |
| 4722. | STVQD |
| 4723. | TVQDI |
| 4724. | VQDIL |
| 4725. | QDILD |
| 4726. | DILDK |
| 4727. | ILDKI |
| 4728. | LDKIT |
| 4729. | DKITT |
| 4730. | KITTD |
| 4731. | ITTDP |
| 4732. | TTDPS |
| 4733. | TDPSL |
| 4734. | DPSLG |
| 4735. | PSLGL |
| 4736. | SLGLL |
| 4737. | LGLLK |
| 4738. | GLLKA |
| 4739. | LLKAF |
| 4740. | LKAFN |
| 4741. | KAFNN |
| 4742. | AFNNF |
| 4743. | FNNFP |
| 4744. | NNFPI |
| 4745. | NFPIT |
| 4746. | FPITN |
| 4747. | PITNK |
| 4748. | ITNKI |
| 4749. | TNKIQ |
| 4750. | NKIQC |
| 4751. | KIQCN |
| 4752. | IQCNG |
| 4753. | QCNGL |
| 4754. | CNGLF |
| 4755. | NGLFT |
| 4756. | GLFTP |
| 4757. | LFTPS |
| 4758. | FTPSN |
| 4759. | TPSNI |
| 4760. | PSNIE |
| 4761. | SNIET |
| 4762. | NIETL |
| 4763. | IETLL |
| 4764. | ETLLG |
| 4765. | TLLGG |
| 4766. | LLGGT |
| 4767. | LGGTE |
| 4768. | GGTEI |
| 4769. | GTEIG |
| 4770. | TEIGK |
| 4771. | EIGKF |
| 4772. | IGKFT |
| 4773. | GKFTV |
| 4774. | KFTVT |
| 4775. | FTVTP |
| 4776. | TVTPK |
| 4777. | VTPKS |
| 4778. | TPKSS |
| 4779. | PKSSG |
| 4780. | KSSGS |
| 4781. | SSGSM |
| 4782. | SGSMF |
| 4783. | GSMFL |
| 4784. | SMFLV |
| 4785. | MFLVS |
| 4786. | FLVSA |
| 4787. | LVSAD |
| 4788. | VSADI |

TABLE 6-continued

| | |
|---|---|
| 4789. | SADII |
| 4790. | ADIIA |
| 4791. | DIIAS |
| 4792. | IIASR |
| 4793. | IASRM |
| 4794. | ASRME |
| 4795. | SRMEG |
| 4796. | RMEGG |
| 4797. | MEGGV |
| 4798. | EGGVV |
| 4799. | GGVVL |
| 4800. | GVVLA |
| 4801. | VVLAL |
| 4802. | VLALV |
| 4803. | LALVR |
| 4804. | ALVRE |
| 4805. | LVREG |
| 4806. | VREGD |
| 4807. | REGDS |
| 4808. | EGDSK |
| 4809. | GDSKP |
| 4810. | DSKPC |
| 4811. | SKPCA |
| 4812. | KPCAI |
| 4813. | PCAIS |
| 4814. | CAISY |
| 4815. | AISYG |
| 4816. | ISYGY |
| 4817. | SYGYS |
| 4818. | YGYSS |
| 4819. | GYSSG |
| 4820. | YSSGV |
| 4821. | SSGVP |
| 4822. | SGVPN |
| 4823. | GVPNL |
| 4824. | VPNLC |
| 4825. | PNLCS |
| 4826. | NLCSL |
| 4827. | LCSLR |
| 4828. | CSLRT |
| 4829. | SLRTS |
| 4830. | LRTSI |
| 4831. | RTSIT |
| 4832. | TSITN |
| 4833. | SITNT |
| 4834. | ITNTG |
| 4835. | TNTGL |
| 4836. | NTGLT |
| 4837. | TGLTP |
| 4838. | GLTPT |
| 4839. | LTPTT |
| 4840. | TPTTY |
| 4841. | PTTYS |
| 4842. | TTYSL |
| 4843. | TYSLR |
| 4844. | YSLRV |
| 4845. | SLRVG |
| 4846. | LRVGG |
| 4847. | RVGGL |
| 4848. | VGGLE |
| 4849. | GGLES |
| 4850. | GLESG |
| 4851. | LESGV |
| 4852. | ESGVV |
| 4853. | SGVVW |
| 4854. | GVVWV |
| 4855. | VVWVN |
| 4856. | VWVNA |
| 4857. | WVNAL |
| 4858. | VNALS |
| 4859. | NALSN |
| 4860. | ALSNG |
| 4861. | LSNGN |
| 4862. | SNGND |
| 4863. | NGNDI |
| 4864. | GNDIL |
| 4865. | NDILG |
| 4866. | DILGI |
| 4867. | ILGIT |
| 4868. | LGITN |

TABLE 6-continued

| | |
|---|---|
| 4869. | GITNT |
| 4870. | ITNTS |
| 4871. | TNTSN |
| 4872. | NTSNV |
| 4873. | TSNVS |
| 4874. | SNVSF |
| 4875. | NVSFL |
| 4876. | VSFLE |
| 4877. | SFLEV |
| 4878. | FLEVI |
| 4879. | LEVIP |
| 4880. | EVIPQ |
| 4881. | VIPQT |
| 4882. | IPQTN |
| 4883. | PQTNA |

5-mer peptides of CT823 (cHtrA, 497 amino acids), ACCESSION# NP 220344.1, GI: 15605558 (SEQ ID NOS: 4884-5376)

| | |
|---|---|
| 4884. | MMKRL |
| 4885. | MKRLL |
| 4886. | KRLLC |
| 4887. | RLLCV |
| 4888. | LLCVL |
| 4889. | LCVLL |
| 4890. | CVLLS |
| 4891. | VLLST |
| 4892. | LLSTS |
| 4893. | LSTSV |
| 4894. | STSVF |
| 4895. | TSVFS |
| 4896. | SVFSS |
| 4897. | VFSSP |
| 4898. | FSSPM |
| 4899. | SSPML |
| 4900. | SPMLG |
| 4901. | PMLGY |
| 4902. | MLGYS |
| 4903. | LGYSA |
| 4904. | GYSAS |
| 4905. | YSASK |
| 4906. | SASKK |
| 4907. | ASKKD |
| 4908. | SKKDS |
| 4909. | KKDSK |
| 4910. | KDSKA |
| 4911. | DSKAD |
| 4912. | SKADI |
| 4913. | KADIC |
| 4914. | ADICL |
| 4915. | DICLA |
| 4916. | ICLAV |
| 4917. | CLAVS |
| 4918. | LAVSS |
| 4919. | AVSSG |
| 4920. | VSSGD |
| 4921. | SSGDQ |
| 4922. | SGDQE |
| 4923. | GDQEV |
| 4924. | DQEVS |
| 4925. | QEVSQ |
| 4926. | EVSQE |
| 4927. | VSQED |
| 4928. | SQEDL |
| 4929. | QEDLL |
| 4930. | EDLLK |
| 4931. | DLLKE |
| 4932. | LLKEV |
| 4933. | LKEVS |
| 4934. | KEVSR |
| 4935. | EVSRG |
| 4936. | VSRGF |
| 4937. | SRGFS |
| 4938. | RGFSR |
| 4939. | GFSRV |
| 4940. | FSRVA |
| 4941. | SRVAA |
| 4942. | RVAAK |
| 4943. | VAAKA |

TABLE 6-continued

| | |
|---|---|
| 4944. | AAKAT |
| 4945. | AKATP |
| 4946. | KATPG |
| 4947. | ATPGV |
| 4948. | TPGVV |
| 4949. | PGVVY |
| 4950. | GVVYI |
| 4951. | VVYIE |
| 4952. | VYIEN |
| 4953. | YIENF |
| 4954. | IENFP |
| 4955. | ENFPK |
| 4956. | NFPKT |
| 4957. | FPKTG |
| 4958. | PKTGN |
| 4959. | KTGNQ |
| 4960. | TGNQA |
| 4961. | GNQAI |
| 4962. | NQAIA |
| 4963. | QAIAS |
| 4964. | AIASP |
| 4965. | IASPG |
| 4966. | ASPGN |
| 4967. | SPGNK |
| 4968. | PGNKR |
| 4969. | GNKRG |
| 4970. | NKRGF |
| 4971. | KRGFQ |
| 4972. | RGFQE |
| 4973. | GFQEN |
| 4974. | FQENP |
| 4975. | QENPF |
| 4976. | ENPFD |
| 4977. | NPFDY |
| 4978. | PFDYF |
| 4979. | FDYFN |
| 4980. | DYFND |
| 4981. | YFNDE |
| 4982. | FNDEF |
| 4983. | NDEFF |
| 4984. | DEFFN |
| 4985. | EFFNR |
| 4986. | FFNRF |
| 4987. | FNRFF |
| 4988. | NRFFG |
| 4989. | RFFGL |
| 4990. | FFGLP |
| 4991. | FGLPS |
| 4992. | GLPSH |
| 4993. | LPSHR |
| 4994. | PSHRE |
| 4995. | SHREQ |
| 4996. | HREQQ |
| 4997. | REQQR |
| 4998. | EQQRP |
| 4999. | QQRPQ |
| 5000. | QRPQQ |
| 5001. | RPQQR |
| 5002. | PQQRD |
| 5003. | QQRDA |
| 5004. | QRDAV |
| 5005. | RDAVR |
| 5006. | DAVRG |
| 5007. | AVRGT |
| 5008. | VRGTG |
| 5009. | RGTGF |
| 5010. | GTGFI |
| 5011. | TGFIV |
| 5012. | GFIVS |
| 5013. | FIVSE |
| 5014. | IVSED |
| 5015. | VSEDG |
| 5016. | SEDGY |
| 5017. | EDGYV |
| 5018. | DGYVV |
| 5019. | GYVVT |
| 5020. | YVVTN |
| 5021. | VVTNH |
| 5022. | VTNHH |
| 5023. | TNHHV |

TABLE 6-continued

| | | |
|---|---|---|
| 5024. | NHHVV | |
| 5025. | HHVVE | |
| 5026. | HVVED | |
| 5027. | VVEDA | |
| 5028. | VEDAG | |
| 5029. | EDAGK | |
| 5030. | DAGKI | |
| 5031. | AGKIH | |
| 5032. | GKIHV | |
| 5033. | KIHVT | |
| 5034. | IHVTL | |
| 5035. | HVTLH | |
| 5036. | VTLHD | |
| 5037. | TLHDG | |
| 5038. | LHDGQ | |
| 5039. | HDGQK | |
| 5040. | DGQKY | |
| 5041. | GQKYT | |
| 5042. | QKYTA | |
| 5043. | KYTAK | |
| 5044. | YTAKI | |
| 5045. | TAKIV | |
| 5046. | AKIVG | |
| 5047. | KIVGL | |
| 5048. | IVGLD | |
| 5049. | VGLDP | |
| 5050. | GLDPK | |
| 5051. | LDPKT | |
| 5052. | DPKTD | |
| 5053. | PKTDL | |
| 5054. | KTDLA | |
| 5055. | TDLAV | |
| 5056. | DLAVI | |
| 5057. | LAVIK | |
| 5058. | AVIKI | |
| 5059. | VIKIQ | |
| 5060. | IKIQA | |
| 5061. | KIQAE | |
| 5062. | IQAEK | |
| 5063. | QAEKL | |
| 5064. | AEKLP | |
| 5065. | EKLPF | |
| 5066. | KLPFL | |
| 5067. | LPFLT | |
| 5068. | PFLTF | |
| 5069. | FLTFG | |
| 5070. | LTFGN | |
| 5071. | TFGNS | |
| 5072. | FGNSD | |
| 5073. | GNSDQ | |
| 5074. | NSDQL | |
| 5075. | SDQLQ | |
| 5076. | DQLQI | |
| 5077. | QLQIG | |
| 5078. | LQIGD | |
| 5079. | QIGDW | |
| 5080. | IGDWA | |
| 5081. | GDWAI | |
| 5082. | DWAIA | |
| 5083. | WAIAI | |
| 5084. | AIAIG | |
| 5085. | IAIGN | |
| 5086. | AIGNP | |
| 5087. | IGNPF | |
| 5088. | GNPFG | |
| 5089. | NPFGL | |
| 5090. | PFGLQ | |
| 5091. | FGLQA | |
| 5092. | GLQAT | |
| 5093. | LQATV | |
| 5094. | QATVT | |
| 5095. | ATVTV | |
| 5096. | TVTVG | |
| 5097. | VTVGV | |
| 5098. | TVGVI | |
| 5099. | VGVIS | |
| 5100. | GVISA | |
| 5101. | VISAK | |
| 5102. | ISAKG | |
| 5103. | SAKGR | |
| 5104. | AKGRN | |
| 5105. | KGRNQ | |
| 5106. | GRNQL | |
| 5107. | RNQLH | |
| 5108. | NQLHI | |
| 5109. | QLHIV | |
| 5110. | LHIVD | |
| 5111. | HIVDF | |
| 5112. | IVDFE | |
| 5113. | VDFED | |
| 5114. | DFEDF | |
| 5115. | FEDFI | |
| 5116. | EDFIQ | |
| 5117. | DFIQT | |
| 5118. | FIQTD | |
| 5119. | IQTDA | |
| 5120. | QTDAA | |
| 5121. | TDAAI | |
| 5122. | DAAIN | |
| 5123. | AAINP | |
| 5124. | AINPG | |
| 5125. | INPGN | |
| 5126. | NPGNS | |
| 5127. | PGNSG | |
| 5128. | GNSGG | |
| 5129. | NSGGP | |
| 5130. | SGGPL | |
| 5131. | GGPLL | |
| 5132. | GPLLN | |
| 5133. | PLLNI | |
| 5134. | LLNIN | |
| 5135. | LNING | |
| 5136. | NINGQ | |
| 5137. | INGQV | |
| 5138. | NGQVI | |
| 5139. | GQVIG | |
| 5140. | QVIGV | |
| 5141. | VIGVN | |
| 5142. | IGVNT | |
| 5143. | GVNTA | |
| 5144. | VNTAI | |
| 5145. | NTAIV | |
| 5146. | TAIVS | |
| 5147. | AIVSG | |
| 5148. | IVSGS | |
| 5149. | VSGSG | |
| 5150. | SGSGG | |
| 5151. | GSGGY | |
| 5152. | SGGYI | |
| 5153. | GGYIG | |
| 5154. | GYIGI | |
| 5155. | YIGIG | |
| 5156. | IGIGF | |
| 5157. | GIGFA | |
| 5158. | IGFAI | |
| 5159. | GFAIP | |
| 5160. | FAIPS | |
| 5161. | AIPSL | |
| 5162. | IPSLM | |
| 5163. | PSLMA | |
| 5164. | SLMAK | |
| 5165. | LMAKR | |
| 5166. | MAKRV | |
| 5167. | AKRVI | |
| 5168. | KRVID | |
| 5169. | RVIDQ | |
| 5170. | VIDQL | |
| 5171. | IDQLI | |
| 5172. | DQLIS | |
| 5173. | QLISD | |
| 5174. | LISDG | |
| 5175. |ISDGQ | |
| 5176. | SDGQV | |
| 5177. | DGQVT | |
| 5178. | GQVTR | |
| 5179. | QVTRG | |
| 5180. | VTRGF | |
| 5181. | TRGFL | |
| 5182. | RGFLG | |
| 5183. | GFLGV | |

TABLE 6-continued

| | |
|---|---|
| 5184. | FLGVT |
| 5185. | LGVTL |
| 5186. | GVTLQ |
| 5187. | VTLQP |
| 5188. | TLQPI |
| 5189. | LQPID |
| 5190. | QPIDS |
| 5191. | PIDSE |
| 5192. | IDSEL |
| 5193. | DSELA |
| 5194. | SELAT |
| 5195. | ELATC |
| 5196. | LATCY |
| 5197. | ATCYK |
| 5198. | TCYKL |
| 5199. | CYKLE |
| 5200. | YKLEK |
| 5201. | KLEKV |
| 5202. | LEKVY |
| 5203. | EKVYG |
| 5204. | KVYGA |
| 5205. | VYGAL |
| 5206. | YGALV |
| 5207. | GALVT |
| 5208. | ALVTD |
| 5209. | LVTDV |
| 5210. | VTDVV |
| 5211. | TDVVK |
| 5212. | DVVKG |
| 5213. | VVKGS |
| 5214. | VKGSP |
| 5215. | KGSPA |
| 5216. | GSPAE |
| 5217. | SPAEK |
| 5218. | PAEKA |
| 5219. | AEKAG |
| 5220. | EKAGL |
| 5221. | KAGLR |
| 5222. | AGLRQ |
| 5223. | GLRQE |
| 5224. | LRQED |
| 5225. | RQEDV |
| 5226. | QEDVI |
| 5227. | EDVIV |
| 5228. | DVIVA |
| 5229. | VIVAY |
| 5230. | IVAYN |
| 5231. | VAYNG |
| 5232. | AYNGK |
| 5233. | YNGKE |
| 5234. | NGKEV |
| 5235. | GKEVE |
| 5236. | KEVES |
| 5237. | EVESL |
| 5238. | VESLS |
| 5239. | ESLSA |
| 5240. | SLSAL |
| 5241. | LSALR |
| 5242. | SALRN |
| 5243. | ALRNA |
| 5244. | LRNAI |
| 5245. | RNAIS |
| 5246. | NAISL |
| 5247. | AISLM |
| 5248. | ISLMM |
| 5249. | SLMMP |
| 5250. | LMMPG |
| 5251. | MMPGT |
| 5252. | MPGTR |
| 5253. | PGTRV |
| 5254. | GTRVV |
| 5255. | TRVVL |
| 5256. | RVVLK |
| 5257. | VVLKI |
| 5258. | VLKIV |
| 5259. | LKIVR |
| 5260. | KIVRE |
| 5261. | IVREG |
| 5262. | VREGK |
| 5263. | REGKT |
| 5264. | EGKTI |
| 5265. | GKTIE |
| 5266. | KTIEI |
| 5267. | TIEIP |
| 5268. | IEIPV |
| 5269. | EIPVT |
| 5270. | IPVTV |
| 5271. | PVTVT |
| 5272. | VTVTQ |
| 5273. | TVTQI |
| 5274. | VTQIP |
| 5275. | TQIPT |
| 5276. | QIPTE |
| 5277. | IPTED |
| 5278. | PTEDG |
| 5279. | TEDGV |
| 5280. | EDGVS |
| 5281. | DGVSA |
| 5282. | GVSAL |
| 5283. | VSALQ |
| 5284. | SALQK |
| 5285. | ALQKM |
| 5286. | LQKMG |
| 5287. | QKMGV |
| 5288. | KMGVR |
| 5289. | MGVRV |
| 5290. | GVRVQ |
| 5291. | VRVQN |
| 5292. | RVQNI |
| 5293. | VQNIT |
| 5294. | QNITP |
| 5295. | NITPE |
| 5296. | ITPEI |
| 5297. | TPEIC |
| 5298. | PEICK |
| 5299. | EICKK |
| 5300. | ICKKL |
| 5301. | CKKLG |
| 5302. | KKLGL |
| 5303. | KLGLA |
| 5304. | LGLAA |
| 5305. | GLAAD |
| 5306. | LAADT |
| 5307. | AADTR |
| 5308. | ADTRG |
| 5309. | DTRGI |
| 5310. | TRGIL |
| 5311. | RGILV |
| 5312. | GILVV |
| 5313. | ILVVA |
| 5314. | LVVAV |
| 5315. | VVAVE |
| 5316. | VAVEA |
| 5317. | AVEAG |
| 5318. | VEAGS |
| 5319. | EAGSP |
| 5320. | AGSPA |
| 5321. | GSPAA |
| 5322. | SPAAS |
| 5323. | PAASA |
| 5324. | AASAG |
| 5325. | ASAGV |
| 5326. | SAGVA |
| 5327. | AGVAP |
| 5328. | GVAPG |
| 5329. | VAPGQ |
| 5330. | APGQL |
| 5331. | PGQLI |
| 5332. | GQLIL |
| 5333. | QLILA |
| 5334. | LILAV |
| 5335. | ILAVN |
| 5336. | LAVNR |
| 5337. | AVNRQ |
| 5338. | VNRQR |
| 5339. | NRQRV |
| 5340. | RQRVA |
| 5341. | QRVAS |
| 5342. | RVASV |
| 5343. | VASVE |

TABLE 6-continued

| | |
|---|---|
| 5344. | ASVEE |
| 5345. | SVEEL |
| 5346. | VEELN |
| 5347. | EELNQ |
| 5348. | ELNQV |
| 5349. | LNQVL |
| 5350. | NQVLK |
| 5351. | QVLKN |
| 5352. | VLKNS |
| 5353. | LKNSK |
| 5354. | KNSKG |
| 5355. | NSKGE |
| 5356. | SKGEN |
| 5357. | KGENV |
| 5358. | GENVL |
| 5359. | ENVLL |
| 5360. | NVLLM |
| 5361. | VLLMV |
| 5362. | LLMVS |
| 5363. | LMVSQ |
| 5364. | MVSQG |
| 5365. | VSQGD |
| 5366. | SQGDV |
| 5367. | QGDVV |
| 5368. | GDVVR |
| 5369. | DVVRF |
| 5370. | VVRFI |
| 5371. | VRFIV |
| 5372. | RFIVL |
| 5373. | FIVLK |
| 5374. | IVLKS |
| 5375. | VLKSD |
| 5376. | LKSDE |

5-mer peptides of CT681 (MOMP, 393 amino acids), ACCESSION# NP 220200.1, GI: 15605414 (SEQ ID NOS: 5377-5765)

| | |
|---|---|
| 5377. | MKKLL |
| 5378. | KKLLK |
| 5379. | KLLKS |
| 5380. | LLKSV |
| 5381. | LKSVL |
| 5382. | KSVLV |
| 5383. | SVLVF |
| 5384. | VLVFA |
| 5385. | LVFAA |
| 5386. | VFAAL |
| 5387. | FAALS |
| 5388. | AALSS |
| 5389. | ALSSA |
| 5390. | LSSAS |
| 5391. | SSASS |
| 5392. | SASSL |
| 5393. | ASSLQ |
| 5394. | SSLQA |
| 5395. | SLQAL |
| 5396. | LQALP |
| 5397. | QALPV |
| 5398. | ALPVG |
| 5399. | LPVGN |
| 5400. | PVGNP |
| 5401. | VGNPA |
| 5402. | GNPAE |
| 5403. | NPAEP |
| 5404. | PAEPS |
| 5405. | AEPSL |
| 5406. | EPSLM |
| 5407. | PSLMI |
| 5408. | SLMID |
| 5409. | LMIDG |
| 5410. | MIDGI |
| 5411. | IDGIL |
| 5412. | DGILW |
| 5413. | GILWE |
| 5414. | ILWEG |
| 5415. | LWEGF |
| 5416. | WEGFG |
| 5417. | EGFGG |
| 5418. | GFGGD |

TABLE 6-continued

| | |
|---|---|
| 5419. | FGGDP |
| 5420. | GGDPC |
| 5421. | GDPCD |
| 5422. | DPCDP |
| 5423. | PCDPC |
| 5424. | CDPCA |
| 5425. | DPCAT |
| 5426. | PCATW |
| 5427. | CATWC |
| 5428. | ATWCD |
| 5429. | TWCDA |
| 5430. | WCDAI |
| 5431. | CDAIS |
| 5432. | DAISM |
| 5433. | AISMR |
| 5434. | ISMRV |
| 5435. | SMRVG |
| 5436. | MRVGY |
| 5437. | RVGYY |
| 5438. | VGYYG |
| 5439. | GYYGD |
| 5440. | YYGDF |
| 5441. | YGDFV |
| 5442. | GDFVF |
| 5443. | DFVFD |
| 5444. | FVFDR |
| 5445. | VFDRV |
| 5446. | FDRVL |
| 5447. | DRVLK |
| 5448. | RVLKT |
| 5449. | VLKTD |
| 5450. | LKTDV |
| 5451. | KTDVN |
| 5452. | TDVNK |
| 5453. | DVNKE |
| 5454. | VNKEF |
| 5455. | NKEFQ |
| 5456. | KEFQM |
| 5457. | EFQMG |
| 5458. | FQMGA |
| 5459. | QMGAK |
| 5460. | MGAKP |
| 5461. | GAKPT |
| 5462. | AKPTT |
| 5463. | KPTTD |
| 5464. | PTTDT |
| 5465. | TTDTG |
| 5466. | TDTGN |
| 5467. | DTGNS |
| 5468. | TGNSA |
| 5469. | GNSAA |
| 5470. | NSAAP |
| 5471. | SAAPS |
| 5472. | AAPST |
| 5473. | APSTL |
| 5474. | PSTLT |
| 5475. | STLTA |
| 5476. | TLTAR |
| 5477. | LTARE |
| 5478. | TAREN |
| 5479. | ARENP |
| 5480. | RENPA |
| 5481. | ENPAY |
| 5482. | NPAYG |
| 5483. | PAYGR |
| 5484. | AYGRH |
| 5485. | YGRHM |
| 5486. | GRHMQ |
| 5487. | RHMQD |
| 5488. | HMQDA |
| 5489. | MQDAE |
| 5490. | QDAEM |
| 5491. | DAEMF |
| 5492. | AEMFT |
| 5493. | EMFTN |
| 5494. | MFTNA |
| 5495. | FTNAA |
| 5496. | TNAAC |
| 5497. | NAACM |
| 5498. | AACMA |

TABLE 6-continued

| | |
|---|---|
| 5499. | ACMAL |
| 5500. | CMALN |
| 5501. | MALNI |
| 5502. | ALNIW |
| 5503. | LNIWD |
| 5504. | NIWDR |
| 5505. | IWDRF |
| 5506. | WDRFD |
| 5507. | DRFDV |
| 5508. | RFDVF |
| 5509. | FDVFC |
| 5510. | DVFCT |
| 5511. | VFCTL |
| 5512. | FCTLG |
| 5513. | CTLGA |
| 5514. | TLGAT |
| 5515. | LGATS |
| 5516. | GATSG |
| 5517. | ATSGY |
| 5518. | TSGYL |
| 5519. | SGYLK |
| 5520. | GYLKG |
| 5521. | YLKGN |
| 5522. | LKGNS |
| 5523. | KGNSA |
| 5524. | GNSAS |
| 5525. | NSASF |
| 5526. | SASFN |
| 5527. | ASFNL |
| 5528. | SFNLV |
| 5529. | FNLVG |
| 5530. | NLVGL |
| 5531. | LVGLF |
| 5532. | VGLFG |
| 5533. | GLFGD |
| 5534. | LFGDN |
| 5535. | FGDNE |
| 5536. | GDNEN |
| 5537. | DNENQ |
| 5538. | NENQK |
| 5539. | ENQKT |
| 5540. | NQKTV |
| 5541. | QKTVK |
| 5542. | KTVKA |
| 5543. | TVKAE |
| 5544. | VKAES |
| 5545. | KAESV |
| 5546. | AESVP |
| 5547. | ESVPN |
| 5548. | SVPNM |
| 5549. | VPNMS |
| 5550. | PNMSF |
| 5551. | NMSFD |
| 5552. | MSFDQ |
| 5553. | SFDQS |
| 5554. | FDQSV |
| 5555. | DQSVV |
| 5556. | QSVVE |
| 5557. | SVVEL |
| 5558. | VVELY |
| 5559. | VELYT |
| 5560. | ELYTD |
| 5561. | LYTDT |
| 5562. | YTDTT |
| 5563. | TDTTF |
| 5564. | DTTFA |
| 5565. | TTFAW |
| 5566. | TFAWS |
| 5567. | FAWSV |
| 5568. | AWSVG |
| 5569. | WSVGA |
| 5570. | SVGAR |
| 5571. | VGARA |
| 5572. | GARAA |
| 5573. | ARAAL |
| 5574. | RAALW |
| 5575. | AALWE |
| 5576. | ALWEC |
| 5577. | LWECG |
| 5578. | WECGC |
| 5579. | ECGCA |
| 5580. | CGCAT |
| 5581. | GCATL |
| 5582. | CATLG |
| 5583. | ATLGA |
| 5584. | TLGAS |
| 5585. | LGASF |
| 5586. | GASFQ |
| 5587. | ASFQY |
| 5588. | SFQYA |
| 5589. | FQYAQ |
| 5590. | QYAQS |
| 5591. | YAQSK |
| 5592. | AQSKP |
| 5593. | QSKPK |
| 5594. | SKPKV |
| 5595. | KPKVE |
| 5596. | PKVEE |
| 5597. | KVEEL |
| 5598. | VEELN |
| 5599. | EELNV |
| 5600. | ELNVL |
| 5601. | LNVLC |
| 5602. | NVLCN |
| 5603. | VLCNA |
| 5604. | LCNAA |
| 5605. | CNAAE |
| 5606. | NAAEF |
| 5607. | AAEFT |
| 5608. | AEFTI |
| 5609. | EFTIN |
| 5610. | FTINK |
| 5611. | TINKP |
| 5612. | INKPK |
| 5613. | NKPKG |
| 5614. | KPKGY |
| 5615. | PKGYV |
| 5616. | KGYVG |
| 5617. | GYVGK |
| 5618. | YVGKE |
| 5619. | VGKEF |
| 5620. | GKEFP |
| 5621. | KEFPL |
| 5622. | EFPLD |
| 5623. | FPLDL |
| 5624. | PLDLT |
| 5625. | LDLTA |
| 5626. | DLTAG |
| 5627. | LTAGT |
| 5628. | TAGTD |
| 5629. | AGTDA |
| 5630. | GTDAA |
| 5631. | TDAAT |
| 5632. | DAATG |
| 5633. | AATGT |
| 5634. | ATGTK |
| 5635. | TGTKD |
| 5636. | GTKDA |
| 5637. | TKDAS |
| 5638. | KDASI |
| 5639. | DASID |
| 5640. | ASIDY |
| 5641. | SIDYH |
| 5642. | IDYHE |
| 5643. | DYHEW |
| 5644. | YHEWQ |
| 5645. | HEWQA |
| 5646. | EWQAS |
| 5647. | WQASL |
| 5648. | QASLA |
| 5649. | ASLAL |
| 5650. | SLALS |
| 5651. | LALSY |
| 5652. | ALSYR |
| 5653. | LSYRL |
| 5654. | SYRLN |
| 5655. | YRLNM |
| 5656. | RLNMF |
| 5657. | LNMFT |
| 5658. | NMFTP |

TABLE 6-continued

| | | |
|---|---|---|
| 5659. | MFTPY | |
| 5660. | FTPYI | |
| 5661. | TPYIG | |
| 5662. | PYIGV | |
| 5663. | YIGVK | |
| 5664. | IGVKW | |
| 5665. | GVKWS | |
| 5666. | VKWSR | |
| 5667. | KWSRA | |
| 5668. | WSRAS | |
| 5669. | SRASF | |
| 5670. | RASFD | |
| 5671. | ASFDA | |
| 5672. | SFDAD | |
| 5673. | FDADT | |
| 5674. | DADTI | |
| 5675. | ADTIR | |
| 5676. | DTIRI | |
| 5677. | TIRIA | |
| 5678. | IRIAQ | |
| 5679. | RIAQP | |
| 5680. | IAQPK | |
| 5681. | AQPKS | |
| 5682. | QPKSA | |
| 5683. | PKSAT | |
| 5684. | KSATA | |
| 5685. | SATAI | |
| 5686. | ATAIF | |
| 5687. | TAIFD | |
| 5688. | AIFDT | |
| 5689. | IFDTT | |
| 5690. | FDTTT | |
| 5691. | DTTTL | |
| 5692. | TTTLN | |
| 5693. | TTLNP | |
| 5694. | TLNPT | |
| 5695. | LNPTI | |
| 5696. | NPTIA | |
| 5697. | PTIAG | |
| 5698. | TIAGA | |
| 5699. | IAGAG | |
| 5700. | AGAGD | |
| 5701. | GAGDV | |
| 5702. | AGDVK | |
| 5703. | GDVKT | |
| 5704. | DVKTG | |
| 5705. | VKTGA | |
| 5706. | KTGAE | |
| 5707. | TGAEG | |
| 5708. | GAEGQ | |
| 5709. | AEGQL | |
| 5710. | EGQLG | |
| 5711. | GQLGD | |
| 5712. | QLGDT | |
| 5713. | LGDTM | |
| 5714. | GDTMQ | |
| 5715. | DTMQI | |
| 5716. | TMQIV | |
| 5717. | MQIVS | |
| 5718. | QIVSL | |
| 5719. | IVSLQ | |
| 5720. | VSLQL | |
| 5721. | SLQLN | |
| 5722. | LQLNK | |
| 5723. | QLNKM | |
| 5724. | LNKMK | |
| 5725. | NKMKS | |
| 5726. | KMKSR | |
| 5727. | MKSRK | |
| 5728. | KSRKS | |
| 5729. | SRKSC | |
| 5730. | RKSCG | |
| 5731. | KSCGI | |
| 5732. | SCGIA | |
| 5733. | CGIAV | |
| 5734. | GIAVG | |
| 5735. | IAVGT | |
| 5736. | AVGTT | |
| 5737. | VGTTI | |
| 5738. | GTTIV | |

TABLE 6-continued

| | | |
|---|---|---|
| 5739. | TTIVD | |
| 5740. | TIVDA | |
| 5741. | IVDAD | |
| 5742. | VDADK | |
| 5743. | DADKY | |
| 5744. | ADKYA | |
| 5745. | DKYAV | |
| 5746. | KYAVT | |
| 5747. | YAVTV | |
| 5748. | AVTVE | |
| 5749. | VTVET | |
| 5750. | TVETR | |
| 5751. | VETRL | |
| 5752. | ETRLI | |
| 5753. | TRLID | |
| 5754. | RLIDE | |
| 5755. | LIDER | |
| 5756. | IDERA | |
| 5757. | DERAA | |
| 5758. | ERAAH | |
| 5759. | RAAHV | |
| 5760. | AAHVN | |
| 5761. | AHVNA | |
| 5762. | HVNAQ | |
| 5763. | VNAQF | |
| 5764. | NAQFR | |
| 5765. | AQFRF | |

5-mer peptides of CT119 (IncA, 273 amino acids), ACCESSION# NP219622.1, GI: 15604838 (SEQ ID NOS: 5766-6034)

| | |
|---|---|
| 5766. | MTTPT |
| 5767. | TTPTL |
| 5768. | TPTLI |
| 5769. | PTLIV |
| 5770. | TLIVT |
| 5771. | LIVTP |
| 5772. | IVTPP |
| 5773. | VTPPS |
| 5774. | TPPSP |
| 5775. | PPSPP |
| 5776. | PSPPA |
| 5777. | SPPAP |
| 5778. | PPAPS |
| 5779. | PAPSY |
| 5780. | APSYS |
| 5781. | PSYSA |
| 5782. | SYSAN |
| 5783. | YSANR |
| 5784. | SANRV |
| 5785. | ANRVP |
| 5786. | NRVPQ |
| 5787. | RVPQP |
| 5788. | VPQPS |
| 5789. | PQPSL |
| 5790. | QPSLM |
| 5791. | PSLMD |
| 5792. | SLMDK |
| 5793. | LMDKI |
| 5794. | MDKIK |
| 5795. | DKIKK |
| 5796. | KIKKI |
| 5797. | IKKIA |
| 5798. | KKIAA |
| 5799. | KIAAI |
| 5800. | IAAIA |
| 5801. | AAIAS |
| 5802. | AIASL |
| 5803. | IASLI |
| 5804. | ASLIL |
| 5805. | SLILI |
| 5806. | LILIG |
| 5807. | ILIGT |
| 5808. | LIGTI |
| 5809. | IGTIG |
| 5810. | GTIGF |
| 5811. | TIGFL |
| 5812. | IGFLA |
| 5813. | GFLAL |

TABLE 6-continued

| | |
|---|---|
| 5814. | FLALL |
| 5815. | LALLG |
| 5816. | ALLGH |
| 5817. | LLGHL |
| 5818. | LGHLV |
| 5819. | GHLVG |
| 5820. | HLVGF |
| 5821. | LVGFL |
| 5822. | VGFLI |
| 5823. | GFLIA |
| 5824. | FLIAP |
| 5825. | LIAPQ |
| 5826. | IAPQI |
| 5827. | APQIT |
| 5828. | PQITI |
| 5829. | QITIV |
| 5830. | ITIVL |
| 5831. | TIVLL |
| 5832. | IVLLA |
| 5833. | VLLAL |
| 5834. | LLALF |
| 5835. | LALFI |
| 5836. | ALFII |
| 5837. | LFIIS |
| 5838. | FIISL |
| 5839. | IISLA |
| 5840. | ISLAG |
| 5841. | SLAGN |
| 5842. | LAGNA |
| 5843. | AGNAL |
| 5844. | GNALY |
| 5845. | NALYL |
| 5846. | ALYLQ |
| 5847. | LYLQK |
| 5848. | YLQKT |
| 5849. | LQKTA |
| 5850. | QKTAN |
| 5851. | KTANL |
| 5852. | TANLH |
| 5853. | ANLHL |
| 5854. | NLHLY |
| 5855. | LHLYQ |
| 5856. | HLYQD |
| 5857. | LYQDL |
| 5858. | YQDLQ |
| 5859. | QDLQR |
| 5860. | DLQRE |
| 5861. | LQREV |
| 5862. | QREVG |
| 5863. | REVGS |
| 5864. | EVGSL |
| 5865. | VGSLK |
| 5866. | GSLKE |
| 5867. | SLKEI |
| 5868. | LKEIN |
| 5869. | KEINF |
| 5870. | EINFM |
| 5871. | INFML |
| 5872. | NFMLS |
| 5873. | FMLSV |
| 5874. | MLSVL |
| 5875. | LSVLQ |
| 5876. | SVLQK |
| 5877. | VLQKE |
| 5878. | LQKEF |
| 5879. | QKEFL |
| 5880. | KEFLH |
| 5881. | EFLHL |
| 5882. | FLHLS |
| 5883. | LHLSK |
| 5884. | HLSKE |
| 5885. | LSKEF |
| 5886. | SKEFA |
| 5887. | KEFAT |
| 5888. | EFATT |
| 5889. | FATTS |
| 5890. | ATTSK |
| 5891. | TTSKD |
| 5892. | TSKDL |
| 5893. | SKDLS |
| 5894. | KDLSA |
| 5895. | DLSAV |
| 5896. | LSAVS |
| 5897. | SAVSQ |
| 5898. | AVSQD |
| 5899. | VSQDF |
| 5900. | SQDFY |
| 5901. | QDFYS |
| 5902. | DFYSC |
| 5903. | FYSCL |
| 5904. | YSCLQ |
| 5905. | SCLQG |
| 5906. | CLQGF |
| 5907. | LQGFR |
| 5908. | QGFRD |
| 5909. | GFRDN |
| 5910. | FRDNY |
| 5911. | RDNYK |
| 5912. | DNYKG |
| 5913. | NYKGF |
| 5914. | YKGFE |
| 5915. | KGFES |
| 5916. | GFESL |
| 5917. | FESLL |
| 5918. | ESLLD |
| 5919. | SLLDE |
| 5920. | LLDEY |
| 5921. | LDEYK |
| 5922. | DEYKN |
| 5923. | EYKNS |
| 5924. | YKNST |
| 5925. | KNSTE |
| 5926. | NSTEE |
| 5927. | STEEM |
| 5928. | TEEMR |
| 5929. | EEMRK |
| 5930. | EMRKL |
| 5931. | MRKLF |
| 5932. | RKLFS |
| 5933. | KLFSQ |
| 5934. | LFSQE |
| 5935. | FSQEI |
| 5936. | SQEII |
| 5937. | QEIIA |
| 5938. | EIIAD |
| 5939. | IIADL |
| 5940. | IADLK |
| 5941. | ADLKG |
| 5942. | DLKGS |
| 5943. | LKGSV |
| 5944. | KGSVA |
| 5945. | GSVAS |
| 5946. | SVASL |
| 5947. | VASLR |
| 5948. | ASLRE |
| 5949. | SLREE |
| 5950. | LREEI |
| 5951. | REEIR |
| 5952. | EEIRF |
| 5953. | EIRFL |
| 5954. | IRFLT |
| 5955. | RFLTP |
| 5956. | FLTPL |
| 5957. | LTPLA |
| 5958. | TPLAE |
| 5959. | PLAEE |
| 5960. | LAEEV |
| 5961. | AEEVR |
| 5962. | EEVRR |
| 5963. | EVRRL |
| 5964. | VRRLA |
| 5965. | RRLAH |
| 5966. | RLAHN |
| 5967. | LAHNQ |
| 5968. | AHNQQ |
| 5969. | HNQQS |
| 5970. | NQQSL |
| 5971. | QQSLT |
| 5972. | QSLTV |
| 5973. | SLTVV |

TABLE 6-continued

| | |
|---|---|
| 5974. | LTVVI |
| 5975. | TVVIE |
| 5976. | VVIEE |
| 5977. | VIEEL |
| 5978. | IEELK |
| 5979. | EELKT |
| 5980. | ELKTI |
| 5981. | LKTIR |
| 5982. | KTIRD |
| 5983. | TIRDS |
| 5984. | IRDSL |
| 5985. | RDSLR |
| 5986. | DSLRD |
| 5987. | SLRDE |
| 5988. | LRDEI |
| 5989. | RDEIG |
| 5990. | DEIGQ |
| 5991. | EIGQL |
| 5992. | IGQLS |
| 5993. | GQLSQ |
| 5994. | QLSQL |
| 5995. | LSQLS |
| 5996. | SQLSK |
| 5997. | QLSKT |
| 5998. | LSKTL |
| 5999. | SKTLT |
| 6000. | KTLTS |
| 6001. | TLTSQ |
| 6002. | LTSQI |
| 6003. | TSQIA |
| 6004. | SQIAL |
| 6005. | QIALQ |
| 6006. | IALQR |
| 6007. | ALQRK |
| 6008. | LQRKE |
| 6009. | QRKES |
| 6010. | RKESS |
| 6011. | KESSD |
| 6012. | ESSDL |
| 6013. | SSDLC |
| 6014. | SDLCS |
| 6015. | DLCSQ |
| 6016. | LCSQI |
| 6017. | CSQIR |
| 6018. | SQIRE |
| 6019. | QIRET |
| 6020. | IRETL |
| 6021. | RETLS |
| 6022. | ETLSS |
| 6023. | TLSSP |
| 6024. | LSSPR |
| 6025. | SSPRK |
| 6026. | SPRKS |
| 6027. | PRKSA |
| 6028. | RKSAS |
| 6029. | KSASP |
| 6030. | SASPS |
| 6031. | ASPST |
| 6032. | SPSTK |
| 6033. | PSTKS |
| 6034. | STKSS |

5-mer peptides of CT813 (inclusion membrane protein, 264 amino acids), ACCESSION# NP 220333.1, GI: 15605547 (SEQ ID NOS: 6035-6294)

| | |
|---|---|
| 6035. | MTTLP |
| 6036. | TTLPN |
| 6037. | TLPNN |
| 6038. | LPNNC |
| 6039. | PNNCT |
| 6040. | NNCTS |
| 6041. | NCTSN |
| 6042. | CTSNS |
| 6043. | TSNSN |
| 6044. | SNSNS |
| 6045. | NSNSI |
| 6046. | SNSIN |
| 6047. | NSINT |
| 6048. | SINTF |
| 6049. | INTFT |
| 6050. | NTFTK |
| 6051. | TFTKD |
| 6052. | FTKDI |
| 6053. | TKDIE |
| 6054. | KDIEM |
| 6055. | DIEMA |
| 6056. | IEMAK |
| 6057. | EMAKQ |
| 6058. | MAKQI |
| 6059. | AKQIQ |
| 6060. | KQIQG |
| 6061. | QIQGS |
| 6062. | IQGSR |
| 6063. | QGSRK |
| 6064. | GSRKD |
| 6065. | SRKDP |
| 6066. | RKDPL |
| 6067. | KDPLA |
| 6068. | DPLAK |
| 6069. | PLAKT |
| 6070. | LAKTS |
| 6071. | AKTSW |
| 6072. | KTSWI |
| 6073. | TSWIA |
| 6074. | SWIAG |
| 6075. | WIAGL |
| 6076. | IAGLI |
| 6077. | AGLIC |
| 6078. | GLICV |
| 6079. | LICVV |
| 6080. | ICVVA |
| 6081. | CVVAG |
| 6082. | VVAGV |
| 6083. | VAGVL |
| 6084. | AGVLG |
| 6085. | GVLGL |
| 6086. | VLGLL |
| 6087. | LGLLA |
| 6088. | GLLAI |
| 6089. | LLAIG |
| 6090. | LAIGI |
| 6091. | AIGIG |
| 6092. | IGIGG |
| 6093. | GIGGC |
| 6094. | IGGCS |
| 6095. | GGCSM |
| 6096. | GCSMA |
| 6097. | CSMAS |
| 6098. | SMASG |
| 6099. | MASGL |
| 6100. | ASGLG |
| 6101. | SGLGL |
| 6102. | GLGLI |
| 6103. | LGLIG |
| 6104. | GLIGA |
| 6105. | LIGAI |
| 6106. | IGAIV |
| 6107. | GAIVA |
| 6108. | AIVAA |
| 6109. | IVAAV |
| 6110. | VAAVI |
| 6111. | AAVIV |
| 6112. | AVIVA |
| 6113. | VIVAV |
| 6114. | IVAVG |
| 6115. | VAVGL |
| 6116. | AVGLC |
| 6117. | VGLCC |
| 6118. | GLCCL |
| 6119. | LCCLV |
| 6120. | CCLVS |
| 6121. | CLVSA |
| 6122. | LVSAL |
| 6123. | VSALC |
| 6124. | SALCL |
| 6125. | ALCLQ |
| 6126. | LCLQV |
| 6127. | CLQVE |
| 6128. | LQVEK |

TABLE 6-continued

| | |
|---|---|
| 6129. | QVEKS |
| 6130. | VEKSQ |
| 6131. | EKSQW |
| 6132. | KSQWW |
| 6133. | SQWWQ |
| 6134. | QWWQK |
| 6135. | WWQKE |
| 6136. | WQKEF |
| 6137. | QKEFE |
| 6138. | KEFES |
| 6139. | EFESW |
| 6140. | FESWI |
| 6141. | ESWIE |
| 6142. | SWIEQ |
| 6143. | WIEQK |
| 6144. | IEQKS |
| 6145. | EQKSQ |
| 6146. | QKSQF |
| 6147. | KSQFR |
| 6148. | SQFRI |
| 6149. | QFRIV |
| 6150. | FRIVM |
| 6151. | RIVMA |
| 6152. | IVMAD |
| 6153. | VMADM |
| 6154. | MADML |
| 6155. | ADMLK |
| 6156. | DMLKA |
| 6157. | MLKAN |
| 6158. | LKANR |
| 6159. | KANRK |
| 6160. | ANRKL |
| 6161. | NRKLQ |
| 6162. | RKLQS |
| 6163. | KLQSE |
| 6164. | LQSEV |
| 6165. | QSEVE |
| 6166. | SEVEF |
| 6167. | EVEFL |
| 6168. | VEFLS |
| 6169. | EFLSK |
| 6170. | FLSKG |
| 6171. | LSKGW |
| 6172. | SKGWS |
| 6173. | KGWSD |
| 6174. | GWSDD |
| 6175. | WSDDT |
| 6176. | SDDTA |
| 6177. | DDTAV |
| 6178. | DTAVH |
| 6179. | TAVHK |
| 6180. | AVHKE |
| 6181. | VHKED |
| 6182. | HKEDV |
| 6183. | KEDVT |
| 6184. | EDVTK |
| 6185. | DVTKY |
| 6186. | VTKYE |
| 6187. | TKYEQ |
| 6188. | KYEQV |
| 6189. | YEQVV |
| 6190. | EQVVE |
| 6191. | QVVEE |
| 6192. | VVEEY |
| 6193. | VEEYA |
| 6194. | EEYAE |
| 6195. | EYAEK |
| 6196. | YAEKI |
| 6197. | AEKIM |
| 6198. | EKIME |
| 6199. | KIMEL |
| 6200. | IMELY |
| 6201. | MELYE |
| 6202. | ELYEE |
| 6203. | LYEET |
| 6204. | YEETG |
| 6205. | EETGV |
| 6206. | ETGVL |
| 6207. | TGVLT |
| 6208. | GVLTI |

TABLE 6-continued

| | |
|---|---|
| 6209. | VLTIE |
| 6210. | LTIEK |
| 6211. | TIEKI |
| 6212. | IEKIN |
| 6213. | EKINL |
| 6214. | KINLQ |
| 6215. | INLQK |
| 6216. | NLQKE |
| 6217. | LQKEK |
| 6218. | QKEKK |
| 6219. | KEKKA |
| 6220. | EKKAW |
| 6221. | KKAWL |
| 6222. | KAWLE |
| 6223. | AWLEE |
| 6224. | WLEEK |
| 6225. | LEEKA |
| 6226. | EEKAE |
| 6227. | EKAEM |
| 6228. | KAEME |
| 6229. | AEMEQ |
| 6230. | EMEQK |
| 6231. | MEQKL |
| 6232. | EQKLT |
| 6233. | QKLTT |
| 6234. | KLTTV |
| 6235. | LTTVT |
| 6236. | TTVTD |
| 6237. | TVTDL |
| 6238. | VTDLE |
| 6239. | TDLEA |
| 6240. | DLEAA |
| 6241. | LEAAK |
| 6242. | EAAKQ |
| 6243. | AAKQQ |
| 6244. | AKQQL |
| 6245. | KQQLE |
| 6246. | QQLEE |
| 6247. | QLEEK |
| 6248. | LEEKV |
| 6249. | EEKVT |
| 6250. | EKVTD |
| 6251. | KVTDL |
| 6252. | VTDLE |
| 6253. | TDLES |
| 6254. | DLESE |
| 6255. | LESEK |
| 6256. | ESEKQ |
| 6257. | SEKQE |
| 6258. | EKQEL |
| 6259. | KQELR |
| 6260. | QELRE |
| 6261. | ELREE |
| 6262. | LREEL |
| 6263. | REELD |
| 6264. | EELDK |
| 6265. | ELDKA |
| 6266. | LDKAI |
| 6267. | DKAIE |
| 6268. | KAIEN |
| 6269. | AIENL |
| 6270. | IENLD |
| 6271. | ENLDE |
| 6272. | NLDEM |
| 6273. | LDEMA |
| 6274. | DEMAY |
| 6275. | EMAYE |
| 6276. | MAYEA |
| 6277. | AYEAM |
| 6278. | YEAME |
| 6279. | EAMEF |
| 6280. | AMEFE |
| 6281. | MEFEK |
| 6282. | EFEKE |
| 6283. | FEKEK |
| 6284. | EKEKH |
| 6285. | KEKHG |
| 6286. | EKHGI |
| 6287. | KHGIK |
| 6288. | HGIKP |

TABLE 6-continued

| | |
|---|---|
| 6289. | GIKPG |
| 6290. | IKPGR |
| 6291. | KPGRR |
| 6292. | PGRRG |
| 6293. | GRRGS |
| 6294. | RRGSI |

5-mer peptides of CT795 (hypothetical protein, 163 amino acids), ACCESSION# NP 220315.1, GI: 15605529 (SEQ ID NOS: 6295-6453)

| | |
|---|---|
| 6295. | MRFLL |
| 6296. | RFLLA |
| 6297. | FLLAL |
| 6298. | LLALF |
| 6299. | LALFS |
| 6300. | ALFSL |
| 6301. | LFSLI |
| 6302. | FSLIL |
| 6303. | SLILV |
| 6304. | LILVL |
| 6305. | ILVLP |
| 6306. | LVLPA |
| 6307. | VLPAT |
| 6308. | LPATE |
| 6309. | PATEA |
| 6310. | ATEAF |
| 6311. | TEAFS |
| 6312. | EAFST |
| 6313. | AFSTE |
| 6314. | FSTED |
| 6315. | STEDK |
| 6316. | TEDKQ |
| 6317. | EDKQC |
| 6318. | DKQCQ |
| 6319. | KQCQQ |
| 6320. | QCQQE |
| 6321. | CQQEA |
| 6322. | QQEAE |
| 6323. | QEAEE |
| 6324. | EAEED |
| 6325. | AEEDC |
| 6326. | EEDCS |
| 6327. | EDCSQ |
| 6328. | DCSQV |
| 6329. | CSQVA |
| 6330. | SQVAD |
| 6331. | QVADT |
| 6332. | VADTC |
| 6333. | ADTCV |
| 6334. | DTCVF |
| 6335. | TCVFY |
| 6336. | CVFYS |
| 6337. | VFYSY |
| 6338. | FYSYA |
| 6339. | YSYAE |
| 6340. | SYAEG |
| 6341. | YAEGL |
| 6342. | AEGLE |
| 6343. | EGLEH |
| 6344. | GLEHA |
| 6345. | LEHAR |
| 6346. | EHARD |
| 6347. | HARDE |
| 6348. | ARDEG |
| 6349. | RDEGK |
| 6350. | DEGKL |
| 6351. | EGKLT |
| 6352. | GKLTL |
| 6353. | KLTLV |
| 6354. | LTLVV |
| 6355. | TLVVL |
| 6356. | LVVLL |
| 6357. | VVLLD |
| 6358. | VLLDT |
| 6359. | LLDTS |
| 6360. | LDTSG |
| 6361. | DTSGY |
| 6362. | TSGYS |
| 6363. | SGYSF |
| 6364. | GYSFE |
| 6365. | YSFET |
| 6366. | SFETL |
| 6367. | FETLA |
| 6368. | ETLAD |
| 6369. | TLADA |
| 6370. | LADAA |
| 6371. | ADAAH |
| 6372. | DAAHA |
| 6373. | AAHAM |
| 6374. | AHAME |
| 6375. | HAMES |
| 6376. | AMESS |
| 6377. | MESSL |
| 6378. | ESSLL |
| 6379. | SSLLS |
| 6380. | SLLST |
| 6381. | LLSTF |
| 6382. | LSTFA |
| 6383. | STFAD |
| 6384. | TFADF |
| 6385. | FADFV |
| 6386. | ADFVV |
| 6387. | DFVVL |
| 6388. | FVVLS |
| 6389. | VVLSR |
| 6390. | VLSRR |
| 6391. | LSRRE |
| 6392. | SRREA |
| 6393. | RREAV |
| 6394. | REAVP |
| 6395. | EAVPL |
| 6396. | AVPLI |
| 6397. | VPLIY |
| 6398. | PLIYP |
| 6399. | LIYPP |
| 6400. | IYPPV |
| 6401. | YPPVP |
| 6402. | PPVPD |
| 6403. | PVPDP |
| 6404. | VPDPM |
| 6405. | PDPMV |
| 6406. | DPMVG |
| 6407. | PMVGE |
| 6408. | MVGEI |
| 6409. | VGEIA |
| 6410. | GEIAL |
| 6411. | EIALF |
| 6412. | IALFL |
| 6413. | ALFLE |
| 6414. | LFLEA |
| 6415. | FLEAF |
| 6416. | LEAFS |
| 6417. | EAFSD |
| 6418. | AFSDQ |
| 6419. | FSDQT |
| 6420. | SDQTF |
| 6421. | DQTFP |
| 6422. | QTFPS |
| 6423. | TFPSQ |
| 6424. | FPSQP |
| 6425. | PSQPV |
| 6426. | SQPVI |
| 6427. | QPVIV |
| 6428. | PVIVT |
| 6429. | VIVTL |
| 6430. | IVTLA |
| 6431. | VTLAI |
| 6432. | TLAIG |
| 6433. | LAIGA |
| 6434. | AIGAS |
| 6435. | IGASS |
| 6436. | GASSA |
| 6437. | ASSAE |
| 6438. | SSAEI |
| 6439. | SAEIM |
| 6440. | AEIMD |
| 6441. | EIMDI |
| 6442. | IMDIT |
| 6443. | MDITE |

TABLE 6-continued

| | |
|---|---|
| 6444. | DITEI |
| 6445. | ITEIP |
| 6446. | TEIPS |
| 6447. | EIPSI |
| 6448. | IPSIN |
| 6449. | PSINP |
| 6450. | SINPE |
| 6451. | INPEF |
| 6452. | NPEFV |
| 6453. | PEFVE |

5-mer peptides of CT621 (hypothetical protein, 832 amino acids), ACCESSION# NP 220138.1, GI: 15605352 (SEQ ID NOS: 6454-7281)

| | |
|---|---|
| 6454. | MNRIH |
| 6455. | NRIHR |
| 6456. | RIHRT |
| 6457. | IHRTQ |
| 6458. | HRTQG |
| 6459. | RTQGS |
| 6460. | TQGSL |
| 6461. | QGSLT |
| 6462. | GSLTD |
| 6463. | SLTDY |
| 6464. | LTDYN |
| 6465. | TDYNS |
| 6466. | DYNST |
| 6467. | YNSTL |
| 6468. | NSTLE |
| 6469. | STLEA |
| 6470. | TLEAI |
| 6471. | LEAIA |
| 6472. | EAIAK |
| 6473. | AIAKK |
| 6474. | IAKKI |
| 6475. | AKKIA |
| 6476. | KKIAK |
| 6477. | KIAKP |
| 6478. | IAKPD |
| 6479. | AKPDS |
| 6480. | KPDSA |
| 6481. | PDSAT |
| 6482. | DSATI |
| 6483. | SATIV |
| 6484. | ATIVS |
| 6485. | TIVSQ |
| 6486. | IVSQV |
| 6487. | VSQVA |
| 6488. | SQVAQ |
| 6489. | QVAQY |
| 6490. | VAQYE |
| 6491. | AQYEQ |
| 6492. | QYEQF |
| 6493. | YEQFK |
| 6494. | EQFKM |
| 6495. | QFKME |
| 6496. | FKMEQ |
| 6497. | KMEQE |
| 6498. | MEQEA |
| 6499. | EQEAL |
| 6500. | QEALK |
| 6501. | EALKA |
| 6502. | ALKAL |
| 6503. | LKALL |
| 6504. | KALLV |
| 6505. | ALLVS |
| 6506. | LLVSF |
| 6507. | LVSFD |
| 6508. | VSFDQ |
| 6509. | SFDQK |
| 6510. | FDQKA |
| 6511. | DQKAD |
| 6512. | QKADQ |
| 6513. | KADQR |
| 6514. | ADQRY |
| 6515. | DQRYR |
| 6516. | QRYRN |
| 6517. | RYRNL |
| 6518. | YRNLI |

TABLE 6-continued

| | |
|---|---|
| 6519. | RNLIQ |
| 6520. | NLIQR |
| 6521. | LIQRL |
| 6522. | IQRLE |
| 6523. | QRLEQ |
| 6524. | RLEQL |
| 6525. | LEQLD |
| 6526. | EQLDV |
| 6527. | QLDVD |
| 6528. | LDVDR |
| 6529. | DVDRQ |
| 6530. | VDRQT |
| 6531. | DRQTG |
| 6532. | RQTGR |
| 6533. | QTGRS |
| 6534. | TGRST |
| 6535. | GRSTE |
| 6536. | RSTES |
| 6537. | STESQ |
| 6538. | TESQH |
| 6539. | ESQHI |
| 6540. | SQHIQ |
| 6541. | QHIQE |
| 6542. | HIQEK |
| 6543. | IQEKP |
| 6544. | QEKPM |
| 6545. | EKPMA |
| 6546. | KPMAS |
| 6547. | PMASL |
| 6548. | MASLQ |
| 6549. | ASLQS |
| 6550. | SLQSE |
| 6551. | LQSEN |
| 6552. | QSENQ |
| 6553. | SENQV |
| 6554. | ENQVV |
| 6555. | NQVVA |
| 6556. | QVVAQ |
| 6557. | VVAQA |
| 6558. | VAQAV |
| 6559. | AQAVV |
| 6560. | QAVVQ |
| 6561. | AVVQS |
| 6562. | VVQSD |
| 6563. | VQSDS |
| 6564. | QSDSS |
| 6565. | SDSSM |
| 6566. | DSSMP |
| 6567. | SSMPI |
| 6568. | SMPIF |
| 6569. | MPIFT |
| 6570. | PIFTG |
| 6571. | IFTGI |
| 6572. | FTGIK |
| 6573. | TGIKQ |
| 6574. | GIKQS |
| 6575. | IKQSW |
| 6576. | KQSWA |
| 6577. | QSWAV |
| 6578. | SWAVR |
| 6579. | WAVRL |
| 6580. | AVRLV |
| 6581. | VRLVQ |
| 6582. | RLVQG |
| 6583. | LVQGI |
| 6584. | VQGIR |
| 6585. | QGIRE |
| 6586. | GIREI |
| 6587. | IREIL |
| 6588. | REILD |
| 6589. | EILDQ |
| 6590. | ILDQV |
| 6591. | LDQVL |
| 6592. | DQVLV |
| 6593. | QVLVD |
| 6594. | VLVDT |
| 6595. | LVDTS |
| 6596. | VDTSL |
| 6597. | DTSLF |
| 6598. | TSLFT |

TABLE 6-continued

| | |
|---|---|
| 6599. | SLFTE |
| 6600. | LFTEE |
| 6601. | FTEEE |
| 6602. | TEEER |
| 6603. | EEERG |
| 6604. | EERGD |
| 6605. | ERGDL |
| 6606. | RGDLL |
| 6607. | GDLLA |
| 6608. | DLLAI |
| 6609. | LLAIR |
| 6610. | LAIRM |
| 6611. | AIRMD |
| 6612. | IRMDA |
| 6613. | RMDAA |
| 6614. | MDAAS |
| 6615. | DAASL |
| 6616. | AASLQ |
| 6617. | ASLQD |
| 6618. | SLQDK |
| 6619. | LQDKQ |
| 6620. | QDKQE |
| 6621. | DKQER |
| 6622. | KQERL |
| 6623. | QERLS |
| 6624. | ERLST |
| 6625. | RLSTE |
| 6626. | LSTED |
| 6627. | STEDI |
| 6628. | TEDIR |
| 6629. | EDIRS |
| 6630. | DIRSL |
| 6631. | IRSLL |
| 6632. | RSLLS |
| 6633. | SLLSL |
| 6634. | LLSLS |
| 6635. | LSLSN |
| 6636. | SLSND |
| 6637. | LSNDV |
| 6638. | SNDVM |
| 6639. | NDVMR |
| 6640. | DVMRV |
| 6641. | VMRVL |
| 6642. | MRVLQ |
| 6643. | RVLQK |
| 6644. | VLQKA |
| 6645. | LQKAS |
| 6646. | QKASV |
| 6647. | KASVS |
| 6648. | ASVSS |
| 6649. | SVSST |
| 6650. | VSSTR |
| 6651. | SSTRQ |
| 6652. | STRQL |
| 6653. | TRQLE |
| 6654. | RQLEL |
| 6655. | QLELI |
| 6656. | LELIQ |
| 6657. | ELIQS |
| 6658. | LIQSL |
| 6659. | IQSLI |
| 6660. | QSLID |
| 6661. | SLIDI |
| 6662. | LIDIF |
| 6663. | IDIFG |
| 6664. | DIFGT |
| 6665. | IFGTE |
| 6666. | FGTEE |
| 6667. | GTEEN |
| 6668. | TEENL |
| 6669. | EENLE |
| 6670. | ENLEQ |
| 6671. | NLEQS |
| 6672. | LEQSF |
| 6673. | EQSFA |
| 6674. | QSFAQ |
| 6675. | SFAQV |
| 6676. | FAQVR |
| 6677. | AQVRL |
| 6678. | QVRLE |
| 6679. | VRLEN |
| 6680. | RLENF |
| 6681. | LENFQ |
| 6682. | ENFQA |
| 6683. | NFQAI |
| 6684. | FQAIL |
| 6685. | QAILS |
| 6686. | AILSV |
| 6687. | ILSVI |
| 6688. | LSVIK |
| 6689. | SVIKE |
| 6690. | VIKER |
| 6691. | IKERL |
| 6692. | KERLT |
| 6693. | ERLTE |
| 6694. | RLTEE |
| 6695. | LTEEE |
| 6696. | TEEEF |
| 6697. | EEEFR |
| 6698. | EEFRV |
| 6699. | EFRVF |
| 6700. | FRVFQ |
| 6701. | RVFQE |
| 6702. | VFQEV |
| 6703. | FQEVS |
| 6704. | QEVSE |
| 6705. | EVSEE |
| 6706. | VSEEI |
| 6707. | SEEIS |
| 6708. | EEISS |
| 6709. | EISSI |
| 6710. | ISSIQ |
| 6711. | SSIQR |
| 6712. | SIQRT |
| 6713. | IQRTS |
| 6714. | QRTSE |
| 6715. | RTSES |
| 6716. | TSESH |
| 6717. | SESHL |
| 6718. | ESHLS |
| 6719. | SHLSP |
| 6720. | HLSPE |
| 6721. | LSPEH |
| 6722. | SPEHI |
| 6723. | PEHIE |
| 6724. | EHIEA |
| 6725. | HIEAI |
| 6726. | IEAIA |
| 6727. | EAIAR |
| 6728. | AIARV |
| 6729. | IARVG |
| 6730. | ARVGG |
| 6731. | RVGGH |
| 6732. | VGGHL |
| 6733. | GGHLS |
| 6734. | GHLSA |
| 6735. | HLSAK |
| 6736. | LSAKI |
| 6737. | SAKIV |
| 6738. | AKIVE |
| 6739. | KIVES |
| 6740. | IVESE |
| 6741. | VESEL |
| 6742. | ESELK |
| 6743. | SELKA |
| 6744. | ELKAS |
| 6745. | LKASQ |
| 6746. | KASQK |
| 6747. | ASQKV |
| 6748. | SQKVD |
| 6749. | QKVDL |
| 6750. | KVDLC |
| 6751. | VDLCQ |
| 6752. | DLCQR |
| 6753. | LCQRI |
| 6754. | CQRIA |
| 6755. | QRIAA |
| 6756. | RIAAM |
| 6757. | IAAMY |
| 6758. | AAMYQ |

TABLE 6-continued

| | |
|---|---|
| 6759. | AMYQE |
| 6760. | MYQEQ |
| 6761. | YQEQV |
| 6762. | QEQVD |
| 6763. | EQVDA |
| 6764. | QVDAV |
| 6765. | VDAVQ |
| 6766. | DAVQA |
| 6767. | AVQAY |
| 6768. | VQAYH |
| 6769. | QAYHS |
| 6770. | AYHSL |
| 6771. | YHSLE |
| 6772. | HSLEQ |
| 6773. | SLEQD |
| 6774. | LEQDA |
| 6775. | EQDAL |
| 6776. | QDALF |
| 6777. | DALFV |
| 6778. | ALFVN |
| 6779. | LFVNS |
| 6780. | FVNSR |
| 6781. | VNSRQ |
| 6782. | NSRQH |
| 6783. | SRQHS |
| 6784. | RQHSH |
| 6785. | QHSHF |
| 6786. | HSHFV |
| 6787. | SHFVQ |
| 6788. | HFVQV |
| 6789. | FVQVI |
| 6790. | VQVIS |
| 6791. | QVISL |
| 6792. | VISLV |
| 6793. | ISLVS |
| 6794. | SLVSS |
| 6795. | LVSSL |
| 6796. | VSSLM |
| 6797. | SSLMH |
| 6798. | SLMHS |
| 6799. | LMHSL |
| 6800. | MHSLS |
| 6801. | HSLSP |
| 6802. | SLSPT |
| 6803. | LSPTS |
| 6804. | SPTSE |
| 6805. | PTSEE |
| 6806. | TSEEE |
| 6807. | SEEER |
| 6808. | EEERI |
| 6809. | EERIL |
| 6810. | ERILL |
| 6811. | RILLN |
| 6812. | ILLNP |
| 6813. | LLNPA |
| 6814. | LNPAM |
| 6815. | NPAMM |
| 6816. | PAMMV |
| 6817. | AMMVS |
| 6818. | MMVSV |
| 6819. | MVSVL |
| 6820. | VSVLP |
| 6821. | SVLPT |
| 6822. | VLPTV |
| 6823. | LPTVR |
| 6824. | PTVRA |
| 6825. | TVRAI |
| 6826. | VRAIG |
| 6827. | RAIGL |
| 6828. | AIGLR |
| 6829. | IGLRF |
| 6830. | GLRFD |
| 6831. | LRFDF |
| 6832. | RFDFL |
| 6833. | FDFLT |
| 6834. | DFLTA |
| 6835. | FLTAE |
| 6836. | LTAEQ |
| 6837. | TAEQQ |
| 6838. | AEQQQ |
| 6839. | EQQQM |
| 6840. | QQQMV |
| 6841. | QQMVN |
| 6842. | QMVNA |
| 6843. | MVNAA |
| 6844. | VNAAV |
| 6845. | NAAVS |
| 6846. | AAVSS |
| 6847. | AVSSL |
| 6848. | VSSLQ |
| 6849. | SSLQQ |
| 6850. | SLQQQ |
| 6851. | LQQQQ |
| 6852. | QQQQL |
| 6853. | QQQLD |
| 6854. | QQLDE |
| 6855. | QLDEF |
| 6856. | LDEFL |
| 6857. | DEFLG |
| 6858. | EFLGV |
| 6859. | FLGVL |
| 6860. | LGVLC |
| 6861. | GVLCA |
| 6862. | VLCAH |
| 6863. | LCAHL |
| 6864. | CAHLV |
| 6865. | AHLVV |
| 6866. | HLVVV |
| 6867. | LVVVN |
| 6868. | VVVNC |
| 6869. | VVNCQ |
| 6870. | VNCQN |
| 6871. | NCQNK |
| 6872. | CQNKE |
| 6873. | QNKET |
| 6874. | NKETG |
| 6875. | KETGL |
| 6876. | ETGLL |
| 6877. | TGLLE |
| 6878. | GLLEG |
| 6879. | LLEGL |
| 6880. | LEGLE |
| 6881. | EGLEE |
| 6882. | GLEES |
| 6883. | LEESF |
| 6884. | EESFS |
| 6885. | ESFSE |
| 6886. | SFSET |
| 6887. | FSETL |
| 6888. | SETLS |
| 6889. | ETLSG |
| 6890. | TLSGL |
| 6891. | LSGLS |
| 6892. | SGLSN |
| 6893. | GLSNN |
| 6894. | LSNNF |
| 6895. | SNNFV |
| 6896. | NNFVL |
| 6897. | NFVLT |
| 6898. | FVLTA |
| 6899. | VLTAK |
| 6900. | LTAKM |
| 6901. | TAKMQ |
| 6902. | AKMQD |
| 6903. | KMQDI |
| 6904. | MQDIL |
| 6905. | QDILQ |
| 6906. | DILQV |
| 6907. | ILQVC |
| 6908. | LQVCS |
| 6909. | QVCSL |
| 6910. | VCSLQ |
| 6911. | CSLQG |
| 6912. | SLQGF |
| 6913. | LQGFV |
| 6914. | QGFVT |
| 6915. | GFVTL |
| 6916. | FVTLA |
| 6917. | VTLAN |
| 6918. | TLANG |

TABLE 6-continued

| | |
|---|---|
| 6919. | LANGD |
| 6920. | ANGDR |
| 6921. | NGDRY |
| 6922. | GDRYE |
| 6923. | DRYEL |
| 6924. | RYELF |
| 6925. | YELFS |
| 6926. | ELFSY |
| 6927. | LFSYN |
| 6928. | FSYND |
| 6929. | SYNDS |
| 6930. | YNDSG |
| 6931. | NDSGE |
| 6932. | DSGEA |
| 6933. | SGEAV |
| 6934. | GEAVC |
| 6935. | EAVCD |
| 6936. | AVCDE |
| 6937. | VCDEI |
| 6938. | CDEIA |
| 6939. | DEIAL |
| 6940. | EIALG |
| 6941. | IALGD |
| 6942. | ALGDG |
| 6943. | LGDGF |
| 6944. | GDGFH |
| 6945. | DGFHK |
| 6946. | GFHKV |
| 6947. | FHKVL |
| 6948. | HKVLG |
| 6949. | KVLGT |
| 6950. | VLGTM |
| 6951. | LGTML |
| 6952. | GTMLA |
| 6953. | TMLAV |
| 6954. | MLAVA |
| 6955. | LAVAL |
| 6956. | AVALS |
| 6957. | VALSQ |
| 6958. | ALSQA |
| 6959. | LSQAE |
| 6960. | SQAEV |
| 6961. | QAEVF |
| 6962. | AEVFK |
| 6963. | EVFKQ |
| 6964. | VFKQE |
| 6965. | FKQEC |
| 6966. | KQECD |
| 6967. | QECDR |
| 6968. | ECDRF |
| 6969. | CDRFI |
| 6970. | DRFIL |
| 6971. | RFILQ |
| 6972. | FILQA |
| 6973. | ILQAD |
| 6974. | LQADS |
| 6975. | QADSE |
| 6976. | ADSEK |
| 6977. | DSEKN |
| 6978. | SEKNM |
| 6979. | EKNMI |
| 6980. | KNMIH |
| 6981. | NMIHK |
| 6982. | MIHKR |
| 6983. | IHKRM |
| 6984. | HKRMV |
| 6985. | KRMVQ |
| 6986. | RMVQG |
| 6987. | MVQGE |
| 6988. | VQGEQ |
| 6989. | QGEQK |
| 6990. | GEQKS |
| 6991. | EQKSL |
| 6992. | QKSLF |
| 6993. | KSLFL |
| 6994. | SLFLT |
| 6995. | LFLTK |
| 6996. | FLTKM |
| 6997. | LTKMQ |
| 6998. | TKMQT |
| 6999. | KMQTE |
| 7000. | MQTEL |
| 7001. | QTELN |
| 7002. | TELNA |
| 7003. | ELNAG |
| 7004. | LNAGK |
| 7005. | NAGKT |
| 7006. | AGKTI |
| 7007. | GKTIA |
| 7008. | KTIAQ |
| 7009. | TIAQT |
| 7010. | IAQTK |
| 7011. | AQTKE |
| 7012. | QTKEV |
| 7013. | TKEVE |
| 7014. | KEVEA |
| 7015. | EVEAS |
| 7016. | VEASP |
| 7017. | EASPL |
| 7018. | ASPLP |
| 7019. | SPLPS |
| 7020. | PLPSA |
| 7021. | LPSAV |
| 7022. | PSAVA |
| 7023. | SAVAS |
| 7024. | AVASV |
| 7025. | VASVL |
| 7026. | ASVLI |
| 7027. | SVLID |
| 7028. | VLIDH |
| 7029. | LIDHY |
| 7030. | IDHYM |
| 7031. | DHYMP |
| 7032. | HYMPK |
| 7033. | YMPKE |
| 7034. | MPKEV |
| 7035. | PKEVE |
| 7036. | KEVEF |
| 7037. | EVEFL |
| 7038. | VEFLE |
| 7039. | EFLEK |
| 7040. | FLEKI |
| 7041. | LEKIS |
| 7042. | EKISS |
| 7043. | KISSR |
| 7044. | ISSRL |
| 7045. | SSRLY |
| 7046. | SRLYY |
| 7047. | RLYYG |
| 7048. | LYYGN |
| 7049. | YYGNK |
| 7050. | YGNKG |
| 7051. | GNKGS |
| 7052. | NKGSD |
| 7053. | KGSDI |
| 7054. | GSDIG |
| 7055. | SDIGN |
| 7056. | DIGNT |
| 7057. | IGNTI |
| 7058. | GNTIL |
| 7059. | NTILD |
| 7060. | TILDA |
| 7061. | ILDAI |
| 7062. | LDAIS |
| 7063. | DAISL |
| 7064. | AISLY |
| 7065. | ISLYV |
| 7066. | SLYVN |
| 7067. | LYVNS |
| 7068. | YVNSA |
| 7069. | VNSAT |
| 7070. | NSATY |
| 7071. | SATYF |
| 7072. | ATYFG |
| 7073. | TYFGF |
| 7074. | YFGFA |
| 7075. | FGFAN |
| 7076. | GFANY |
| 7077. | FANYI |
| 7078. | ANYIG |

TABLE 6-continued

| | |
|---|---|
| 7079. | NYIGQ |
| 7080. | YIGQP |
| 7081. | IGQPP |
| 7082. | GQPPV |
| 7083. | QPPVV |
| 7084. | PPVVG |
| 7085. | PVVGK |
| 7086. | VVGKT |
| 7087. | VGKTR |
| 7088. | GKTRE |
| 7089. | KTREN |
| 7090. | TRENT |
| 7091. | RENIF |
| 7092. | ENIFA |
| 7093. | NIFAG |
| 7094. | IFAGS |
| 7095. | FAGSA |
| 7096. | AGSAD |
| 7097. | GSADN |
| 7098. | SADNA |
| 7099. | ADNAK |
| 7100. | DNAKA |
| 7101. | NAKAK |
| 7102. | AKAKL |
| 7103. | KAKLD |
| 7104. | AKLDE |
| 7105. | KLDEE |
| 7106. | LDEEK |
| 7107. | DEEKK |
| 7108. | EEKKQ |
| 7109. | EKKQV |
| 7110. | KKQVD |
| 7111. | KQVDV |
| 7112. | QVDVF |
| 7113. | VDVFL |
| 7114. | DVFLE |
| 7115. | VFLEI |
| 7116. | FLEIT |
| 7117. | LEITE |
| 7118. | EITEA |
| 7119. | ITEAA |
| 7120. | TEAAK |
| 7121. | EAAKT |
| 7122. | AAKTT |
| 7123. | AKTTV |
| 7124. | KTTVT |
| 7125. | TTVTN |
| 7126. | TVTNQ |
| 7127. | VTNQQ |
| 7128. | TNQQS |
| 7129. | NQQSA |
| 7130. | QQSAV |
| 7131. | QSAVT |
| 7132. | SAVTN |
| 7133. | AVTND |
| 7134. | VTNDD |
| 7135. | TNDDK |
| 7136. | NDDKL |
| 7137. | DDKLS |
| 7138. | DKLST |
| 7139. | KLSTE |
| 7140. | LSTEQ |
| 7141. | STEQK |
| 7142. | TEQKA |
| 7143. | EQKAK |
| 7144. | QKAKI |
| 7145. | KAKIK |
| 7146. | AKIKA |
| 7147. | KIKAE |
| 7148. | IKAEL |
| 7149. | KAELT |
| 7150. | AELTQ |
| 7151. | ELTQY |
| 7152. | LTQYT |
| 7153. | TQYTD |
| 7154. | QYTDM |
| 7155. | YTDML |
| 7156. | TDMLN |
| 7157. | DMLNA |
| 7158. | MLNAI |

TABLE 6-continued

| | |
|---|---|
| 7159. | LNAIS |
| 7160. | NAISN |
| 7161. | AISNS |
| 7162. | ISNSL |
| 7163. | SNSLT |
| 7164. | NSLTS |
| 7165. | SLTSL |
| 7166. | LTSLK |
| 7167. | TSLKT |
| 7168. | SLKTQ |
| 7169. | LKTQL |
| 7170. | KTQLA |
| 7171. | TQLAP |
| 7172. | QLAPL |
| 7173. | LAPLS |
| 7174. | APLSV |
| 7175. | PLSVS |
| 7176. | LSVST |
| 7177. | SVSTV |
| 7178. | VSTVE |
| 7179. | STVEG |
| 7180. | TVEGV |
| 7181. | VEGVD |
| 7182. | EGVDG |
| 7183. | GVDGV |
| 7184. | VDGVF |
| 7185. | DGVFE |
| 7186. | GVFEV |
| 7187. | VFEVK |
| 7188. | FEVKN |
| 7189. | EVKNG |
| 7190. | VKNGI |
| 7191. | KNGIP |
| 7192. | NGIPG |
| 7193. | GIPGE |
| 7194. | IPGEN |
| 7195. | PGENG |
| 7196. | GENGK |
| 7197. | ENGKN |
| 7198. | NGKNW |
| 7199. | GKNWR |
| 7200. | KNWRL |
| 7201. | NWRLV |
| 7202. | WRLVL |
| 7203. | RLVLQ |
| 7204. | LVLQT |
| 7205. | VLQTL |
| 7206. | LQTLE |
| 7207. | QTLED |
| 7208. | TLEDT |
| 7209. | LEDTV |
| 7210. | EDTVV |
| 7211. | DTVVS |
| 7212. | TVVSG |
| 7213. | VVSGE |
| 7214. | VSGEV |
| 7215. | SGEVG |
| 7216. | GEVGS |
| 7217. | EVGSP |
| 7218. | VGSPT |
| 7219. | GSPTN |
| 7220. | SPTNI |
| 7221. | PTNIG |
| 7222. | TNIGM |
| 7223. | NIGMF |
| 7224. | IGMFQ |
| 7225. | GMFQM |
| 7226. | MFQMQ |
| 7227. | FQMQA |
| 7228. | QMQAL |
| 7229. | MQALV |
| 7230. | QALVH |
| 7231. | ALVHL |
| 7232. | LVHLN |
| 7233. | VHLNQ |
| 7234. | HLNQQ |
| 7235. | LNQQA |
| 7236. | NQQAY |
| 7237. | QQAYA |
| 7238. | QAYAD |

TABLE 6-continued

| | |
|---|---|
| 7239. | AYADM |
| 7240. | YADMG |
| 7241. | ADMGQ |
| 7242. | DMGQN |
| 7243. | MGQNF |
| 7244. | GQNFQ |
| 7245. | QNFQL |
| 7246. | NFQLE |
| 7247. | FQLEL |
| 7248. | QLELQ |
| 7249. | LELQM |
| 7250. | ELQMH |
| 7251. | LQMHL |
| 7252. | QMHLT |
| 7253. | MHLTS |
| 7254. | HLTSM |
| 7255. | LTSMQ |
| 7256. | TSMQQ |
| 7257. | SMQQE |
| 7258. | MQQEW |
| 7259. | QQEWM |
| 7260. | QEWMV |
| 7261. | EWMVV |
| 7262. | WMVVA |
| 7263. | MVVAT |
| 7264. | VVATS |
| 7265. | VATSL |
| 7266. | ATSLQ |
| 7267. | TSLQL |
| 7268. | SLQLL |
| 7269. | LQLLN |
| 7270. | QLLNQ |
| 7271. | LLNQI |
| 7272. | LNQIY |
| 7273. | NQIYL |
| 7274. | QIYLG |
| 7275. | IYLGL |
| 7276. | YLGLA |
| 7277. | LGLAR |
| 7278. | GLARN |
| 7279. | LARNL |
| 7280. | ARNLL |
| 7281. | RNLLR |

5-mer peptides of CT622 (hypothetical protein, 647 amino acids), ACCESSION# NP 220139.1, GI: 15605353 (SEQ ID NOS: 7282-7924)

| | |
|---|---|
| 7282. | MESGP |
| 7283. | ESGPE |
| 7284. | SGPES |
| 7285. | GPESV |
| 7286. | PESVS |
| 7287. | ESVSS |
| 7288. | SVSSN |
| 7289. | VSSNQ |
| 7290. | SSNQS |
| 7291. | SNQSS |
| 7292. | NQSSM |
| 7293. | QSSMN |
| 7294. | SSMNP |
| 7295. | SMNPI |
| 7296. | MNPII |
| 7297. | NPIIN |
| 7298. | PIING |
| 7299. | IINGQ |
| 7300. | INGQI |
| 7301. | NGQIA |
| 7302. | GQIAS |
| 7303. | QIASN |
| 7304. | IASNS |
| 7305. | ASNSE |
| 7306. | SNSET |
| 7307. | NSETK |
| 7308. | SETKE |
| 7309. | ETKES |
| 7310. | TKEST |
| 7311. | KESTK |
| 7312. | ESTKE |
| 7313. | STKES |

TABLE 6-continued

| | |
|---|---|
| 7314. | TKESE |
| 7315. | KESEA |
| 7316. | ESEAS |
| 7317. | SEASP |
| 7318. | EASPS |
| 7319. | ASPSA |
| 7320. | SPSAS |
| 7321. | PSASS |
| 7322. | SASSS |
| 7323. | ASSSV |
| 7324. | SSSVS |
| 7325. | SSVSS |
| 7326. | SVSSW |
| 7327. | VSSWS |
| 7328. | SSWSF |
| 7329. | SWSFL |
| 7330. | WSFLS |
| 7331. | SFLSS |
| 7332. | FLSSA |
| 7333. | LSSAK |
| 7334. | SSAKH |
| 7335. | SAKHA |
| 7336. | AKHAL |
| 7337. | KHALI |
| 7338. | HALIS |
| 7339. | ALISL |
| 7340. | LISLR |
| 7341. | ISLRD |
| 7342. | SLRDA |
| 7343. | LRDAI |
| 7344. | RDAIL |
| 7345. | DAILN |
| 7346. | AILNK |
| 7347. | ILNKN |
| 7348. | LNKNS |
| 7349. | NKNSS |
| 7350. | KNSSP |
| 7351. | NSSPT |
| 7352. | SSPTD |
| 7353. | SPTDS |
| 7354. | PTDSL |
| 7355. | TDSLS |
| 7356. | DSLSQ |
| 7357. | SLSQL |
| 7358. | LSQLE |
| 7359. | SQLEA |
| 7360. | QLEAS |
| 7361. | LEAST |
| 7362. | EASTS |
| 7363. | ASTST |
| 7364. | STSTS |
| 7365. | TSTST |
| 7366. | STSTV |
| 7367. | TSTVT |
| 7368. | STVTR |
| 7369. | TVTRV |
| 7370. | VTRVA |
| 7371. | TRVAA |
| 7372. | RVAAR |
| 7373. | VAARD |
| 7374. | AARDY |
| 7375. | ARDYN |
| 7376. | RDYNE |
| 7377. | DYNEA |
| 7378. | YNEAK |
| 7379. | NEAKS |
| 7380. | EAKSN |
| 7381. | AKSNF |
| 7382. | KSNFD |
| 7383. | SNFDT |
| 7384. | NFDTA |
| 7385. | FDTAK |
| 7386. | DTAKS |
| 7387. | TAKSG |
| 7388. | AKSGL |
| 7389. | KSGLE |
| 7390. | SGLEN |
| 7391. | GLENA |
| 7392. | LENAT |
| 7393. | ENATT |

TABLE 6-continued

| | |
|---|---|
| 7394. | NATTL |
| 7395. | ATTLA |
| 7396. | TTLAE |
| 7397. | TLAEY |
| 7398. | LAEYE |
| 7399. | AEYET |
| 7400. | EYETK |
| 7401. | YETKM |
| 7402. | ETKMA |
| 7403. | TKMAD |
| 7404. | KMADL |
| 7405. | MADLM |
| 7406. | ADLMA |
| 7407. | DLMAA |
| 7408. | LMAAL |
| 7409. | MAALQ |
| 7410. | AALQD |
| 7411. | ALQDM |
| 7412. | LQDME |
| 7413. | QDMER |
| 7414. | DMERL |
| 7415. | MERLA |
| 7416. | ERLAK |
| 7417. | RLAKQ |
| 7418. | LAKQK |
| 7419. | AKQKA |
| 7420. | KQKAE |
| 7421. | QKAEV |
| 7422. | KAEVT |
| 7423. | AEVTR |
| 7424. | EVTRI |
| 7425. | VTRIK |
| 7426. | TRIKE |
| 7427. | RIKEA |
| 7428. | IKEAL |
| 7429. | KEALQ |
| 7430. | EALQE |
| 7431. | ALQEK |
| 7432. | LQEKQ |
| 7433. | QEKQE |
| 7434. | EKQEV |
| 7435. | KQEVI |
| 7436. | QEVID |
| 7437. | EVIDK |
| 7438. | VIDKL |
| 7439. | IDKLN |
| 7440. | DKLNQ |
| 7441. | KLNQL |
| 7442. | LNQLV |
| 7443. | NQLVK |
| 7444. | QLVKL |
| 7445. | LVKLE |
| 7446. | VKLEK |
| 7447. | KLEKQ |
| 7448. | LEKQN |
| 7449. | EKQNQ |
| 7450. | KQNQT |
| 7451. | QNQTL |
| 7452. | NQTLK |
| 7453. | QTLKE |
| 7454. | TLKET |
| 7455. | LKETL |
| 7456. | KETLT |
| 7457. | ETLTT |
| 7458. | TLTTT |
| 7459. | LTTTD |
| 7460. | TTTDS |
| 7461. | TTDSA |
| 7462. | TDSAD |
| 7463. | DSADQ |
| 7464. | SADQI |
| 7465. | ADQIP |
| 7466. | DQIPA |
| 7467. | QIPAI |
| 7468. | IPAIN |
| 7469. | PAINS |
| 7470. | AINSQ |
| 7471. | INSQL |
| 7472. | NSQLE |
| 7473. | SQLEI |
| 7474. | QLEIN |
| 7475. | LEINK |
| 7476. | EINKN |
| 7477. | INKNS |
| 7478. | NKNSA |
| 7479. | KNSAD |
| 7480. | NSADQ |
| 7481. | SADQI |
| 7482. | ADQII |
| 7483. | DQIIK |
| 7484. | QIIKD |
| 7485. | IIKDL |
| 7486. | IKDLE |
| 7487. | KDLEG |
| 7488. | DLEGQ |
| 7489. | LEGQN |
| 7490. | EGQNI |
| 7491. | GQNIS |
| 7492. | QNISY |
| 7493. | NISYE |
| 7494. | ISYEA |
| 7495. | SYEAV |
| 7496. | YEAVL |
| 7497. | EAVLT |
| 7498. | AVLTN |
| 7499. | VLTNA |
| 7500. | LTNAG |
| 7501. | TNAGE |
| 7502. | NAGEV |
| 7503. | AGEVI |
| 7504. | GEVIK |
| 7505. | EVIKA |
| 7506. | VIKAS |
| 7507. | IKASS |
| 7508. | KASSE |
| 7509. | ASSEA |
| 7510. | SSEAG |
| 7511. | SEAGI |
| 7512. | EAGIK |
| 7513. | AGIKL |
| 7514. | GIKLG |
| 7515. | IKLGQ |
| 7516. | KLGQA |
| 7517. | LGQAL |
| 7518. | GQALQ |
| 7519. | QALQS |
| 7520. | ALQSI |
| 7521. | LQSIV |
| 7522. | QSIVD |
| 7523. | SIVDA |
| 7524. | IVDAG |
| 7525. | VDAGD |
| 7526. | DAGDQ |
| 7527. | AGDQS |
| 7528. | GDQSQ |
| 7529. | DQSQA |
| 7530. | QSQAA |
| 7531. | SQAAV |
| 7532. | QAAVL |
| 7533. | AAVLQ |
| 7534. | AVLQA |
| 7535. | VLQAQ |
| 7536. | LQAQQ |
| 7537. | QAQQN |
| 7538. | AQQNN |
| 7539. | QQNNS |
| 7540. | QNNSP |
| 7541. | NNSPD |
| 7542. | NSPDN |
| 7543. | SPDNI |
| 7544. | PDNIA |
| 7545. | DNIAA |
| 7546. | NIAAT |
| 7547. | IAATK |
| 7548. | AATKK |
| 7549. | ATKKL |
| 7550. | TKKLI |
| 7551. | KKLID |
| 7552. | KLIDA |
| 7553. | LIDAA |

TABLE 6-continued

| | |
|---|---|
| 7554. | IDAAE |
| 7555. | DAAET |
| 7556. | AAETK |
| 7557. | AETKV |
| 7558. | ETKVN |
| 7559. | TKVNE |
| 7560. | KVNEL |
| 7561. | VNELK |
| 7562. | NELKQ |
| 7563. | ELKQE |
| 7564. | LKQEH |
| 7565. | KQEHT |
| 7566. | QEHTG |
| 7567. | EHTGL |
| 7568. | HTGLT |
| 7569. | TGLTD |
| 7570. | GLTDS |
| 7571. | LTDSP |
| 7572. | TDSPL |
| 7573. | DSPLV |
| 7574. | SPLVK |
| 7575. | PLVKK |
| 7576. | LVKKA |
| 7577. | VKKAE |
| 7578. | KKAEE |
| 7579. | KAEEQ |
| 7580. | AEEQI |
| 7581. | EEQIS |
| 7582. | EQISQ |
| 7583. | QISQA |
| 7584. | ISQAQ |
| 7585. | SQAQK |
| 7586. | QAQKD |
| 7587. | AQKDI |
| 7588. | QKDIQ |
| 7589. | KDIQE |
| 7590. | DIQEI |
| 7591. | IQEIK |
| 7592. | QEIKP |
| 7593. | EIKPS |
| 7594. | IKPSG |
| 7595. | KPSGS |
| 7596. | PSGSD |
| 7597. | SGSDI |
| 7598. | GSDIP |
| 7599. | SDIPI |
| 7600. | DIPIV |
| 7601. | IPIVG |
| 7602. | PIVGP |
| 7603. | IVGPS |
| 7604. | VGPSG |
| 7605. | GPSGS |
| 7606. | PSGSA |
| 7607. | SGSAA |
| 7608. | GSAAS |
| 7609. | SAASA |
| 7610. | AASAG |
| 7611. | ASAGS |
| 7612. | SAGSA |
| 7613. | AGSAV |
| 7614. | GSAVG |
| 7615. | SAVGA |
| 7616. | AVGAL |
| 7617. | VGALK |
| 7618. | GALKS |
| 7619. | ALKSS |
| 7620. | LKSSN |
| 7621. | KSSNN |
| 7622. | SSNNS |
| 7623. | SNNSG |
| 7624. | NNSGR |
| 7625. | NSGRI |
| 7626. | SGRIS |
| 7627. | GRISL |
| 7628. | RISLL |
| 7629. | ISLLL |
| 7630. | SLLLD |
| 7631. | LLLDD |
| 7632. | LLDDV |
| 7633. | LDDVD |

TABLE 6-continued

| | |
|---|---|
| 7634. | DDVDN |
| 7635. | DVDNE |
| 7636. | VDNEM |
| 7637. | DNEMA |
| 7638. | NEMAA |
| 7639. | EMAAI |
| 7640. | MAAIA |
| 7641. | AAIAM |
| 7642. | AIAMQ |
| 7643. | IAMQG |
| 7644. | AMQGF |
| 7645. | MQGFR |
| 7646. | QGFRS |
| 7647. | GFRSM |
| 7648. | FRSMI |
| 7649. | RSMIE |
| 7650. | SMIEQ |
| 7651. | MIEQF |
| 7652. | IEQFN |
| 7653. | EQFNV |
| 7654. | QFNVN |
| 7655. | FNVNN |
| 7656. | NVNNP |
| 7657. | VNNPA |
| 7658. | NNPAT |
| 7659. | NPATA |
| 7660. | PATAK |
| 7661. | ATAKE |
| 7662. | TAKEL |
| 7663. | AKELQ |
| 7664. | KELQA |
| 7665. | ELQAM |
| 7666. | LQAME |
| 7667. | QAMEA |
| 7668. | AMEAQ |
| 7669. | MEAQL |
| 7670. | EAQLT |
| 7671. | AQLTA |
| 7672. | QLTAM |
| 7673. | LTAMS |
| 7674. | TAMSD |
| 7675. | AMSDQ |
| 7676. | MSDQL |
| 7677. | SDQLV |
| 7678. | DQLVG |
| 7679. | QLVGA |
| 7680. | LVGAD |
| 7681. | VGADG |
| 7682. | GADGE |
| 7683. | ADGEL |
| 7684. | DGELP |
| 7685. | GELPA |
| 7686. | ELPAE |
| 7687. | LPAEI |
| 7688. | PAEIQ |
| 7689. | AEIQA |
| 7690. | EIQAI |
| 7691. | IQAIK |
| 7692. | QAIKD |
| 7693. | AIKDA |
| 7694. | IKDAL |
| 7695. | KDALA |
| 7696. | DALAQ |
| 7697. | ALAQA |
| 7698. | LAQAL |
| 7699. | AQALK |
| 7700. | QALKQ |
| 7701. | ALKQP |
| 7702. | LKQPS |
| 7703. | KQPST |
| 7704. | QPSTD |
| 7705. | PSTDG |
| 7706. | STDGL |
| 7707. | TDGLA |
| 7708. | DGLAT |
| 7709. | GLATA |
| 7710. | LATAM |
| 7711. | ATAMG |
| 7712. | TAMGQ |
| 7713. | AMGQV |

TABLE 6-continued

| | |
|---|---|
| 7714. | MGQVA |
| 7715. | GQVAF |
| 7716. | QVAFA |
| 7717. | VAFAA |
| 7718. | AFAAA |
| 7719. | FAAAK |
| 7720. | AAAKV |
| 7721. | AAKVG |
| 7722. | AKVGG |
| 7723. | KVGGG |
| 7724. | VGGGS |
| 7725. | GGGSA |
| 7726. | GGSAG |
| 7727. | GSAGT |
| 7728. | SAGTA |
| 7729. | AGTAG |
| 7730. | GTAGT |
| 7731. | TAGTV |
| 7732. | AGTVQ |
| 7733. | GTVQM |
| 7734. | TVQMN |
| 7735. | VQMNV |
| 7736. | QMNVK |
| 7737. | MNVKQ |
| 7738. | NVKQL |
| 7739. | VKQLY |
| 7740. | KQLYK |
| 7741. | QLYKT |
| 7742. | LYKTA |
| 7743. | YKTAF |
| 7744. | KTAFS |
| 7745. | TAFSS |
| 7746. | AFSST |
| 7747. | FSSTS |
| 7748. | SSTSS |
| 7749. | STSSS |
| 7750. | TSSSS |
| 7751. | SSSSY |
| 7752. | SSSYA |
| 7753. | SSYAA |
| 7754. | SYAAA |
| 7755. | YAAAL |
| 7756. | AAALS |
| 7757. | AALSD |
| 7758. | ALSDG |
| 7759. | LSDGY |
| 7760. | SDGYS |
| 7761. | DGYSA |
| 7762. | GYSAY |
| 7763. | YSAYK |
| 7764. | SAYKT |
| 7765. | AYKTL |
| 7766. | YKTLN |
| 7767. | KTLNS |
| 7768. | TLNSL |
| 7769. | LNSLY |
| 7770. | NSLYS |
| 7771. | SLYSE |
| 7772. | LYSES |
| 7773. | YSESR |
| 7774. | SESRS |
| 7775. | ESRSG |
| 7776. | SRSGV |
| 7777. | RSGVQ |
| 7778. | SGVQS |
| 7779. | GVQSA |
| 7780. | VQSAI |
| 7781. | QSAIS |
| 7782. | SAISQ |
| 7783. | AISQT |
| 7784. | ISQTA |
| 7785. | SQTAN |
| 7786. | QTANP |
| 7787. | TANPA |
| 7788. | ANPAL |
| 7789. | NPALS |
| 7790. | PALSR |
| 7791. | ALSRS |
| 7792. | LSRSV |
| 7793. | SRSVS |
| 7794. | RSVSR |
| 7795. | SVSRS |
| 7796. | VSRSG |
| 7797. | SRSGI |
| 7798. | RSGIE |
| 7799. | SGIES |
| 7800. | GIESQ |
| 7801. | IESQG |
| 7802. | ESQGR |
| 7803. | SQGRS |
| 7804. | QGRSA |
| 7805. | GRSAD |
| 7806. | RSADA |
| 7807. | SADAS |
| 7808. | ADASQ |
| 7809. | DASQR |
| 7810. | ASQRA |
| 7811. | SQRAA |
| 7812. | QRAAE |
| 7813. | RAAET |
| 7814. | AAETI |
| 7815. | AETIV |
| 7816. | ETIVR |
| 7817. | TIVRD |
| 7818. | IVRDS |
| 7819. | VRDSQ |
| 7820. | RDSQT |
| 7821. | DSQTL |
| 7822. | SQTLG |
| 7823. | QTLGD |
| 7824. | TLGDV |
| 7825. | LGDVY |
| 7826. | GDVYS |
| 7827. | DVYSR |
| 7828. | VYSRL |
| 7829. | YSRLQ |
| 7830. | SRLQV |
| 7831. | RLQVL |
| 7832. | LQVLD |
| 7833. | QVLDS |
| 7834. | VLDSL |
| 7835. | LDSLM |
| 7836. | DSLMS |
| 7837. | SLMST |
| 7838. | LMSTI |
| 7839. | MSTIV |
| 7840. | STIVS |
| 7841. | TIVSN |
| 7842. | IVSNP |
| 7843. | VSNPQ |
| 7844. | SNPQV |
| 7845. | NPQVN |
| 7846. | PQVNQ |
| 7847. | QVNQE |
| 7848. | VNQEE |
| 7849. | NQEEI |
| 7850. | QEEIM |
| 7851. | EEIMQ |
| 7852. | EIMQK |
| 7853. | IMQKL |
| 7854. | MQKLT |
| 7855. | QKLTA |
| 7856. | KLTAS |
| 7857. | LTASI |
| 7858. | TASIS |
| 7859. | ASISK |
| 7860. | SISKA |
| 7861. | ISKAP |
| 7862. | SKAPQ |
| 7863. | KAPQF |
| 7864. | APQFG |
| 7865. | PQFGY |
| 7866. | QFGYP |
| 7867. | FGYPA |
| 7868. | GYPAV |
| 7869. | YPAVQ |
| 7870. | PAVQN |
| 7871. | AVQNS |
| 7872. | VQNSA |
| 7873. | QNSAD |

TABLE 6-continued

| | |
|---|---|
| 7874. | NSADS |
| 7875. | SADSL |
| 7876. | ADSLQ |
| 7877. | DSLQK |
| 7878. | SLQKF |
| 7879. | LQKFA |
| 7880. | QKFAA |
| 7881. | KFAAQ |
| 7882. | FAAQL |
| 7883. | AAQLE |
| 7884. | AQLER |
| 7885. | QLERE |
| 7886. | LEREF |
| 7887. | EREFV |
| 7888. | REFVD |
| 7889. | EFVDG |
| 7890. | FVDGE |
| 7891. | VDGER |
| 7892. | DGERS |
| 7893. | GERSL |
| 7894. | ERSLA |
| 7895. | RSLAE |
| 7896. | SLAES |
| 7897. | LAESR |
| 7898. | AESRE |
| 7899. | ESREN |
| 7900. | SRENA |
| 7901. | RENAF |
| 7902. | ENAFR |

TABLE 6-continued

| | |
|---|---|
| 7903. | NAFRK |
| 7904. | AFRKQ |
| 7905. | FRKQP |
| 7906. | RKQPA |
| 7907. | KQPAF |
| 7908. | QPAFI |
| 7909. | PAFIQ |
| 7910. | AFIQQ |
| 7911. | FIQQV |
| 7912. | IQQVL |
| 7913. | QQVLV |
| 7914. | QVLVN |
| 7915. | VLVNI |
| 7916. | LVNIA |
| 7917. | VNIAS |
| 7918. | NIASL |
| 7919. | IASLF |
| 7920. | ASLFS |
| 7921. | SLFSG |
| 7922. | LFSGY |
| 7923. | FSGYL |
| 7924. | SGYLS |

Amino Acid Sequences of *Chlamydia trachomatis* Proteins CT443, CT381, CT875, CT147, HSP60, CT376 and CT557, CT858 (CPAF), Pgp3, CT823 (cHtrA), CT681 (14014P), CT119 (IncA) and CT813 (All sequences are available from this website: www.ncbi.nlm.nih.gov/protein/15605169)

CT443 (OmcB or CRP60, 553 amino acids), ACCESSION#: NP 219955.1, GI: 15605169
(SEQ ID NO: 7925)

```
  1 mrigdpmnkl irravtifav tsvaslfasg vletsmaesl stnvisladt kakdntshks
 61 kkarknhske tpvdrkevap vheskatgpk qdscfgrmyt vkvnddrnve itqavpeyat
121 vgspypieit atgkrdcvdv iitqqlpcea efvrsdpatt ptadgklvwk idrlgqgeks
181 kitvwvkplk egccftaatv cacpeirsvt kcgqpaicvk qegpenaclr cpvvykiniv
241 nqgtatarnv vvenpvpdgy ahssgqrvlt ftlgdmqpge hrtitvefcp lkrgratnia
301 tvsycgghkn tasvttvine pcvqvsiaga dwsyvckpve yvisvsnpgd lvlrdvvved
361 tlspgvtvle aagaqiscnk vvwtvkelnp geslqykylv raqtpgqftn nvvvkscsdc
421 gtctscaeat tywkgvaath mcvvdtcdpv cvgentvyri cvtnrgsaed tnvslmlkfs
481 kelqpvsfsg ptkgtitgnt vvfdslprlg sketvefsvt lkavsagdar geailssdtl
541 tvpvsdtent hiy
```

CT381 (ArtJ, 257 amino acids), ACCESSION# NP 219890.1, GI: 15605105
(SEQ ID NO: 7926)

```
  1 mcikrkktwi aflavvcsfc ltgclkeggd snsekfivgt natyppfefv dkrgevvgfd
 61 idlareisnk lgktldvref sfdalilnlk qhridavitg msitpsrlke ilmipyygee
121 ikhlvlvfkg enkhplpltq yrsvavqtgt ygeaylqsls evhirsfdst levlmevmhg
181 kspvavleps iaqvvlkdfp alstatidlp edqwvlgygi gvasdrpala lkieaavqei
241 rkegvlaele qkwglnn
```

CT875 (hypothetical protein, 591 amino acids), ACCESSION#: NP 219502.1, GI: 15604718
(SEQ ID NO: 7927)

```
  1 msirgvggng nsripshngd gsnrrsqntk gnnkvedrvc slyssrsnen respyavvdv
 61 ssmiestpts gettrasrgv fsrfqrglvr vadkvrravq cawssystrr ssatraaesg
121 sssrtargas sgyreyspsa arglrlmftd fwrtrylrqt spmagvfgnl dvnearlmaa
181 ytsecadhle anklagpdgv aaareiakrw eqrvrdlqdk gaarkllndp lgrrtpnyqs
241 knpgeytvgn smfydgpqva nlqnvdtgfw ldmsnlsdvv lsreiqtglr aratleesmp
```

-continued

```
301 mlenleerfr rlqetcdaar teieesgwtr esasrmegde aqgpsraqqa fqsfvnecns 361 iefsfgsfge hvrvlcarvs rglaaageai rrcfscckgs thryaprddl spegaslaet 421 larfaddmgi ergadgtydi plvddwrrgv psiegegsds iyeimmpiye vmdmdletrr 481 sfavqqghyq dprasdydlp rasdydlprs pyptpplppr yqlqnmdvea gfreavyasf 541 vagmynyvvt qpqeripnsq qvegilrdml tngsqtfrdl mrrwnrevdr e
```

CT147 (hypothetical protein, 1449 amino acids), ACCESSION# NP 219650.1,
GI: 15604866

(SEQ ID NO: 7928)

```
   1 manpstpsfn hsdlslqgrl rassqqctqa gqgdpqplsp esrgltsnfs trrdlidvve 61 esietakgse lkklriyeia lkiltiigaa ilfavplcml lgvplwipiv tcigvgiafs 121 iakgclqkrc qqireeyral hlyhryllsn kdsidgtlls rfdirfrkae eklhgldldk 181 reanhplead krydfaglah qryqvdaalg isssqdafwr gvaqqvksvk ddvvlgdkas 241 tdlypiaqqa lqaagvgfsg aagkeslldl akslsslfaw gsqvgkdshe alqqyqmrfl 301 sspilatwcg agfsasaqdf vlkgenildi asenhtkmqn aikrvqlvsv lgkmrnwkek 361 idtliqnknl dqdslrklyq diekamhkvc iedgvstsiq tqvrkvtqky lrqdlqelln 421 kkaplnesdl skmqkgissc anlvvtlles qlgtsgqtpi keveesiyrd liatilqmgs 481 aaggvtplvd gvhkairegk alrselsram slhprqsflg vqsaveklqa firdpkwgas 541 avhtsaeetl aqkqkfvsdl triqtsladw reryglfeet klnhivstdf vsrteafldt 601 lknvaeacsl eqavaelkdc edamkadlth veqkmnptei esareefkrl meelagiqeq 661 leqiaqpiye egvsgerlll ntvffhpevl rkkvqakeas lealtkgeqp sptkkktlkq 721 lsegceyfss lvskinalkt ilegsrgkki asqdirqlig ltdelalels sfqqdslesl 781 lygleglsip aasieqkkgs pksssiaekv vyashqrvhn gvkakvnrtl eafsqlikgl 841 rgslrnamit kavvaavlsv afsclaialf svqltwlpim lcvlalvlea ipsalsiwve 901 krnwkyevas lakqlvsdgr klpypdlgdq nikhlekird vygldgvael rvaeaallgv 961 qklpeeqkqe slksavkalr adakvlnkkf kklpesyqpq hsevtgvqgv teqesrddvl 1021 vaqdmaaiee lqdqyhaacl qfesystrfl aeqrkakfle ellvqkrrdv shlshqeahy 1081 tqvvshlkel ismrkgastq haskeeistk mrellslddq llkahtaqdv nrdnsingql 1141 qqqfkklsee gslqkvkall elnmclgnag qtlyhsrlkr evfeaslsgt srqllqyged 1201 lfasydgsdr sallrfvlgs gyemiseass elkslrkrwk rsasqaaiap edyekvcrvl 1261 erflkardsl rpklglplgk ssdatvglqh qirdnqrvka rvtacyqesc rnvlqhledw 1321 vrktrqesae cqkvetkire fcqkagsken laestemlfs sleedlnkip ldvlrailrs 1381 lsskvlhird qklelekleee qfaktnaivk akeaefekng evwhnqyqml ksqmeklesq 1441 krrltdkke
```

HSP60 (CT110, 544 amino acids), ACCESSION# AAS19616.1, GI: 42541742

(SEQ ID NO: 7929)

```
   1 mvaknikyne earkkiqkgv ktlaeavkvt lgpkgrhvvi dksfgspqvt kdgvtvakev 61 eladkhenmg aqmvkevask tadkagdgtt tatvlaeaiy teglrnvtag anpmdlkrgi 121 dkavkvvvdq irkiskpvqh hkeiaqvati sanndaeign liaeamekvg kngsitveea 181 kgfetvldvv egmnfnrgyl ssyfatnpet qecvledalv liydkkisgi kdflpvlqqv 241 aesgrplli aediegeala tivvnrirgg frvcavkapg fgdrrkamle diailtggql 301 iseelgmkle nanlamlgka kkvivskedt tivegmgeke alearcesik kqiedsssdy 361 dkeklqerla klsggvavir vgaateiemk ekkdrvddaq hatiaaveeg ilpggggtali 421 rciptleafl pmltnedeqi garivlkals aplkqiaana gkegaiifqq vmsrsanegy
```

```
481 dalrdaytdm leagildpak vtrsalesaa svagllltte aliaeipeek paaapampga 541 gmdy
```

CT376 (malate dehydrogenase, 326 amino acids) ACCESSION# NP 219885.1, GI: 15605100

(SEQ ID NO: 7930)

```
  1 mvsqtvsvav tggtgqiays flfslahgdv fgldcgidlr iydipgtera lsgvrmeldd 61 gafpllqrvq vttslhdafd gidaafligs vprgpgmerr dllkkngeif atqgkalntt 121 akrdakifvv gnpvntncwi amnhaprllr knfhamlrld qnrmhsmlsh raevplsavs 181 qvvvwgnhsa kqvpdftqal indrpiaeti adrdwlenim vpsvqsrgsa vieargkssa 241 asaaralaea arsiyqpkeg ewfssgvcsd hnpyglpedl ifgfpcrmla tgeyeviprl 301 pwdafirgkm qisldeilqe kasvsl
```

CT557 (dihydrolipoamide dehydrogenase, 465 amino acids), ACCESSION# NP 220072.1, GI: 15605286

(SEQ ID NO: 7931)

```
  1 mneafdcvvi gagpggyvaa itaaqaglkt aliekreagg tclnrgcips kallagaevv 61 tqirhadqfg ihvegfsiny pamvqrkdsv vrsirdglng lirsnkitvf sgrgslisst 121 evkilgenps vikahsiila tgseprafpg ipfsaespri lcstgvlnlk eipqkmaiig 181 ggvigcefas lfhtlgsevs vieassqila lnnpdisktm fdkftrqglr fvleasysni 241 edigdrvrlt ingnveeydy vlvsigrrin tenigldkag vicdergvip tdatmrtnvp 301 niyaigditg kwqlahvash qgiiaarnia ghkeeidysa vpsviftfpe vasvglspta 361 aqqqkipvkv tkfpfraigk avamgeadgf aaiishettq qilgayvigp hassliseit 421 lavrneltlp ciyetihahp tlaevwaesa llavdtplhm ppakk
```

CT858 (CPAF, total of 609 amino acids), ACCESSION# AAC68456.1, GI: 3329332

(SEQ ID NO: 7932)

```
  1 mgfwrtsimk mnriwllllt fssaihspvq geslvcknal qdlsflehll qvkyapktwk 61 eqylgwdlvq ssysaqqklr tqenpstsfc qqvladfigg lndfhagvtf faiesaylpy 121 tvqkssdgrf yfvdimtfss eirvgdelle vdgapvqdvl atlygsnhkg taaeesaalr 181 tlfsrmaslg hkvpsgrttl kirrpfgttr evrvkwryvp egvgdlatia psirapqlqk 241 smrsffpkkd dafhrssslf yspmvphfwa elrnhyatsg lksgynigst dgflpvigpv 301 iweseglfra yissvtdgdg kshkvgflri ptyswqdmed fdpsgpppwe efakiiqvfs 361 sntealiidq tnnpggsvly lyallsmltd rplelpkhrm iltqdevvda ldwltllenv 421 dtnvesrlal gdnmegytvd lqvaeylksf grqvincwsk gdielstpip lfgfekihph 481 prvqyskpic vlineqdfsc adffpvvlkd ndralivgtr tagaggfvfn vqfpnrtgik 541 tcsltgslav rehgafieni gvephidlpf tandirykgy seyldkvkkl vcqlinndgt 601 iilaedgsf
```

Pgp3 (plasmid-encoded secretion protein, 264 amino acids), ACCESSION# ADI51551.1, GI: 297749006

(SEQ ID NO: 7933)

```
  1 mgnsgfylyn tencvfadni kvgqmteplk dqqiilgtks tpvaakmtas dgisltvsnn 61 sstnasitig ldaekayqli leklgnqild giadtivdst vqdildkitt dpslgllkaf 121 nnfpitnkiq cnglftpsni etllggteig kftvtpkssg smflvsadii asrmeggvvl 181 alvregdskp caisygyssg vpnlcslrts itntgltptt yslrvggles gvvwvnalsn 241 gndilgitnt snvsflevip qtna
```

CT823 (cHtrA, 497 amino acids), ACCESSION# NP 220344.1, GI: 15605558

(SEQ ID NO: 7934)

```
  1 mmkrllcvll stsvfsspml gysaskkdsk adiclavssg dgevsgedll kevsrgfsrv 61 aakatpgvvy ienfpktgnq aiaspgnkrg fqenpfdyfn deffnrffgl pshreqqrpq
```

```
121 qrdavrgtgf ivsedgyvvt nhhvvedagk ihvtlhdgqk ytakivgldp ktdlavikiq 181 aeklpfltfg nsdqlqigdw aiaignpfgl qatvtvgvis akgrnqlhiv dfedfiqtda 241 ainpgnsggp llningqvig vntaivsgsg gyigigfaip slmakrvidq lisdgqvtrg 301 flgvtlqpid selatcykle kvygalvtdv vkgspaekag lrqedvivay ngkeveslsa 361 lrnaislmmp gtrvvlkivr egktieipvt vtqiptedgv salqkmgvrv qnitpeickk 421 lglaadtrgi lvvaveagsp aasagvapgq lilavnrqrv asveelnqvl knskgenvll 481 mvsqgdvvrf ivlksde
```

CT681 (MOMP, 393 amino acids), ACCESSION# NP 220200.1, GI: 15605414
(SEQ ID NO: 7935)
```
  1 mkkllksvlv faalssassl qalpvgnpae pslmidgilw egfggdpcdp catwcdaism 61 rvgyygdfvf drvlktdvnk efqmgakptt dtgnsaapst ltarenpayg rhmqdaemft 121 naacmalniw drfdvfctlg atsgylkgns asfnlvglfg dnenqktvka esvpnmsfdq 181 svvelytdtt fawsvgaraa lwecgcatlg asfqyaqskp kveelnvlcn aaeftinkpk 241 gyvgkefpld ltagtdaatg tkdasidyhe wqaslalsyr lnmftpyigv kwsrasfdad 301 tiriaqpksa taifdttlln ptiagagdvk tgaegqlgdt mqivslqlnk mksrkscgia 361 vgttivdadk yavtvetrli deraahvnaq frf
```

CT119 (IncA, 273 amino acids), ACCESSION# NP 219622.1, GI: 15604838
(SEQ ID NO: 7936)
```
  1 mttptlivtp psppapsysa nrvpqpslmd kikkiaaias liligtigfl allghlvgfl 61 iapqitivll alfiislagn alylqktanl hlyqdlqrev gslkeinfml svlqkeflhl 121 skefattskd lsavsqdfys clqgfrdnyk gfeslldeyk nsteemrklf sqeiiadlkg 181 svaslreeir fltplaeevr rlahnqqslt vvieelktir dslrdeigql sqlsktltsq 241 ialqrkessd lcsqiretls sprksaspst kss
```

CT813 (inclusion membrane protein, 264 amino acids), ACCESSION#
NP 220333.1, GI: 15605547
(SEQ ID NO: 7937)
```
  1 mttlpnncts nsnsintftk diemakqiqg srkdplakts wiaglicvva gvlgllaigi 61 ggcsmasglg ligaivaavi vavglcclvs alclqveksq wwqkefeswi eqksqfrivm 121 admlkanrkl qseveflskg wsddtavhke dvtkyeqvve eyaekimely eetgvltiek 181 inlqkekkaw leekaemeqk lttvtdleaa kqqleekvtd lesekqelre eldkaienld 241 emayeamefe kekhgikpgr rgsi
```

CT795 (hypothetical protein, 163 amino acids), ACCESSION# NP 220315.1,
GI: 15605529
(SEQ ID NO: 7938)
```
  1 mrfllalfsl ilvlpateaf stedkqcqqe aeedcsqvad tcvfysyaeg lehardegkl 61 tivvlldtsg ysfetladaa hamessllst fadfvvlsrr eavpliyppv pdpmvgeial 121 fleafsdqtf psqpvivtla igassaeimd iteipsinpe fve
```

CT621 (hypothetical protein, 832 amino acids), ACCESSION# NP 220138.1,
GI: 15605352
(SEQ ID NO: 7939)
```
  1 mnrihrtqgs ltdynstlea iakkiakpds ativsqvaqy eqfkmeqeal kallvsfdqk 61 adqryrnliq rleqldvdrq tgrstesqhi qekpmaslqs enqvvaqavv qsdssmpift 121 gikqswavrl vqgireildq vlvdtslfte eergdllair mdaaslqdkq erlstedirs 181 llslsndvmr vlqkasysst rqleliqsli difgteenle qsfaqvrlen fqailsvike 241 rlteeefrvf qevseeissi qrtseshlsp ehieaiarvg ghlsakives elkasqkvdl 301 cqriaamyqe qvdavqayhs leqdalfvns rqhshfvqvi slvsslmhsl sptseeeril 361 lnpammvsvl ptvraiglrf dfltaeqqqm vnaavsslqq qqldeflgvl cahlvvvncq
```

```
421 nketgllegl eesfsetlsg lsnnfvltak mqdilqvcsl qgfvtlangd ryelfsynds 481 geavcdeial gdgfhkvlgt mlavalsqae vfkqecdrfi lqadseknmi hkrmvqgeqk 541 slfltkmqte lnagktiaqt keveasplps avasvlidhy mpkeveflek issrlyygnk 601 gsdigntild aislyvnsat yfgfanyigq ppvvgktren ifagsadnak akldeekkqv 661 dvfleiteaa kttvtnqqsa vtnddklste qkakikaelt qytdmlnais nsltslktql 721 aplsvstveg vdgvfevkng ipgengknwr lvlqtledtv vsgevgsptn igmfqmqalv 781 hlnqqayadm gqnfqlelqm hltsmqqewm vvatslqlln qiylglarnl lr CT622 (hypothetical protein, 647 amino acids), ACCESSION# NP 220139.1,
GI: 15605353
                                                    (SEQ ID NO: 7940)
  1 mesgpesyss nqssmnpiin gqiasnsetk estkeseasp sasssvssws flssakhali 61 slrdailnkn ssptdslsql eastststvt rvaardynea ksnfdtaksg lenattlaey 121 etkmadlmaa lqdmerlakq kaevtrikea lqekqevidk lnqlvklekq nqtlketltt 181 tdsadqipai nsqleinkns adqiikdleg qnisyeavlt nagevikass eagiklgqal 241 qsivdagdqs qaavlqaqqn nspdniaatk klidaaetkv nelkqehtgl tdsplvkkae 301 eqisqaqkdi qeikpsgsdi pivgpsgsaa sagsavgalk ssnnsgrisl llddvdnema 361 aiamqgfrsm ieqfnvnnpa takelqamea qltamsdqlv gadgelpaei qaikdalaqa 421 lkqpstdgla tamgqvafaa akvgggsagt agtvqmnvkq lyktafssts sssyaaalsd 481 gysayktlns lysesrsgvq saisqtanpa lsrsysrsgi esqgrsadas qraaetivrd 541 sqtlgdvysr lqvldslmst ivsnpqvnqe eimqkltasi skapqfgypa vqnsadslqk 601 faaqlerefv dgerslaesr enafrkqpaf iqqvlvnias lfsgyls
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09046530B2). An electronic copy of the "Sequence Listing" will also be available from the USPTO upon request and payment of the fee set forth in 37 CFR 1.19(b)(3).

What is claimed is:

1. A method of identifying an infertile female subject for whom in vitro fertilization or surgical repair of fallopian tube damage is indicated to treat the subject's infertility, comprising:
    (a) contacting a biological sample from the subject with a diagnostic panel comprising an antigen of each of Chlamydia trachomatis CT443 or an immunologically reactive fragment thereof, Chlamydia trachomatis CT381 or an immunologically reactive fragment thereof, and Chlamydia trachomatis CT875 or an immunologically reactive fragment thereof;
    (b) detecting formation of an antigen/antibody complex with each of the antigen of Chlamydia trachomatis CT443 or an immunologically reactive fragment thereof and the antigen of Chlamydia trachomatis CT381 or an immunologically reactive fragment thereof and detecting the absence of formation of an antigen/antibody complex with the antigen of Chlamydia trachomatis CT875 or an immunologically reactive fragment thereof in the sample, wherein the detection of an antigen/antibody complex with each of the antigen of Chlamydia trachomatis CT443 or an immunologically reactive fragment thereof and the antigen of Chlamydia trachomatis CT381 or an immunologically reactive fragment thereof and detection of the absence of formation of an antigen/antibody complex with the antigen of Chlamydia trachomatis CT875 or an immunologically reactive fragment thereof in the sample identifies the subject as having tubal factor infertility, thereby identifying the subject as a subject for whom in vitro fertilization or surgical repair of fallopian tube damage is indicated to treat the subject's infertility; and
    (c) treating the subject identified in step (b) as having tubal factor infertility by in vitro fertilization or surgical repair of fallopian tube damage.

2. The method of claim 1, wherein the tubal factor infertility is caused by chlamydial infection.

3. The method of claim 1, wherein the subject is a human female.

4. The method of claim 1, wherein the biological sample is any body fluid in which antibodies can be detected.

5. The method of claim 1, wherein the biological sample is diluted 1:1000.

6. The method of claim 1, wherein the antigen of the CT443 protein or immunologically reactive fragment thereof is a C terminal fragment.

7. The method of claim 1, further comprising contacting the biological sample of (a) with an additional antigen selected from the group consisting of *Chlamydia trachomatis* HSP60 or an immunologically reactive fragment thereof, *Chlamydia trachomatis* CT376 or an immunologically reactive fragment thereof, *Chlamydia trachomatis* CT557 or an immunologically reactive fragment thereof and any combination thereof, and an antigen/antibody complex is detected in the sample for each of said additional antigen(s).

\* \* \* \* \*

UNITED STATES PATENT AND TRADEMARK OFFICE
CERTIFICATE OF CORRECTION

PATENT NO. : 9,046,530 B2
APPLICATION NO. : 13/691260
DATED : June 2, 2015
INVENTOR(S) : Zhong Page 1 of 1

It is certified that error appears in the above-identified patent and that said Letters Patent is hereby corrected as shown below:

In the Specification:
Column 16, Line 16: Please correct "(ETA)," to read -- (EIA), --
Column 20, Line 32: Please correct "304 ml" to read -- 30 µg/ml --
Column 144, Table 6 Notes, Line 24: Please correct "CT681 (14014P)," to read -- CT681 (MOMP), --

Signed and Sealed this
Seventeenth Day of May, 2016

Michelle K. Lee
*Director of the United States Patent and Trademark Office*